(12) United States Patent
Bowie et al.

(10) Patent No.: US 11,104,919 B2
(45) Date of Patent: Aug. 31, 2021

(54) CELL-FREE METABOLIC PATHWAY FOR GLUCOSE METABOLISM WITH A MOLECULAR PURGE VALVE

(71) Applicant: The Regents of the University of California, Oakland, CA (US)

(72) Inventors: James U. Bowie, Culver City, CA (US); Tyler P. Korman, Sierra Madre, CA (US); Paul H. Opgenorth, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 21 days.

(21) Appl. No.: 15/744,049

(22) PCT Filed: Jul. 21, 2016

(86) PCT No.: PCT/US2016/043260
§ 371 (c)(1),
(2) Date: Jan. 11, 2018

(87) PCT Pub. No.: WO2017/015429
PCT Pub. Date: Jan. 26, 2017

(65) Prior Publication Data
US 2018/0201958 A1 Jul. 19, 2018

Related U.S. Application Data

(60) Provisional application No. 62/195,142, filed on Jul. 21, 2015.

(51) Int. Cl.
*C12P 7/16* (2006.01)
*C12P 7/62* (2006.01)

(52) U.S. Cl.
CPC .............. *C12P 7/16* (2013.01); *C12P 7/625* (2013.01); *C12Y 101/01044* (2013.01); *C12Y 202/01001* (2013.01); *C12Y 202/01002* (2013.01); *C12Y 203/01008* (2013.01); *C12Y 301/01031* (2013.01); *C12Y 401/02009* (2013.01); *C12Y 401/02013* (2013.01); *C12Y 401/02022* (2013.01); *C12Y 501/03001* (2013.01); *C12Y 503/01001* (2013.01); *C12Y 503/01006* (2013.01); *C12Y 503/01009* (2013.01); *Y02E 50/10* (2013.01)

(58) Field of Classification Search
None
See application file for complete search history.

(56) References Cited

U.S. PATENT DOCUMENTS

| 10,196,653 | B2 * | 2/2019 | Bowie | C12Y 102/01051 |
|---|---|---|---|---|
| 2002/0011863 | A1 | 8/2002 | Kawase et al. | |
| 2003/0233675 | A1 | 12/2003 | Cao et al. | |
| 2009/0162881 | A1 | 6/2009 | Okamura et al. | |
| 2011/0124073 | A1 | 5/2011 | Devroe et al. | |
| 2013/0030164 | A1 | 1/2013 | Yoshida et al. | |
| 2014/0058056 | A1 | 2/2014 | Burgard et al. | |
| 2017/0183688 | A1 | 6/2017 | Bowie et al. | |

FOREIGN PATENT DOCUMENTS

| WO | 2010/051527 A2 | 5/2010 |
|---|---|---|
| WO | 2014/018757 A1 | 1/2014 |
| WO | 2014/153036 A1 | 9/2014 |
| WO | 2014/197702 A1 | 12/2014 |
| WO | 2015/153929 A2 | 10/2015 |

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
Bologna et al. J Bacteriol. Aug. 2007; 189(16): 5937-5946 (Year: 2007).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Mohri, Mineko, International Preliminary Report on Patentability, PCT/US2016/043260, The International Bureau of WIPO, dated Feb. 1, 2018.
Thomas, Shane, International Search Report and Written Opinion, PCT/US2016/043260, U.S. Patent and Trademark Office, dated Jan. 13, 2017.
Bogorad et al., "Synthetic non-oxidative glycolysis enables complete carbon conservation," Nature, 502:693-698, Oct. 31, 2013.
Kohara et al., C65173 Yuji Kohara Unpublished cDNA Caeonohabditis Elegans cDNA clone yk406c5 5, mRNA sequence; GenBank Accession No. C65173, Jul. 2006.
Korman et al., "A synthetic biochemistry system for the in vitro production of isoprene from glycolysis intermediates," Protein Science, 23:576-585, Feb. 6, 2014.
Opgenorth et al., "A synthetic biochemistry molecular purge valve module that maintains redox balance," Nat. Commun., vol. 5, pp. 4113, Jun. 17, 2014.
Wade et al., GenBank Accession No. G86673, Sep. 6, 2002.
Callura et al., "Genetic switchboard for synthetic biology applications", PNAS, Apr. 10, 2012, vol. 109, No. 15, pp. 5850-5855.
Korsner, Sven-Erik, Office Action, European Patent Office, Application No. 16828516.1, dated Sep. 25, 2019.
Korman et al., "Development and use of a molecular purge valve to maintain reduction/oxidation balance in synthetic biochemistry systems", 29th Annual Symposium of the Protein Society, Jul. 22-25, 2015, Barcelona, Spain, p. 60, Retrieved from the Internet: URL:https://onlinelibrary.wiley.com/doi/epdf/10.1002/pro.2823 [retrieved Dec. 19, 2018].

(Continued)

*Primary Examiner* — Christian L Fronda
(74) *Attorney, Agent, or Firm* — Gavrilovich, Dodd & Lindsey LLP

(57) ABSTRACT

Provided is an engineered pathway that can function in a cell-free system, cellular system or a combination thereof to convert a sugar to a chemical or biofuel.

6 Claims, 13 Drawing Sheets
Specification includes a Sequence Listing.

(56) References Cited

OTHER PUBLICATIONS

Korsner, Sven-Erik, Extended European Search Report, European Patent Office, Application No. 16828516.1, dated Feb. 11, 2019.
Opgenorth, "A synthetic biochemistry molecular purge valve module that maintains redox balance", 28th Annual Symposium of the Protein Society, Jul. 2014, San Diego, CA, pp. 151-152, Retrieved from the Internet: URL:https://onlinelibrary.wiley.com/doi/epdf/10.1002/pro.2504 [retrieved on Dec. 19, 2018].
Opgenorth, "Production of bio-based chemicals in vivo and in vitro", University of California Dissertation, 2015, p. i-xi, 1-103, Retrieved from the Internet: URL:https://cloudfront.escholarship.org/dist/prd/content/qt05k8b5zq/qt05k8b5zq.pdf?t=nxcsuh [retrieved Dec. 20, 2018].
Opgenorth, "A synthetic biochemistry module for production of bio-based chemicals from glucose", Nature Chemical Biology, vol. 12, Apr. 11, 2016, pp. 393-395.
Su et al., "Alleviating redox imbalance enhances 7-dehydrocholesterol production in engineered *Saccharomyces cerevisiae*", PLOS One, vol. 10, Jun. 22, 2015, pp. 1-15.
Grozinger, Thilo, Office Action, European Patent Office, Application No. 16828516.1, dated Feb. 24, 2021.

\* cited by examiner

Mutant PDH is NADP+ Specific
Wild-Type PDH is NAD+ Specific

- Molecular Purge Valve = WT PDH, Mutant PDH, and NoxE
- >80% Conversion of Pyruvate to polyhydroxybutyrate (PHB) or isoprene
- Demonstrates carbon flux in the presence of high NADPH concentration

SEQUENCE LISTING

<160> NUMBER OF SEQ ID NOS: 64

<210> SEQ ID NO 1
<211> LENGTH: 2478
<212> TYPE: DNA
<213> ORGANISM: Bifidobacterium adolescentis
<220> FEATURE:
<221> NAME/KEY: CDS
<222> LOCATION: (1)..(2478)

<400> SEQUENCE: 1

```
atg acg agt cct gtt att ggc acc cct tgg aag aag ctg aac gct ccg      48
Met Thr Ser Pro Val Ile Gly Thr Pro Trp Lys Lys Leu Asn Ala Pro
1               5                   10                  15 gtt tcc gag gaa gct atc gaa ggc gtg gat aag tac tgg cgc gca gcc      96
Val Ser Glu Glu Ala Ile Glu Gly Val Asp Lys Tyr Trp Arg Ala Ala
            20                  25                  30 aac tac ctc tcc atc ggc cag atc tat ctg cgt agc aac ccg ctg atg     144
Asn Tyr Leu Ser Ile Gly Gln Ile Tyr Leu Arg Ser Asn Pro Leu Met
        35                  40                  45 aag gag cct ttc acc cgc gaa gac gtc aag cac cgt ctg gtc ggt cac     192
Lys Glu Pro Phe Thr Arg Glu Asp Val Lys His Arg Leu Val Gly His
    50                  55                  60 tgg ggc acc acc ccg ggc ctg aac ttc ctc atc ggc cac atc aac cgt     240
Trp Gly Thr Thr Pro Gly Leu Asn Phe Leu Ile Gly His Ile Asn Arg
65                  70                  75                  80 ctc att gct gat cac cag cag aac act gtg atc atc atg ggc ccg ggc     288
Leu Ile Ala Asp His Gln Gln Asn Thr Val Ile Ile Met Gly Pro Gly
                85                  90                  95 cac ggc ggc ccg gct ggt acc gct cag tcc tac ctg gac ggc acc tac     336
His Gly Gly Pro Ala Gly Thr Ala Gln Ser Tyr Leu Asp Gly Thr Tyr
            100                 105                 110 acc gag tac ttc ccg aac atc acc aag gat gag gct ggc ctg cag aag     384
Thr Glu Tyr Phe Pro Asn Ile Thr Lys Asp Glu Ala Gly Leu Gln Lys
        115                 120                 125 ttc ttc cgc cag ttc tcc tac ccg ggt ggc atc ccg tcc cac tac gct     432
Phe Phe Arg Gln Phe Ser Tyr Pro Gly Gly Ile Pro Ser His Tyr Ala
    130                 135                 140 ccg gag acc ccg ggc tcc atc cac gaa ggc ggc gag ctg ggt tac gcc     480
Pro Glu Thr Pro Gly Ser Ile His Glu Gly Gly Glu Leu Gly Tyr Ala
145                 150                 155                 160
```

-continued

| | | |
|---|---|---|
| ctg tcc cac gcc tac ggc gct gtg atg aac aac ccg agc ctg ttc gtc<br>Leu Ser His Ala Tyr Gly Ala Val Met Asn Asn Pro Ser Leu Phe Val<br>165 170 175 | 528 | |
| ccg gcc atc gtc ggc gac ggt gaa gct gag acc ggc ccg ctg gcc acc<br>Pro Ala Ile Val Gly Asp Gly Glu Ala Glu Thr Gly Pro Leu Ala Thr<br>180 185 190 | 576 | |
| ggc tgg cag tcc aac aag ctc atc aac ccg cgc acc gac ggt atc gtg<br>Gly Trp Gln Ser Asn Lys Leu Ile Asn Pro Arg Thr Asp Gly Ile Val<br>195 200 205 | 624 | |
| ctg ccg atc ctg cac ctc aac ggc tac aag atc gcc aac ccg acc atc<br>Leu Pro Ile Leu His Leu Asn Gly Tyr Lys Ile Ala Asn Pro Thr Ile<br>210 215 220 | 672 | |
| ctg tcc cgc atc tcc gac gaa gag ctc cac gag ttc ttc cac ggc atg<br>Leu Ser Arg Ile Ser Asp Glu Glu Leu His Glu Phe Phe His Gly Met<br>225 230 235 240 | 720 | |
| ggc tat gag ccg tac gag ttc gtc gct ggc ttc gac aac gag gat cac<br>Gly Tyr Glu Pro Tyr Glu Phe Val Ala Gly Phe Asp Asn Glu Asp His<br>245 250 255 | 768 | |
| ctg tcg atc cac cgt cgt ttc gcc gag ctg ttc gag acc gtc ttc gac<br>Leu Ser Ile His Arg Arg Phe Ala Glu Leu Phe Glu Thr Val Phe Asp<br>260 265 270 | 816 | |
| gag atc tgc gac atc aag gcc gcc gct cag acc gac gac atg act cgt<br>Glu Ile Cys Asp Ile Lys Ala Ala Ala Gln Thr Asp Asp Met Thr Arg<br>275 280 285 | 864 | |
| ccg ttc tac ccg atg atc atc ttc cgt acc ccg aag ggc tgg acc tgc<br>Pro Phe Tyr Pro Met Ile Ile Phe Arg Thr Pro Lys Gly Trp Thr Cys<br>290 295 300 | 912 | |
| ccg aag ttc atc gac ggc aag aag acc gag ggc tcc tgg cgt tcc cac<br>Pro Lys Phe Ile Asp Gly Lys Lys Thr Glu Gly Ser Trp Arg Ser His<br>305 310 315 320 | 960 | |
| cag gtg ccg ctg gct tcc gcc cgc gat acc gag gcc cac ttc gag gtc<br>Gln Val Pro Leu Ala Ser Ala Arg Asp Thr Glu Ala His Phe Glu Val<br>325 330 335 | 1008 | |
| ctc aag aac tgg ctc gag tcc tac aag ccg gaa gag ctg ttc gac gag<br>Leu Lys Asn Trp Leu Glu Ser Tyr Lys Pro Glu Glu Leu Phe Asp Glu<br>340 345 350 | 1056 | |
| aac ggc gcc gtg aag ccg gaa gtc acc gcc ttc atg ccg acc ggc gaa<br>Asn Gly Ala Val Lys Pro Glu Val Thr Ala Phe Met Pro Thr Gly Glu<br>355 360 365 | 1104 | |
| ctg cgc atc ggt gag aac ccg aac gcc aac ggt ggc cgc atc cgc gaa<br>Leu Arg Ile Gly Glu Asn Pro Asn Ala Asn Gly Gly Arg Ile Arg Glu<br>370 375 380 | 1152 | |
| gag ctg aag ctg ccg aag ctg gaa gac tac gag gtc aag gaa gtc gcc<br>Glu Leu Lys Leu Pro Lys Leu Glu Asp Tyr Glu Val Lys Glu Val Ala<br>385 390 395 400 | 1200 | |
| gag tac ggc cac ggc tgg ggc cag ctc gag gcc acc cgt cgt ctg ggc<br>Glu Tyr Gly His Gly Trp Gly Gln Leu Glu Ala Thr Arg Arg Leu Gly<br>405 410 415 | 1248 | |
| gtc tac acc cgc gac atc atc aag aac aac ccg gac tcc ttc cgt atc<br>Val Tyr Thr Arg Asp Ile Ile Lys Asn Asn Pro Asp Ser Phe Arg Ile<br>420 425 430 | 1296 | |
| ttc gga ccg gat gag acc gct tcc aac cgt ctg cag gcc gct tac gac<br>Phe Gly Pro Asp Glu Thr Ala Ser Asn Arg Leu Gln Ala Ala Tyr Asp<br>435 440 445 | 1344 | |
| gtc acc aac aag cag tgg gac gcc ggc tac ctg tcc gct cag gtc gac<br>Val Thr Asn Lys Gln Trp Asp Ala Gly Tyr Leu Ser Ala Gln Val Asp<br>450 455 460 | 1392 | |
| gag cac atg gct gtc acc ggc cag gtc acc gag cag ctt tcc gag cac<br>Glu His Met Ala Val Thr Gly Gln Val Thr Glu Gln Leu Ser Glu His<br>465 470 475 480 | 1440 | |

-continued

| | |
|---|---|
| cag atg gaa ggc ttc ctc gag ggc tac ctg ctg acc ggc cgt cac ggc<br>Gln Met Glu Gly Phe Leu Glu Gly Tyr Leu Leu Thr Gly Arg His Gly<br>                     485                       490                   495 | 1488 |
| atc tgg agc tcc tat gag tcc ttc gtg cac gtg atc gac tcc atg ctg<br>Ile Trp Ser Ser Tyr Glu Ser Phe Val His Val Ile Asp Ser Met Leu<br>500                       505                       510 | 1536 |
| aac cag cac gcc aag tgg ctc gag gct acc gtc cgc gag att ccg tgg<br>Asn Gln His Ala Lys Trp Leu Glu Ala Thr Val Arg Glu Ile Pro Trp<br>       515                   520                   525 | 1584 |
| cgc aag ccg atc tcc tcc atg aac ctg ctc gtc tcc tcc cac gtg tgg<br>Arg Lys Pro Ile Ser Ser Met Asn Leu Leu Val Ser Ser His Val Trp<br>530                       535                       540 | 1632 |
| cgt cag gat cac aac ggc ttc tcc cac cag gat ccg ggt gtc acc tcc<br>Arg Gln Asp His Asn Gly Phe Ser His Gln Asp Pro Gly Val Thr Ser<br>545                       550                   555                   560 | 1680 |
| gtc ctg ctg aac aag tgc ttc aac aac gat cac gtg atc ggc atc tac<br>Val Leu Leu Asn Lys Cys Phe Asn Asn Asp His Val Ile Gly Ile Tyr<br>                     565                   570                   575 | 1728 |
| ttc ccg gtg gat tcc aac atg ctg ctc gct gtg gct gag aag tgc tac<br>Phe Pro Val Asp Ser Asn Met Leu Leu Ala Val Ala Glu Lys Cys Tyr<br>580                       585                       590 | 1776 |
| aag tcc acc aac aag atc aac gcc atc atc gcc ggc aag cag ccg gcc<br>Lys Ser Thr Asn Lys Ile Asn Ala Ile Ile Ala Gly Lys Gln Pro Ala<br>       595                   600                   605 | 1824 |
| gcc acc tgg ctg acc ctg gac gaa gct cgc gcc gag ctc gag aag ggt<br>Ala Thr Trp Leu Thr Leu Asp Glu Ala Arg Ala Glu Leu Glu Lys Gly<br>610                       615                       620 | 1872 |
| gct gcc gag tgg aag tgg gct tcc aac gtg aag tcc aac gat gag gct<br>Ala Ala Glu Trp Lys Trp Ala Ser Asn Val Lys Ser Asn Asp Glu Ala<br>625                       630                   635                   640 | 1920 |
| cag atc gtg ctc gcc gcc acc ggt gat gtt ccg act cag gaa atc atg<br>Gln Ile Val Leu Ala Ala Thr Gly Asp Val Pro Thr Gln Glu Ile Met<br>                     645                   650                   655 | 1968 |
| gcc gct gcc gac aag ctg gac gcc atg ggc atc aag ttc aag gtc gtc<br>Ala Ala Ala Asp Lys Leu Asp Ala Met Gly Ile Lys Phe Lys Val Val<br>660                       665                       670 | 2016 |
| aac gtg gtt gac ctg gtc aag ctg cag tcc gcc aag gag aac aac gag<br>Asn Val Val Asp Leu Val Lys Leu Gln Ser Ala Lys Glu Asn Asn Glu<br>                     675                   680                   685 | 2064 |
| gcc ctc tcc gat gag gag ttc gct gag ctg ttc acc gag gac aag ccg<br>Ala Leu Ser Asp Glu Glu Phe Ala Glu Leu Phe Thr Glu Asp Lys Pro<br>690                       695                       700 | 2112 |
| gtc ctg ttc gct tac cac tcc tat gcc cgc gat gtg cgt ggt ctg atc<br>Val Leu Phe Ala Tyr His Ser Tyr Ala Arg Asp Val Arg Gly Leu Ile<br>705                       710                   715                   720 | 2160 |
| tac gat cgc ccg aac cac gac aac ttc aac gtt cac ggc tac gag gag<br>Tyr Asp Arg Pro Asn His Asp Asn Phe Asn Val His Gly Tyr Glu Glu<br>                     725                   730                   735 | 2208 |
| cag ggc tcc acc acc acc ccg tac gac atg gtt cgc gtg aac aac atc<br>Gln Gly Ser Thr Thr Thr Pro Tyr Asp Met Val Arg Val Asn Asn Ile<br>740                       745                       750 | 2256 |
| gat cgc tac gag ctc cag gct gaa gct ctg cgc atg att gac gct gac<br>Asp Arg Tyr Glu Leu Gln Ala Glu Ala Leu Arg Met Ile Asp Ala Asp<br>       755                   760                   765 | 2304 |
| aag tac gcc gac aag atc aac gag ctc gag gcc ttc cgt cag gaa gcc<br>Lys Tyr Ala Asp Lys Ile Asn Glu Leu Glu Ala Phe Arg Gln Glu Ala<br>770                       775                       780 | 2352 |
| ttc cag ttc gct gtc gac aac ggc tac gat cac ccg gat tac acc gac<br>Phe Gln Phe Ala Val Asp Asn Gly Tyr Asp His Pro Asp Tyr Thr Asp | 2400 |

| | | | | | | | | | | | | | | | 785 | | | | | 790 | | | | | 795 | | | | | 800 | | |
|---|---|---|---|---|---|---|---|---|---|---|---|---|---|---|---|---|---|---|---|---|---|---|---|---|---|---|---|---|---|---|---|---|

```
                        785                 790                 795                 800
tgg gtc tac tcc ggt gtc aac acc aac aag cag ggt gct atc tcc gct      2448
Trp Val Tyr Ser Gly Val Asn Thr Asn Lys Gln Gly Ala Ile Ser Ala
                805                 810                 815 acc gcc gca acc gct ggc gat aac gag tga                              2478
Thr Ala Ala Thr Ala Gly Asp Asn Glu
                820                 825

<210> SEQ ID NO 2
<211> LENGTH: 825
<212> TYPE: PRT
<213> ORGANISM: Bifidobacterium adolescentis

<400> SEQUENCE: 2

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
                20                  25                  30

Asn Tyr Leu Ser Ile Gly Gln Ile Tyr Leu Arg Ser Asn Pro Leu Met
            35                  40                  45

Lys Glu Pro Phe Thr Arg Glu Asp Val Lys His Arg Leu Val Gly His
        50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Met Gly Pro Gly
                85                  90                  95

His Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Ile Asn Pro Arg Thr Asp Gly Ile Val
        195                 200                 205

Leu Pro Ile Leu His Leu Asn Gly Tyr Lys Ile Ala Asn Pro Thr Ile
210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270

Glu Ile Cys Asp Ile Lys Ala Ala Ala Gln Thr Asp Asp Met Thr Arg
        275                 280                 285

Pro Phe Tyr Pro Met Ile Ile Phe Arg Thr Pro Lys Gly Trp Thr Cys
290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
```

-continued

```
                325                 330                 335
Leu Lys Asn Trp Leu Glu Ser Tyr Lys Pro Glu Glu Leu Phe Asp Glu
            340                 345                 350
Asn Gly Ala Val Lys Pro Glu Val Thr Ala Phe Met Pro Thr Gly Glu
        355                 360                 365
Leu Arg Ile Gly Glu Asn Pro Asn Ala Asn Gly Gly Arg Ile Arg Glu
    370                 375                 380
Glu Leu Lys Leu Pro Lys Leu Glu Asp Tyr Glu Val Lys Glu Val Ala
385                 390                 395                 400
Glu Tyr Gly His Gly Trp Gly Gln Leu Glu Ala Thr Arg Arg Leu Gly
                405                 410                 415
Val Tyr Thr Arg Asp Ile Ile Lys Asn Asn Pro Asp Ser Phe Arg Ile
            420                 425                 430
Phe Gly Pro Asp Glu Thr Ala Ser Asn Arg Leu Gln Ala Ala Tyr Asp
        435                 440                 445
Val Thr Asn Lys Gln Trp Asp Ala Gly Tyr Leu Ser Ala Gln Val Asp
    450                 455                 460
Glu His Met Ala Val Thr Gly Gln Val Thr Glu Gln Leu Ser Glu His
465                 470                 475                 480
Gln Met Glu Gly Phe Leu Glu Gly Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ser Ser Met Asn Leu Leu Val Ser Ser His Val Trp
    530                 535                 540
Arg Gln Asp His Asn Gly Phe Ser His Gln Asp Pro Gly Val Thr Ser
545                 550                 555                 560
Val Leu Leu Asn Lys Cys Phe Asn Asn Asp His Val Ile Gly Ile Tyr
                565                 570                 575
Phe Pro Val Asp Ser Asn Met Leu Leu Ala Val Ala Glu Lys Cys Tyr
            580                 585                 590
Lys Ser Thr Asn Lys Ile Asn Ala Ile Ile Ala Gly Lys Gln Pro Ala
        595                 600                 605
Ala Thr Trp Leu Thr Leu Asp Glu Ala Arg Ala Glu Leu Glu Lys Gly
    610                 615                 620
Ala Ala Glu Trp Lys Trp Ala Ser Asn Val Lys Ser Asn Asp Glu Ala
625                 630                 635                 640
Gln Ile Val Leu Ala Ala Thr Gly Asp Val Pro Thr Gln Glu Ile Met
                645                 650                 655
Ala Ala Ala Asp Lys Leu Asp Ala Met Gly Ile Lys Phe Lys Val Val
            660                 665                 670
Asn Val Val Asp Leu Val Lys Leu Gln Ser Ala Lys Glu Asn Asn Glu
        675                 680                 685
Ala Leu Ser Asp Glu Glu Phe Ala Glu Leu Phe Thr Glu Asp Lys Pro
    690                 695                 700
Val Leu Phe Ala Tyr His Ser Tyr Ala Arg Asp Val Arg Gly Leu Ile
705                 710                 715                 720
Tyr Asp Arg Pro Asn His Asp Asn Phe Asn Val His Gly Tyr Glu Glu
                725                 730                 735
Gln Gly Ser Thr Thr Pro Tyr Asp Met Val Arg Val Asn Asn Ile
            740                 745                 750
```

```
Asp Arg Tyr Glu Leu Gln Ala Glu Ala Leu Arg Met Ile Asp Ala Asp
        755                 760                 765

Lys Tyr Ala Asp Lys Ile Asn Glu Leu Glu Ala Phe Arg Gln Glu Ala
        770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
                805                 810                 815

Thr Ala Thr Ala Gly Asp Asn Glu
        820                 825

<210> SEQ ID NO 3
<211> LENGTH: 999
<212> TYPE: DNA
<213> ORGANISM: Escherichia coli
<220> FEATURE:
<221> NAME/KEY: CDS
<222> LOCATION: (1)..(999)

<400> SEQUENCE: 3
```

| | | | | | | | | | | | | | | | | |
|---|---|---|---|---|---|---|---|---|---|---|---|---|---|---|---|---|
| atg | aaa | acg | tta | ggt | gaa | ttt | att | gtc | gaa | aag | cag | cac | gag | ttt | tct | 48 |
| Met | Lys | Thr | Leu | Gly | Glu | Phe | Ile | Val | Glu | Lys | Gln | His | Glu | Phe | Ser | |
| 1 | | | | 5 | | | | | 10 | | | | | 15 | | |
| cat | gct | acc | ggt | gag | ctc | act | gct | ttg | ctg | tcg | gca | ata | aaa | ctg | ggc | 96 |
| His | Ala | Thr | Gly | Glu | Leu | Thr | Ala | Leu | Leu | Ser | Ala | Ile | Lys | Leu | Gly | |
| | | | 20 | | | | | 25 | | | | | 30 | | | |
| gcc | aag | att | atc | cat | cgc | gat | atc | aac | aaa | gca | gga | ctg | gtt | gat | atc | 144 |
| Ala | Lys | Ile | Ile | His | Arg | Asp | Ile | Asn | Lys | Ala | Gly | Leu | Val | Asp | Ile | |
| | | 35 | | | | | 40 | | | | | 45 | | | | |
| ctg | ggt | gcc | agc | ggt | gct | gag | aac | gtg | cag | ggc | gag | gtt | cag | cag | aaa | 192 |
| Leu | Gly | Ala | Ser | Gly | Ala | Glu | Asn | Val | Gln | Gly | Glu | Val | Gln | Gln | Lys | |
| 50 | | | | | 55 | | | | | 60 | | | | | | |
| ctc | gac | ttg | ttc | gct | aat | gaa | aaa | ctg | aaa | gcc | gca | ctg | aaa | gca | cgc | 240 |
| Leu | Asp | Leu | Phe | Ala | Asn | Glu | Lys | Leu | Lys | Ala | Ala | Leu | Lys | Ala | Arg | |
| 65 | | | | | 70 | | | | | 75 | | | | | 80 | |
| gat | atc | gtt | gcg | ggc | att | gcc | tct | gaa | gaa | gaa | gat | gag | att | gtc | gtc | 288 |
| Asp | Ile | Val | Ala | Gly | Ile | Ala | Ser | Glu | Glu | Glu | Asp | Glu | Ile | Val | Val | |
| | | | | 85 | | | | | 90 | | | | | 95 | | |
| ttt | gaa | ggc | tgt | gaa | cac | gca | aaa | tac | gtg | gtg | ctg | atg | gac | ccc | ctg | 336 |
| Phe | Glu | Gly | Cys | Glu | His | Ala | Lys | Tyr | Val | Val | Leu | Met | Asp | Pro | Leu | |
| | | | | 100 | | | | | 105 | | | | | 110 | | |
| gat | ggc | tcg | tcc | aac | atc | gat | gtt | aac | gtc | tct | gtc | ggt | acc | att | ttc | 384 |
| Asp | Gly | Ser | Ser | Asn | Ile | Asp | Val | Asn | Val | Ser | Val | Gly | Thr | Ile | Phe | |
| | | | 115 | | | | | 120 | | | | | 125 | | | |
| tcc | atc | tac | cgc | cgc | gtt | acg | cct | gtt | ggc | acg | ccg | gta | acg | gaa | gaa | 432 |
| Ser | Ile | Tyr | Arg | Arg | Val | Thr | Pro | Val | Gly | Thr | Pro | Val | Thr | Glu | Glu | |
| | | 130 | | | | | 135 | | | | | 140 | | | | |
| gat | ttc | ctc | cag | cct | ggt | aac | aaa | cag | gtt | gcg | gca | ggt | tac | gtg | gta | 480 |
| Asp | Phe | Leu | Gln | Pro | Gly | Asn | Lys | Gln | Val | Ala | Ala | Gly | Tyr | Val | Val | |
| 145 | | | | | 150 | | | | | 155 | | | | | 160 | |
| tac | ggc | tcc | tct | acc | atg | ctg | gtt | tac | acc | acc | gga | tgc | ggt | gtt | cac | 528 |
| Tyr | Gly | Ser | Ser | Thr | Met | Leu | Val | Tyr | Thr | Thr | Gly | Cys | Gly | Val | His | |
| | | | | 165 | | | | | 170 | | | | | 175 | | |
| gcc | ttt | act | tac | gat | cct | tcg | ctc | ggc | gtt | ttc | tgc | ctg | tgc | cag | gaa | 576 |
| Ala | Phe | Thr | Tyr | Asp | Pro | Ser | Leu | Gly | Val | Phe | Cys | Leu | Cys | Gln | Glu | |
| | | | | 180 | | | | | 185 | | | | | 190 | | |
| cgg | atg | cgc | ttc | ccg | gag | aaa | ggc | aaa | acc | tac | tcc | atc | aac | gaa | gga | 624 |
| Arg | Met | Arg | Phe | Pro | Glu | Lys | Gly | Lys | Thr | Tyr | Ser | Ile | Asn | Glu | Gly | |
| | | | 195 | | | | | 200 | | | | | 205 | | | |

```
aac tac att aag ttt ccg aac ggg gtg aag aag tac att aaa ttc tgc      672
Asn Tyr Ile Lys Phe Pro Asn Gly Val Lys Lys Tyr Ile Lys Phe Cys
210                 215                 220 cag gaa gaa gat aaa tcc acc aac cgc cct tat acc tca cgt tat atc      720
Gln Glu Glu Asp Lys Ser Thr Asn Arg Pro Tyr Thr Ser Arg Tyr Ile
225                 230                 235                 240 ggt tca ctg gtc gcg gat ttc cac cgt aac ctg ctg aaa ggc ggt att      768
Gly Ser Leu Val Ala Asp Phe His Arg Asn Leu Leu Lys Gly Gly Ile
        245                 250                 255 tat ctc tac cca agc acc gcc agc cac ccg gac ggc aaa ctg cgt ttg      816
Tyr Leu Tyr Pro Ser Thr Ala Ser His Pro Asp Gly Lys Leu Arg Leu
        260                 265                 270 ctg tat gag tgc aac ccg atg gca ttc ctg gcg gaa caa gcg ggc ggt      864
Leu Tyr Glu Cys Asn Pro Met Ala Phe Leu Ala Glu Gln Ala Gly Gly
        275                 280                 285 aaa gcg agc gat ggc aaa gag cgt att ctg gat atc atc ccg gaa acc      912
Lys Ala Ser Asp Gly Lys Glu Arg Ile Leu Asp Ile Ile Pro Glu Thr
290                 295                 300 ctg cac cag cgc cgt tca ttc ttt gtc ggc aac gac cat atg gtt gaa      960
Leu His Gln Arg Arg Ser Phe Phe Val Gly Asn Asp His Met Val Glu
305                 310                 315                 320 gat gtc gaa cgc ttt atc cgt gag ttc ccg gac gcg taa                  999
Asp Val Glu Arg Phe Ile Arg Glu Phe Pro Asp Ala
                325                 330
```

<210> SEQ ID NO 4
<211> LENGTH: 332
<212> TYPE: PRT
<213> ORGANISM: Escherichia coli

<400> SEQUENCE: 4

```
Met Lys Thr Leu Gly Glu Phe Ile Val Glu Lys Gln His Glu Phe Ser
1               5                   10                  15

His Ala Thr Gly Glu Leu Thr Ala Leu Leu Ser Ala Ile Lys Leu Gly
            20                  25                  30

Ala Lys Ile Ile His Arg Asp Ile Asn Lys Ala Gly Leu Val Asp Ile
        35                  40                  45

Leu Gly Ala Ser Gly Ala Glu Asn Val Gln Gly Glu Val Gln Gln Lys
    50                  55                  60

Leu Asp Leu Phe Ala Asn Glu Lys Leu Lys Ala Leu Lys Ala Arg
65                  70                  75              80

Asp Ile Val Ala Gly Ile Ala Ser Glu Glu Asp Glu Ile Val Val
                85                  90                  95

Phe Glu Gly Cys Glu His Ala Lys Tyr Val Val Leu Met Asp Pro Leu
            100                 105                 110

Asp Gly Ser Ser Asn Ile Asp Val Asn Val Ser Val Gly Thr Ile Phe
        115                 120                 125

Ser Ile Tyr Arg Arg Val Thr Pro Val Gly Thr Pro Val Thr Glu Glu
    130                 135                 140

Asp Phe Leu Gln Pro Gly Asn Lys Gln Val Ala Ala Gly Tyr Val Val
145                 150                 155                 160

Tyr Gly Ser Ser Thr Met Leu Val Tyr Thr Thr Gly Cys Gly Val His
                165                 170                 175

Ala Phe Thr Tyr Asp Pro Ser Leu Gly Val Phe Cys Leu Cys Gln Glu
            180                 185                 190

Arg Met Arg Phe Pro Glu Lys Gly Lys Thr Tyr Ser Ile Asn Glu Gly
        195                 200                 205
```

```
Asn Tyr Ile Lys Phe Pro Asn Gly Val Lys Lys Tyr Ile Lys Phe Cys
    210                 215                 220

Gln Glu Glu Asp Lys Ser Thr Asn Arg Pro Tyr Thr Ser Arg Tyr Ile
225                 230                 235                 240

Gly Ser Leu Val Ala Asp Phe His Arg Asn Leu Leu Lys Gly Gly Ile
                245                 250                 255

Tyr Leu Tyr Pro Ser Thr Ala Ser His Pro Asp Gly Lys Leu Arg Leu
            260                 265                 270

Leu Tyr Glu Cys Asn Pro Met Ala Phe Leu Ala Glu Gln Ala Gly Gly
        275                 280                 285

Lys Ala Ser Asp Gly Lys Glu Arg Ile Leu Asp Ile Ile Pro Glu Thr
290                 295                 300

Leu His Gln Arg Arg Ser Phe Phe Val Gly Asn Asp His Met Val Glu
305                 310                 315                 320

Asp Val Glu Arg Phe Ile Arg Glu Phe Pro Asp Ala
                325                 330
```

<210> SEQ ID NO 5
<211> LENGTH: 678
<212> TYPE: DNA
<213> ORGANISM: Escherichia coli
<220> FEATURE:
<221> NAME/KEY: CDS
<222> LOCATION: (1)..(678)

<400> SEQUENCE: 5

```
atg aaa cag tat ttg att gcc ccc tca att ctg tcg gct gat ttt gcc    48
Met Lys Gln Tyr Leu Ile Ala Pro Ser Ile Leu Ser Ala Asp Phe Ala
1               5                   10                  15 cgc ctg ggt gaa gat acc gca aaa gcc ctg gca gct ggc gct gat gtc    96
Arg Leu Gly Glu Asp Thr Ala Lys Ala Leu Ala Ala Gly Ala Asp Val
            20                  25                  30 gtg cat ttt gac gtc atg gat aac cac tat gtt ccc aat ctg acg att   144
Val His Phe Asp Val Met Asp Asn His Tyr Val Pro Asn Leu Thr Ile
        35                  40                  45 ggg cca atg gtg ctg aaa tcc ttg cgt aac tat ggc att acc gcc cct   192
Gly Pro Met Val Leu Lys Ser Leu Arg Asn Tyr Gly Ile Thr Ala Pro
    50                  55                  60 atc gac gta cac ctg atg gtg aaa ccc gtc gat cgc att gtg cct gat   240
Ile Asp Val His Leu Met Val Lys Pro Val Asp Arg Ile Val Pro Asp
65                  70                  75                  80 ttc gct gcc gct ggt gcc agc atc att acc ttt cat cca gaa gcc tcc   288
Phe Ala Ala Ala Gly Ala Ser Ile Ile Thr Phe His Pro Glu Ala Ser
                85                  90                  95 gag cat gtt gac cgc acg ctg caa ctg att aaa gaa aat ggc tgt aaa   336
Glu His Val Asp Arg Thr Leu Gln Leu Ile Lys Glu Asn Gly Cys Lys
            100                 105                 110 gcg ggt ctg gta ttt aac ccg gcg aca cct ctg agc tat ctg gat tac   384
Ala Gly Leu Val Phe Asn Pro Ala Thr Pro Leu Ser Tyr Leu Asp Tyr
        115                 120                 125 gtg atg gat aag ctg gat gtg atc ctg ctg atg tcc gtc aac cct ggt   432
Val Met Asp Lys Leu Asp Val Ile Leu Leu Met Ser Val Asn Pro Gly
    130                 135                 140 ttc ggc ggt cag tct ttc att cct caa aca ctg gat aaa ctg cgc gaa   480
Phe Gly Gly Gln Ser Phe Ile Pro Gln Thr Leu Asp Lys Leu Arg Glu
145                 150                 155                 160 gta cgt cgc cgt atc gac gag tct ggc ttt gac att cga cta gaa gtg   528
Val Arg Arg Arg Ile Asp Glu Ser Gly Phe Asp Ile Arg Leu Glu Val
                165                 170                 175
```

```
gac  ggt  ggc  gtg  aag  gtg  aac  aac  att  ggc  gaa  atc  gct  gcg  gcg  ggc         576
Asp  Gly  Gly  Val  Lys  Val  Asn  Asn  Ile  Gly  Glu  Ile  Ala  Ala  Ala  Gly
          180                      185                      190 gcg  gat  atg  ttc  gtc  gcc  ggt  tcg  gca  atc  ttc  gac  cag  cca  gac  tac         624
Ala  Asp  Met  Phe  Val  Ala  Gly  Ser  Ala  Ile  Phe  Asp  Gln  Pro  Asp  Tyr
          195                      200                      205 aaa  aaa  gtc  att  gat  gaa  atg  cgc  agt  gaa  ctg  gca  aag  gta  agt  cat         672
Lys  Lys  Val  Ile  Asp  Glu  Met  Arg  Ser  Glu  Leu  Ala  Lys  Val  Ser  His
          210                      215                      220 gaa  taa                                                                                678
Glu
225

<210> SEQ ID NO 6
<211> LENGTH: 225
<212> TYPE: PRT
<213> ORGANISM: Escherichia coli

<400> SEQUENCE: 6

Met  Lys  Gln  Tyr  Leu  Ile  Ala  Pro  Ser  Ile  Leu  Ser  Ala  Asp  Phe  Ala
1                   5                       10                      15

Arg  Leu  Gly  Glu  Asp  Thr  Ala  Lys  Ala  Leu  Ala  Ala  Gly  Ala  Asp  Val
               20                      25                      30

Val  His  Phe  Asp  Val  Met  Asp  Asn  His  Tyr  Val  Pro  Asn  Leu  Thr  Ile
          35                      40                      45

Gly  Pro  Met  Val  Leu  Lys  Ser  Leu  Arg  Asn  Tyr  Gly  Ile  Thr  Ala  Pro
     50                      55                      60

Ile  Asp  Val  His  Leu  Met  Val  Lys  Pro  Val  Asp  Arg  Ile  Val  Pro  Asp
65                   70                      75                      80

Phe  Ala  Ala  Ala  Gly  Ala  Ser  Ile  Ile  Thr  Phe  His  Pro  Glu  Ala  Ser
                85                      90                      95

Glu  His  Val  Asp  Arg  Thr  Leu  Gln  Leu  Ile  Lys  Glu  Asn  Gly  Cys  Lys
               100                     105                     110

Ala  Gly  Leu  Val  Phe  Asn  Pro  Ala  Thr  Pro  Leu  Ser  Tyr  Leu  Asp  Tyr
          115                     120                     125

Val  Met  Asp  Lys  Leu  Asp  Val  Ile  Leu  Leu  Met  Ser  Val  Asn  Pro  Gly
     130                     135                     140

Phe  Gly  Gly  Gln  Ser  Phe  Ile  Pro  Gln  Thr  Leu  Asp  Lys  Leu  Arg  Glu
145                     150                     155                     160

Val  Arg  Arg  Arg  Ile  Asp  Glu  Ser  Gly  Phe  Asp  Ile  Arg  Leu  Glu  Val
                165                     170                     175

Asp  Gly  Gly  Val  Lys  Val  Asn  Asn  Ile  Gly  Glu  Ile  Ala  Ala  Ala  Gly
          180                     185                     190

Ala  Asp  Met  Phe  Val  Ala  Gly  Ser  Ala  Ile  Phe  Asp  Gln  Pro  Asp  Tyr
          195                     200                     205

Lys  Lys  Val  Ile  Asp  Glu  Met  Arg  Ser  Glu  Leu  Ala  Lys  Val  Ser  His
          210                     215                     220

Glu
225

<210> SEQ ID NO 7
<211> LENGTH: 660
<212> TYPE: DNA
<213> ORGANISM: Escherichia coli
<220> FEATURE:
<221> NAME/KEY: CDS
<222> LOCATION: (1)..(660)

<400> SEQUENCE: 7
```

```
atg acg cag gat gaa ttg aaa aaa gca gta gga tgg gcg gca ctt cag      48
Met Thr Gln Asp Glu Leu Lys Lys Ala Val Gly Trp Ala Ala Leu Gln
1               5                   10                  15 tat gtt cag ccc ggc acc att gtt ggt gta ggt aca ggt tcc acc gcc      96
Tyr Val Gln Pro Gly Thr Ile Val Gly Val Gly Thr Gly Ser Thr Ala
                20                  25                  30 gca cac ttt att gac gcg ctc ggt aca atg aaa ggc cag att gaa ggg     144
Ala His Phe Ile Asp Ala Leu Gly Thr Met Lys Gly Gln Ile Glu Gly
            35                  40                  45 gcc gtt tcc agt tca gat gct tcc act gaa aaa ctg aaa agc ctc ggc     192
Ala Val Ser Ser Ser Asp Ala Ser Thr Glu Lys Leu Lys Ser Leu Gly
        50                  55                  60 att cac gtt ttt gat ctc aac gaa gtc gac agc ctt ggc atc tac gtt     240
Ile His Val Phe Asp Leu Asn Glu Val Asp Ser Leu Gly Ile Tyr Val
65                  70                  75                  80 gat ggc gca gat gaa atc aac ggc cac atg caa atg atc aaa ggc ggc     288
Asp Gly Ala Asp Glu Ile Asn Gly His Met Gln Met Ile Lys Gly Gly
                85                  90                  95 ggc gcg gcg ctg acc cgt gaa aaa atc att gct tcg gtt gca gaa aaa     336
Gly Ala Ala Leu Thr Arg Glu Lys Ile Ile Ala Ser Val Ala Glu Lys
                100                 105                 110 ttt atc tgt att gca gac gct tcc aag cag gtt gat att ctg ggt aaa     384
Phe Ile Cys Ile Ala Asp Ala Ser Lys Gln Val Asp Ile Leu Gly Lys
            115                 120                 125 ttc ccg ctg cca gta gaa gtt atc ccg atg gca cgt agt gca gtg gcg     432
Phe Pro Leu Pro Val Glu Val Ile Pro Met Ala Arg Ser Ala Val Ala
        130                 135                 140 cgt cag ctg gtg aaa ctg ggc ggt cgt ccg gaa tac cgt cag ggc gtg     480
Arg Gln Leu Val Lys Leu Gly Gly Arg Pro Glu Tyr Arg Gln Gly Val
145                 150                 155                 160 gtg acc gat aat ggc aac gtg atc ctc gac gtc cac ggc atg gaa atc     528
Val Thr Asp Asn Gly Asn Val Ile Leu Asp Val His Gly Met Glu Ile
                165                 170                 175 ctt gac ccg ata gcg atg gaa aac gcc ata aat gcg att cct ggc gtg     576
Leu Asp Pro Ile Ala Met Glu Asn Ala Ile Asn Ala Ile Pro Gly Val
            180                 185                 190 gtg act gtt ggc ttg ttt gct aac cgt ggc gcg gac gtt gcg ctg att     624
Val Thr Val Gly Leu Phe Ala Asn Arg Gly Ala Asp Val Ala Leu Ile
        195                 200                 205 ggc aca cct gac ggt gtc aaa acc att gtg aaa tga                     660
Gly Thr Pro Asp Gly Val Lys Thr Ile Val Lys
        210                 215
```

<210> SEQ ID NO 8
<211> LENGTH: 219
<212> TYPE: PRT
<213> ORGANISM: Escherichia coli

<400> SEQUENCE: 8

```
Met Thr Gln Asp Glu Leu Lys Lys Ala Val Gly Trp Ala Ala Leu Gln
1               5                   10                  15

Tyr Val Gln Pro Gly Thr Ile Val Gly Val Gly Thr Gly Ser Thr Ala
                20                  25                  30

Ala His Phe Ile Asp Ala Leu Gly Thr Met Lys Gly Gln Ile Glu Gly
            35                  40                  45

Ala Val Ser Ser Ser Asp Ala Ser Thr Glu Lys Leu Lys Ser Leu Gly
        50                  55                  60

Ile His Val Phe Asp Leu Asn Glu Val Asp Ser Leu Gly Ile Tyr Val
65                  70                  75                  80
```

```
Asp Gly Ala Asp Glu Ile Asn Gly His Met Gln Met Ile Lys Gly Gly
                 85                  90                  95

Gly Ala Ala Leu Thr Arg Glu Lys Ile Ile Ala Ser Val Ala Glu Lys
            100                 105                 110

Phe Ile Cys Ile Ala Asp Ala Ser Lys Gln Val Asp Ile Leu Gly Lys
        115                 120                 125

Phe Pro Leu Pro Val Glu Val Ile Pro Met Ala Arg Ser Ala Val Ala
    130                 135                 140

Arg Gln Leu Val Lys Leu Gly Arg Pro Glu Tyr Arg Gln Gly Val
145                 150                 155                 160

Val Thr Asp Asn Gly Asn Val Ile Leu Asp Val His Gly Met Glu Ile
                165                 170                 175

Leu Asp Pro Ile Ala Met Glu Asn Ala Ile Asn Ala Ile Pro Gly Val
            180                 185                 190

Val Thr Val Gly Leu Phe Ala Asn Arg Gly Ala Asp Val Ala Leu Ile
        195                 200                 205

Gly Thr Pro Asp Gly Val Lys Thr Ile Val Lys
    210                 215

<210> SEQ ID NO 9
<211> LENGTH: 954
<212> TYPE: DNA
<213> ORGANISM: Escherichia coli
<220> FEATURE:
<221> NAME/KEY: CDS
<222> LOCATION: (1)..(954)

<400> SEQUENCE: 9 atg acg gac aaa ttg acc tcc ctt cgt cag tac acc acc gta gtg gcc     48
Met Thr Asp Lys Leu Thr Ser Leu Arg Gln Tyr Thr Thr Val Val Ala
1               5                   10                  15 gac act ggg gac atc gcg gca atg aag ctg tat caa ccg cag gat gcc     96
Asp Thr Gly Asp Ile Ala Ala Met Lys Leu Tyr Gln Pro Gln Asp Ala
            20                  25                  30 aca acc aac cct tct ctc att ctt aac gca gcg cag att ccg gaa tac    144
Thr Thr Asn Pro Ser Leu Ile Leu Asn Ala Ala Gln Ile Pro Glu Tyr
        35                  40                  45 cgt aag ttg att gat gat gct gtc gcc tgg gcg aaa cag cag agc aac    192
Arg Lys Leu Ile Asp Asp Ala Val Ala Trp Ala Lys Gln Gln Ser Asn
    50                  55                  60 gat cgc gcg cag cag atc gtg gac gcg acc gac aaa ctg gca gta aat    240
Asp Arg Ala Gln Gln Ile Val Asp Ala Thr Asp Lys Leu Ala Val Asn
65                  70                  75                  80 att ggt ctg gaa atc ctg aaa ctg gtt ccg ggc cgt atc tca act gaa    288
Ile Gly Leu Glu Ile Leu Lys Leu Val Pro Gly Arg Ile Ser Thr Glu
                85                  90                  95 gtt gat gcg cgt ctt tcc tat gac acc gaa gcg tca att gcg aaa gca    336
Val Asp Ala Arg Leu Ser Tyr Asp Thr Glu Ala Ser Ile Ala Lys Ala
            100                 105                 110 aaa cgc ctg atc aaa ctc tac aac gat gct ggt att agc aac gat cgt    384
Lys Arg Leu Ile Lys Leu Tyr Asn Asp Ala Gly Ile Ser Asn Asp Arg
        115                 120                 125 att ctg atc aaa ctg gct tct acc tgg cag ggt atc cgt gct gca gaa    432
Ile Leu Ile Lys Leu Ala Ser Thr Trp Gln Gly Ile Arg Ala Ala Glu
    130                 135                 140 cag ctg gaa aaa gaa ggc atc aac tgt aac ctg acc ctg ctg ttc tcc    480
Gln Leu Glu Lys Glu Gly Ile Asn Cys Asn Leu Thr Leu Leu Phe Ser
145                 150                 155                 160
```

```
ttc gct cag gct cgt gct tgt gcg gaa gcg ggc gtg ttc ctg atc tcg       528
Phe Ala Gln Ala Arg Ala Cys Ala Glu Ala Gly Val Phe Leu Ile Ser
                165                 170                 175 ccg ttt gtt ggc cgt att ctt gac tgg tac aaa gcg aat acc gat aag       576
Pro Phe Val Gly Arg Ile Leu Asp Trp Tyr Lys Ala Asn Thr Asp Lys
            180                 185                 190 aaa gag tac gct ccg gca gaa gat ccg ggc gtg gtt tct gta tct gaa       624
Lys Glu Tyr Ala Pro Ala Glu Asp Pro Gly Val Val Ser Val Ser Glu
        195                 200                 205 atc tac cag tac tac aaa gag cac ggt tat gaa acc gtg gtt atg ggc       672
Ile Tyr Gln Tyr Tyr Lys Glu His Gly Tyr Glu Thr Val Val Met Gly
    210                 215                 220 gca agc ttc cgt aac atc ggc gaa att ctg gaa ctg gca ggc tgc gac       720
Ala Ser Phe Arg Asn Ile Gly Glu Ile Leu Glu Leu Ala Gly Cys Asp
225                 230                 235                 240 cgt ctg acc atc gca ccg gca ctg ctg aaa gag ctg gcg gag agc gaa       768
Arg Leu Thr Ile Ala Pro Ala Leu Leu Lys Glu Leu Ala Glu Ser Glu
                245                 250                 255 ggg gct atc gaa cgt aaa ctg tct tac acc ggc gaa gtg aaa gcg cgt       816
Gly Ala Ile Glu Arg Lys Leu Ser Tyr Thr Gly Glu Val Lys Ala Arg
            260                 265                 270 ccg gcg cgt atc act gag tcc gag ttc ctg tgg cag cac aac cag gat       864
Pro Ala Arg Ile Thr Glu Ser Glu Phe Leu Trp Gln His Asn Gln Asp
        275                 280                 285 cca atg gca gta gat aaa ctg gcg gaa ggt atc cgt aag ttt gct att       912
Pro Met Ala Val Asp Lys Leu Ala Glu Gly Ile Arg Lys Phe Ala Ile
    290                 295                 300 gac cag gaa aaa ctg gaa aaa atg atc ggc gat ctg ctg taa               954
Asp Gln Glu Lys Leu Glu Lys Met Ile Gly Asp Leu Leu
305                 310                 315

<210> SEQ ID NO 10
<211> LENGTH: 317
<212> TYPE: PRT
<213> ORGANISM: Escherichia coli

<400> SEQUENCE: 10

Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
    50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
    130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
```

```
                      165                 170                 175
Pro Phe Val Gly Arg Ile Leu Asp Trp Tyr Lys Ala Asn Thr Asp Lys
                180                 185                 190

Lys Glu Tyr Ala Pro Ala Glu Asp Pro Gly Val Val Ser Val Ser Glu
            195                 200                 205

Ile Tyr Gln Tyr Tyr Lys Glu His Gly Tyr Glu Thr Val Val Met Gly
210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
        275                 280                 285

Pro Met Ala Val Asp Lys Leu Ala Glu Gly Ile Arg Lys Phe Ala Ile
    290                 295                 300

Asp Gln Glu Lys Leu Glu Lys Met Ile Gly Asp Leu Leu
305                 310                 315

<210> SEQ ID NO 11
<211> LENGTH: 1992
<212> TYPE: DNA
<213> ORGANISM: Escherichia coli
<220> FEATURE:
<221> NAME/KEY: CDS
<222> LOCATION: (1)..(1992)

<400> SEQUENCE: 11 atg tcc tca cgt aaa gag ctt gcc aat gct att cgt gcg ctg agc atg      48
Met Ser Ser Arg Lys Glu Leu Ala Asn Ala Ile Arg Ala Leu Ser Met
1               5                   10                  15 gac gca gta cag aaa gcc aaa tcc ggt cac ccg ggt gcc cct atg ggt      96
Asp Ala Val Gln Lys Ala Lys Ser Gly His Pro Gly Ala Pro Met Gly
            20                  25                  30 atg gct gac att gcc gaa gtc ctg tgg cgt gat ttc ctg aaa cac aac     144
Met Ala Asp Ile Ala Glu Val Leu Trp Arg Asp Phe Leu Lys His Asn
        35                  40                  45 ccg cag aat ccg tcc tgg gct gac cgt gac cgc ttc gtg ctg tcc aac     192
Pro Gln Asn Pro Ser Trp Ala Asp Arg Asp Arg Phe Val Leu Ser Asn
    50                  55                  60 ggc cac ggc tcc atg ctg atc tac agc ctg ctg cac ctc acc ggt tac     240
Gly His Gly Ser Met Leu Ile Tyr Ser Leu Leu His Leu Thr Gly Tyr
65                  70                  75                  80 gat ctg ccg atg gaa gaa ctg aaa aac ttc cgt cag ctg cac tct aaa     288
Asp Leu Pro Met Glu Glu Leu Lys Asn Phe Arg Gln Leu His Ser Lys
                85                  90                  95 act ccg ggt cac ccg gaa gtg ggt tac acc gct ggt gtg gaa acc acc     336
Thr Pro Gly His Pro Glu Val Gly Tyr Thr Ala Gly Val Glu Thr Thr
            100                 105                 110 acc ggt ccg ctg ggt cag ggt att gcc aac gca gtc ggt atg gcg att     384
Thr Gly Pro Leu Gly Gln Gly Ile Ala Asn Ala Val Gly Met Ala Ile
        115                 120                 125 gca gaa aaa acg ctg gcg gcg cag ttt aac cgt ccg ggc cac gac att     432
Ala Glu Lys Thr Leu Ala Ala Gln Phe Asn Arg Pro Gly His Asp Ile
    130                 135                 140 gtc gac cac tac acc tac gcc ttc atg ggc gac ggc tgc atg atg gaa     480
Val Asp His Tyr Thr Tyr Ala Phe Met Gly Asp Gly Cys Met Met Glu
145                 150                 155                 160
```

```
ggc atc tcc cac gaa gtt tgc tct ctg gcg ggt acg ctg aag ctg ggt        528
Gly Ile Ser His Glu Val Cys Ser Leu Ala Gly Thr Leu Lys Leu Gly
            165                 170                 175 aaa ctg att gca ttc tac gat gac aac ggt att tct atc gat ggt cac        576
Lys Leu Ile Ala Phe Tyr Asp Asp Asn Gly Ile Ser Ile Asp Gly His
        180                 185                 190 gtt gaa ggc tgg ttc acc gac gac acc gca atg cgt ttc gaa gct tac        624
Val Glu Gly Trp Phe Thr Asp Asp Thr Ala Met Arg Phe Glu Ala Tyr
            195                 200                 205 ggc tgg cac gtt att cgc gac atc gac ggt cat gac gcg gca tct atc        672
Gly Trp His Val Ile Arg Asp Ile Asp Gly His Asp Ala Ala Ser Ile
    210                 215                 220 aaa cgc gca gta gaa gaa gcg cgc gca gtg act gac aaa cct tcc ctg        720
Lys Arg Ala Val Glu Glu Ala Arg Ala Val Thr Asp Lys Pro Ser Leu
225                 230                 235                 240 ctg atg tgc aaa acc atc atc ggt ttc ggt tcc ccg aac aaa gcc ggt        768
Leu Met Cys Lys Thr Ile Ile Gly Phe Gly Ser Pro Asn Lys Ala Gly
                245                 250                 255 acc cac gac tcc cac ggt gcg ccg ctg ggc gac gct gaa att gcc ctg        816
Thr His Asp Ser His Gly Ala Pro Leu Gly Asp Ala Glu Ile Ala Leu
            260                 265                 270 acc cgc gaa caa ctg ggc tgg aaa tat gcg ccg ttc gaa atc ccg tct        864
Thr Arg Glu Gln Leu Gly Trp Lys Tyr Ala Pro Phe Glu Ile Pro Ser
        275                 280                 285 gaa atc tat gct cag tgg gat gcg aaa gaa gca ggc cag gcg aaa gaa        912
Glu Ile Tyr Ala Gln Trp Asp Ala Lys Glu Ala Gly Gln Ala Lys Glu
    290                 295                 300 tcc gca tgg aac gag aaa ttc gct gct tac gcg aaa gct tat ccg cag        960
Ser Ala Trp Asn Glu Lys Phe Ala Ala Tyr Ala Lys Ala Tyr Pro Gln
305                 310                 315                 320 gaa gcc gct gaa ttt acc cgc cgt atg aaa ggc gaa atg ccg tct gac       1008
Glu Ala Ala Glu Phe Thr Arg Arg Met Lys Gly Glu Met Pro Ser Asp
                325                 330                 335 ttc gac gct aaa gcg aaa gag ttc atc gct aaa ctg cag gct aat ccg       1056
Phe Asp Ala Lys Ala Lys Glu Phe Ile Ala Lys Leu Gln Ala Asn Pro
            340                 345                 350 gcg aaa atc gcc agc cgt aaa gcg tct cag aat gct atc gaa gcg ttc       1104
Ala Lys Ile Ala Ser Arg Lys Ala Ser Gln Asn Ala Ile Glu Ala Phe
        355                 360                 365 ggt ccg ctg ttg ccg gaa ttc ctc ggc ggt tct gct gac ctg gcg ccg       1152
Gly Pro Leu Leu Pro Glu Phe Leu Gly Gly Ser Ala Asp Leu Ala Pro
    370                 375                 380 tct aac ctg acc ctg tgg tct ggt tct aaa gca atc aac gaa gat gct       1200
Ser Asn Leu Thr Leu Trp Ser Gly Ser Lys Ala Ile Asn Glu Asp Ala
385                 390                 395                 400 gcg ggt aac tac atc cac tac ggt gtt cgc gag ttc ggt atg acc gcg       1248
Ala Gly Asn Tyr Ile His Tyr Gly Val Arg Glu Phe Gly Met Thr Ala
                405                 410                 415 att gct aac ggt atc tcc ctg cac ggt ggc ttc ctg ccg tac acc tcc       1296
Ile Ala Asn Gly Ile Ser Leu His Gly Gly Phe Leu Pro Tyr Thr Ser
            420                 425                 430 acc ttc ctg atg ttc gtg gaa tac gca cgt aac gcc gta cgt atg gct       1344
Thr Phe Leu Met Phe Val Glu Tyr Ala Arg Asn Ala Val Arg Met Ala
        435                 440                 445 gcg ctg atg aaa cag cgt cag gtg atg gtt tac acc cac gac tcc atc       1392
Ala Leu Met Lys Gln Arg Gln Val Met Val Tyr Thr His Asp Ser Ile
    450                 455                 460 ggt ctg ggc gaa gac ggc ccg act cac cag ccg gtt gag cag gtc gct       1440
Gly Leu Gly Glu Asp Gly Pro Thr His Gln Pro Val Glu Gln Val Ala
```

```
                            465                 470                 475                 480
tct ctg cgc gta acc ccg aac atg tct aca tgg cgt ccg tgt gac cag                        1488
Ser Leu Arg Val Thr Pro Asn Met Ser Thr Trp Arg Pro Cys Asp Gln
                            485                 490                 495 gtt gaa tcc gcg gtc gcg tgg aaa tac ggt gtt gag cgt cag gac ggc                        1536
Val Glu Ser Ala Val Ala Trp Lys Tyr Gly Val Glu Arg Gln Asp Gly
            500                 505                 510 ccg acc gca ctg atc ctc tcc cgt cag aac ctg gcg cag cag gaa cga                        1584
Pro Thr Ala Leu Ile Leu Ser Arg Gln Asn Leu Ala Gln Gln Glu Arg
        515                 520                 525 act gaa gag caa ctg gca aac atc gcg cgc ggt ggt tat gtg ctg aaa                        1632
Thr Glu Glu Gln Leu Ala Asn Ile Ala Arg Gly Gly Tyr Val Leu Lys
    530                 535                 540 gac tgc gcc ggt cag ccg gaa ctg att ttc atc gct acc ggt tca gaa                        1680
Asp Cys Ala Gly Gln Pro Glu Leu Ile Phe Ile Ala Thr Gly Ser Glu
545                 550                 555                 560 gtt gaa ctg gct gtt gct gcc tac gaa aaa ctg act gcc gaa ggc gtg                        1728
Val Glu Leu Ala Val Ala Ala Tyr Glu Lys Leu Thr Ala Glu Gly Val
                565                 570                 575 aaa gcg cgc gtg gtg tcc atg ccg tct acc gac gca ttt gac aag cag                        1776
Lys Ala Arg Val Val Ser Met Pro Ser Thr Asp Ala Phe Asp Lys Gln
            580                 585                 590 gat gct gct tac cgt gaa tcc gta ctg ccg aaa gcg gtt act gca cgc                        1824
Asp Ala Ala Tyr Arg Glu Ser Val Leu Pro Lys Ala Val Thr Ala Arg
        595                 600                 605 gtt gct gta gaa gcg ggt att gct gac tac tgg tac aag tat gtt ggc                        1872
Val Ala Val Glu Ala Gly Ile Ala Asp Tyr Trp Tyr Lys Tyr Val Gly
    610                 615                 620 ctg aac ggt gct atc gtc ggt atg acc acc ttc ggt gaa tct gct ccg                        1920
Leu Asn Gly Ala Ile Val Gly Met Thr Thr Phe Gly Glu Ser Ala Pro
625                 630                 635                 640 gca gag ctg ctg ttt gaa gag ttc ggc ttc act gtt gat aac gtt gtt                        1968
Ala Glu Leu Leu Phe Glu Glu Phe Gly Phe Thr Val Asp Asn Val Val
                645                 650                 655 gcg aaa gca aaa gaa ctg ctg taa                                                        1992
Ala Lys Ala Lys Glu Leu Leu
            660
```

<210> SEQ ID NO 12
<211> LENGTH: 663
<212> TYPE: PRT
<213> ORGANISM: Escherichia coli

<400> SEQUENCE: 12

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110
```

```
Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
```

```
              530               535                540
Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
                580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
            610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
            660

<210> SEQ ID NO 13
<211> LENGTH: 768
<212> TYPE: DNA
<213> ORGANISM: Escherichia coli
<220> FEATURE:
<221> NAME/KEY: CDS
<222> LOCATION: (1)..(768)

<400> SEQUENCE: 13
```

| | | |
|---|---|---|
| atg cga cat cct tta gtg atg ggt aac tgg aaa ctg aac ggc agc cgc | 48 | |
| Met Arg His Pro Leu Val Met Gly Asn Trp Lys Leu Asn Gly Ser Arg | | |
| 1               5                  10                  15 | | |
| cac atg gtt cac gag ctg gtt tct aac ctg cgt aaa gag ctg gca ggt | 96 | |
| His Met Val His Glu Leu Val Ser Asn Leu Arg Lys Glu Leu Ala Gly | | |
|             20                  25                  30 | | |
| gtt gct ggc tgt gcg gtt gca atc gca cca ccg gaa atg tat atc gat | 144 | |
| Val Ala Gly Cys Ala Val Ala Ile Ala Pro Pro Glu Met Tyr Ile Asp | | |
|         35                  40                  45 | | |
| atg gcg aag cgc gaa gct gaa ggc agc cac atc atg ctg ggt gcg caa | 192 | |
| Met Ala Lys Arg Glu Ala Glu Gly Ser His Ile Met Leu Gly Ala Gln | | |
|     50                  55                  60 | | |
| aac gtg gac ctg aac ctg tcc ggc gca ttc acc ggt gaa acc tct gct | 240 | |
| Asn Val Asp Leu Asn Leu Ser Gly Ala Phe Thr Gly Glu Thr Ser Ala | | |
| 65                  70                  75                  80 | | |
| gct atg ctg aaa gac atc ggc gca cag tac atc atc atc ggt cac tct | 288 | |
| Ala Met Leu Lys Asp Ile Gly Ala Gln Tyr Ile Ile Ile Gly His Ser | | |
|                 85                  90                  95 | | |
| gaa cgt cgt act tac cac aaa gaa tct gac gaa ctg atc gcg aaa aaa | 336 | |
| Glu Arg Arg Thr Tyr His Lys Glu Ser Asp Glu Leu Ile Ala Lys Lys | | |
|             100                 105                 110 | | |
| ttc gcg gtg ctg aaa gag cag ggc ctg act ccg gtt ctg tgc atc ggt | 384 | |
| Phe Ala Val Leu Lys Glu Gln Gly Leu Thr Pro Val Leu Cys Ile Gly | | |
|         115                 120                 125 | | |
| gaa acc gaa gct gaa aat gaa gcg ggc aaa act gaa gaa gtt tgc gca | 432 | |
| Glu Thr Glu Ala Glu Asn Glu Ala Gly Lys Thr Glu Glu Val Cys Ala | | |
|     130                 135                 140 | | |
| cgt cag atc gac gcg gta ctg aaa act cag ggt gct gcg gca ttc gaa | 480 | |
| Arg Gln Ile Asp Ala Val Leu Lys Thr Gln Gly Ala Ala Ala Phe Glu | | |
| 145                 150                 155                 160 | | |
| ggt gcg gtt atc gct tac gaa cct gta tgg gca atc ggt act ggc aaa | 528 | |
| Gly Ala Val Ile Ala Tyr Glu Pro Val Trp Ala Ile Gly Thr Gly Lys | | |

```
                                165                 170                 175
tct gca act ccg gct cag gca cag gct gtt cac aaa ttc atc cgt gac       576
Ser Ala Thr Pro Ala Gln Ala Gln Ala Val His Lys Phe Ile Arg Asp
            180                 185                 190 cac atc gct aaa gtt gac gct aac atc gct gaa caa gtg atc att cag       624
His Ile Ala Lys Val Asp Ala Asn Ile Ala Glu Gln Val Ile Ile Gln
            195                 200                 205 tac ggc ggc tct gta aac gcg tct aac gct gca gaa ctg ttt gct cag       672
Tyr Gly Gly Ser Val Asn Ala Ser Asn Ala Ala Glu Leu Phe Ala Gln
        210                 215                 220 ccg gat atc gac ggc gcg ctg gtt ggt ggt gct tct ctg aaa gct gac       720
Pro Asp Ile Asp Gly Ala Leu Val Gly Gly Ala Ser Leu Lys Ala Asp
225                 230                 235                 240 gcc ttc gca gta atc gtt aaa gct gca gaa gcg gct aaa cag gct taa       768
Ala Phe Ala Val Ile Val Lys Ala Ala Glu Ala Ala Lys Gln Ala
                    245                 250                 255

<210> SEQ ID NO 14
<211> LENGTH: 255
<212> TYPE: PRT
<213> ORGANISM: Escherichia coli

<400> SEQUENCE: 14

Met Arg His Pro Leu Val Met Gly Asn Trp Lys Leu Asn Gly Ser Arg
1               5                   10                  15

His Met Val His Glu Leu Val Ser Asn Leu Arg Lys Glu Leu Ala Gly
                20                  25                  30

Val Ala Gly Cys Ala Val Ala Ile Ala Pro Pro Glu Met Tyr Ile Asp
            35                  40                  45

Met Ala Lys Arg Glu Ala Glu Gly Ser His Ile Met Leu Gly Ala Gln
        50                  55                  60

Asn Val Asp Leu Asn Leu Ser Gly Ala Phe Thr Gly Glu Thr Ser Ala
65                  70                  75                  80

Ala Met Leu Lys Asp Ile Gly Ala Gln Tyr Ile Ile Ile Gly His Ser
                85                  90                  95

Glu Arg Arg Thr Tyr His Lys Glu Ser Asp Glu Leu Ile Ala Lys Lys
            100                 105                 110

Phe Ala Val Leu Lys Glu Gln Gly Leu Thr Pro Val Leu Cys Ile Gly
        115                 120                 125

Glu Thr Glu Ala Glu Asn Glu Ala Gly Lys Thr Glu Glu Val Cys Ala
130                 135                 140

Arg Gln Ile Asp Ala Val Leu Lys Thr Gln Gly Ala Ala Ala Phe Glu
145                 150                 155                 160

Gly Ala Val Ile Ala Tyr Glu Pro Val Trp Ala Ile Gly Thr Gly Lys
                165                 170                 175

Ser Ala Thr Pro Ala Gln Ala Gln Ala Val His Lys Phe Ile Arg Asp
            180                 185                 190

His Ile Ala Lys Val Asp Ala Asn Ile Ala Glu Gln Val Ile Ile Gln
        195                 200                 205

Tyr Gly Gly Ser Val Asn Ala Ser Asn Ala Ala Glu Leu Phe Ala Gln
    210                 215                 220

Pro Asp Ile Asp Gly Ala Leu Val Gly Gly Ala Ser Leu Lys Ala Asp
225                 230                 235                 240

Ala Phe Ala Val Ile Val Lys Ala Ala Glu Ala Ala Lys Gln Ala
                245                 250                 255
```

<210> SEQ ID NO 15
<211> LENGTH: 1080
<212> TYPE: DNA
<213> ORGANISM: Escherichia coli
<220> FEATURE:
<221> NAME/KEY: CDS
<222> LOCATION: (1)..(1080)

<400> SEQUENCE: 15

| | | | | | | | | | | | | | | | | |
|---|---|---|---|---|---|---|---|---|---|---|---|---|---|---|---|---|
| atg | tct | aag | att | ttt | gat | ttc | gta | aaa | cct | ggc | gta | atc | act | ggt | gat | 48 |
| Met | Ser | Lys | Ile | Phe | Asp | Phe | Val | Lys | Pro | Gly | Val | Ile | Thr | Gly | Asp | |
| 1 | | | | 5 | | | | | 10 | | | | | 15 | | |
| gac | gta | cag | aaa | gtt | ttc | cag | gta | gca | aaa | gaa | aac | aac | ttc | gca | ctg | 96 |
| Asp | Val | Gln | Lys | Val | Phe | Gln | Val | Ala | Lys | Glu | Asn | Asn | Phe | Ala | Leu | |
| | | | 20 | | | | | 25 | | | | | 30 | | | |
| cca | gca | gta | aac | tgc | gtc | ggt | act | gac | tcc | atc | aac | gcc | gta | ctg | gaa | 144 |
| Pro | Ala | Val | Asn | Cys | Val | Gly | Thr | Asp | Ser | Ile | Asn | Ala | Val | Leu | Glu | |
| | 35 | | | | | 40 | | | | | 45 | | | | | |
| acc | gct | gct | aaa | gtt | aaa | gcg | ccg | gtt | atc | gtt | cag | ttc | tcc | aac | ggt | 192 |
| Thr | Ala | Ala | Lys | Val | Lys | Ala | Pro | Val | Ile | Val | Gln | Phe | Ser | Asn | Gly | |
| 50 | | | | | 55 | | | | | 60 | | | | | | |
| ggt | gct | tcc | ttt | atc | gct | ggt | aaa | ggc | gtg | aaa | tct | gac | gtt | ccg | cag | 240 |
| Gly | Ala | Ser | Phe | Ile | Ala | Gly | Lys | Gly | Val | Lys | Ser | Asp | Val | Pro | Gln | |
| 65 | | | | 70 | | | | | 75 | | | | | 80 | | |
| ggt | gct | gct | atc | ctg | ggc | gcg | atc | tct | ggt | gcg | cat | cac | gtt | cac | cag | 288 |
| Gly | Ala | Ala | Ile | Leu | Gly | Ala | Ile | Ser | Gly | Ala | His | His | Val | His | Gln | |
| | | | | 85 | | | | | 90 | | | | | 95 | | |
| atg | gct | gaa | cat | tat | ggt | gtt | ccg | gtt | atc | ctg | cac | act | gac | cac | tgc | 336 |
| Met | Ala | Glu | His | Tyr | Gly | Val | Pro | Val | Ile | Leu | His | Thr | Asp | His | Cys | |
| | | | 100 | | | | | 105 | | | | | 110 | | | |
| gcg | aag | aaa | ctg | ctg | ccg | tgg | atc | gac | ggt | ctg | ttg | gac | gcg | ggt | gaa | 384 |
| Ala | Lys | Lys | Leu | Leu | Pro | Trp | Ile | Asp | Gly | Leu | Leu | Asp | Ala | Gly | Glu | |
| | 115 | | | | | 120 | | | | | 125 | | | | | |
| aaa | cac | ttc | gca | gct | acc | ggt | aag | ccg | ctg | ttc | tct | tct | cac | atg | atc | 432 |
| Lys | His | Phe | Ala | Ala | Thr | Gly | Lys | Pro | Leu | Phe | Ser | Ser | His | Met | Ile | |
| 130 | | | | | 135 | | | | | 140 | | | | | | |
| gac | ctg | tct | gaa | gaa | tct | ctg | caa | gag | aac | atc | gaa | atc | tgc | tct | aaa | 480 |
| Asp | Leu | Ser | Glu | Glu | Ser | Leu | Gln | Glu | Asn | Ile | Glu | Ile | Cys | Ser | Lys | |
| 145 | | | | | 150 | | | | | 155 | | | | | 160 | |
| tac | ctg | gag | cgc | atg | tcc | aaa | atc | ggc | atg | act | ctg | gaa | atc | gaa | ctg | 528 |
| Tyr | Leu | Glu | Arg | Met | Ser | Lys | Ile | Gly | Met | Thr | Leu | Glu | Ile | Glu | Leu | |
| | | | | 165 | | | | | 170 | | | | | 175 | | |
| ggt | tgc | acc | ggt | ggt | gaa | gaa | gac | ggc | gtg | gac | aac | agc | cac | atg | gac | 576 |
| Gly | Cys | Thr | Gly | Gly | Glu | Glu | Asp | Gly | Val | Asp | Asn | Ser | His | Met | Asp | |
| | | | 180 | | | | | 185 | | | | | 190 | | | |
| gct | tct | gca | ctg | tac | acc | cag | ccg | gaa | gac | gtt | gat | tac | gca | tac | acc | 624 |
| Ala | Ser | Ala | Leu | Tyr | Thr | Gln | Pro | Glu | Asp | Val | Asp | Tyr | Ala | Tyr | Thr | |
| | 195 | | | | | 200 | | | | | 205 | | | | | |
| gaa | ctg | agc | aaa | atc | agc | ccg | cgt | ttc | acc | atc | gca | gcg | tcc | ttc | ggt | 672 |
| Glu | Leu | Ser | Lys | Ile | Ser | Pro | Arg | Phe | Thr | Ile | Ala | Ala | Ser | Phe | Gly | |
| 210 | | | | | 215 | | | | | 220 | | | | | | |
| aac | gta | cac | ggt | gtt | tac | aag | ccg | ggt | aac | gtg | gtt | ctg | act | ccg | acc | 720 |
| Asn | Val | His | Gly | Val | Tyr | Lys | Pro | Gly | Asn | Val | Val | Leu | Thr | Pro | Thr | |
| 225 | | | | | 230 | | | | | 235 | | | | | 240 | |
| atc | ctg | cgt | gat | tct | cag | gaa | tat | gtt | tcc | aag | aaa | cac | aac | ctg | ccg | 768 |
| Ile | Leu | Arg | Asp | Ser | Gln | Glu | Tyr | Val | Ser | Lys | Lys | His | Asn | Leu | Pro | |
| | | | | 245 | | | | | 250 | | | | | 255 | | |
| cac | aac | agc | ctg | aac | ttc | gta | ttc | cac | ggt | ggt | tcc | ggt | tct | act | gct | 816 |
| His | Asn | Ser | Leu | Asn | Phe | Val | Phe | His | Gly | Gly | Ser | Gly | Ser | Thr | Ala | |
| | | | 260 | | | | | 265 | | | | | 270 | | | |
| cag | gaa | atc | aaa | gac | tcc | gta | agc | tac | ggc | gta | gta | aaa | atg | aac | atc | 864 |

-continued

```
                Gln Glu Ile Lys Asp Ser Val Ser Tyr Gly Val Val Lys Met Asn Ile
                            275                 280                 285 gat acc gat acc caa tgg gca acc tgg gaa ggc gtt ctg aac tac tac              912
Asp Thr Asp Thr Gln Trp Ala Thr Trp Glu Gly Val Leu Asn Tyr Tyr
290                 295                 300 aaa gcg aac gaa gct tat ctg cag ggt cag ctg ggt aac ccg aaa ggc              960
Lys Ala Asn Glu Ala Tyr Leu Gln Gly Gln Leu Gly Asn Pro Lys Gly
305                 310                 315                 320 gaa gat cag ccg aac aag aaa tac tac gat ccg cgc gta tgg ctg cgt             1008
Glu Asp Gln Pro Asn Lys Lys Tyr Tyr Asp Pro Arg Val Trp Leu Arg
                325                 330                 335 gcc ggt cag act tcg atg atc gct cgt ctg gag aaa gca ttc cag gaa             1056
Ala Gly Gln Thr Ser Met Ile Ala Arg Leu Glu Lys Ala Phe Gln Glu
            340                 345                 350 ctg aac gcg atc gac gtt ctg taa                                              1080
Leu Asn Ala Ile Asp Val Leu
                355
```

<210> SEQ ID NO 16
<211> LENGTH: 359
<212> TYPE: PRT
<213> ORGANISM: Escherichia coli

<400> SEQUENCE: 16

```
Met Ser Lys Ile Phe Asp Phe Val Lys Pro Gly Val Ile Thr Gly Asp
1               5                   10                  15

Asp Val Gln Lys Val Phe Gln Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Ala Lys Val Lys Ala Pro Val Ile Val Gln Phe Ser Asn Gly
    50                  55                  60

Gly Ala Ser Phe Ile Ala Gly Lys Gly Val Lys Ser Asp Val Pro Gln
65                  70                  75                  80

Gly Ala Ala Ile Leu Gly Ala Ile Ser Gly Ala His His Val His Gln
                85                  90                  95

Met Ala Glu His Tyr Gly Val Pro Val Ile Leu His Thr Asp His Cys
            100                 105                 110

Ala Lys Lys Leu Leu Pro Trp Ile Asp Gly Leu Leu Asp Ala Gly Glu
        115                 120                 125

Lys His Phe Ala Ala Thr Gly Lys Pro Leu Phe Ser Ser His Met Ile
    130                 135                 140

Asp Leu Ser Glu Glu Ser Leu Gln Glu Asn Ile Glu Ile Cys Ser Lys
145                 150                 155                 160

Tyr Leu Glu Arg Met Ser Lys Ile Gly Met Thr Leu Glu Ile Glu Leu
                165                 170                 175

Gly Cys Thr Gly Gly Glu Glu Asp Gly Val Asp Asn Ser His Met Asp
            180                 185                 190

Ala Ser Ala Leu Tyr Thr Gln Pro Glu Asp Val Asp Tyr Ala Tyr Thr
        195                 200                 205

Glu Leu Ser Lys Ile Ser Pro Arg Phe Thr Ile Ala Ala Ser Phe Gly
    210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys Lys His Asn Leu Pro
                245                 250                 255
```

```
His Asn Ser Leu Asn Phe Val Phe His Gly Gly Ser Gly Thr Ala
            260                 265                 270

Gln Glu Ile Lys Asp Ser Val Ser Tyr Gly Val Val Lys Met Asn Ile
        275                 280                 285

Asp Thr Asp Thr Gln Trp Ala Thr Trp Glu Gly Val Leu Asn Tyr Tyr
    290                 295                 300

Lys Ala Asn Glu Ala Tyr Leu Gln Gly Gln Leu Gly Asn Pro Lys Gly
305                 310                 315                 320

Glu Asp Gln Pro Asn Lys Lys Tyr Tyr Asp Pro Arg Val Trp Leu Arg
                325                 330                 335

Ala Gly Gln Thr Ser Met Ile Ala Arg Leu Glu Lys Ala Phe Gln Glu
            340                 345                 350

Leu Asn Ala Ile Asp Val Leu
            355

<210> SEQ ID NO 17
<211> LENGTH: 1341
<212> TYPE: DNA
<213> ORGANISM: Lactococcus lactis
<220> FEATURE:
<221> NAME/KEY: CDS
<222> LOCATION: (1)..(1341)

<400> SEQUENCE: 17
```

| | | | | | | | | | | | | | | | | |
|---|---|---|---|---|---|---|---|---|---|---|---|---|---|---|---|---|
| atg | aaa | atc | gta | gtt | atc | ggt | acg | aac | cac | gca | ggc | att | gct | aca | gca | 48 |
| Met | Lys | Ile | Val | Val | Ile | Gly | Thr | Asn | His | Ala | Gly | Ile | Ala | Thr | Ala | |
| 1 | | | | 5 | | | | | 10 | | | | | 15 | | |
| aat | aca | tta | att | gat | cga | tat | cca | ggc | cat | gag | att | gtt | atg | att | gac | 96 |
| Asn | Thr | Leu | Ile | Asp | Arg | Tyr | Pro | Gly | His | Glu | Ile | Val | Met | Ile | Asp | |
| | | | 20 | | | | | 25 | | | | | 30 | | | |
| cgt | aac | agt | aat | atg | agt | tac | ttg | ggg | tgt | ggg | aca | gct | att | tgg | gtc | 144 |
| Arg | Asn | Ser | Asn | Met | Ser | Tyr | Leu | Gly | Cys | Gly | Thr | Ala | Ile | Trp | Val | |
| | 35 | | | | | 40 | | | | | 45 | | | | | |
| gga | aga | caa | att | gaa | aaa | cca | gat | gag | ctg | ttt | tat | gcc | aaa | gca | gaa | 192 |
| Gly | Arg | Gln | Ile | Glu | Lys | Pro | Asp | Glu | Leu | Phe | Tyr | Ala | Lys | Ala | Glu | |
| 50 | | | | | 55 | | | | | 60 | | | | | | |
| gat | ttt | gaa | aaa | aag | gga | gta | aag | ata | tta | aca | gaa | aca | gaa | gtt | tca | 240 |
| Asp | Phe | Glu | Lys | Lys | Gly | Val | Lys | Ile | Leu | Thr | Glu | Thr | Glu | Val | Ser | |
| 65 | | | | | 70 | | | | | 75 | | | | | 80 | |
| gaa | att | gac | ttt | act | aat | aaa | atg | att | tat | gcc | aag | tca | aaa | act | gga | 288 |
| Glu | Ile | Asp | Phe | Thr | Asn | Lys | Met | Ile | Tyr | Ala | Lys | Ser | Lys | Thr | Gly | |
| | | | | 85 | | | | | 90 | | | | | 95 | | |
| gaa | aag | att | aca | gaa | agt | tat | gat | aaa | ctc | gtt | ctg | gca | aca | ggt | tca | 336 |
| Glu | Lys | Ile | Thr | Glu | Ser | Tyr | Asp | Lys | Leu | Val | Leu | Ala | Thr | Gly | Ser | |
| | | | 100 | | | | | 105 | | | | | 110 | | | |
| cgt | cca | att | att | cct | aac | ttg | cca | gga | aaa | gat | ctt | aaa | ggc | att | cat | 384 |
| Arg | Pro | Ile | Ile | Pro | Asn | Leu | Pro | Gly | Lys | Asp | Leu | Lys | Gly | Ile | His | |
| | 115 | | | | | 120 | | | | | 125 | | | | | |
| ttt | tta | aaa | ctt | ttt | caa | gaa | ggg | caa | gcc | att | gac | gaa | gag | ttt | gct | 432 |
| Phe | Leu | Lys | Leu | Phe | Gln | Glu | Gly | Gln | Ala | Ile | Asp | Glu | Glu | Phe | Ala | |
| 130 | | | | | 135 | | | | | 140 | | | | | | |
| aag | aat | gat | gtg | aaa | cgg | att | gct | gtg | att | ggt | gct | ggt | tat | att | ggg | 480 |
| Lys | Asn | Asp | Val | Lys | Arg | Ile | Ala | Val | Ile | Gly | Ala | Gly | Tyr | Ile | Gly | |
| 145 | | | | | 150 | | | | | 155 | | | | | 160 | |
| aca | gaa | att | gct | gaa | gct | gcc | aaa | cgt | cgt | gga | aaa | gaa | gtc | cta | ctt | 528 |
| Thr | Glu | Ile | Ala | Glu | Ala | Ala | Lys | Arg | Arg | Gly | Lys | Glu | Val | Leu | Leu | |
| | | | | 165 | | | | | 170 | | | | | 175 | | |
| ttt | gat | gca | gaa | agt | act | tca | ctt | gct | tca | tat | tat | gat | gaa | gag | ttt | 576 |
| Phe | Asp | Ala | Glu | Ser | Thr | Ser | Leu | Ala | Ser | Tyr | Tyr | Asp | Glu | Glu | Phe | |
| | | | 180 | | | | | 185 | | | | | 190 | | | |

```
gct aaa ggg atg gat gaa aat ctt gcc caa cat gga att gaa ctc cat      624
Ala Lys Gly Met Asp Glu Asn Leu Ala Gln His Gly Ile Glu Leu His
        195                 200                 205 ttt ggg gaa tta gct caa gag ttt aag gca aat gaa aaa ggt cat gta      672
Phe Gly Glu Leu Ala Gln Glu Phe Lys Ala Asn Glu Lys Gly His Val
    210                 215                 220 tca cag att gta act aat aaa tca act tat gat gtt gac ctc gtt att      720
Ser Gln Ile Val Thr Asn Lys Ser Thr Tyr Asp Val Asp Leu Val Ile
225                 230                 235                 240 aat tgt att ggc ttt aca gcc aat agt gca ttg gct ggt gaa cat tta      768
Asn Cys Ile Gly Phe Thr Ala Asn Ser Ala Leu Ala Gly Glu His Leu
                245                 250                 255 gaa acc ttt aaa aat gga gca atc aaa gtg gat aaa cat caa caa agt      816
Glu Thr Phe Lys Asn Gly Ala Ile Lys Val Asp Lys His Gln Gln Ser
            260                 265                 270 agt gac cca gat gtt tct gct gta gga gat gtt gcc aca atc tat tct      864
Ser Asp Pro Asp Val Ser Ala Val Gly Asp Val Ala Thr Ile Tyr Ser
        275                 280                 285 aat gct tta caa gac ttc acc tac att gcc ctt gcc tca aac gct gtt      912
Asn Ala Leu Gln Asp Phe Thr Tyr Ile Ala Leu Ala Ser Asn Ala Val
    290                 295                 300 cgc tca ggg att gtt gct ggt cat aat att gga gga aaa tca ata gag      960
Arg Ser Gly Ile Val Ala Gly His Asn Ile Gly Gly Lys Ser Ile Glu
305                 310                 315                 320 tct gtt ggt gta caa ggt tct aat gga atc tct att ttt ggt tac aat     1008
Ser Val Gly Val Gln Gly Ser Asn Gly Ile Ser Ile Phe Gly Tyr Asn
                325                 330                 335 atg act tct acg ggc ttg tcg gtt aaa gct gcg aaa aaa atc ggc cta     1056
Met Thr Ser Thr Gly Leu Ser Val Lys Ala Ala Lys Lys Ile Gly Leu
            340                 345                 350 gaa gtt tca ttt agt gat ttt gaa gat aag caa aaa gca tgg ttc ctt     1104
Glu Val Ser Phe Ser Asp Phe Glu Asp Lys Gln Lys Ala Trp Phe Leu
        355                 360                 365 cat gaa aat aat gat agt gtg aaa att cgt atc gtt tat gaa aca aaa     1152
His Glu Asn Asn Asp Ser Val Lys Ile Arg Ile Val Tyr Glu Thr Lys
    370                 375                 380 aat cgc aga att att ggt gct caa ctt gct agc aag agt gaa ata att     1200
Asn Arg Arg Ile Ile Gly Ala Gln Leu Ala Ser Lys Ser Glu Ile Ile
385                 390                 395                 400 gca gga aat att aat atg ttt agt tta gct att caa gaa aag aaa acg     1248
Ala Gly Asn Ile Asn Met Phe Ser Leu Ala Ile Gln Glu Lys Lys Thr
                405                 410                 415 att gat gaa tta gcc tta ctt gat tta ttc ttc tta cca cac ttc aat     1296
Ile Asp Glu Leu Ala Leu Leu Asp Leu Phe Phe Leu Pro His Phe Asn
            420                 425                 430 agt cca tat aat tac atg act gtt gca gct tta aat gca aaa taa         1341
Ser Pro Tyr Asn Tyr Met Thr Val Ala Ala Leu Asn Ala Lys
        435                 440                 445

<210> SEQ ID NO 18
<211> LENGTH: 446
<212> TYPE: PRT
<213> ORGANISM: Lactococcus lactis

<400> SEQUENCE: 18

Met Lys Ile Val Val Ile Gly Thr Asn His Ala Gly Ile Ala Thr Ala
1               5                   10                  15

Asn Thr Leu Ile Asp Arg Tyr Pro Gly His Glu Ile Val Met Ile Asp
            20                  25                  30
```

```
Arg Asn Ser Asn Met Ser Tyr Leu Gly Cys Gly Thr Ala Ile Trp Val
         35                  40                  45
Gly Arg Gln Ile Glu Lys Pro Asp Glu Leu Phe Tyr Ala Lys Ala Glu
 50                  55                  60
Asp Phe Glu Lys Lys Gly Val Lys Ile Leu Thr Glu Thr Glu Val Ser
 65                  70                  75                  80
Glu Ile Asp Phe Thr Asn Lys Met Ile Tyr Ala Lys Ser Lys Thr Gly
                 85                  90                  95
Glu Lys Ile Thr Glu Ser Tyr Asp Lys Leu Val Leu Ala Thr Gly Ser
                100                 105                 110
Arg Pro Ile Ile Pro Asn Leu Pro Gly Lys Asp Leu Lys Gly Ile His
                115                 120                 125
Phe Leu Lys Leu Phe Gln Glu Gly Gln Ala Ile Asp Glu Glu Phe Ala
130                 135                 140
Lys Asn Asp Val Lys Arg Ile Ala Val Ile Gly Ala Gly Tyr Ile Gly
145                 150                 155                 160
Thr Glu Ile Ala Glu Ala Ala Lys Arg Arg Gly Lys Glu Val Leu Leu
                165                 170                 175
Phe Asp Ala Glu Ser Thr Ser Leu Ala Ser Tyr Tyr Asp Glu Glu Phe
                180                 185                 190
Ala Lys Gly Met Asp Glu Asn Leu Ala Gln His Gly Ile Glu Leu His
                195                 200                 205
Phe Gly Glu Leu Ala Gln Glu Phe Lys Ala Asn Glu Lys Gly His Val
                210                 215                 220
Ser Gln Ile Val Thr Asn Lys Ser Thr Tyr Asp Val Asp Leu Val Ile
225                 230                 235                 240
Asn Cys Ile Gly Phe Thr Ala Asn Ser Ala Leu Ala Gly Glu His Leu
                245                 250                 255
Glu Thr Phe Lys Asn Gly Ala Ile Lys Val Asp Lys His Gln Gln Ser
                260                 265                 270
Ser Asp Pro Asp Val Ser Ala Val Gly Asp Val Ala Thr Ile Tyr Ser
                275                 280                 285
Asn Ala Leu Gln Asp Phe Thr Tyr Ile Ala Leu Ala Ser Asn Ala Val
290                 295                 300
Arg Ser Gly Ile Val Ala Gly His Asn Ile Gly Gly Lys Ser Ile Glu
305                 310                 315                 320
Ser Val Gly Val Gln Gly Ser Asn Gly Ile Ser Ile Phe Gly Tyr Asn
                325                 330                 335
Met Thr Ser Thr Gly Leu Ser Val Lys Ala Ala Lys Lys Ile Gly Leu
                340                 345                 350
Glu Val Ser Phe Ser Asp Phe Glu Asp Lys Gln Lys Ala Trp Phe Leu
                355                 360                 365
His Glu Asn Asn Asp Ser Val Lys Ile Arg Ile Val Tyr Glu Thr Lys
                370                 375                 380
Asn Arg Arg Ile Ile Gly Ala Gln Leu Ala Ser Lys Ser Glu Ile Ile
385                 390                 395                 400
Ala Gly Asn Ile Asn Met Phe Ser Leu Ala Ile Gln Glu Lys Lys Thr
                405                 410                 415
Ile Asp Glu Leu Ala Leu Leu Asp Leu Phe Phe Leu Pro His Phe Asn
                420                 425                 430
Ser Pro Tyr Asn Tyr Met Thr Val Ala Ala Leu Asn Ala Lys
                435                 440                 445
```

```
<210> SEQ ID NO 19
<211> LENGTH: 317
<212> TYPE: PRT
<213> ORGANISM: Geobacillus stearothermophilus

<400> SEQUENCE: 19

Met Glu Gln Trp Leu Val Gly Ile Asp Leu Gly Gly Thr Thr Thr Lys
1               5                   10                  15

Met Ala Phe Ile Thr Glu Asp Gly Ile Ile Val His Lys Trp Glu Ile
            20                  25                  30

Pro Thr Asp Thr Ser Asn Arg Gly Glu Arg Ile Val Ala His Ile Ala
        35                  40                  45

Arg Ser Leu Asp Glu Thr Leu Ala Arg Leu Gly Gly Thr Lys Glu Gln
50                  55                  60

Leu Leu Ala Ile Gly Ile Gly Ala Pro Gly Pro Val Gln Glu Glu Thr
65                  70                  75                  80

Gly Met Leu Tyr Glu Ala Val Asn Leu Gly Trp Lys His Tyr Pro Leu
                85                  90                  95

Lys Arg Gln Leu Glu Glu Thr Gly Leu Pro Val Ala Val Asp Asn
            100                 105                 110

Asp Ala Asn Ile Ala Ala Leu Gly Glu Met Trp Lys Gly Ala Gly Gly
        115                 120                 125

Gly Ala Arg His Leu Leu Phe Val Thr Leu Gly Thr Gly Val Gly Gly
130                 135                 140

Gly Val Ile Ala Asn Gly Ala Ile Val Arg Gly Thr Asn Gly Ala Gly
145                 150                 155                 160

Gly Glu Ile Gly His Met Thr Met Val Ala Asp Gly Ala Pro Cys
                165                 170                 175

Asn Cys Gly Lys Thr Gly Cys Leu Glu Thr Ile Ala Ser Ala Thr Gly
            180                 185                 190

Ile Val Arg Ile Ala Gly Glu Lys Leu Ala Ala Ser Glu Arg Pro Ser
        195                 200                 205

Ala Leu Arg Gly Gly Asp Val Thr Ala Lys Ala Val Phe Asp Ala Ala
210                 215                 220

Lys Thr Gly Asp Ala Leu Ala Leu Glu Val Val Glu Val Thr Arg
225                 230                 235                 240

Tyr Leu Gly Leu Ala Leu Ala Asn Ala Ala Asn Val Thr Asn Pro Glu
                245                 250                 255

Lys Ile Val Ile Gly Gly Val Ser Lys Ala Gly Ala Leu Leu Val
            260                 265                 270

Glu His Val Ala Ala His Phe Arg Arg Tyr Ala Phe Pro Arg Val Ala
        275                 280                 285

Ala Gly Ala Glu Ile Val Leu Ala Thr Leu Gly Asn Asp Ala Gly Val
290                 295                 300

Ile Gly Gly Ala Trp Leu Ala Lys Ser Leu Ile Gly Ala
305                 310                 315

<210> SEQ ID NO 20
<211> LENGTH: 319
<212> TYPE: PRT
<213> ORGANISM: Geobacillus stearothermophilus

<400> SEQUENCE: 20

Met Lys Arg Ile Gly Val Leu Thr Ser Gly Gly Asp Ser Pro Gly Met
1               5                   10                  15

Asn Ala Ala Ile Arg Ser Val Val Arg Lys Ala Ile Tyr His Gly Val
```

```
                       20                  25                  30
Glu Val Tyr Gly Val Tyr His Gly Tyr Ala Gly Leu Ile Ala Gly Asn
                35                  40                  45

Ile Lys Lys Leu Glu Val Gly Asp Val Gly Asp Ile Ile His Arg Gly
         50                  55                  60

Gly Thr Ile Leu Tyr Thr Ala Arg Cys Pro Glu Phe Lys Thr Glu Glu
 65                  70                  75                  80

Gly Gln Lys Lys Gly Ile Glu Gln Leu Lys Lys His Gly Ile Glu Gly
                 85                  90                  95

Leu Val Val Ile Gly Gly Asp Gly Ser Tyr Gln Gly Ala Lys Lys Leu
            100                 105                 110

Thr Glu His Gly Phe Pro Cys Val Gly Val Pro Gly Thr Ile Asp Asn
        115                 120                 125

Asp Ile Pro Gly Thr Asp Phe Thr Ile Gly Phe Asp Thr Ala Leu Asn
    130                 135                 140

Thr Val Ile Asp Ala Ile Asp Lys Ile Arg Asp Thr Ala Thr Ser His
145                 150                 155                 160

Glu Arg Thr Tyr Val Ile Glu Val Met Gly Arg His Ala Gly Asp Ile
                165                 170                 175

Ala Leu Trp Ser Gly Leu Ala Gly Gly Ala Glu Thr Ile Leu Ile Pro
            180                 185                 190

Glu Ala Asp Tyr Asp Met Asn Asp Val Ile Ala Arg Leu Lys Arg Gly
        195                 200                 205

His Glu Arg Gly Lys Lys His Ser Ile Ile Ile Val Ala Glu Gly Val
    210                 215                 220

Gly Ser Gly Val Asp Phe Gly Arg Gln Ile Gln Glu Ala Thr Gly Phe
225                 230                 235                 240

Glu Thr Arg Val Thr Val Leu Gly His Val Gln Arg Gly Gly Ser Pro
                245                 250                 255

Thr Ala Phe Asp Arg Val Leu Ala Ser Arg Leu Gly Ala Arg Ala Val
            260                 265                 270

Glu Leu Leu Leu Glu Gly Lys Gly Gly Arg Cys Val Gly Ile Gln Asn
        275                 280                 285

Asn Gln Leu Val Asp His Asp Ile Ala Glu Ala Leu Ala Asn Lys His
    290                 295                 300

Thr Ile Asp Gln Arg Met Tyr Ala Leu Ser Lys Glu Leu Ser Ile
305                 310                 315

<210> SEQ ID NO 21
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 21 atg gcg gta acg caa aca gcc cag gcc tgt gac ctg gtc att ttc ggc      48
Met Ala Val Thr Gln Thr Ala Gln Ala Cys Asp Leu Val Ile Phe Gly
1               5                  10                  15 gcg aaa ggc gac ctt gcg cgt cgt aaa ttg ctg cct tcc ctg tat caa      96
Ala Lys Gly Asp Leu Ala Arg Arg Lys Leu Leu Pro Ser Leu Tyr Gln
                20                  25                  30 ctg gaa aaa gcc ggt cag ctc aac ccg gac acc cgg att atc ggc gta     144
Leu Glu Lys Ala Gly Gln Leu Asn Pro Asp Thr Arg Ile Ile Gly Val
            35                  40                  45
```

```
ggg cgt gct gac tgg gat aaa gcg gca tat acc aaa gtt gtc cgc gag       192
Gly Arg Ala Asp Trp Asp Lys Ala Ala Tyr Thr Lys Val Val Arg Glu
        50                  55                  60 gcg ctc gaa act ttc atg aaa gaa acc att gat gaa ggt tta tgg gac       240
Ala Leu Glu Thr Phe Met Lys Glu Thr Ile Asp Glu Gly Leu Trp Asp
 65                  70                  75                  80 acc ctg agt gca cgt ctg gat ttt tgt aat ctc gat gtc aat gac act       288
Thr Leu Ser Ala Arg Leu Asp Phe Cys Asn Leu Asp Val Asn Asp Thr
                     85                  90                  95 gct gca ttc agc cgt ctc ggc gcg atg ctg gat caa aaa aat cgt atc       336
Ala Ala Phe Ser Arg Leu Gly Ala Met Leu Asp Gln Lys Asn Arg Ile
                100                 105                 110 acc att aac tac ttt gcc atg ccg ccc agc act ttt ggc gca att tgc       384
Thr Ile Asn Tyr Phe Ala Met Pro Pro Ser Thr Phe Gly Ala Ile Cys
            115                 120                 125 aaa ggg ctt ggc gag gca aaa ctg aat gct aaa ccg gca cgc gta gtc       432
Lys Gly Leu Gly Glu Ala Lys Leu Asn Ala Lys Pro Ala Arg Val Val
130                 135                 140 atg gag aaa ccg ctg ggg acg tcg ctg gcg acc tcg cag gaa atc aat       480
Met Glu Lys Pro Leu Gly Thr Ser Leu Ala Thr Ser Gln Glu Ile Asn
145                 150                 155                 160 gat cag gtt ggc gaa tac ttc gag gag tgc cag gtt tac cgt atc gac       528
Asp Gln Val Gly Glu Tyr Phe Glu Glu Cys Gln Val Tyr Arg Ile Asp
                165                 170                 175 cac tat ctt ggt aaa gaa acg gtg ctg aac ctg ttg gcg ctg cgt ttt       576
His Tyr Leu Gly Lys Glu Thr Val Leu Asn Leu Leu Ala Leu Arg Phe
                180                 185                 190 gct aac tcc ctg ttt gtg aat aac tgg gac aat cgc acc att gat cat       624
Ala Asn Ser Leu Phe Val Asn Asn Trp Asp Asn Arg Thr Ile Asp His
            195                 200                 205 gtt gag att acc gtg gca gaa gaa gtg ggg atc gaa ggg cgc tgg ggc       672
Val Glu Ile Thr Val Ala Glu Glu Val Gly Ile Glu Gly Arg Trp Gly
210                 215                 220 tat ttt gat aaa gcc ggt cag atg cgc gac atg atc cag aac cac ctg       720
Tyr Phe Asp Lys Ala Gly Gln Met Arg Asp Met Ile Gln Asn His Leu
225                 230                 235                 240 ctg caa att ctt tgc atg att gcg atg tct ccg ccg tct gac ctg agc       768
Leu Gln Ile Leu Cys Met Ile Ala Met Ser Pro Pro Ser Asp Leu Ser
                245                 250                 255 gca gac agc atc cgc gat gaa aaa gtg aaa gta ctg aag tct ctg cgc       816
Ala Asp Ser Ile Arg Asp Glu Lys Val Lys Val Leu Lys Ser Leu Arg
                260                 265                 270 cgc atc gac cgc tcc aac gta cgc gaa aaa acc gta cgc ggg caa tat       864
Arg Ile Asp Arg Ser Asn Val Arg Glu Lys Thr Val Arg Gly Gln Tyr
            275                 280                 285 act gcg ggc ttc gcc cag ggc aaa aaa gtg ccg gga tat ctg gaa gaa       912
Thr Ala Gly Phe Ala Gln Gly Lys Lys Val Pro Gly Tyr Leu Glu Glu
290                 295                 300 gag ggc gcg aac aag agc agc aat aca gaa act ttc gtg gcg atc cgc       960
Glu Gly Ala Asn Lys Ser Ser Asn Thr Glu Thr Phe Val Ala Ile Arg
305                 310                 315                 320 gtc gac att gat aac tgg cgc tgg gcc ggt gtg cca ttc tac ctg cgt      1008
Val Asp Ile Asp Asn Trp Arg Trp Ala Gly Val Pro Phe Tyr Leu Arg
                325                 330                 335 act ggt aaa cgt ctg ccg acc aaa tgt tct gaa gtc gtg gtc tat ttc      1056
Thr Gly Lys Arg Leu Pro Thr Lys Cys Ser Glu Val Val Val Tyr Phe
                340                 345                 350 aaa aca cct gaa ctg aat ctg ttt aaa gaa tcg tgg cag gat ctg ccg      1104
Lys Thr Pro Glu Leu Asn Leu Phe Lys Glu Ser Trp Gln Asp Leu Pro
            355                 360                 365
```

```
cag aat aaa ctg act atc cgt ctg caa cct gat gaa ggc gtg gat atc   1152
Gln Asn Lys Leu Thr Ile Arg Leu Gln Pro Asp Glu Gly Val Asp Ile
    370                 375                 380 cag gta ctg aat aaa gtt cct ggc ctt gac cac aaa cat aac ctg caa   1200
Gln Val Leu Asn Lys Val Pro Gly Leu Asp His Lys His Asn Leu Gln
385                 390                 395                 400 atc acc aag ctg gat ctg agc tat tca gaa acc ttt aat cag acg cat   1248
Ile Thr Lys Leu Asp Leu Ser Tyr Ser Glu Thr Phe Asn Gln Thr His
                405                 410                 415 ctg gcg gat gcc tat gaa cgt ttg ctg ctg gaa acc atg cgt ggt att   1296
Leu Ala Asp Ala Tyr Glu Arg Leu Leu Leu Glu Thr Met Arg Gly Ile
            420                 425                 430 cag gca ctg ttt gta cgt cgc gac gaa gtg gaa gaa gcc tgg aaa tgg   1344
Gln Ala Leu Phe Val Arg Arg Asp Glu Val Glu Glu Ala Trp Lys Trp
        435                 440                 445 gta gac tcc att act gag gcg tgg gcg atg gac aat gat gcg ccg aaa   1392
Val Asp Ser Ile Thr Glu Ala Trp Ala Met Asp Asn Asp Ala Pro Lys
    450                 455                 460 ccg tat cag gcc gga acc tgg gga ccc gtt gcc tcg gtg gcg atg att   1440
Pro Tyr Gln Ala Gly Thr Trp Gly Pro Val Ala Ser Val Ala Met Ile
465                 470                 475                 480 acc cgt gat ggt cgt tcc tgg aat gag ttt gag taa                   1476
Thr Arg Asp Gly Arg Ser Trp Asn Glu Phe Glu
                485                 490
```

<210> SEQ ID NO 22
<211> LENGTH: 491
<212> TYPE: PRT
<213> ORGANISM: Escherichia coli

<400> SEQUENCE: 22

```
Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205
```

Val Glu Ile Thr Val Ala Glu Val Gly Ile Glu Gly Arg Trp Gly
210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
            245                 250                 255

Ala Asp Ser Ile Arg Asp Glu Lys Val Lys Val Leu Lys Ser Leu Arg
            260                 265                 270

Arg Ile Asp Arg Ser Asn Val Arg Glu Lys Thr Val Arg Gly Gln Tyr
        275                 280                 285

Thr Ala Gly Phe Ala Gln Gly Lys Lys Val Pro Gly Tyr Leu Glu Glu
290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Tyr Phe
                340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Glu Ala Trp Lys Trp
        435                 440                 445

Val Asp Ser Ile Thr Glu Ala Trp Ala Met Asp Asn Asp Ala Pro Lys
450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 23
<211> LENGTH: 497
<212> TYPE: PRT
<213> ORGANISM: Geobacillus stearothermophilus

<400> SEQUENCE: 23

Met Asp Asn Met Asn Pro Lys Ser Ile Ile Val Ile Phe Gly Ala Thr
1               5                   10                  15

Gly Asp Leu Ala Lys Arg Lys Leu Phe Pro Ser Leu Tyr Arg Leu Tyr
            20                  25                  30

Glu Lys Gly His Leu Asn Glu Gln Phe Ala Val Val Gly Val Ala Arg
        35                  40                  45

Arg Pro Leu Ser Ala Asp Glu Phe Arg Asn Tyr Val Arg Asp Ser Val
    50                  55                  60

Glu Thr Ala Phe His Gln Lys Leu Ala Asp Glu Arg Phe Thr Ser His
65                  70                  75                  80

Phe Tyr Tyr His Pro Phe Asp Val Thr Glu Ala Glu Ser Tyr Gln Arg

```
            85                  90                  95
Leu Lys Ser Leu Leu Glu Gln Leu Asp Gly Thr Tyr Lys Thr Glu Gly
            100                 105                 110

Asn Arg Ile Phe Tyr Leu Ala Met Ala Pro Glu Phe Phe Gly Thr Val
            115                 120                 125

Thr Ser Arg Leu Gln Ser Glu Gly Leu Thr Glu Thr His Gly Phe Lys
            130                 135                 140

Arg Leu Val Ile Glu Lys Pro Phe Gly His Asp Leu Ala Ser Ala Glu
145                 150                 155                 160

Lys Leu Asn Asp Glu Ile Arg Arg Val Phe Ser Glu Arg Glu Ile Tyr
                    165                 170                 175

Arg Ile Asp His Tyr Leu Gly Lys Glu Met Val Gln Asn Ile Glu Val
                180                 185                 190

Ile Arg Phe Ser Asn Ala Ile Phe Glu Pro Leu Trp Asn Asn Arg Phe
            195                 200                 205

Ile Ala Asn Ile Gln Ile Thr Ser Ser Glu Thr Leu Gly Val Glu Asp
            210                 215                 220

Arg Gly Arg Tyr Tyr Asp His Ser Gly Ala Leu Arg Asp Met Val Gln
225                 230                 235                 240

Asn His Met Leu Gln Met Val Ala Leu Leu Ala Met Glu Pro Pro Ile
                    245                 250                 255

Lys Leu Thr Thr Asp Asp Ile Arg His Glu Lys Val Lys Val Leu Arg
                260                 265                 270

Ala Leu Arg Pro Ile Ala His Asp Glu Val Asp Arg Tyr Phe Val Arg
            275                 280                 285

Gly Gln Tyr Gly Arg Gly Val Ile His Gly Lys His Val Pro Ala Tyr
            290                 295                 300

Arg Glu Glu Pro Asn Val Asp Pro Asn Ser Asn Thr Glu Thr Phe Val
305                 310                 315                 320

Ala Gly Lys Leu Leu Ile Asp Asn Phe Arg Trp Ala Gly Val Pro Phe
                    325                 330                 335

Tyr Ile Arg Thr Gly Lys Arg Met Ala Glu Lys Ser Thr Lys Ile Val
                340                 345                 350

Val Gln Phe Lys Asp Val Pro Met Asn Leu Tyr Tyr Arg Thr Asn Glu
            355                 360                 365

Thr Ile Ala Pro Asn Leu Leu Val Ile His Ile Gln Pro Asp Glu Gly
            370                 375                 380

Ile Thr Leu His Leu Asn Gly Lys Lys Thr Gly Glu Ser Thr Thr Ile
385                 390                 395                 400

Thr Ala Pro Phe Gln Leu Asp Tyr Cys Asn Asn Cys Ile Asp Gly Ile
                    405                 410                 415

Asn Thr Pro Glu Ala Tyr Glu Lys Leu Leu Tyr Asp Cys Met Arg Gly
                420                 425                 430

Asp Ala Thr Asn Phe Thr His Trp Asp Glu Val Ala Ala Ser Trp Gln
            435                 440                 445

Phe Val Asp Pro Ile Ser Glu Val Trp Thr Thr Lys Ala Ser Asp
            450                 455                 460

Phe Pro Asn Tyr Ala Ala Gly Ser Met Gly Pro Ala Ala Ala Asp Lys
465                 470                 475                 480

Leu Leu Lys Gln Asp Gly Phe His Trp Trp Pro Ile Glu His Pro Arg
                    485                 490                 495

Pro
```

<210> SEQ ID NO 24
<211> LENGTH: 497
<212> TYPE: PRT
<213> ORGANISM: Geobacillus stearothermophilus

<400> SEQUENCE: 24

```
Met Asp Asn Met Asn Pro Lys Ser Ile Ile Val Ile Phe Gly Ala Thr
 1               5                  10                  15
Gly Asp Leu Ala Lys Arg Lys Leu Phe Pro Ser Leu Tyr Arg Leu Tyr
             20                  25                  30
Glu Lys Gly His Leu Asn Glu Gln Phe Ala Val Val Gly Val Asp Arg
         35                  40                  45
Arg Pro Leu Ser Ala Asp Glu Phe Arg Asn Tyr Val Arg Asp Ser Val
     50                  55                  60
Glu Thr Ala Phe His Gln Lys Leu Ala Asp Arg Phe Thr Ser His
 65                  70                  75                  80
Phe Tyr Tyr His Pro Phe Asp Val Thr Glu Ala Glu Ser Tyr Gln Arg
                 85                  90                  95
Leu Lys Ser Leu Leu Glu Gln Leu Asp Gly Thr Tyr Lys Thr Glu Gly
            100                 105                 110
Asn Arg Ile Phe Tyr Leu Ala Met Ala Pro Glu Phe Phe Gly Thr Val
        115                 120                 125
Thr Ser Arg Leu Gln Ser Glu Gly Leu Thr Thr His Gly Phe Lys
    130                 135                 140
Arg Leu Val Ile Glu Lys Pro Phe Gly His Asp Leu Ala Ser Ala Glu
145                 150                 155                 160
Lys Leu Asn Asp Glu Ile Arg Arg Val Phe Ser Arg Glu Ile Tyr
                165                 170                 175
Arg Ile Asp His Tyr Leu Gly Lys Glu Met Val Gln Asn Ile Glu Val
            180                 185                 190
Ile Arg Phe Ser Asn Ala Ile Phe Glu Pro Leu Trp Asn Asn Arg Phe
        195                 200                 205
Ile Ala Asn Ile Gln Ile Thr Ser Ser Glu Thr Leu Gly Val Glu Asp
    210                 215                 220
Arg Gly Arg Tyr Tyr Asp His Ser Gly Ala Leu Arg Asp Met Val Gln
225                 230                 235                 240
Asn His Met Leu Gln Met Val Ala Leu Leu Ala Met Glu Pro Pro Ile
                245                 250                 255
Lys Leu Thr Thr Asp Asp Ile Arg His Glu Lys Val Lys Val Leu Arg
            260                 265                 270
Ala Leu Arg Pro Ile Ala His Asp Glu Val Asp Arg Tyr Phe Val Arg
        275                 280                 285
Gly Gln Tyr Gly Arg Gly Val Ile Gly Lys His Val Pro Ala Tyr
    290                 295                 300
Arg Glu Glu Pro Asn Val Asp Pro Asn Ser Asn Thr Glu Thr Phe Val
305                 310                 315                 320
Ala Gly Lys Leu Leu Ile Asp Asn Phe Arg Trp Ala Gly Val Pro Phe
                325                 330                 335
Tyr Ile Arg Thr Gly Lys Arg Met Ala Glu Lys Ser Thr Lys Ile Val
            340                 345                 350
Val Gln Phe Lys Asp Val Pro Met Asn Leu Tyr Tyr Arg Thr Asn Glu
        355                 360                 365
Thr Ile Ala Pro Asn Leu Leu Val Ile His Ile Gln Pro Asp Glu Gly
    370                 375                 380
```

```
Ile Thr Leu His Leu Asn Gly Lys Lys Thr Gly Glu Ser Thr Thr Ile
385                 390                 395                 400

Thr Ala Pro Phe Gln Leu Asp Tyr Cys Asn Asn Cys Ile Asp Gly Ile
                405                 410                 415

Asn Thr Pro Glu Ala Tyr Glu Lys Leu Leu Tyr Asp Cys Met Arg Gly
                420                 425                 430

Asp Ala Thr Asn Phe Thr His Trp Asp Glu Val Ala Ala Ser Trp Gln
                435                 440                 445

Phe Val Asp Pro Ile Ser Glu Val Trp Thr Asn Thr Lys Ala Ser Asp
450                 455                 460

Phe Pro Asn Tyr Ala Ala Gly Ser Met Gly Pro Ala Ala Ala Asp Lys
465                 470                 475                 480

Leu Leu Lys Gln Asp Gly Phe His Trp Trp Pro Ile Glu His Pro Arg
                485                 490                 495

Pro

<210> SEQ ID NO 25
<211> LENGTH: 996
<212> TYPE: DNA
<213> ORGANISM: Escherichia coli
<220> FEATURE:
<221> NAME/KEY: CDS
<222> LOCATION: (1)..(996)

<400> SEQUENCE: 25 atg aag caa aca gtt tat atc gcc agc cct gag agc cag caa att cac        48
Met Lys Gln Thr Val Tyr Ile Ala Ser Pro Glu Ser Gln Gln Ile His
1               5                   10                  15 gtc tgg aat ctg aat cat gaa ggc gca ctg acg ctg aca cag gtt gtc        96
Val Trp Asn Leu Asn His Glu Gly Ala Leu Thr Leu Thr Gln Val Val
                20                  25                  30 gat gtg ccg ggg cag gtg cag ccg atg gtg gtc agc ccg gac aaa cgt       144
Asp Val Pro Gly Gln Val Gln Pro Met Val Val Ser Pro Asp Lys Arg
            35                  40                  45 tat ctc tat gtt ggt gtt cgc cct gag ttt cgc gtc ctg gcg tat cgt       192
Tyr Leu Tyr Val Gly Val Arg Pro Glu Phe Arg Val Leu Ala Tyr Arg
        50                  55                  60 atc gcc ccg gac gat ggc gca ctg acc ttt gcc gca gag tct gcg ctg       240
Ile Ala Pro Asp Asp Gly Ala Leu Thr Phe Ala Ala Glu Ser Ala Leu
65                  70                  75                  80 ccg ggt agt ccg acg cat att tcc acc gat cac cag ggg cag ttt gtc       288
Pro Gly Ser Pro Thr His Ile Ser Thr Asp His Gln Gly Gln Phe Val
                85                  90                  95 ttt gta ggt tct tac aat gcg ggt aac gtg agc gta acg cgt ctg gaa       336
Phe Val Gly Ser Tyr Asn Ala Gly Asn Val Ser Val Thr Arg Leu Glu
            100                 105                 110 gat ggc ctg cca gtg ggc gtc gtc gat gtg gtc gag ggg ctg gac ggt       384
Asp Gly Leu Pro Val Gly Val Val Asp Val Val Glu Gly Leu Asp Gly
        115                 120                 125 tgc cat tcc gcc aat atc tca ccg gac aac cgt acg ctg tgg gtt ccg       432
Cys His Ser Ala Asn Ile Ser Pro Asp Asn Arg Thr Leu Trp Val Pro
130                 135                 140 gca tta aag cag gat cgc att tgc ctg ttt acg gtc agc gat gat ggt       480
Ala Leu Lys Gln Asp Arg Ile Cys Leu Phe Thr Val Ser Asp Asp Gly
145                 150                 155                 160 cat ctc gtg gcg cag gac cct gcg gaa gtg acc acc gtt gaa ggg gcc       528
His Leu Val Ala Gln Asp Pro Ala Glu Val Thr Thr Val Glu Gly Ala
                165                 170                 175
```

```
ggc ccg cgt cat atg gta ttc cat cca aac gaa caa tat gcg tat tgc      576
Gly Pro Arg His Met Val Phe His Pro Asn Glu Gln Tyr Ala Tyr Cys
            180                 185                 190 gtc aat gag tta aac agc tca gtg gat gtc tgg gaa ctg aaa gat ccg      624
Val Asn Glu Leu Asn Ser Ser Val Asp Val Trp Glu Leu Lys Asp Pro
        195                 200                 205 cac ggt aat atc gaa tgt gtc cag acg ctg gat atg atg ccg gaa aac      672
His Gly Asn Ile Glu Cys Val Gln Thr Leu Asp Met Met Pro Glu Asn
    210                 215                 220 ttc tcc gac acc cgt tgg gcg gct gat att cat atc acc ccg gat ggt      720
Phe Ser Asp Thr Arg Trp Ala Ala Asp Ile His Ile Thr Pro Asp Gly
225                 230                 235                 240 cgc cat tta tac gcc tgc gac cgt acc gcc agc ctg att acc gtt ttc      768
Arg His Leu Tyr Ala Cys Asp Arg Thr Ala Ser Leu Ile Thr Val Phe
                245                 250                 255 agc gtt tcg gaa gat ggc agc gtg ttg agt aaa gaa ggc ttc cag cca      816
Ser Val Ser Glu Asp Gly Ser Val Leu Ser Lys Glu Gly Phe Gln Pro
            260                 265                 270 acg gaa acc cag ccg cgc ggc ttc aat gtt gat cac agc ggc aag tat      864
Thr Glu Thr Gln Pro Arg Gly Phe Asn Val Asp His Ser Gly Lys Tyr
        275                 280                 285 ctg att gcc gcc ggg caa aaa tct cac cac atc tcg gta tac gaa att      912
Leu Ile Ala Ala Gly Gln Lys Ser His His Ile Ser Val Tyr Glu Ile
    290                 295                 300 gtt ggc gag cag ggg cta ctg cat gaa aaa ggc cgc tat gcg gtc ggg      960
Val Gly Glu Gln Gly Leu Leu His Glu Lys Gly Arg Tyr Ala Val Gly
305                 310                 315                 320 cag gga cca atg tgg gtg gtg gtt aac gca cac taa                      996
Gln Gly Pro Met Trp Val Val Val Asn Ala His
                325                 330

<210> SEQ ID NO 26
<211> LENGTH: 331
<212> TYPE: PRT
<213> ORGANISM: Escherichia coli

<400> SEQUENCE: 26

Met Lys Gln Thr Val Tyr Ile Ala Ser Pro Glu Ser Gln Gln Ile His
1               5                   10                  15

Val Trp Asn Leu Asn His Glu Gly Ala Leu Thr Leu Thr Gln Val Val
            20                  25                  30

Asp Val Pro Gly Gln Val Gln Pro Met Val Val Ser Pro Asp Lys Arg
        35                  40                  45

Tyr Leu Tyr Val Gly Val Arg Pro Glu Phe Arg Val Leu Ala Tyr Arg
    50                  55                  60

Ile Ala Pro Asp Asp Gly Ala Leu Thr Phe Ala Ala Glu Ser Ala Leu
65                  70                  75                  80

Pro Gly Ser Pro Thr His Ile Ser Thr Asp His Gln Gly Gln Phe Val
                85                  90                  95

Phe Val Gly Ser Tyr Asn Ala Gly Asn Val Ser Val Thr Arg Leu Glu
            100                 105                 110

Asp Gly Leu Pro Val Gly Val Val Asp Val Val Glu Gly Leu Asp Gly
        115                 120                 125

Cys His Ser Ala Asn Ile Ser Pro Asp Asn Arg Thr Leu Trp Val Pro
    130                 135                 140

Ala Leu Lys Gln Asp Arg Ile Cys Leu Phe Thr Val Ser Asp Asp Gly
145                 150                 155                 160

His Leu Val Ala Gln Asp Pro Ala Glu Val Thr Thr Val Glu Gly Ala
```

```
                      165                 170                 175
Gly Pro Arg His Met Val Phe His Pro Asn Glu Gln Tyr Ala Tyr Cys
                180                 185                 190

Val Asn Glu Leu Asn Ser Ser Val Asp Val Trp Glu Leu Lys Asp Pro
            195                 200                 205

His Gly Asn Ile Glu Cys Val Gln Thr Leu Asp Met Met Pro Glu Asn
        210                 215                 220

Phe Ser Asp Thr Arg Trp Ala Asp Ile His Ile Thr Pro Asp Gly
225                 230                 235                 240

Arg His Leu Tyr Ala Cys Asp Arg Thr Ala Ser Leu Ile Thr Val Phe
                245                 250                 255

Ser Val Ser Glu Asp Gly Ser Val Leu Ser Lys Glu Gly Phe Gln Pro
            260                 265                 270

Thr Glu Thr Gln Pro Arg Gly Phe Asn Val Asp His Ser Gly Lys Tyr
        275                 280                 285

Leu Ile Ala Ala Gly Gln Lys Ser His His Ile Ser Val Tyr Glu Ile
    290                 295                 300

Val Gly Glu Gln Gly Leu Leu His Glu Lys Gly Arg Tyr Ala Val Gly
305                 310                 315                 320

Gln Gly Pro Met Trp Val Val Asn Ala His
                325                 330

<210> SEQ ID NO 27
<211> LENGTH: 470
<212> TYPE: PRT
<213> ORGANISM: Geobacillus thermodenitrificans

<400> SEQUENCE: 27

Met Ala Lys Gln Gln Ile Gly Val Ile Gly Leu Ala Val Met Gly Lys
1               5                   10                  15

Asn Leu Ala Leu Asn Ile Glu Ser Arg Gly Tyr Ser Val Ala Val Tyr
            20                  25                  30

Asn Arg Ser Arg Glu Lys Thr Asp Glu Phe Leu Glu Glu Ala Lys Gly
        35                  40                  45

Lys Asn Ile Val Gly Thr Tyr Ser Ile Glu Glu Phe Val Asn Ala Leu
    50                  55                  60

Glu Lys Pro Arg Lys Ile Leu Leu Met Val Lys Ala Gly Ala Pro Thr
65                  70                  75                  80

Asp Ala Thr Ile Glu Gln Leu Lys Pro Tyr Leu Glu Lys Gly Asp Ile
                85                  90                  95

Leu Ile Asp Gly Gly Asn Thr Tyr Phe Lys Asp Thr Gln Arg Arg Asn
            100                 105                 110

Glu Glu Leu Ala Lys Leu Gly Ile His Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala His Glu Leu Val Arg Pro Ile Phe Glu Ala Ile Ala
145                 150                 155                 160

Ala Lys Val Asp Gly Glu Pro Cys Thr Thr Tyr Ile Gly Pro Asp Gly
                165                 170                 175

Ala Gly His Tyr Val Lys Met Val His Asn Gly Ile Glu Tyr Gly Asp
            180                 185                 190

Met Gln Leu Ile Ala Glu Ala Tyr Phe Leu Leu Lys His Val Leu Gly
        195                 200                 205
```

Met Asp Ala Ala Glu Leu His Glu Val Phe Ala Asp Trp Asn Lys Gly
210                 215                 220

Glu Leu Asn Ser Tyr Leu Ile Glu Ile Thr Ala Asp Ile Phe Thr Lys
225                 230                 235                 240

Ile Asp Asp Glu Thr Gly Lys Pro Leu Val Asp Val Ile Leu Asp Lys
                245                 250                 255

Ala Gly Gln Lys Gly Thr Gly Lys Trp Thr Ser Gln Asn Ala Leu Asp
                260                 265                 270

Leu Gly Val Pro Leu Pro Ile Thr Glu Ser Val Phe Ala Arg Phe
                275                 280                 285

Ile Ser Ala Met Lys Asp Glu Arg Val Lys Ala Ser Lys Leu Leu Ser
290                 295                 300

Gly Pro Ala Val Lys Pro Phe Glu Gly Asp Arg Asp His Phe Ile Glu
305                 310                 315                 320

Ala Val Arg Arg Ala Leu Tyr Met Ser Lys Ile Cys Ser Tyr Ala Gln
                325                 330                 335

Gly Phe Ala Gln Met Lys Ala Ala Ser Asp Glu Tyr Asn Trp Asn Leu
                340                 345                 350

Arg Tyr Gly Asp Ile Ala Met Ile Phe Arg Gly Gly Cys Ile Ile Arg
                355                 360                 365

Ala Gln Phe Leu Gln Lys Ile Lys Glu Ala Tyr Asp Arg Asp Pro Ala
370                 375                 380

Leu Pro Asn Leu Leu Leu Asp Pro Tyr Phe Lys Asn Ile Val Glu Ser
385                 390                 395                 400

Tyr Gln Asp Ser Leu Arg Glu Ile Val Ala Thr Ala Ala Met Arg Gly
                405                 410                 415

Ile Pro Val Pro Ala Phe Ala Ser Ala Leu Ala Tyr Tyr Asp Ser Tyr
                420                 425                 430

Arg Asn Glu Val Leu Pro Ala Asn Leu Ile Gln Ala Gln Arg Asp Tyr
                435                 440                 445

Phe Gly Ala His Thr Tyr Glu Arg Val Asp Lys Glu Gly Ile Phe His
                450                 455                 460

Thr Glu Trp Leu Ala Lys
465                 470

<210> SEQ ID NO 28
<211> LENGTH: 470
<212> TYPE: PRT
<213> ORGANISM: Artificial Sequence
<220> FEATURE:
<223> OTHER INFORMATION: Mutant Gnd (mGnd)

<400> SEQUENCE: 28

Met Ala Lys Gln Gln Ile Gly Val Ile Gly Leu Ala Val Met Gly Lys
1               5                   10                  15

Asn Leu Ala Leu Asn Ile Glu Ser Arg Gly Tyr Ser Val Ala Val Tyr
                20                  25                  30

Asp Tyr Ser Arg Glu Leu Thr Asp Glu Phe Leu Glu Glu Ala Lys Gly
                35                  40                  45

Lys Asn Ile Val Gly Thr Tyr Ser Ile Glu Glu Phe Val Asn Ala Leu
                50                  55                  60

Glu Lys Pro Arg Lys Ile Leu Leu Met Val Lys Ala Gly Ala Pro Thr
65                  70                  75                  80

Asp Ala Thr Ile Glu Gln Leu Lys Pro Tyr Leu Glu Lys Gly Asp Ile
                85                  90                  95

```
Leu Ile Asp Gly Gly Asn Thr Tyr Phe Lys Asp Thr Gln Arg Arg Asn
                100                 105                 110

Glu Glu Leu Ala Lys Leu Gly Ile His Phe Ile Gly Thr Gly Val Ser
            115                 120                 125

Gly Gly Glu Glu Gly Ala Leu Lys Gly Pro Ser Ile Met Pro Gly Gly
        130                 135                 140

Gln Lys Glu Ala His Glu Leu Val Arg Pro Ile Phe Glu Ala Ile Ala
145                 150                 155                 160

Ala Lys Val Asp Gly Glu Pro Cys Thr Thr Tyr Ile Gly Pro Asp Gly
                165                 170                 175

Ala Gly His Tyr Val Lys Met Val His Asn Gly Ile Glu Tyr Gly Asp
            180                 185                 190

Met Gln Leu Ile Ala Glu Ala Tyr Phe Leu Leu Lys His Val Leu Gly
        195                 200                 205

Met Asp Ala Ala Glu Leu His Glu Val Phe Ala Asp Trp Asn Lys Gly
210                 215                 220

Glu Leu Asn Ser Tyr Leu Ile Glu Ile Thr Ala Asp Ile Phe Thr Lys
225                 230                 235                 240

Ile Asp Asp Glu Thr Gly Lys Pro Leu Val Asp Val Ile Leu Asp Lys
                245                 250                 255

Ala Gly Gln Lys Gly Thr Gly Lys Trp Thr Ser Gln Asn Ala Leu Asp
            260                 265                 270

Leu Gly Val Pro Leu Pro Ile Ile Thr Glu Ser Val Phe Ala Arg Phe
        275                 280                 285

Ile Ser Ala Met Lys Asp Glu Arg Val Lys Ala Ser Lys Leu Leu Ser
290                 295                 300

Gly Pro Ala Val Lys Pro Phe Glu Gly Asp Arg Asp His Phe Ile Glu
305                 310                 315                 320

Ala Val Arg Arg Ala Leu Tyr Met Ser Lys Ile Cys Ser Tyr Ala Gln
                325                 330                 335

Gly Phe Ala Gln Met Lys Ala Ala Ser Asp Glu Tyr Asn Trp Asn Leu
            340                 345                 350

Arg Tyr Gly Asp Ile Ala Met Ile Phe Arg Gly Gly Cys Ile Ile Arg
        355                 360                 365

Ala Gln Phe Leu Gln Lys Ile Lys Glu Ala Tyr Asp Arg Asp Pro Ala
370                 375                 380

Leu Pro Asn Leu Leu Leu Asp Pro Tyr Phe Lys Asn Ile Val Glu Ser
385                 390                 395                 400

Tyr Gln Asp Ser Leu Arg Glu Ile Val Ala Thr Ala Met Arg Gly
                405                 410                 415

Ile Pro Val Pro Ala Phe Ala Ser Ala Leu Ala Tyr Tyr Asp Ser Tyr
            420                 425                 430

Arg Asn Glu Val Leu Pro Ala Asn Leu Ile Gln Ala Gln Arg Asp Tyr
        435                 440                 445

Phe Gly Ala His Thr Tyr Glu Arg Val Asp Lys Glu Gly Ile Phe His
450                 455                 460

Thr Glu Trp Leu Ala Lys
465                 470

<210> SEQ ID NO 29
<211> LENGTH: 335
<212> TYPE: PRT
<213> ORGANISM: Geobacillus stearothermophilus

<400> SEQUENCE: 29
```

Met Ala Val Lys Val Gly Ile Asn Gly Phe Gly Arg Ile Gly Arg Asn
1               5                   10                  15

Val Phe Arg Ala Ala Leu Lys Asn Pro Asp Ile Glu Val Val Ala Val
                20                  25                  30

Asn Asp Leu Thr Asp Ala Asn Thr Leu Ala His Leu Leu Lys Tyr Asp
            35                  40                  45

Ser Val His Gly Arg Leu Asp Ala Glu Val Ser Val Asn Gly Asn Asn
        50                  55                  60

Leu Val Val Asn Gly Lys Glu Ile Ile Val Lys Ala Glu Arg Asp Pro
65                  70                  75                  80

Glu Asn Leu Ala Trp Gly Glu Ile Gly Val Asp Ile Val Val Glu Ser
                85                  90                  95

Thr Gly Arg Phe Thr Lys Arg Glu Asp Ala Ala Lys His Leu Glu Ala
            100                 105                 110

Gly Ala Lys Lys Val Ile Ile Ser Ala Pro Ala Lys Asn Glu Asp Ile
        115                 120                 125

Thr Ile Val Met Gly Val Asn Gln Asp Lys Tyr Asp Pro Lys Ala His
    130                 135                 140

His Val Ile Ser Asn Ala Ser Cys Thr Thr Asn Cys Leu Ala Pro Phe
145                 150                 155                 160

Ala Lys Val Leu His Glu Gln Phe Gly Ile Val Arg Gly Met Met Thr
                165                 170                 175

Thr Val His Ser Tyr Thr Asn Asp Gln Arg Ile Leu Asp Leu Pro His
            180                 185                 190

Lys Asp Leu Arg Arg Ala Arg Ala Ala Glu Ser Ile Ile Pro Thr
        195                 200                 205

Thr Thr Gly Ala Ala Lys Ala Val Ala Leu Val Leu Pro Glu Leu Lys
    210                 215                 220

Gly Lys Leu Asn Gly Met Ala Met Arg Val Pro Thr Pro Asn Val Ser
225                 230                 235                 240

Val Val Asp Leu Val Ala Glu Leu Glu Lys Glu Val Thr Val Glu Glu
                245                 250                 255

Val Asn Ala Ala Leu Lys Ala Ala Ala Glu Gly Glu Leu Lys Gly Ile
            260                 265                 270

Leu Ala Tyr Ser Glu Glu Pro Leu Val Ser Arg Asp Tyr Asn Gly Ser
        275                 280                 285

Thr Val Ser Ser Thr Ile Asp Ala Leu Ser Thr Met Val Ile Asp Gly
    290                 295                 300

Lys Met Val Lys Val Val Ser Trp Tyr Asp Asn Glu Thr Gly Tyr Ser
305                 310                 315                 320

His Arg Val Val Asp Leu Ala Ala Tyr Ile Ala Ser Lys Gly Leu
                325                 330                 335

<210> SEQ ID NO 30
<211> LENGTH: 335
<212> TYPE: PRT
<213> ORGANISM: Artificial Sequence
<220> FEATURE:
<223> OTHER INFORMATION: Mutant Gap (mGap) (D34A/L35R/T35K)

<400> SEQUENCE: 30

Met Ala Val Lys Val Gly Ile Asn Gly Phe Gly Arg Ile Gly Arg Asn
1               5                   10                  15

Val Phe Arg Ala Ala Leu Lys Asn Pro Asp Ile Glu Val Val Ala Val
                20                  25                  30

```
Asn Ala Arg Lys Asp Ala Asn Thr Leu Ala His Leu Leu Lys Tyr Asp
            35                  40                  45

Ser Val His Gly Arg Leu Asp Ala Glu Val Ser Val Asn Gly Asn Asn
 50                  55                  60

Leu Val Val Asn Gly Lys Glu Ile Ile Val Lys Ala Glu Arg Asp Pro
 65                  70                  75                  80

Glu Asn Leu Ala Trp Gly Glu Ile Gly Val Asp Ile Val Val Glu Ser
                 85                  90                  95

Thr Gly Arg Phe Thr Lys Arg Glu Asp Ala Ala Lys His Leu Glu Ala
                 100                 105                 110

Gly Ala Lys Lys Val Ile Ile Ser Ala Pro Ala Lys Asn Glu Asp Ile
                 115                 120                 125

Thr Ile Val Met Gly Val Asn Gln Asp Lys Tyr Asp Pro Lys Ala His
 130                 135                 140

His Val Ile Ser Asn Ala Ser Cys Thr Thr Asn Cys Leu Ala Pro Phe
145                 150                 155                 160

Ala Lys Val Leu His Glu Gln Phe Gly Ile Val Arg Gly Met Met Thr
                 165                 170                 175

Thr Val His Ser Tyr Thr Asn Asp Gln Arg Ile Leu Asp Leu Pro His
                 180                 185                 190

Lys Asp Leu Arg Arg Ala Arg Ala Ala Glu Ser Ile Ile Pro Thr
                 195                 200                 205

Thr Thr Gly Ala Ala Lys Ala Val Leu Val Leu Pro Glu Leu Lys
 210                 215                 220

Gly Lys Leu Asn Gly Met Ala Met Arg Val Pro Thr Pro Asn Val Ser
225                 230                 235                 240

Val Val Asp Leu Val Ala Glu Leu Glu Lys Glu Val Thr Val Glu Glu
                 245                 250                 255

Val Asn Ala Ala Leu Lys Ala Ala Glu Gly Glu Leu Lys Gly Ile
                 260                 265                 270

Leu Ala Tyr Ser Glu Glu Pro Leu Val Ser Arg Asp Tyr Asn Gly Ser
                 275                 280                 285

Thr Val Ser Ser Thr Ile Asp Ala Leu Ser Thr Met Val Ile Asp Gly
                 290                 295                 300

Lys Met Val Lys Val Val Ser Trp Tyr Asp Asn Glu Thr Gly Tyr Ser
305                 310                 315                 320

His Arg Val Val Asp Leu Ala Ala Tyr Ile Ala Ser Lys Gly Leu
                 325                 330                 335

<210> SEQ ID NO 31
<211> LENGTH: 335
<212> TYPE: PRT
<213> ORGANISM: Artificial sequence
<220> FEATURE:
<223> OTHER INFORMATION: Mutant Gap (mGap)(P188D)

<400> SEQUENCE: 31

Met Ala Val Lys Val Gly Ile Asn Gly Phe Gly Arg Ile Gly Arg Asn
1               5                   10                  15

Val Phe Arg Ala Ala Leu Lys Asn Pro Asp Ile Glu Val Ala Val
                 20                  25                  30

Asn Asp Leu Thr Asp Ala Asn Thr Leu Ala His Leu Leu Lys Tyr Asp
            35                  40                  45

Ser Val His Gly Arg Leu Asp Ala Glu Val Ser Val Asn Gly Asn Asn
 50                  55                  60
```

```
Leu Val Val Asn Gly Lys Glu Ile Ile Val Lys Ala Glu Arg Asp Pro
 65                  70                  75                  80

Glu Asn Leu Ala Trp Gly Glu Ile Gly Val Asp Ile Val Val Glu Ser
                 85                  90                  95

Thr Gly Arg Phe Thr Lys Arg Glu Asp Ala Ala Lys His Leu Glu Ala
            100                 105                 110

Gly Ala Lys Lys Val Ile Ile Ser Ala Pro Ala Lys Asn Glu Asp Ile
        115                 120                 125

Thr Ile Val Met Gly Val Asn Gln Asp Lys Tyr Asp Pro Lys Ala His
130                 135                 140

His Val Ile Ser Asn Ala Ser Cys Thr Thr Asn Cys Leu Ala Pro Phe
145                 150                 155                 160

Ala Lys Val Leu His Glu Gln Phe Gly Ile Val Arg Gly Met Met Thr
                165                 170                 175

Thr Val His Ser Tyr Thr Asn Asp Gln Arg Ile Leu Asp Leu Asp His
            180                 185                 190

Lys Asp Leu Arg Arg Ala Arg Ala Ala Ala Glu Ser Ile Ile Pro Thr
        195                 200                 205

Thr Thr Gly Ala Ala Lys Ala Val Ala Leu Val Leu Pro Glu Leu Lys
210                 215                 220

Gly Lys Leu Asn Gly Met Ala Met Arg Val Pro Thr Pro Asn Val Ser
225                 230                 235                 240

Val Val Asp Leu Val Ala Glu Leu Glu Lys Glu Val Thr Val Glu Glu
                245                 250                 255

Val Asn Ala Ala Leu Lys Ala Ala Glu Gly Glu Leu Lys Gly Ile
            260                 265                 270

Leu Ala Tyr Ser Glu Glu Pro Leu Val Ser Arg Asp Tyr Asn Gly Ser
        275                 280                 285

Thr Val Ser Ser Thr Ile Asp Ala Leu Ser Thr Met Val Ile Asp Gly
290                 295                 300

Lys Met Val Lys Val Val Ser Trp Tyr Asp Asn Glu Thr Gly Tyr Ser
305                 310                 315                 320

His Arg Val Val Asp Leu Ala Ala Tyr Ile Ala Ser Lys Gly Leu
                325                 330                 335

<210> SEQ ID NO 32
<211> LENGTH: 394
<212> TYPE: PRT
<213> ORGANISM: Geobacillus stearothermophilus

<400> SEQUENCE: 32

Met Asn Lys Lys Thr Ile Arg Asp Val Asp Val Arg Gly Lys Arg Val
1               5                   10                  15

Phe Cys Arg Val Asp Phe Asn Val Pro Met Glu Gln Gly Ala Ile Thr
                20                  25                  30

Asp Asp Thr Arg Ile Arg Ala Ala Leu Pro Thr Ile Arg Tyr Leu Ile
            35                  40                  45

Glu His Gly Ala Lys Val Ile Leu Ala Ser His Leu Gly Arg Pro Lys
        50                  55                  60

Gly Lys Val Val Glu Glu Leu Arg Leu Asp Ala Val Ala Lys Arg Leu
65                  70                  75                  80

Gly Glu Leu Leu Glu Arg Pro Val Ala Lys Thr Asn Glu Ala Val Gly
                85                  90                  95

Asp Glu Val Lys Ala Ala Val Asp Arg Leu Asn Glu Gly Asp Val Leu
```

```
                100                 105                 110
Leu Leu Glu Asn Val Arg Phe Tyr Pro Gly Glu Glu Lys Asn Asp Pro
            115                 120                 125

Glu Leu Ala Lys Ala Phe Ala Glu Leu Ala Asp Leu Tyr Val Asn Asp
130                 135                 140

Ala Phe Gly Ala Ala His Arg Ala His Ala Ser Thr Glu Gly Ile Ala
145                 150                 155                 160

His Tyr Leu Pro Ala Val Ala Gly Phe Leu Met Glu Lys Glu Leu Glu
                165                 170                 175

Val Leu Gly Lys Ala Leu Ser Asn Pro Asp Arg Pro Phe Thr Ala Ile
            180                 185                 190

Ile Gly Gly Ala Lys Val Lys Asp Lys Ile Gly Val Ile Asp Asn Leu
        195                 200                 205

Leu Glu Lys Val Asp Asn Leu Ile Ile Gly Gly Leu Ala Tyr Thr
    210                 215                 220

Phe Val Lys Ala Leu Gly His Asp Val Gly Lys Ser Leu Leu Glu Glu
225                 230                 235                 240

Asp Lys Ile Glu Leu Ala Lys Ser Phe Met Glu Lys Ala Lys Glu Lys
                245                 250                 255

Gly Val Arg Phe Tyr Met Pro Val Asp Val Val Ala Asp Arg Phe
            260                 265                 270

Ala Asn Asp Ala Asn Thr Lys Val Val Pro Ile Asp Ala Ile Pro Ala
            275                 280                 285

Asp Trp Ser Ala Leu Asp Ile Gly Pro Lys Thr Arg Glu Leu Tyr Arg
        290                 295                 300

Asp Val Ile Arg Glu Ser Lys Leu Val Val Trp Asn Gly Pro Met Gly
305                 310                 315                 320

Val Phe Glu Met Asp Ala Phe Ala His Gly Thr Lys Ala Ile Ala Glu
                325                 330                 335

Ala Leu Ala Glu Ala Leu Asp Thr Tyr Ser Val Ile Gly Gly Gly Asp
            340                 345                 350

Ser Ala Ala Ala Val Glu Lys Phe Gly Leu Ala Asp Lys Met Asp His
        355                 360                 365

Ile Ser Thr Gly Gly Gly Ala Ser Leu Glu Phe Met Glu Gly Lys Gln
    370                 375                 380

Leu Pro Gly Val Val Ala Leu Glu Asp Lys
385                 390

<210> SEQ ID NO 33
<211> LENGTH: 1365
<212> TYPE: DNA
<213> ORGANISM: Escherichia coli
<220> FEATURE:
<221> NAME/KEY: CDS
<222> LOCATION: (1)..(1365)

<400> SEQUENCE: 33 atg agc gat aat gac act atc gta gcc cag gcc acg cct ccg gga cgt      48
Met Ser Asp Asn Asp Thr Ile Val Ala Gln Ala Thr Pro Pro Gly Arg
1               5                   10                  15 ggc ggc gtt ggc atc ctg cgc atc tcc ggc ttc aaa gcc cgt gaa gtt      96
Gly Gly Val Gly Ile Leu Arg Ile Ser Gly Phe Lys Ala Arg Glu Val
                20                  25                  30 gcc gaa acc gtg ctg ggt aaa ctg cct aag ccg cgc tac gcc gat tat     144
Ala Glu Thr Val Leu Gly Lys Leu Pro Lys Pro Arg Tyr Ala Asp Tyr
            35                  40                  45
```

| | | |
|---|---|---|
| ctt ccg ttt aaa gac gcc gac ggc agc gtg ctc gat cag ggg att gcg<br>Leu Pro Phe Lys Asp Ala Asp Gly Ser Val Leu Asp Gln Gly Ile Ala<br>50                       55                         60 | | 192 |
| cta tgg ttc cct ggc ccg aac tcg ttc acc ggc gaa gat gtg ctg gaa<br>Leu Trp Phe Pro Gly Pro Asn Ser Phe Thr Gly Glu Asp Val Leu Glu<br>65                    70                    75                   80 | | 240 |
| ctg caa ggt cat ggc ggt ccg gtg atc ctc gac ctg ctg tta aaa cgc<br>Leu Gln Gly His Gly Gly Pro Val Ile Leu Asp Leu Leu Leu Lys Arg<br>                    85                    90                   95 | | 288 |
| att ctg acc att ccc ggc ctg cgg att gct cgc cct ggt gag ttt tcc<br>Ile Leu Thr Ile Pro Gly Leu Arg Ile Ala Arg Pro Gly Glu Phe Ser<br>                100                  105                  110 | | 336 |
| gaa cgc gcg ttt ctt aac gat aaa ctt gac tta gcc cag gcc gag gcg<br>Glu Arg Ala Phe Leu Asn Asp Lys Leu Asp Leu Ala Gln Ala Glu Ala<br>                115                  120                  125 | | 384 |
| att gcc gat ctt atc gac gcc agt tcg gaa cag gcg gcc cgt tcg gca<br>Ile Ala Asp Leu Ile Asp Ala Ser Ser Glu Gln Ala Ala Arg Ser Ala<br>         130                  135                  140 | | 432 |
| ctt aac tcg ctg caa ggc gca ttc tcc gca cgg gtt aat cat ctg gta<br>Leu Asn Ser Leu Gln Gly Ala Phe Ser Ala Arg Val Asn His Leu Val<br>145                      150                  155                  160 | | 480 |
| gaa gcc ctc acc cac ttg cgc att tac gtc gaa gcg gca att gat ttc<br>Glu Ala Leu Thr His Leu Arg Ile Tyr Val Glu Ala Ala Ile Asp Phe<br>                165                  170                  175 | | 528 |
| ccc gat gaa gag atc gat ttc ctc tcc gac gga aaa att gaa gcc cag<br>Pro Asp Glu Glu Ile Asp Phe Leu Ser Asp Gly Lys Ile Glu Ala Gln<br>         180                  185                  190 | | 576 |
| ctc aat gac gtt att gcc gat ctt gat gca gtg cgt gct gaa gca cgt<br>Leu Asn Asp Val Ile Ala Asp Leu Asp Ala Val Arg Ala Glu Ala Arg<br>                195                  200                  205 | | 624 |
| cag ggt agt ttg ttg cgc gaa ggg atg aaa gtg gtg att gcc gga cgt<br>Gln Gly Ser Leu Leu Arg Glu Gly Met Lys Val Val Ile Ala Gly Arg<br>         210                  215                  220 | | 672 |
| cct aac gcc ggt aaa tcg agc ctg tta aac gcg ctg gcg ggg cgt gaa<br>Pro Asn Ala Gly Lys Ser Ser Leu Leu Asn Ala Leu Ala Gly Arg Glu<br>225                      230                  235                  240 | | 720 |
| gcg gca atc gta acc gat atc gcc gga act acg cgt gac gtg ctg cgt<br>Ala Ala Ile Val Thr Asp Ile Ala Gly Thr Thr Arg Asp Val Leu Arg<br>                245                  250                  255 | | 768 |
| gag cat atc cac att gac gga atg ccg ctg cat atc atc gat acc gcc<br>Glu His Ile His Ile Asp Gly Met Pro Leu His Ile Ile Asp Thr Ala<br>         260                  265                  270 | | 816 |
| ggg cta cgt gaa gcc agt gac gaa gta gaa cgt att ggt atc gag cgc<br>Gly Leu Arg Glu Ala Ser Asp Glu Val Glu Arg Ile Gly Ile Glu Arg<br>                275                  280                  285 | | 864 |
| gcg tgg cag gaa att gaa cag gcc gac cgc gtg ctg ttt atg gtc gat<br>Ala Trp Gln Glu Ile Glu Gln Ala Asp Arg Val Leu Phe Met Val Asp<br>         290                  295                  300 | | 912 |
| ggc acc aca aca gac gcc gtg gat ccg gca gag atc tgg ccg gaa ttt<br>Gly Thr Thr Thr Asp Ala Val Asp Pro Ala Glu Ile Trp Pro Glu Phe<br>305                      310                  315                  320 | | 960 |
| att gcc cgt ctg cca gcg aaa ctg ccg atc acc gtg gtg cgc aat aaa<br>Ile Ala Arg Leu Pro Ala Lys Leu Pro Ile Thr Val Val Arg Asn Lys<br>                325                  330                  335 | | 1008 |
| gcc gat atc acc ggc gaa acg ctg gga atg agt gaa gtg aac ggt cac<br>Ala Asp Ile Thr Gly Glu Thr Leu Gly Met Ser Glu Val Asn Gly His<br>         340                  345                  350 | | 1056 |
| gcg tta att cgt ctc tcg gca agg act ggt gaa ggc gtg gac gtg ctg<br>Ala Leu Ile Arg Leu Ser Ala Arg Thr Gly Glu Gly Val Asp Val Leu<br>                355                  360                  365 | | 1104 |

```
cgt aac cat ctc aaa cag agc atg ggc ttt gac acc aac atg gaa ggc    1152
Arg Asn His Leu Lys Gln Ser Met Gly Phe Asp Thr Asn Met Glu Gly
        370                 375                 380 ggc ttc ctg gcg cgt cgt cgc cac cta cag gcg ctg gaa cag gca gcg    1200
Gly Phe Leu Ala Arg Arg Arg His Leu Gln Ala Leu Glu Gln Ala Ala
385                 390                 395                 400 gaa cat cta caa cag ggc aaa gcg caa ctg ttg gga gcc tgg gca ggt    1248
Glu His Leu Gln Gln Gly Lys Ala Gln Leu Leu Gly Ala Trp Ala Gly
                405                 410                 415 gaa ctg ctg gcg gaa gag ttg cgt ctg gca cag cag aac tta agc gaa    1296
Glu Leu Leu Ala Glu Glu Leu Arg Leu Ala Gln Gln Asn Leu Ser Glu
        420                 425                 430 atc acc ggg gaa ttt act tca gac gac ctg ctg ggg cgg att ttc tcc    1344
Ile Thr Gly Glu Phe Thr Ser Asp Asp Leu Leu Gly Arg Ile Phe Ser
        435                 440                 445 agc ttc tgt att ggt aag taa                                        1365
Ser Phe Cys Ile Gly Lys
        450
```

<210> SEQ ID NO 34
<211> LENGTH: 454
<212> TYPE: PRT
<213> ORGANISM: Escherichia coli

<400> SEQUENCE: 34

```
Met Ser Asp Asn Asp Thr Ile Val Ala Gln Ala Thr Pro Pro Gly Arg
1               5                   10                  15

Gly Gly Val Gly Ile Leu Arg Ile Ser Gly Phe Lys Ala Arg Glu Val
            20                  25                  30

Ala Glu Thr Val Leu Gly Lys Leu Pro Lys Pro Arg Tyr Ala Asp Tyr
        35                  40                  45

Leu Pro Phe Lys Asp Ala Asp Gly Ser Val Leu Asp Gln Gly Ile Ala
    50                  55                  60

Leu Trp Phe Pro Gly Pro Asn Ser Phe Thr Gly Glu Asp Val Leu Glu
65                  70                  75                  80

Leu Gln Gly His Gly Gly Pro Val Ile Leu Asp Leu Leu Leu Lys Arg
                85                  90                  95

Ile Leu Thr Ile Pro Gly Leu Arg Ile Ala Arg Pro Gly Glu Phe Ser
            100                 105                 110

Glu Arg Ala Phe Leu Asn Asp Lys Leu Asp Leu Ala Gln Ala Glu Ala
        115                 120                 125

Ile Ala Asp Leu Ile Asp Ala Ser Ser Glu Gln Ala Ala Arg Ser Ala
    130                 135                 140

Leu Asn Ser Leu Gln Gly Ala Phe Ser Ala Arg Val Asn His Leu Val
145                 150                 155                 160

Glu Ala Leu Thr His Leu Arg Ile Tyr Val Glu Ala Ala Ile Asp Phe
                165                 170                 175

Pro Asp Glu Glu Ile Asp Phe Leu Ser Asp Gly Lys Ile Glu Ala Gln
            180                 185                 190

Leu Asn Asp Val Ile Ala Asp Leu Asp Ala Val Arg Ala Glu Ala Arg
        195                 200                 205

Gln Gly Ser Leu Leu Arg Glu Gly Met Lys Val Val Ile Ala Gly Arg
    210                 215                 220

Pro Asn Ala Gly Lys Ser Ser Leu Leu Asn Ala Leu Ala Gly Arg Glu
225                 230                 235                 240

Ala Ala Ile Val Thr Asp Ile Ala Gly Thr Thr Arg Asp Val Leu Arg
```

```
                    245                 250                 255
Glu His Ile His Ile Asp Gly Met Pro Leu His Ile Ile Asp Thr Ala
                260                 265                 270
Gly Leu Arg Glu Ala Ser Asp Glu Val Glu Arg Ile Gly Ile Glu Arg
            275                 280                 285
Ala Trp Gln Glu Ile Glu Gln Ala Asp Arg Val Leu Phe Met Val Asp
    290                 295                 300
Gly Thr Thr Thr Asp Ala Val Asp Pro Ala Glu Ile Trp Pro Glu Phe
305                 310                 315                 320
Ile Ala Arg Leu Pro Ala Lys Leu Pro Ile Thr Val Val Arg Asn Lys
                325                 330                 335
Ala Asp Ile Thr Gly Glu Thr Leu Gly Met Ser Glu Val Asn Gly His
                340                 345                 350
Ala Leu Ile Arg Leu Ser Ala Arg Thr Gly Glu Gly Val Asp Val Leu
            355                 360                 365
Arg Asn His Leu Lys Gln Ser Met Gly Phe Asp Thr Asn Met Glu Gly
        370                 375                 380
Gly Phe Leu Ala Arg Arg His Leu Gln Ala Leu Glu Gln Ala Ala
385                 390                 395                 400
Glu His Leu Gln Gln Gly Lys Ala Gln Leu Leu Gly Ala Trp Ala Gly
                405                 410                 415
Glu Leu Leu Ala Glu Leu Arg Leu Ala Gln Gln Asn Leu Ser Glu
                420                 425                 430
Ile Thr Gly Glu Phe Thr Ser Asp Asp Leu Leu Gly Arg Ile Phe Ser
            435                 440                 445
Ser Phe Cys Ile Gly Lys
    450

<210> SEQ ID NO 35
<211> LENGTH: 1389
<212> TYPE: DNA
<213> ORGANISM: Geobacillus thermodenitrificans
<220> FEATURE:
<221> NAME/KEY: CDS
<222> LOCATION: (1)..(1389)

<400> SEQUENCE: 35 atg aca gaa ttt gat aca att gcc gct att tcg acg ccg atg gga gaa      48
Met Thr Glu Phe Asp Thr Ile Ala Ala Ile Ser Thr Pro Met Gly Glu
1               5                   10                  15 ggg gcg atc gcc att gtt cgg ctg agc ggg gat gag gcg gta gag atc      96
Gly Ala Ile Ala Ile Val Arg Leu Ser Gly Asp Glu Ala Val Glu Ile
                20                  25                  30 gcc gat cgg ctt ttc cgc agc cca act gga aag cag ctg aaa gac gtg     144
Ala Asp Arg Leu Phe Arg Ser Pro Thr Gly Lys Gln Leu Lys Asp Val
            35                  40                  45 ccg tca cac acg att cat tat ggg cat att gtt gac cca aaa agc ggg     192
Pro Ser His Thr Ile His Tyr Gly His Ile Val Asp Pro Lys Ser Gly
        50                  55                  60 cgg atc gtt gag gaa gtg atg gta tcg gtc atg cgg gcg ccg aaa aca     240
Arg Ile Val Glu Glu Val Met Val Ser Val Met Arg Ala Pro Lys Thr
65                  70                  75                  80 ttt acg cgt gaa gat gta gta gag att aat tgc cat ggc ggg ttc gtt     288
Phe Thr Arg Glu Asp Val Val Glu Ile Asn Cys His Gly Gly Phe Val
                85                  90                  95 tcc gtc aat cgg gtg ttg cag ctt gtg ctc gcg aac ggg gcg cgt ctc     336
Ser Val Asn Arg Val Leu Gln Leu Val Leu Ala Asn Gly Ala Arg Leu
                100                 105                 110
```

```
                                                   -continued gcc gag ccg ggg gag ttt acg aag cga gcg ttt tta aac ggg cgc atc     384
Ala Glu Pro Gly Glu Phe Thr Lys Arg Ala Phe Leu Asn Gly Arg Ile
            115                 120                 125 gac tta tcc cag gct gaa gcg gtc att gac ctc att cgc gcc aaa acg     432
Asp Leu Ser Gln Ala Glu Ala Val Ile Asp Leu Ile Arg Ala Lys Thr
130                 135                 140 gat cga gcg atg aac gtc gcc ttg cag caa atg gag ggg cgc ttg tcg     480
Asp Arg Ala Met Asn Val Ala Leu Gln Gln Met Glu Gly Arg Leu Ser
145                 150                 155                 160 aaa ttg atc cgc gaa ttg cgg cag acg att tta gaa acg ttg gcg cac     528
Lys Leu Ile Arg Glu Leu Arg Gln Thr Ile Leu Glu Thr Leu Ala His
                165                 170                 175 gtt gaa gtc aac atc gac tat ccg gaa tac gat gat gtc gag gag atg     576
Val Glu Val Asn Ile Asp Tyr Pro Glu Tyr Asp Asp Val Glu Glu Met
            180                 185                 190 acg ccg cgt cta cta aaa gag aaa gca gaa tac gtg cgt ggg caa att     624
Thr Pro Arg Leu Leu Lys Glu Lys Ala Glu Tyr Val Arg Gly Gln Ile
        195                 200                 205 gaa aaa ctg ctt tcg acc gct acc caa ggg aaa att ttg cgc gaa ggt     672
Glu Lys Leu Leu Ser Thr Ala Thr Gln Gly Lys Ile Leu Arg Glu Gly
    210                 215                 220 ttg gcg acg gtt att atc ggg cgg ccg aac gtc ggc aag tcc tca ctg     720
Leu Ala Thr Val Ile Ile Gly Arg Pro Asn Val Gly Lys Ser Ser Leu
225                 230                 235                 240 tta aat gcg ctt gct cac gaa aac cga gcg atc gtc act gat att ccg     768
Leu Asn Ala Leu Ala His Glu Asn Arg Ala Ile Val Thr Asp Ile Pro
                245                 250                 255 gga acg acg cgc gat gtc atc gaa gag tat gtc aac gtt cgc ggt gtg     816
Gly Thr Thr Arg Asp Val Ile Glu Glu Tyr Val Asn Val Arg Gly Val
            260                 265                 270 ccg ctc cgc ttg att gat acg gcc ggc atc cgt gaa aca gaa gat att     864
Pro Leu Arg Leu Ile Asp Thr Ala Gly Ile Arg Glu Thr Glu Asp Ile
        275                 280                 285 gtt gaa cgg att ggc gtc gag cgc tca cgg caa atg ttg aag aag gcc     912
Val Glu Arg Ile Gly Val Glu Arg Ser Arg Gln Met Leu Lys Lys Ala
    290                 295                 300 gat tta att ttg ctt gtt ttg aac tat cat gaa ccg ctg aca gaa gag     960
Asp Leu Ile Leu Leu Val Leu Asn Tyr His Glu Pro Leu Thr Glu Glu
305                 310                 315                 320 gat gag cgg ctg ttt gca atg aca gaa gga atg gat gtt att gtt atc    1008
Asp Glu Arg Leu Phe Ala Met Thr Glu Gly Met Asp Val Ile Val Ile
                325                 330                 335 gtc aat aaa acg gat ttg cct cag aac att gat ata gag cgg gtc aaa    1056
Val Asn Lys Thr Asp Leu Pro Gln Asn Ile Asp Ile Glu Arg Val Lys
            340                 345                 350 gag ctt gcg gct ggc cgg ccg att gtg gca aca tca cta ttg tgt gaa    1104
Glu Leu Ala Ala Gly Arg Pro Ile Val Ala Thr Ser Leu Leu Cys Glu
        355                 360                 365 cga gga att gat gaa ctg gaa aaa gcg att gct gac tta ttt ttt ggt    1152
Arg Gly Ile Asp Glu Leu Glu Lys Ala Ile Ala Asp Leu Phe Phe Gly
    370                 375                 380 ggt gaa ctc gaa gcc ggc gat ttg act tat gtc tcg aat tcc cgg cat    1200
Gly Glu Leu Glu Ala Gly Asp Leu Thr Tyr Val Ser Asn Ser Arg His
385                 390                 395                 400 atc gcg ttg ctc gaa cag gcg aaa aag gcg atc gaa gat gcg ctg tcc    1248
Ile Ala Leu Leu Glu Gln Ala Lys Lys Ala Ile Glu Asp Ala Leu Ser
                405                 410                 415 ggc att gat gtt ggc atg ccg gtc gat ctc gtt caa atc gat ttg cgc    1296
Gly Ile Asp Val Gly Met Pro Val Asp Leu Val Gln Ile Asp Leu Arg
```

```
                    420                 425                 430
cgc gcg tgg gag ctg ctt ggc gaa atc gtt ggc gat aca gtg cat gaa    1344
Arg Ala Trp Glu Leu Leu Gly Glu Ile Val Gly Asp Thr Val His Glu
            435                 440                 445 agc ctg att gat cag ctg ttt gcc caa ttt tgt tta gga aaa taa        1389
Ser Leu Ile Asp Gln Leu Phe Ala Gln Phe Cys Leu Gly Lys
    450                 455                 460
```

<210> SEQ ID NO 36
<211> LENGTH: 462
<212> TYPE: PRT
<213> ORGANISM: Geobacillus thermodenitrificans

<400> SEQUENCE: 36

```
Met Thr Glu Phe Asp Thr Ile Ala Ala Ile Ser Thr Pro Met Gly Glu
1               5                   10                  15

Gly Ala Ile Ala Ile Val Arg Leu Ser Gly Asp Glu Ala Val Glu Ile
            20                  25                  30

Ala Asp Arg Leu Phe Arg Ser Pro Thr Gly Lys Gln Leu Lys Asp Val
        35                  40                  45

Pro Ser His Thr Ile His Tyr Gly His Ile Val Asp Pro Lys Ser Gly
    50                  55                  60

Arg Ile Val Glu Glu Val Met Val Ser Val Met Arg Ala Pro Lys Thr
65                  70                  75                  80

Phe Thr Arg Glu Asp Val Val Glu Ile Asn Cys His Gly Gly Phe Val
                85                  90                  95

Ser Val Asn Arg Val Leu Gln Leu Val Leu Ala Asn Gly Ala Arg Leu
            100                 105                 110

Ala Glu Pro Gly Glu Phe Thr Lys Arg Ala Phe Leu Asn Gly Arg Ile
        115                 120                 125

Asp Leu Ser Gln Ala Glu Ala Val Ile Asp Leu Ile Arg Ala Lys Thr
    130                 135                 140

Asp Arg Ala Met Asn Val Ala Leu Gln Gln Met Glu Gly Arg Leu Ser
145                 150                 155                 160

Lys Leu Ile Arg Glu Leu Arg Gln Thr Ile Leu Glu Thr Leu Ala His
                165                 170                 175

Val Glu Val Asn Ile Asp Tyr Pro Glu Tyr Asp Asp Val Glu Glu Met
            180                 185                 190

Thr Pro Arg Leu Leu Lys Glu Lys Ala Glu Tyr Val Arg Gly Gln Ile
        195                 200                 205

Glu Lys Leu Leu Ser Thr Ala Thr Gln Gly Lys Ile Leu Arg Glu Gly
    210                 215                 220

Leu Ala Thr Val Ile Ile Gly Arg Pro Asn Val Gly Lys Ser Ser Leu
225                 230                 235                 240

Leu Asn Ala Leu Ala His Glu Asn Arg Ala Ile Val Thr Asp Ile Pro
                245                 250                 255

Gly Thr Thr Arg Asp Val Ile Glu Glu Tyr Val Asn Val Arg Gly Val
            260                 265                 270

Pro Leu Arg Leu Ile Asp Thr Ala Gly Ile Arg Glu Thr Glu Asp Ile
        275                 280                 285

Val Glu Arg Ile Gly Val Glu Arg Ser Arg Gln Met Leu Lys Lys Ala
    290                 295                 300

Asp Leu Ile Leu Leu Val Leu Asn Tyr His Glu Pro Leu Thr Glu Glu
305                 310                 315                 320

Asp Glu Arg Leu Phe Ala Met Thr Glu Gly Met Asp Val Ile Val Ile
```

```
                    325                 330                 335
Val Asn Lys Thr Asp Leu Pro Gln Asn Ile Asp Ile Glu Arg Val Lys
                340                 345                 350

Glu Leu Ala Ala Gly Arg Pro Ile Val Ala Thr Ser Leu Leu Cys Glu
            355                 360                 365

Arg Gly Ile Asp Glu Leu Glu Lys Ala Ile Ala Asp Leu Phe Phe Gly
        370                 375                 380

Gly Glu Leu Glu Ala Gly Asp Leu Thr Tyr Val Ser Asn Ser Arg His
385                 390                 395                 400

Ile Ala Leu Leu Glu Gln Ala Lys Lys Ala Ile Glu Asp Ala Leu Ser
                405                 410                 415

Gly Ile Asp Val Gly Met Pro Val Asp Leu Val Gln Ile Asp Leu Arg
                420                 425                 430

Arg Ala Trp Glu Leu Leu Gly Glu Ile Val Gly Asp Thr Val His Glu
            435                 440                 445

Ser Leu Ile Asp Gln Leu Phe Ala Gln Phe Cys Leu Gly Lys
    450                 455                 460

<210> SEQ ID NO 37
<211> LENGTH: 1152
<212> TYPE: DNA
<213> ORGANISM: Escherichia coli
<220> FEATURE:
<221> NAME/KEY: CDS
<222> LOCATION: (1)..(1152)

<400> SEQUENCE: 37 atg ttt gaa cca atg gaa ctt acc aat gac gcg gtg att aaa gtc atc      48
Met Phe Glu Pro Met Glu Leu Thr Asn Asp Ala Val Ile Lys Val Ile
1               5                   10                  15 ggc gtc ggc ggc ggc ggt aat gct gtt gaa cac atg gtg cgc gag          96
Gly Val Gly Gly Gly Gly Gly Asn Ala Val Glu His Met Val Arg Glu
            20                  25                  30 cgc att gaa ggt gtt gaa ttc ttc gcg gta aat acc gat gca caa gcg     144
Arg Ile Glu Gly Val Glu Phe Phe Ala Val Asn Thr Asp Ala Gln Ala
        35                  40                  45 ctg cgt aaa aca gcg gtt gga cag acg att caa atc ggt agc ggt atc     192
Leu Arg Lys Thr Ala Val Gly Gln Thr Ile Gln Ile Gly Ser Gly Ile
    50                  55                  60 acc aaa gga ctg ggc gct ggc gct aat cca gaa gtt ggc cgc aat gcg     240
Thr Lys Gly Leu Gly Ala Gly Ala Asn Pro Glu Val Gly Arg Asn Ala
65                  70                  75                  80 gct gat gag gat cgc gat gca ttg cgt gcg gcg ctg gaa ggt gca gac     288
Ala Asp Glu Asp Arg Asp Ala Leu Arg Ala Ala Leu Glu Gly Ala Asp
                85                  90                  95 atg gtc ttt att gct gcg ggt atg ggt ggt ggt acc ggt aca ggt gca     336
Met Val Phe Ile Ala Ala Gly Met Gly Gly Gly Thr Gly Thr Gly Ala
            100                 105                 110 gca cca gtc gtc gct gaa gtg gca aaa gat ttg ggt atc ctg acc gtt     384
Ala Pro Val Val Ala Glu Val Ala Lys Asp Leu Gly Ile Leu Thr Val
        115                 120                 125 gct gtc gtc act aag cct ttc aac ttt gaa ggc aag aag cgt atg gca     432
Ala Val Val Thr Lys Pro Phe Asn Phe Glu Gly Lys Lys Arg Met Ala
    130                 135                 140 ttc gcg gag cag ggg atc act gaa ctg tcc aag cat gtg gac tct ctg     480
Phe Ala Glu Gln Gly Ile Thr Glu Leu Ser Lys His Val Asp Ser Leu
145                 150                 155                 160 atc act atc ccg aac gac aaa ctg ctg aaa gtt ctg ggc cgc ggt atc     528
Ile Thr Ile Pro Asn Asp Lys Leu Leu Lys Val Leu Gly Arg Gly Ile
```

```
tcc ctg ctg gat gcg ttt ggc gca gcg aac gat gta ctg aaa ggc gct    576
Ser Leu Leu Asp Ala Phe Gly Ala Ala Asn Asp Val Leu Lys Gly Ala
        180                 185                 190 gtg caa ggt atc gct gaa ctg att act cgt ccg ggt ttg atg aac gtg    624
Val Gln Gly Ile Ala Glu Leu Ile Thr Arg Pro Gly Leu Met Asn Val
            195                 200                 205 gac ttt gca gac gta cgc acc gta atg tct gag atg ggc tac gca atg    672
Asp Phe Ala Asp Val Arg Thr Val Met Ser Glu Met Gly Tyr Ala Met
210                 215                 220 atg ggt tct ggc gtg gcg agc ggt gaa gac cgt gcg gaa gaa gct gct    720
Met Gly Ser Gly Val Ala Ser Gly Glu Asp Arg Ala Glu Glu Ala Ala
225                 230                 235                 240 gaa atg gct atc tct tct ccg ctg ctg gaa gat atc gac ctg tct ggc    768
Glu Met Ala Ile Ser Ser Pro Leu Leu Glu Asp Ile Asp Leu Ser Gly
                245                 250                 255 gcg cgc ggc gtg ctg gtt aac atc acg gcg ggc ttc gac ctg cgt ctg    816
Ala Arg Gly Val Leu Val Asn Ile Thr Ala Gly Phe Asp Leu Arg Leu
            260                 265                 270 gat gag ttc gaa acg gta ggt aac acc atc cgt gca ttt gct tcc gac    864
Asp Glu Phe Glu Thr Val Gly Asn Thr Ile Arg Ala Phe Ala Ser Asp
        275                 280                 285 aac gcg act gtg gtt atc ggt act tct ctt gac ccg gat atg aat gac    912
Asn Ala Thr Val Val Ile Gly Thr Ser Leu Asp Pro Asp Met Asn Asp
290                 295                 300 gag ctg cgc gta acc gtt gtt gcg aca ggt atc ggc atg gac aaa cgt    960
Glu Leu Arg Val Thr Val Val Ala Thr Gly Ile Gly Met Asp Lys Arg
305                 310                 315                 320 cct gaa atc act ctg gtg acc aat aag cag gtt cag cag cca gtg atg   1008
Pro Glu Ile Thr Leu Val Thr Asn Lys Gln Val Gln Gln Pro Val Met
                325                 330                 335 gat cgc tac cag cag cat ggg atg gct ccg ctg acc cag gag cag aag   1056
Asp Arg Tyr Gln Gln His Gly Met Ala Pro Leu Thr Gln Glu Gln Lys
            340                 345                 350 ccg gtt gct aaa gtc gtg aat gac aat gcg ccg caa act gcg aaa gag   1104
Pro Val Ala Lys Val Val Asn Asp Asn Ala Pro Gln Thr Ala Lys Glu
        355                 360                 365 ccg gat tat ctg gat atc cca gca ttc ctg cgt aag caa gct gat taa   1152
Pro Asp Tyr Leu Asp Ile Pro Ala Phe Leu Arg Lys Gln Ala Asp
370                 375                 380
```

<210> SEQ ID NO 38
<211> LENGTH: 383
<212> TYPE: PRT
<213> ORGANISM: Escherichia coli

<400> SEQUENCE: 38

```
Met Phe Glu Pro Met Glu Leu Thr Asn Asp Ala Val Ile Lys Val Ile
1               5                   10                  15

Gly Val Gly Gly Gly Gly Gly Asn Ala Val Glu His Met Val Arg Glu
            20                  25                  30

Arg Ile Glu Gly Val Glu Phe Phe Ala Val Asn Thr Asp Ala Gln Ala
        35                  40                  45

Leu Arg Lys Thr Ala Val Gly Gln Thr Ile Gln Ile Gly Ser Gly Ile
    50                  55                  60

Thr Lys Gly Leu Gly Ala Gly Ala Asn Pro Glu Val Gly Arg Asn Ala
65                  70                  75                  80

Ala Asp Glu Asp Arg Asp Ala Leu Arg Ala Ala Leu Glu Gly Ala Asp
                85                  90                  95
```

```
Met Val Phe Ile Ala Ala Gly Met Gly Gly Thr Gly Thr Gly Ala
            100                 105                 110

Ala Pro Val Val Ala Glu Val Ala Lys Asp Leu Gly Ile Leu Thr Val
        115                 120                 125

Ala Val Val Thr Lys Pro Phe Asn Phe Glu Gly Lys Lys Arg Met Ala
        130                 135                 140

Phe Ala Glu Gln Gly Ile Thr Glu Leu Ser Lys His Val Asp Ser Leu
145                 150                 155                 160

Ile Thr Ile Pro Asn Asp Lys Leu Leu Lys Val Leu Gly Arg Gly Ile
                165                 170                 175

Ser Leu Leu Asp Ala Phe Gly Ala Ala Asn Asp Val Leu Lys Gly Ala
                180                 185                 190

Val Gln Gly Ile Ala Glu Leu Ile Thr Arg Pro Gly Leu Met Asn Val
        195                 200                 205

Asp Phe Ala Asp Val Arg Thr Val Met Ser Glu Met Gly Tyr Ala Met
        210                 215                 220

Met Gly Ser Gly Val Ala Ser Gly Glu Asp Arg Ala Glu Glu Ala Ala
225                 230                 235                 240

Glu Met Ala Ile Ser Ser Pro Leu Leu Glu Asp Ile Asp Leu Ser Gly
                245                 250                 255

Ala Arg Gly Val Leu Val Asn Ile Thr Ala Gly Phe Asp Leu Arg Leu
                260                 265                 270

Asp Glu Phe Glu Thr Val Gly Asn Thr Ile Arg Ala Phe Ala Ser Asp
        275                 280                 285

Asn Ala Thr Val Val Ile Gly Thr Ser Leu Asp Pro Asp Met Asn Asp
        290                 295                 300

Glu Leu Arg Val Thr Val Val Ala Thr Gly Ile Gly Met Asp Lys Arg
305                 310                 315                 320

Pro Glu Ile Thr Leu Val Thr Asn Lys Gln Val Gln Gln Pro Val Met
                325                 330                 335

Asp Arg Tyr Gln Gln His Gly Met Ala Pro Leu Thr Gln Glu Gln Lys
                340                 345                 350

Pro Val Ala Lys Val Val Asn Asp Asn Ala Pro Gln Thr Ala Lys Glu
                355                 360                 365

Pro Asp Tyr Leu Asp Ile Pro Ala Phe Leu Arg Lys Gln Ala Asp
                370                 375                 380

<210> SEQ ID NO 39
<211> LENGTH: 1380
<212> TYPE: DNA
<213> ORGANISM: Escherichia coli
<220> FEATURE:
<221> NAME/KEY: CDS
<222> LOCATION: (1)..(1380)

<400> SEQUENCE: 39 atg gaa tct att caa ccc tgg att gaa aaa ttt att aag caa gca cag      48
Met Glu Ser Ile Gln Pro Trp Ile Glu Lys Phe Ile Lys Gln Ala Gln
1               5                   10                  15 caa caa cgt tcg caa tcc act aaa gat tat cca acg tct tac cgt aac      96
Gln Gln Arg Ser Gln Ser Thr Lys Asp Tyr Pro Thr Ser Tyr Arg Asn
            20                  25                  30 ctg cga gta aaa ttg agt ttc ggt tat ggt aat ttt acg tct att ccc     144
Leu Arg Val Lys Leu Ser Phe Gly Tyr Gly Asn Phe Thr Ser Ile Pro
        35                  40                  45 tgg ttt gca ttt ctt gga gaa ggt cag gaa gct tct aac ggt ata tat     192
```

```
                Trp Phe Ala Phe Leu Gly Glu Gly Gln Glu Ala Ser Asn Gly Ile Tyr
                    50              55                  60 ccc gtt att ctc tat tat aaa gat ttt gat gag ttg gtt ttg gct tat         240
Pro Val Ile Leu Tyr Tyr Lys Asp Phe Asp Glu Leu Val Leu Ala Tyr
65              70                  75                  80 ggt ata agc gac acg aat gaa cca cat gcc caa tgg cag ttc tct tca         288
Gly Ile Ser Asp Thr Asn Glu Pro His Ala Gln Trp Gln Phe Ser Ser
                85                  90                  95 gac ata cct aaa aca atc gca gag tat ttt cag gca act tcg ggt gta         336
Asp Ile Pro Lys Thr Ile Ala Glu Tyr Phe Gln Ala Thr Ser Gly Val
            100                 105                 110 tat cct aaa aaa tac gga cag tcc tat tac gcc tgt tcc caa aaa gtc         384
Tyr Pro Lys Lys Tyr Gly Gln Ser Tyr Tyr Ala Cys Ser Gln Lys Val
        115                 120                 125 tca cag ggt att gat tac acc cga ttt gcc tct atg ctg gac aac ata         432
Ser Gln Gly Ile Asp Tyr Thr Arg Phe Ala Ser Met Leu Asp Asn Ile
    130                 135                 140 atc aac gac tat aaa tta ata ttt aat tct ggc aag agt gtt att cca         480
Ile Asn Asp Tyr Lys Leu Ile Phe Asn Ser Gly Lys Ser Val Ile Pro
145                 150                 155                 160 cct atg tca aaa act gaa tca tac tgt ctg gaa gat gcg tta aat gat         528
Pro Met Ser Lys Thr Glu Ser Tyr Cys Leu Glu Asp Ala Leu Asn Asp
                165                 170                 175 ttg ttt atc cct gaa acc aca ata gag acg ata ctc aaa cga tta acc         576
Leu Phe Ile Pro Glu Thr Thr Ile Glu Thr Ile Leu Lys Arg Leu Thr
            180                 185                 190 atc aaa aaa aat att atc ctc cag ggg ccg ccc ggc gtt gga aaa acc         624
Ile Lys Lys Asn Ile Ile Leu Gln Gly Pro Pro Gly Val Gly Lys Thr
        195                 200                 205 ttt gtt gca cgc cgt ctg gct tac ttg ctg aca gga gaa aag gct ccg         672
Phe Val Ala Arg Arg Leu Ala Tyr Leu Leu Thr Gly Glu Lys Ala Pro
    210                 215                 220 caa cgc gtc aat atg gtt cag ttc cat caa tct tat agc tat gag gat         720
Gln Arg Val Asn Met Val Gln Phe His Gln Ser Tyr Ser Tyr Glu Asp
225                 230                 235                 240 ttt ata cag ggc tat cgt ccg aat ggc gtc ggc ttc cga cgt aaa gac         768
Phe Ile Gln Gly Tyr Arg Pro Asn Gly Val Gly Phe Arg Arg Lys Asp
                245                 250                 255 ggc ata ttt tac aat ttt tgt cag caa gct aaa gag cag cca gag aaa         816
Gly Ile Phe Tyr Asn Phe Cys Gln Gln Ala Lys Glu Gln Pro Glu Lys
            260                 265                 270 aag tat att ttt att ata gat gaa atc aat cgt gcc aat ctc agt aaa         864
Lys Tyr Ile Phe Ile Ile Asp Glu Ile Asn Arg Ala Asn Leu Ser Lys
        275                 280                 285 gta ttt ggc gaa gtg atg atg tta atg gaa cat gat aaa cga ggt gaa         912
Val Phe Gly Glu Val Met Met Leu Met Glu His Asp Lys Arg Gly Glu
    290                 295                 300 aac tgg tct gtt ccc cta acc tac tcc gaa aac gat gaa gaa cga ttc         960
Asn Trp Ser Val Pro Leu Thr Tyr Ser Glu Asn Asp Glu Glu Arg Phe
305                 310                 315                 320 tat gtc ccg gag aat gtt tat atc atc ggt tta atg aat act gcc gat        1008
Tyr Val Pro Glu Asn Val Tyr Ile Ile Gly Leu Met Asn Thr Ala Asp
                325                 330                 335 cgc tct ctg gcc gtt gtt gac tat gcc cta cgc aga cga ttt tct ttc        1056
Arg Ser Leu Ala Val Val Asp Tyr Ala Leu Arg Arg Arg Phe Ser Phe
            340                 345                 350 ata gat att gag cca ggt ttt gat aca cca cag ttc cgg aat ttt tta        1104
Ile Asp Ile Glu Pro Gly Phe Asp Thr Pro Gln Phe Arg Asn Phe Leu
        355                 360                 365
```

```
ctg aat aaa aaa gca gaa cct tca ttt gtt gag tct tta tgc caa aaa      1152
Leu Asn Lys Lys Ala Glu Pro Ser Phe Val Glu Ser Leu Cys Gln Lys
        370                 375                 380 atg aac gag ttg aac cag gaa atc agc aaa gag gcc act atc ctt ggg      1200
Met Asn Glu Leu Asn Gln Glu Ile Ser Lys Glu Ala Thr Ile Leu Gly
385                 390                 395                 400 aaa gga ttc cgc att ggg cat agt tac ttc tgc tgt ggg ttg gaa gat      1248
Lys Gly Phe Arg Ile Gly His Ser Tyr Phe Cys Cys Gly Leu Glu Asp
                405                 410                 415 ggc acc tct ccg gat acg caa tgg ctt aat gaa att gtg atg acg gat      1296
Gly Thr Ser Pro Asp Thr Gln Trp Leu Asn Glu Ile Val Met Thr Asp
            420                 425                 430 atc gcc cct tta ctc gaa gaa tat ttc ttt gat gac ccc tat aaa caa      1344
Ile Ala Pro Leu Leu Glu Glu Tyr Phe Phe Asp Asp Pro Tyr Lys Gln
        435                 440                 445 cag aaa tgg acc aac aaa tta tta ggg gac tca tag                      1380
Gln Lys Trp Thr Asn Lys Leu Leu Gly Asp Ser
    450                 455

<210> SEQ ID NO 40
<211> LENGTH: 459
<212> TYPE: PRT
<213> ORGANISM: Escherichia coli

<400> SEQUENCE: 40

Met Glu Ser Ile Gln Pro Trp Ile Glu Lys Phe Ile Lys Gln Ala Gln
1               5                   10                  15

Gln Gln Arg Ser Gln Ser Thr Lys Asp Tyr Pro Thr Ser Tyr Arg Asn
            20                  25                  30

Leu Arg Val Lys Leu Ser Phe Gly Tyr Gly Asn Phe Thr Ser Ile Pro
        35                  40                  45

Trp Phe Ala Phe Leu Gly Glu Gly Gln Glu Ala Ser Asn Gly Ile Tyr
    50                  55                  60

Pro Val Ile Leu Tyr Tyr Lys Asp Phe Asp Glu Leu Val Leu Ala Tyr
65                  70                  75                  80

Gly Ile Ser Asp Thr Asn Glu Pro His Ala Gln Trp Gln Phe Ser Ser
                85                  90                  95

Asp Ile Pro Lys Thr Ile Ala Glu Tyr Phe Gln Ala Thr Ser Gly Val
            100                 105                 110

Tyr Pro Lys Lys Tyr Gly Gln Ser Tyr Tyr Ala Cys Ser Gln Lys Val
        115                 120                 125

Ser Gln Gly Ile Asp Tyr Thr Arg Phe Ala Ser Met Leu Asp Asn Ile
    130                 135                 140

Ile Asn Asp Tyr Lys Leu Ile Phe Asn Ser Gly Lys Ser Val Ile Pro
145                 150                 155                 160

Pro Met Ser Lys Thr Glu Ser Tyr Cys Leu Glu Asp Ala Leu Asn Asp
                165                 170                 175

Leu Phe Ile Pro Glu Thr Thr Ile Glu Thr Ile Leu Lys Arg Leu Thr
            180                 185                 190

Ile Lys Lys Asn Ile Ile Leu Gln Gly Pro Pro Gly Val Gly Lys Thr
        195                 200                 205

Phe Val Ala Arg Arg Leu Ala Tyr Leu Leu Thr Gly Glu Lys Ala Pro
    210                 215                 220

Gln Arg Val Asn Met Val Gln Phe His Gln Ser Tyr Ser Tyr Glu Asp
225                 230                 235                 240

Phe Ile Gln Gly Tyr Arg Pro Asn Gly Val Gly Phe Arg Arg Lys Asp
                245                 250                 255
```

```
Gly Ile Phe Tyr Asn Phe Cys Gln Gln Ala Lys Glu Gln Pro Glu Lys
            260                 265                 270

Lys Tyr Ile Phe Ile Ile Asp Glu Ile Asn Arg Ala Asn Leu Ser Lys
        275                 280                 285

Val Phe Gly Glu Val Met Met Leu Met Glu His Asp Lys Arg Gly Glu
    290                 295                 300

Asn Trp Ser Val Pro Leu Thr Tyr Ser Glu Asn Asp Glu Arg Phe
305                 310                 315                 320

Tyr Val Pro Glu Asn Val Tyr Ile Ile Gly Leu Met Asn Thr Ala Asp
                325                 330                 335

Arg Ser Leu Ala Val Val Asp Tyr Ala Leu Arg Arg Phe Ser Phe
            340                 345                 350

Ile Asp Ile Glu Pro Gly Phe Asp Thr Pro Gln Phe Arg Asn Phe Leu
            355                 360                 365

Leu Asn Lys Lys Ala Glu Pro Ser Phe Val Glu Ser Leu Cys Gln Lys
    370                 375                 380

Met Asn Glu Leu Asn Gln Glu Ile Ser Lys Glu Ala Thr Ile Leu Gly
385                 390                 395                 400

Lys Gly Phe Arg Ile Gly His Ser Tyr Phe Cys Cys Gly Leu Glu Asp
                405                 410                 415

Gly Thr Ser Pro Asp Thr Gln Trp Leu Asn Glu Ile Val Met Thr Asp
            420                 425                 430

Ile Ala Pro Leu Leu Glu Glu Tyr Phe Phe Asp Asp Pro Tyr Lys Gln
            435                 440                 445

Gln Lys Trp Thr Asn Lys Leu Leu Gly Asp Ser
    450                 455

<210> SEQ ID NO 41
<211> LENGTH: 1047
<212> TYPE: DNA
<213> ORGANISM: Escherichia coli
<220> FEATURE:
<221> NAME/KEY: CDS
<222> LOCATION: (1)..(1047)

<400> SEQUENCE: 41 gtg gaa cag ccc gtg ata cct gtc cgt aat atc tat tac atg ctt acc      48
Val Glu Gln Pro Val Ile Pro Val Arg Asn Ile Tyr Tyr Met Leu Thr
1               5                   10                  15 tat gca tgg ggt tat tta cag gaa att aag cag gca aac ctt gaa gcc      96
Tyr Ala Trp Gly Tyr Leu Gln Glu Ile Lys Gln Ala Asn Leu Glu Ala
            20                  25                  30 ata ccc ggt aac aat ctt ctt gat atc ctg ggg tat gta tta aat aaa     144
Ile Pro Gly Asn Asn Leu Leu Asp Ile Leu Gly Tyr Val Leu Asn Lys
        35                  40                  45 ggg gtt tta cag ctt tca cgc cga ggg ctt gag ctt gat tac aat cct     192
Gly Val Leu Gln Leu Ser Arg Arg Gly Leu Glu Leu Asp Tyr Asn Pro
    50                  55                  60 aac acc gag atc att cct ggc atc aaa ggg cga ata gag ttt gct aaa     240
Asn Thr Glu Ile Ile Pro Gly Ile Lys Gly Arg Ile Glu Phe Ala Lys
65                  70                  75                  80 aca ata cgc ggc ttc cat ctt aat cat ggg aaa acc gtc agt act ttt     288
Thr Ile Arg Gly Phe His Leu Asn His Gly Lys Thr Val Ser Thr Phe
                85                  90                  95 gat atg ctt aat gaa gac acg ctg gct aac cga att ata aaa agc aca     336
Asp Met Leu Asn Glu Asp Thr Leu Ala Asn Arg Ile Ile Lys Ser Thr
            100                 105                 110
```

| | | |
|---|---|---|
| tta gcc ata tta att aag cat gaa aag tta aat tca act atc aga gat<br>Leu Ala Ile Leu Ile Lys His Glu Lys Leu Asn Ser Thr Ile Arg Asp<br>115                    120                    125 | | 384 |
| gaa gct cgt tca ctt tat aga aaa tta ccg ggc att agc act ctt cat<br>Glu Ala Arg Ser Leu Tyr Arg Lys Leu Pro Gly Ile Ser Thr Leu His<br>130                    135                    140 | | 432 |
| tta act ccg cag cat ttc agc tat ctg aat ggc gga aaa aat acg cgt<br>Leu Thr Pro Gln His Phe Ser Tyr Leu Asn Gly Gly Lys Asn Thr Arg<br>145                    150                    155                    160 | | 480 |
| tat tat aaa ttc gtt atc agt gtc tgc aaa ttc atc gtc aat aat tct<br>Tyr Tyr Lys Phe Val Ile Ser Val Cys Lys Phe Ile Val Asn Asn Ser<br>                  165                    170                    175 | | 528 |
| att cca ggt caa aac aaa gga cac tac cgt ttc tat gat ttt gaa aga<br>Ile Pro Gly Gln Asn Lys Gly His Tyr Arg Phe Tyr Asp Phe Glu Arg<br>                  180                    185                    190 | | 576 |
| aac gaa aaa gag atg tca tta ctt tat caa aag ttt ctt tat gaa ttt<br>Asn Glu Lys Glu Met Ser Leu Leu Tyr Gln Lys Phe Leu Tyr Glu Phe<br>              195                    200                    205 | | 624 |
| tgc cgt cgt gaa tta acg tct gca aac aca acc cgc tct tat tta aaa<br>Cys Arg Arg Glu Leu Thr Ser Ala Asn Thr Thr Arg Ser Tyr Leu Lys<br>210                    215                    220 | | 672 |
| tgg gat gca tcg agt ata tcg gat cag tca ctt aat ttg tta cct cga<br>Trp Asp Ala Ser Ser Ile Ser Asp Gln Ser Leu Asn Leu Leu Pro Arg<br>225                    230                    235                    240 | | 720 |
| atg gaa act gac atc acc att cgc tca tca gaa aaa ata ctt atc gtt<br>Met Glu Thr Asp Ile Thr Ile Arg Ser Ser Glu Lys Ile Leu Ile Val<br>                        245                    250                    255 | | 768 |
| gac gcc aaa tac tat aag agc att ttt tca cga cga atg gga aca gaa<br>Asp Ala Lys Tyr Tyr Lys Ser Ile Phe Ser Arg Arg Met Gly Thr Glu<br>                  260                    265                    270 | | 816 |
| aaa ttt cat tcg caa aat ctt tat caa ctg atg aat tac tta tgg tcg<br>Lys Phe His Ser Gln Asn Leu Tyr Gln Leu Met Asn Tyr Leu Trp Ser<br>              275                    280                    285 | | 864 |
| tta aag cct gaa aat ggc gaa aac ata ggg ggg tta tta ata tat ccc<br>Leu Lys Pro Glu Asn Gly Glu Asn Ile Gly Gly Leu Leu Ile Tyr Pro<br>290                    295                    300 | | 912 |
| cac gta gat acc gca gtg aaa cat cgt tat aaa att aat ggc ttc gat<br>His Val Asp Thr Ala Val Lys His Arg Tyr Lys Ile Asn Gly Phe Asp<br>305                    310                    315                    320 | | 960 |
| att ggc ttg tgt acc gtc aat tta ggt cag gaa tgg ccg tgt ata cat<br>Ile Gly Leu Cys Thr Val Asn Leu Gly Gln Glu Trp Pro Cys Ile His<br>                  325                    330                    335 | | 1008 |
| caa gaa tta ctc gac att ttc gat gaa tat ctc aaa taa<br>Gln Glu Leu Leu Asp Ile Phe Asp Glu Tyr Leu Lys<br>              340                    345 | | 1047 |

<210> SEQ ID NO 42
<211> LENGTH: 348
<212> TYPE: PRT
<213> ORGANISM: Escherichia coli

<400> SEQUENCE: 42

Val Glu Gln Pro Val Ile Pro Val Arg Asn Ile Tyr Tyr Met Leu Thr
1                  5                        10                    15

Tyr Ala Trp Gly Tyr Leu Gln Glu Ile Lys Gln Ala Asn Leu Glu Ala
                  20                    25                    30

Ile Pro Gly Asn Asn Leu Leu Asp Ile Leu Gly Tyr Val Leu Asn Lys
                35                    40                    45

Gly Val Leu Gln Leu Ser Arg Arg Gly Leu Glu Leu Asp Tyr Asn Pro
50                    55                    60

```
Asn Thr Glu Ile Ile Pro Gly Ile Lys Gly Arg Ile Glu Phe Ala Lys
 65                  70                  75                  80

Thr Ile Arg Gly Phe His Leu Asn His Gly Lys Val Ser Thr Phe
             85                  90                  95

Asp Met Leu Asn Glu Asp Thr Leu Ala Asn Arg Ile Ile Lys Ser Thr
                100                 105                 110

Leu Ala Ile Leu Ile Lys His Glu Lys Leu Asn Ser Thr Ile Arg Asp
                115                 120                 125

Glu Ala Arg Ser Leu Tyr Arg Lys Leu Pro Gly Ile Ser Thr Leu His
            130                 135                 140

Leu Thr Pro Gln His Phe Ser Tyr Leu Asn Gly Gly Lys Asn Thr Arg
145                 150                 155                 160

Tyr Tyr Lys Phe Val Ile Ser Val Cys Lys Phe Ile Val Asn Asn Ser
                165                 170                 175

Ile Pro Gly Gln Asn Lys Gly His Tyr Arg Phe Tyr Asp Phe Glu Arg
            180                 185                 190

Asn Glu Lys Glu Met Ser Leu Leu Tyr Gln Lys Phe Leu Tyr Glu Phe
        195                 200                 205

Cys Arg Arg Glu Leu Thr Ser Ala Asn Thr Thr Arg Ser Tyr Leu Lys
    210                 215                 220

Trp Asp Ala Ser Ser Ile Ser Asp Gln Ser Leu Asn Leu Leu Pro Arg
225                 230                 235                 240

Met Glu Thr Asp Ile Thr Ile Arg Ser Ser Glu Lys Ile Leu Ile Val
                245                 250                 255

Asp Ala Lys Tyr Tyr Lys Ser Ile Phe Ser Arg Arg Met Gly Thr Glu
                260                 265                 270

Lys Phe His Ser Gln Asn Leu Tyr Gln Leu Met Asn Tyr Leu Trp Ser
            275                 280                 285

Leu Lys Pro Glu Asn Gly Glu Asn Ile Gly Gly Leu Leu Ile Tyr Pro
        290                 295                 300

His Val Asp Thr Ala Val Lys His Arg Tyr Lys Ile Asn Gly Phe Asp
305                 310                 315                 320

Ile Gly Leu Cys Thr Val Asn Leu Gly Gln Glu Trp Pro Cys Ile His
                325                 330                 335

Gln Glu Leu Leu Asp Ile Phe Asp Glu Tyr Leu Lys
            340                 345

<210> SEQ ID NO 43
<211> LENGTH: 511
<212> TYPE: PRT
<213> ORGANISM: Geobacillus stearothermophilus

<400> SEQUENCE: 43

Met Ser Lys Lys Pro Val Ala Leu Ile Ile Leu Asp Gly Phe Ala Leu
  1               5                  10                  15

Arg Asp Glu Thr Tyr Gly Asn Ala Val Ala Gln Ala Asn Lys Pro Asn
             20                  25                  30

Phe Asp Arg Tyr Trp Asn Glu Tyr Pro His Thr Thr Leu Lys Ala Cys
         35                  40                  45

Gly Glu Ala Val Gly Leu Pro Glu Gly Gln Met Gly Asn Ser Glu Val
     50                  55                  60

Gly His Leu Asn Ile Gly Ala Gly Arg Ile Val Tyr Gln Ser Leu Thr
 65                  70                  75                  80

Arg Ile Asn Ile Ala Ile Arg Glu Gly Glu Phe Asp Arg Asn Glu Thr
```

```
              85                  90                  95
Phe Leu Ala Ala Met Asn His Val Lys Gln His Gly Thr Ser Leu His
            100                 105                 110
Leu Phe Gly Leu Leu Ser Asp Gly Gly Val His Ser His Ile His His
            115                 120                 125
Leu Tyr Ala Leu Leu Arg Leu Ala Lys Glu Gly Val Lys Arg Val
            130                 135                 140
Tyr Ile His Gly Phe Leu Asp Gly Arg Asp Val Gly Pro Gln Thr Ala
145                 150                 155                 160
Pro Gln Tyr Ile Lys Glu Leu Gln Glu Lys Ile Lys Glu Tyr Gly Val
                165                 170                 175
Gly Glu Ile Ala Thr Leu Ser Gly Arg Tyr Tyr Ser Met Asp Arg Asp
            180                 185                 190
Lys Arg Trp Asp Arg Val Glu Lys Ala Tyr Arg Ala Met Val Tyr Gly
            195                 200                 205
Glu Gly Pro Thr Tyr Arg Asp Pro Leu Glu Cys Ile Glu Asp Ser Tyr
            210                 215                 220
Lys His Gly Ile Tyr Asp Glu Phe Val Leu Pro Ser Val Ile Val Arg
225                 230                 235                 240
Glu Asp Gly Arg Pro Val Ala Thr Ile Gln Asp Asn Asp Ala Ile Ile
                245                 250                 255
Phe Tyr Asn Phe Arg Pro Asp Arg Ala Ile Gln Ile Ser Asn Thr Phe
            260                 265                 270
Thr Asn Glu Asp Phe Arg Glu Phe Asp Arg Gly Pro Lys His Pro Lys
            275                 280                 285
His Leu Phe Phe Val Cys Leu Thr His Phe Ser Glu Thr Val Lys Gly
            290                 295                 300
Tyr Val Ala Phe Lys Pro Thr Asn Leu Asp Asn Thr Ile Gly Glu Val
305                 310                 315                 320
Leu Ser Gln His Gly Leu Arg Gln Leu Arg Ile Ala Glu Thr Glu Lys
                325                 330                 335
Tyr Pro His Val Thr Phe Phe Met Ser Gly Gly Arg Glu Glu Lys Phe
            340                 345                 350
Pro Gly Glu Asp Arg Ile Leu Ile Asn Ser Pro Lys Val Pro Thr Tyr
            355                 360                 365
Asp Leu Lys Pro Glu Met Ser Ala Tyr Glu Val Thr Asp Ala Leu Leu
            370                 375                 380
Lys Glu Ile Glu Ala Asp Lys Tyr Asp Ala Ile Ile Leu Asn Tyr Ala
385                 390                 395                 400
Asn Pro Asp Met Val Gly His Ser Gly Lys Leu Glu Pro Thr Ile Lys
                405                 410                 415
Ala Val Glu Ala Val Asp Glu Cys Leu Gly Lys Val Val Asp Ala Ile
            420                 425                 430
Leu Ala Lys Gly Gly Ile Ala Ile Ile Thr Ala Asp His Gly Asn Ala
            435                 440                 445
Asp Glu Val Leu Thr Pro Asp Gly Lys Pro Gln Thr Ala His Thr Thr
            450                 455                 460
Asn Pro Val Pro Val Ile Val Thr Lys Lys Gly Ile Lys Leu Arg Asp
465                 470                 475                 480
Gly Gly Ile Leu Gly Asp Leu Ala Pro Thr Met Leu Asp Leu Leu Gly
                485                 490                 495
Leu Pro Gln Pro Lys Glu Met Thr Gly Lys Ser Leu Ile Val Lys
            500                 505                 510
```

<210> SEQ ID NO 44
<211> LENGTH: 437
<212> TYPE: PRT
<213> ORGANISM: Escherichia coli

<400> SEQUENCE: 44

```
Met Ser Lys Ile Val Lys Ile Ile Gly Arg Glu Ile Ile Asp Ser Arg
1               5                   10                  15
Gly Asn Pro Thr Val Glu Ala Glu Val His Leu Glu Gly Gly Phe Val
            20                  25                  30
Gly Met Ala Ala Ala Pro Ser Gly Ala Ser Thr Gly Ser Arg Glu Ala
        35                  40                  45
Leu Glu Leu Arg Asp Gly Asp Lys Ser Arg Phe Leu Gly Lys Gly Val
    50                  55                  60
Thr Lys Ala Val Ala Ala Val Asn Gly Pro Ile Ala Gln Ala Leu Ile
65                  70                  75                  80
Gly Lys Asp Ala Lys Asp Gln Ala Gly Ile Asp Lys Ile Met Ile Asp
                85                  90                  95
Leu Asp Gly Thr Glu Lys Lys Ser Lys Phe Gly Ala Asn Ala Ile Leu
            100                 105                 110
Ala Val Ser Leu Ala Asn Ala Lys Ala Ala Ala Ala Lys Gly Met
        115                 120                 125
Pro Leu Tyr Glu His Ile Ala Glu Leu Asn Gly Thr Pro Gly Lys Tyr
    130                 135                 140
Ser Met Pro Val Pro Met Met Asn Ile Ile Asn Gly Gly Glu His Ala
145                 150                 155                 160
Asp Asn Asn Val Asp Ile Gln Glu Phe Met Ile Gln Pro Val Gly Ala
                165                 170                 175
Lys Thr Val Lys Glu Ala Ile Arg Met Gly Ser Glu Val Phe His His
            180                 185                 190
Leu Ala Lys Val Leu Lys Ala Lys Gly Met Asn Thr Ala Val Gly Asp
        195                 200                 205
Glu Gly Gly Tyr Ala Pro Asn Leu Gly Ser Asn Asp Glu Ala Leu Ala
    210                 215                 220
Val Ile Ala Glu Ala Val Lys Ala Ala Gly Tyr Glu Leu Gly Lys Asp
225                 230                 235                 240
Ile Thr Leu Ala Met Asp Cys Ala Ala Ser Glu Phe Tyr Lys Asp Gly
                245                 250                 255
Lys Tyr Val Leu Ala Gly Glu Gly Asn Lys Ala Phe Thr Ser Glu Glu
            260                 265                 270
Phe Thr His Phe Leu Glu Glu Leu Thr Lys Gln Tyr Pro Ile Val Ser
        275                 280                 285
Ile Glu Asp Gly Leu Asp Glu Ser Asp Trp Asp Gly Phe Ala Tyr Gln
    290                 295                 300
Thr Lys Val Leu Gly Asp Lys Ile Gln Leu Val Gly Asp Asp Leu Phe
305                 310                 315                 320
Val Thr Asn Thr Lys Ile Leu Lys Glu Gly Ile Glu Lys Gly Ile Ala
                325                 330                 335
Asn Ser Tyr Leu Ile Lys Phe Asn Gln Ile Gly Ser Leu Thr Glu Thr
            340                 345                 350
Leu Ala Ala Ile Lys Met Ala Lys Asp Ala Gly Tyr Thr Ala Val Ile
        355                 360                 365
Ser His Arg Ser Gly Glu Thr Glu Asp Ala Thr Ile Ala Asp Leu Ala
```

```
                370                 375                 380
Val Gly Thr Ala Ala Gly Gln Ile Lys Thr Gly Ser Met Ser Arg Ser
385                 390                 395                 400

Asp Arg Val Ala Lys Tyr Asn Gln Leu Ile Arg Ile Glu Glu Ala Leu
            405                 410                 415

Gly Glu Lys Ala Arg Thr Thr Val Val Lys Arg Ser Lys Ala Arg His
            420                 425                 430

Lys Thr Asp Phe Ile
            435

<210> SEQ ID NO 45
<211> LENGTH: 587
<212> TYPE: PRT
<213> ORGANISM: Geobacillus stearothermophilus

<400> SEQUENCE: 45

Met Lys Arg Lys Thr Lys Ile Val Cys Thr Ile Gly Pro Ala Ser Glu
1               5                   10                  15

Ser Val Asp Lys Leu Val Gln Leu Met Glu Ala Gly Met Asn Val Ala
                20                  25                  30

Arg Leu Asn Phe Ser His Gly Asp His Glu Glu His Gly Arg Arg Ile
            35                  40                  45

Ala Asn Ile Arg Glu Ala Ala Lys Arg Thr Gly Arg Thr Val Ala Ile
50                  55                  60

Leu Leu Asp Thr Lys Gly Pro Glu Ile Arg Thr His Asn Met Glu Asn
65                  70                  75                  80

Gly Ala Ile Glu Leu Lys Glu Gly Ser Lys Leu Val Ile Ser Met Ser
                85                  90                  95

Glu Val Leu Gly Thr Pro Glu Lys Ile Ser Val Thr Tyr Pro Ser Leu
            100                 105                 110

Ile Asp Asp Val Ser Val Gly Ala Lys Ile Leu Leu Asp Asp Gly Leu
        115                 120                 125

Ile Ser Leu Glu Val Asn Ala Val Asp Lys Gln Ala Gly Glu Ile Val
    130                 135                 140

Thr Thr Val Leu Asn Gly Gly Val Leu Lys Asn Lys Lys Gly Val Asn
145                 150                 155                 160

Val Pro Gly Val Lys Val Asn Leu Pro Gly Ile Thr Glu Lys Asp Arg
                165                 170                 175

Ala Asp Ile Leu Phe Gly Ile Arg Gln Gly Ile Asp Phe Ile Ala Ala
            180                 185                 190

Ser Phe Val Arg Arg Ala Ser Asp Val Leu Glu Ile Arg Glu Leu Leu
        195                 200                 205

Glu Ala His Asp Ala Leu His Ile Gln Ile Ile Ala Lys Ile Glu Asn
    210                 215                 220

Glu Glu Gly Val Ala Asn Ile Asp Glu Ile Leu Glu Ala Ala Asp Gly
225                 230                 235                 240

Leu Met Val Ala Arg Gly Asp Leu Gly Val Glu Ile Pro Ala Glu Glu
                245                 250                 255

Val Pro Leu Ile Gln Lys Leu Leu Ile Lys Lys Cys Asn Met Leu Gly
            260                 265                 270

Lys Pro Val Ile Thr Ala Thr Gln Met Leu Asp Ser Met Gln Arg Asn
        275                 280                 285

Pro Arg Pro Thr Arg Ala Glu Ala Ser Asp Val Ala Asn Ala Ile Phe
    290                 295                 300
```

```
Asp Gly Thr Asp Ala Val Met Leu Ser Gly Glu Thr Ala Ala Gly Gln
305                 310                 315                 320

Tyr Pro Val Glu Ala Val Lys Thr Met His Gln Ile Ala Leu Arg Thr
                325                 330                 335

Glu Gln Ala Leu Glu His Arg Asp Ile Leu Ser Gln Arg Thr Lys Glu
                340                 345                 350

Ser Gln Thr Thr Ile Thr Asp Ala Ile Gly Gln Ser Val Ala His Thr
                355                 360                 365

Ala Leu Asn Leu Asp Val Ala Ala Ile Val Thr Pro Thr Val Ser Gly
                370                 375                 380

Lys Thr Pro Gln Met Val Ala Lys Tyr Arg Pro Lys Ala Pro Ile Ile
385                 390                 395                 400

Ala Val Thr Ser Asn Glu Ala Val Ser Arg Arg Leu Ala Leu Val Trp
                405                 410                 415

Gly Val Tyr Thr Lys Glu Ala Pro His Val Asn Thr Thr Asp Glu Met
                420                 425                 430

Leu Asp Val Ala Val Asp Ala Ala Val Arg Ser Gly Leu Val Lys His
                435                 440                 445

Gly Asp Leu Val Val Ile Thr Ala Gly Val Pro Val Gly Glu Thr Gly
450                 455                 460

Ser Thr Asn Leu Met Lys Val His Val Ile Ser Asp Leu Leu Ala Lys
465                 470                 475                 480

Gly Gln Gly Ile Gly Arg Lys Ser Ala Phe Gly Lys Ala Val Val Ala
                485                 490                 495

Lys Thr Ala Glu Glu Ala Arg Gln Lys Met Val Asp Gly Gly Ile Leu
                500                 505                 510

Val Thr Val Ser Thr Asp Ala Asp Met Met Pro Ala Ile Glu Lys Ala
                515                 520                 525

Ala Ala Ile Ile Thr Glu Gly Gly Leu Thr Ser His Ala Ala Val
                530                 535                 540

Val Gly Leu Ser Leu Gly Ile Pro Val Ile Val Gly Val Glu Asn Ala
545                 550                 555                 560

Thr Thr Leu Phe Lys Asp Gly Gln Glu Ile Thr Val Asp Gly Gly Phe
                565                 570                 575

Gly Ala Val Tyr Arg Gly His Ala Ser Val Leu
                580                 585

<210> SEQ ID NO 46
<211> LENGTH: 475
<212> TYPE: PRT
<213> ORGANISM: Zymomonas mobilis

<400> SEQUENCE: 46

Met Thr Glu Gly Leu Phe Pro Arg Gly Arg Lys Val Arg Val Val Ser
1               5                   10                  15

Thr Leu Gly Pro Ala Ser Ser Thr Ala Glu Gln Ile Arg Asp Arg Phe
                20                  25                  30

Leu Ala Gly Ala Asp Val Phe Arg Ile Asn Met Ser His Gly Thr His
                35                  40                  45

Asp Glu Lys Lys Val Ile Val Asp Asn Ile Arg Ala Leu Glu Lys Glu
                50                  55                  60

Phe Asn Arg Pro Thr Thr Ile Leu Phe Asp Leu Gln Gly Pro Lys Leu
65                  70                  75                  80

Arg Val Gly Asp Phe Lys Glu Gly Lys Val Gln Leu Lys Glu Gly Gln
                85                  90                  95
```

Thr Phe Thr Phe Asp Gln Asp Pro Thr Leu Gly Asp Glu Thr Arg Val
            100                 105                 110

Asn Leu Pro His Pro Glu Ile Phe Lys Ala Leu Asp Lys Gly His Arg
            115                 120                 125

Leu Leu Leu Asp Asp Gly Lys Ile Val Val Arg Cys Val Glu Ser Ser
            130                 135                 140

Pro Thr Lys Ile Val Thr Arg Val Glu Val Pro Gly Pro Leu Ser Asp
145                 150                 155                 160

His Lys Gly Phe Asn Val Pro Asp Val Ile Pro Leu Ala Ala Leu
            165                 170                 175

Thr Pro Lys Asp Arg Lys Asp Leu Asp Phe Ala Leu Lys Glu Lys Ala
            180                 185                 190

Asp Trp Val Ala Leu Ser Phe Val Gln Arg Val Glu Asp Val Ile Glu
            195                 200                 205

Ala Lys Glu Leu Ile Lys Gly Arg Ala Pro Leu Leu Val Lys Leu Glu
            210                 215                 220

Lys Pro Ala Ala Ile Glu Asn Leu Glu Ser Ile Leu Ala Ala Thr Asp
225                 230                 235                 240

Ala Val Met Val Ala Arg Gly Asp Leu Gly Val Glu Cys Leu Pro Glu
            245                 250                 255

Ser Val Pro Pro Thr Gln Lys Arg Ile Val Glu Arg Ser Arg Gln Leu
            260                 265                 270

Gly Lys Pro Val Val Val Ala Thr Ala Met Leu Glu Ser Met Ile Lys
            275                 280                 285

Ala Pro Ala Pro Thr Arg Ala Glu Val Ser Asp Val Ala Asn Ala Ile
            290                 295                 300

Tyr Glu Gly Ala Asp Gly Ile Met Leu Ser Ala Glu Ser Ala Ala Gly
305                 310                 315                 320

Asp Trp Pro His Glu Ala Val Asn Met Met His Arg Ile Ala Ser Tyr
            325                 330                 335

Val Glu Asn Ala Pro Gly Tyr Ile Glu Arg Val Arg Phe Thr Pro Thr
            340                 345                 350

Pro Ala Glu Pro Thr Thr Val Asp Ala Leu Ala Glu Asn Ala Ser Lys
            355                 360                 365

Thr Ala Glu Thr Val Gly Ala Lys Ala Ile Ile Val Phe Thr Glu Thr
            370                 375                 380

Gly Lys Thr Ala Gln Arg Val Ser Arg Ala Arg Pro Val Ala Pro Ile
385                 390                 395                 400

Leu Ser Leu Thr Pro Asp Ala Glu Val Ala Arg Arg Leu Gly Leu Val
            405                 410                 415

Trp Gly Ala Gln Pro Val Gln Val Ser Thr Val Lys Thr Leu Asp Glu
            420                 425                 430

Ala Lys Lys Leu Ala Ala Glu Thr Ala Lys Lys Tyr Gly Phe Ala Lys
            435                 440                 445

Ala Gly Asp Lys Leu Val Val Val Ala Gly Glu Pro Phe Gly Lys Ala
            450                 455                 460

Gly Thr Thr Asn Ile Val Asp Val Ile Glu Ala
465                 470                 475

<210> SEQ ID NO 47
<211> LENGTH: 531
<212> TYPE: PRT
<213> ORGANISM: Oryctolagus cuniculus

<400> SEQUENCE: 47

```
Met Ser Lys Ser His Ser Glu Ala Gly Ser Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Ala Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Met Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Asp Val Gly Ser Lys Val Tyr Val
                165                 170                 175

Asp Asp Gly Leu Ile Ser Leu Gln Val Lys Gln Lys Gly Pro Asp Phe
            180                 185                 190

Leu Val Thr Glu Val Glu Asn Gly Gly Phe Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ala Asp Val His Glu Val Arg Lys
                245                 250                 255

Ile Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Ile Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Met Phe His Arg Lys Leu Phe Glu Glu Leu Ala Arg
385                 390                 395                 400

Ala Ser Ser His Ser Thr Asp Leu Met Glu Ala Met Ala Met Gly Ser
                405                 410                 415
```

-continued

```
Val Glu Ala Ser Tyr Lys Cys Leu Ala Ala Leu Ile Val Leu Thr
            420                 425                 430

Glu Ser Gly Arg Ser Ala His Gln Val Ala Arg Tyr Arg Pro Arg Ala
            435                 440                 445

Pro Ile Ile Ala Val Thr Arg Asn His Gln Thr Ala Arg Gln Ala His
            450                 455                 460

Leu Tyr Arg Gly Ile Phe Pro Val Val Cys Lys Asp Pro Val Gln Glu
465                 470                 475                 480

Ala Trp Ala Glu Asp Val Asp Leu Arg Val Asn Leu Ala Met Asn Val
                485                 490                 495

Gly Lys Ala Arg Gly Phe Phe Lys Lys Gly Asp Val Val Ile Val Leu
                500                 505                 510

Thr Gly Trp Arg Pro Gly Ser Gly Phe Thr Asn Thr Met Arg Val Val
                515                 520                 525

Pro Val Pro
        530

<210> SEQ ID NO 48
<211> LENGTH: 568
<212> TYPE: PRT
<213> ORGANISM: Zymomonas mobilis

<400> SEQUENCE: 48

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Ala Asp Ala Leu Gly Gly Ala Val
225                 230                 235                 240

Ala Thr Met Ala Ala Ala Lys Ser Phe Phe Pro Glu Glu Asn Pro His
```

```
            245                 250                 255
Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565

<210> SEQ ID NO 49
<211> LENGTH: 464
<212> TYPE: PRT
<213> ORGANISM: Salmonella enterica

<400> SEQUENCE: 49

Met Asn Thr Ser Glu Leu Glu Thr Leu Ile Arg Thr Ile Leu Ser Glu
1               5                   10                  15

Gln Leu Thr Thr Pro Ala Gln Thr Pro Val Gln Pro Gly Lys Gly
            20                  25                  30

Ile Phe Gln Ser Val Ser Glu Ala Ile Asp Ala Ala His Gln Ala Phe
        35                  40                  45
```

```
Leu Arg Tyr Gln Gln Cys Pro Leu Lys Thr Arg Ser Ala Ile Ile Ser
    50              55                  60

Ala Met Arg Gln Glu Leu Thr Pro Leu Leu Ala Pro Leu Ala Glu Glu
65              70                  75                  80

Ser Ala Asn Glu Thr Gly Met Gly Asn Lys Glu Asp Lys Phe Leu Lys
                85                  90                  95

Asn Lys Ala Ala Leu Asp Asn Thr Pro Gly Val Glu Asp Leu Thr Thr
            100                 105                 110

Thr Ala Leu Thr Gly Asp Gly Met Val Leu Phe Glu Tyr Ser Pro
        115                 120                 125

Phe Gly Val Ile Gly Ser Val Ala Pro Ser Thr Asn Pro Thr Glu Thr
    130                 135                 140

Ile Ile Asn Asn Ser Ile Ser Met Leu Ala Ala Gly Asn Ser Ile Tyr
145                 150                 155                 160

Phe Ser Pro His Pro Gly Ala Lys Lys Val Ser Leu Lys Leu Ile Ser
                165                 170                 175

Leu Ile Glu Glu Ile Ala Phe Arg Cys Cys Gly Ile Arg Asn Leu Val
            180                 185                 190

Val Thr Val Ala Glu Pro Thr Phe Glu Ala Thr Gln Gln Met Met Ala
        195                 200                 205

His Pro Arg Ile Ala Val Leu Ala Ile Thr Gly Gly Pro Gly Ile Val
    210                 215                 220

Ala Met Gly Met Lys Ser Gly Lys Lys Val Ile Gly Ala Gly Ala Gly
225                 230                 235                 240

Asn Pro Pro Cys Ile Val Asp Glu Thr Ala Asp Leu Val Lys Ala Ala
                245                 250                 255

Glu Asp Ile Ile Asn Gly Ala Ser Phe Asp Tyr Asn Leu Pro Cys Ile
            260                 265                 270

Ala Glu Lys Ser Leu Ile Val Val Glu Ser Val Ala Glu Arg Leu Val
        275                 280                 285

Gln Gln Met Gln Thr Phe Gly Ala Leu Leu Leu Ser Pro Ala Asp Thr
    290                 295                 300

Asp Lys Leu Arg Ala Val Cys Leu Pro Glu Gly Gln Ala Asn Lys Lys
305                 310                 315                 320

Leu Val Gly Lys Ser Pro Ser Ala Met Leu Glu Ala Ala Gly Ile Ala
                325                 330                 335

Val Pro Ala Lys Ala Pro Arg Leu Leu Ile Ala Leu Val Asn Ala Asp
            340                 345                 350

Asp Pro Trp Val Thr Ser Glu Gln Leu Met Pro Met Leu Pro Val Val
        355                 360                 365

Lys Val Ser Asp Phe Asp Ser Ala Leu Ala Leu Ala Leu Lys Val Glu
    370                 375                 380

Glu Gly Leu His His Thr Ala Ile Met His Ser Gln Asn Val Ser Arg
385                 390                 395                 400

Leu Asn Leu Ala Ala Arg Thr Leu Gln Thr Ser Ile Phe Val Lys Asn
                405                 410                 415

Gly Pro Ser Tyr Ala Gly Ile Gly Val Gly Gly Glu Gly Phe Thr Thr
            420                 425                 430

Phe Thr Ile Ala Thr Pro Thr Gly Glu Gly Thr Thr Ser Ala Arg Thr
        435                 440                 445

Phe Ala Arg Ser Arg Arg Cys Val Leu Thr Asn Gly Phe Ser Ile Arg
450                 455                 460
```

```
<210> SEQ ID NO 50
<211> LENGTH: 253
<212> TYPE: PRT
<213> ORGANISM: Geobacillus stearothermophilus

<400> SEQUENCE: 50

Met Arg Lys Pro Ile Ile Ala Gly Asn Trp Lys Met His Lys Thr Leu
1               5                   10                  15

Ala Glu Ala Val Gln Phe Val Glu Asp Val Lys Gly His Val Pro Pro
            20                  25                  30

Ala Asp Glu Val Ile Ser Val Val Cys Ala Pro Phe Leu Phe Leu Asp
        35                  40                  45

Arg Leu Val Gln Ala Ala Asp Gly Thr Asp Leu Lys Ile Gly Ala Gln
    50                  55                  60

Thr Met His Phe Ala Asp Gln Gly Ala Tyr Thr Gly Glu Val Ser Pro
65                  70                  75                  80

Val Met Leu Lys Asp Leu Gly Val Thr Tyr Val Ile Leu Gly His Ser
                85                  90                  95

Glu Arg Arg Gln Met Phe Ala Glu Thr Asp Glu Thr Val Asn Lys Lys
            100                 105                 110

Val Leu Ala Ala Phe Thr Arg Gly Leu Ile Pro Ile Ile Cys Cys Gly
        115                 120                 125

Glu Ser Leu Glu Glu Arg Glu Ala Gly Gln Thr Asn Ala Val Val Ala
    130                 135                 140

Ser Gln Val Glu Lys Ala Leu Ala Gly Leu Thr Pro Glu Gln Val Lys
145                 150                 155                 160

Gln Ala Val Ile Ala Tyr Glu Pro Ile Trp Ala Ile Gly Thr Gly Lys
                165                 170                 175

Ser Ser Thr Pro Glu Asp Ala Asn Ser Val Cys Gly His Ile Arg Ser
            180                 185                 190

Val Val Ser Arg Leu Phe Gly Pro Glu Ala Ala Glu Ala Ile Arg Ile
        195                 200                 205

Gln Tyr Gly Gly Ser Val Lys Pro Asp Asn Ile Arg Asp Phe Leu Ala
    210                 215                 220

Gln Gln Gln Ile Asp Gly Pro Leu Val Gly Gly Ala Ser Leu Glu Pro
225                 230                 235                 240

Ala Ser Phe Leu Gln Leu Val Glu Ala Gly Arg His Glu
                245                 250

<210> SEQ ID NO 51
<211> LENGTH: 287
<212> TYPE: PRT
<213> ORGANISM: Geobacillus stearothermophilus

<400> SEQUENCE: 51

Met Ser Leu Val Ser Met Lys Glu Met Leu Asn Glu Ala Leu Arg Gly
1               5                   10                  15

Lys Tyr Ala Val Gly Gln Phe Asn Ile Asn Asn Leu Glu Trp Thr Gln
            20                  25                  30

Ala Ile Leu Ala Ala Ala Glu Glu Lys Ser Pro Val Ile Leu Gly
        35                  40                  45

Val Ser Glu Gly Ala Ala Arg Tyr Met Gly Gly Phe Lys Thr Val Val
    50                  55                  60

Asn Met Val Lys Gly Leu Met Glu Asp Met Asn Ile Thr Val Pro Val
65                  70                  75                  80

Ala Ile His Leu Asp His Gly Ser Ser Phe Glu Lys Cys Lys Ala Ala
```

```
                    85                  90                  95
Ile Asp Ala Gly Phe Thr Ser Val Met Ile Asp Ala Ser His His Pro
            100                 105                 110

Phe Glu Glu Asn Val Arg Ile Thr Ser Gln Val Val Glu Tyr Ala His
            115                 120                 125

Ala Arg Gly Val Ser Val Glu Ala Glu Leu Gly Ile Val Gly Gly Gln
        130                 135                 140

Glu Asp Asp Val Val Gly Glu Gly Val Ile Tyr Ala Asp Pro Lys Glu
145                 150                 155                 160

Cys Glu Glu Leu Val Lys Arg Thr Gly Ile Asp Cys Leu Ala Pro Ala
                165                 170                 175

Leu Gly Ser Val His Gly Pro Tyr Lys Gly Glu Pro Lys Leu Gly Phe
            180                 185                 190

Ala Glu Met Glu Lys Ile Arg Asp Leu Thr Gly Ile Pro Leu Val Leu
            195                 200                 205

His Gly Gly Thr Gly Ile Pro Thr Glu Gln Ile Gln Arg Ala Ile Ser
        210                 215                 220

Leu Gly Thr Ser Lys Ile Asn Val Asn Thr Glu Asn Gln Ile Ala Phe
225                 230                 235                 240

Thr Lys Ala Val Arg Glu Leu Leu Ala Lys Asp Pro Asn Val Tyr Asp
                245                 250                 255

Pro Arg Lys Ile Ile Gly Pro Gly Arg Asp Ala Ile Lys Ala Thr Val
            260                 265                 270

Ile Gly Lys Met Arg Glu Phe Gly Ser Ser Gly Lys Ala Ala Gln
            275                 280                 285

<210> SEQ ID NO 52
<211> LENGTH: 309
<212> TYPE: PRT
<213> ORGANISM: Escherichia coli

<400> SEQUENCE: 52

Met Val Arg Ile Tyr Thr Leu Thr Leu Ala Pro Ser Leu Asp Ser Ala
1               5                   10                  15

Thr Ile Thr Pro Gln Ile Tyr Pro Glu Gly Lys Leu Arg Cys Thr Ala
            20                  25                  30

Pro Val Phe Glu Pro Gly Gly Gly Gly Ile Asn Val Ala Arg Ala Ile
        35                  40                  45

Ala His Leu Gly Gly Ser Ala Thr Ala Ile Phe Pro Ala Gly Gly Ala
    50                  55                  60

Thr Gly Glu His Leu Val Ser Leu Leu Ala Asp Glu Asn Val Pro Val
65                  70                  75                  80

Ala Thr Val Glu Ala Lys Asp Trp Thr Arg Gln Asn Leu His Val His
                85                  90                  95

Val Glu Ala Ser Gly Glu Gln Tyr Arg Phe Val Met Pro Gly Ala Ala
            100                 105                 110

Leu Asn Glu Asp Glu Phe Arg Gln Leu Glu Glu Gln Val Leu Glu Ile
            115                 120                 125

Glu Ser Gly Ala Ile Leu Val Ile Ser Gly Ser Leu Pro Pro Gly Val
        130                 135                 140

Lys Leu Glu Lys Leu Thr Gln Leu Ile Ser Ala Ala Gln Lys Gln Gly
145                 150                 155                 160

Ile Arg Cys Ile Val Asp Ser Ser Gly Glu Ala Leu Ser Ala Ala Leu
                165                 170                 175
```

```
Ala Ile Gly Asn Ile Glu Leu Val Lys Pro Asn Gln Lys Glu Leu Ser
            180                 185                 190

Ala Leu Val Asn Arg Glu Leu Thr Gln Pro Asp Asp Val Arg Lys Ala
            195                 200                 205

Ala Gln Glu Ile Val Asn Ser Gly Lys Ala Lys Arg Val Val Val Ser
            210                 215                 220

Leu Gly Pro Gln Gly Ala Leu Gly Val Asp Ser Glu Asn Cys Ile Gln
225                 230                 235                 240

Val Val Pro Pro Val Lys Ser Gln Ser Thr Val Gly Ala Gly Asp
            245                 250                 255

Ser Met Val Gly Ala Met Thr Leu Lys Leu Ala Glu Asn Ala Ser Leu
            260                 265                 270

Glu Glu Met Val Arg Phe Gly Val Ala Ala Gly Ser Ala Ala Thr Leu
            275                 280                 285

Asn Gln Gly Thr Arg Leu Cys Ser His Asp Asp Thr Gln Lys Ile Tyr
            290                 295                 300

Ala Tyr Leu Ser Arg
305

<210> SEQ ID NO 53
<211> LENGTH: 319
<212> TYPE: PRT
<213> ORGANISM: Geobacillus stearothermophilus

<400> SEQUENCE: 53

Met Lys Arg Ile Gly Val Leu Thr Ser Gly Gly Asp Ser Pro Gly Met
1               5                   10                  15

Asn Ala Ala Ile Arg Ser Val Val Arg Lys Ala Ile Tyr His Gly Val
            20                  25                  30

Glu Val Tyr Gly Val Tyr His Gly Tyr Ala Gly Leu Ile Ala Gly Asn
            35                  40                  45

Ile Lys Lys Leu Glu Val Gly Asp Val Gly Asp Ile Ile His Arg Gly
        50                  55                  60

Gly Thr Ile Leu Tyr Thr Ala Arg Cys Pro Glu Phe Lys Thr Glu Glu
65                  70                  75                  80

Gly Gln Lys Lys Gly Ile Glu Gln Leu Lys Lys His Gly Ile Glu Gly
            85                  90                  95

Leu Val Val Ile Gly Gly Asp Gly Ser Tyr Gln Gly Ala Lys Lys Leu
            100                 105                 110

Thr Glu His Gly Phe Pro Cys Val Gly Val Pro Gly Thr Ile Asp Asn
            115                 120                 125

Asp Ile Pro Gly Thr Asp Phe Thr Ile Gly Phe Asp Thr Ala Leu Asn
        130                 135                 140

Thr Val Ile Asp Ala Ile Asp Lys Ile Arg Asp Thr Ala Thr Ser His
145                 150                 155                 160

Glu Arg Thr Tyr Val Ile Glu Val Met Gly Arg His Ala Gly Asp Ile
            165                 170                 175

Ala Leu Trp Ser Gly Leu Ala Gly Gly Ala Glu Thr Ile Leu Ile Pro
            180                 185                 190

Glu Ala Asp Tyr Asp Met Asn Asp Val Ile Ala Arg Leu Lys Arg Gly
            195                 200                 205

His Glu Ala Gly Lys Lys His Ser Ile Ile Ile Val Ala Glu Gly Val
            210                 215                 220

Gly Ser Gly Val Asp Phe Gly Arg Gln Ile Gln Glu Ala Thr Gly Phe
225                 230                 235                 240
```

-continued

Glu Thr Arg Val Thr Val Leu Gly His Val Gln Arg Gly Gly Ser Pro
            245                 250                 255

Thr Ala Phe Asp Arg Val Leu Ala Ser Arg Leu Gly Ala Arg Ala Val
        260                 265                 270

Glu Leu Leu Leu Glu Gly Lys Gly Gly Arg Cys Val Gly Ile Gln Asn
            275                 280                 285

Asn Gln Leu Val Asp His Asp Ile Ala Glu Ala Leu Ala Asn Lys His
        290                 295                 300

Thr Ile Asp Gln Arg Met Tyr Ala Leu Ser Lys Glu Leu Ser Ile
305                 310                 315

<210> SEQ ID NO 54
<211> LENGTH: 742
<212> TYPE: PRT
<213> ORGANISM: Mycobacterium tuberculosis

<400> SEQUENCE: 54

Met Met Ser Asn Asp Arg Lys Val Thr Glu Ile Glu Asn Ser Pro Val
1               5                   10                  15

Thr Glu Val Arg Pro Glu Glu His Ala Trp Tyr Pro Asp Asp Ser Ala
            20                  25                  30

Leu Ala Ala Pro Pro Ala Ala Thr Pro Ala Ala Ile Ser Asp Gln Leu
        35                  40                  45

Pro Ser Asp Arg Tyr Leu Asn Arg Glu Leu Ser Trp Leu Asp Phe Asn
    50                  55                  60

Ala Arg Val Leu Ala Leu Ala Asp Lys Ser Met Pro Leu Leu Glu
65                  70                  75                  80

Arg Ala Lys Phe Leu Ala Ile Phe Ala Ser Asn Leu Asp Glu Phe Tyr
                85                  90                  95

Met Val Arg Val Ala Gly Leu Lys Arg Arg Asp Glu Met Gly Leu Ser
            100                 105                 110

Val Arg Ser Ala Asp Gly Leu Thr Pro Arg Glu Gln Leu Gly Arg Ile
        115                 120                 125

Gly Glu Gln Thr Gln Gln Leu Ala Ser Arg His Ala Arg Val Phe Leu
    130                 135                 140

Asp Ser Val Leu Pro Ala Leu Gly Glu Glu Gly Ile Tyr Ile Val Thr
145                 150                 155                 160

Trp Ala Asp Leu Asp Gln Ala Glu Arg Asp Arg Leu Ser Thr Tyr Phe
                165                 170                 175

Asn Glu Gln Val Phe Pro Val Leu Thr Pro Leu Ala Val Asp Pro Ala
            180                 185                 190

His Pro Phe Pro Phe Val Ser Gly Leu Ser Leu Asn Leu Ala Val Thr
        195                 200                 205

Val Arg Gln Pro Glu Asp Gly Thr Gln His Phe Ala Arg Val Lys Val
    210                 215                 220

Pro Asp Asn Val Asp Arg Phe Val Glu Leu Ala Ala Arg Glu Ala Ser
225                 230                 235                 240

Glu Glu Ala Ala Gly Thr Glu Gly Arg Thr Ala Leu Arg Phe Leu Pro
                245                 250                 255

Met Glu Glu Leu Ile Ala Ala Phe Leu Pro Val Leu Phe Pro Gly Met
            260                 265                 270

Glu Ile Val Glu His His Ala Phe Arg Ile Thr Arg Asn Ala Asp Phe
        275                 280                 285

Glu Val Glu Glu Asp Arg Asp Glu Asp Leu Leu Gln Ala Leu Glu Arg

```
            290                 295                 300
Glu Leu Ala Arg Arg Arg Phe Gly Ser Pro Val Arg Leu Glu Ile Ala
305                 310                 315                 320

Asp Asp Met Thr Glu Ser Met Leu Glu Leu Leu Arg Glu Leu Asp
            325                 330                 335

Val His Pro Gly Asp Val Ile Glu Val Pro Gly Leu Leu Asp Leu Ser
            340                 345                 350

Ser Leu Trp Gln Ile Tyr Ala Val Asp Arg Pro Thr Leu Lys Asp Arg
            355                 360                 365

Thr Phe Val Pro Ala Thr His Pro Ala Phe Ala Glu Arg Glu Thr Pro
            370                 375                 380

Lys Ser Ile Phe Ala Thr Leu Arg Glu Gly Asp Val Leu Val His His
385                 390                 395                 400

Pro Tyr Asp Ser Phe Ser Thr Ser Val Gln Arg Phe Ile Glu Gln Ala
            405                 410                 415

Ala Ala Asp Pro Asn Val Leu Ala Ile Lys Gln Thr Leu Tyr Arg Thr
            420                 425                 430

Ser Gly Asp Ser Pro Ile Val Arg Ala Leu Ile Asp Ala Ala Glu Ala
            435                 440                 445

Gly Lys Gln Val Val Ala Leu Val Glu Ile Lys Ala Arg Phe Asp Glu
            450                 455                 460

Gln Ala Asn Ile Ala Trp Ala Arg Ala Leu Glu Gln Ala Gly Val His
465                 470                 475                 480

Val Ala Tyr Gly Leu Val Gly Leu Lys Thr His Cys Lys Thr Ala Leu
            485                 490                 495

Val Val Arg Arg Glu Gly Pro Thr Ile Arg Arg Tyr Cys His Val Gly
            500                 505                 510

Thr Gly Asn Tyr Asn Ser Lys Thr Ala Arg Leu Tyr Glu Asp Val Gly
            515                 520                 525

Leu Leu Thr Ala Ala Pro Asp Ile Gly Ala Asp Leu Thr Asp Leu Phe
            530                 535                 540

Asn Ser Leu Thr Gly Tyr Ser Arg Lys Leu Ser Tyr Arg Asn Leu Leu
545                 550                 555                 560

Val Ala Pro His Gly Ile Arg Ala Gly Ile Ile Asp Arg Val Glu Arg
            565                 570                 575

Glu Val Ala Ala His Arg Ala Glu Gly Ala His Asn Gly Lys Gly Arg
            580                 585                 590

Ile Arg Leu Lys Met Asn Ala Leu Val Asp Glu Gln Val Ile Asp Ala
            595                 600                 605

Leu Tyr Arg Ala Ser Arg Ala Gly Val Arg Ile Glu Val Val Val Arg
            610                 615                 620

Gly Ile Cys Ala Leu Arg Pro Gly Ala Gln Gly Ile Ser Glu Asn Ile
625                 630                 635                 640

Ile Val Arg Ser Ile Leu Gly Arg Phe Leu Glu His Ser Arg Ile Leu
            645                 650                 655

His Phe Arg Ala Ile Asp Glu Phe Trp Ile Gly Ser Ala Asp Met Met
            660                 665                 670

His Arg Asn Leu Asp Arg Arg Val Glu Val Met Ala Gln Val Lys Asn
            675                 680                 685

Pro Arg Leu Thr Ala Gln Leu Asp Glu Leu Phe Glu Ser Ala Leu Asp
            690                 695                 700

Pro Cys Thr Arg Cys Trp Glu Leu Gly Pro Asp Gly Gln Trp Thr Ala
705                 710                 715                 720
```

-continued

Ser Pro Gln Glu Gly His Ser Val Arg Asp His Gln Glu Ser Leu Met
                725                 730                 735

Glu Arg His Arg Ser Pro
            740

<210> SEQ ID NO 55
<211> LENGTH: 801
<212> TYPE: PRT
<213> ORGANISM: Pseudomonas aeruginosa

<400> SEQUENCE: 55

Met Ser Gln Ile Leu Pro Ser Gln Asp Glu Leu Leu Ala His Ala Ala
1               5                   10                  15

Ala Glu Pro Ala Phe Ala Ala Trp Leu Gln Gly His Gly Pro Leu Gln
            20                  25                  30

His Ser Ala Glu Thr Arg Ala Val Phe Arg Thr Ala His Gln Leu
        35                  40                  45

Val Gln Ala Gly Leu Gln Pro Asp Leu Ala Ser Val Tyr Gln Leu Phe
    50                  55                  60

Arg Ala Leu Asp Arg Leu Thr Ala Ser Ala Leu Arg Ile Val Val His
65                  70                  75                  80

Met Thr Tyr Ala Arg Arg Ile Arg Leu Asp Gly Gln Pro Leu Gln Ala
                85                  90                  95

Glu Asp Phe Lys Thr Gln Pro Glu Gly His Thr Gly Gly Ala Leu Asn
            100                 105                 110

Met Val Pro Ala Tyr Ala Gly Tyr Leu Ala Leu Asn Val Leu Thr Gly
        115                 120                 125

Lys Thr Arg Ala Trp Leu Met Gly Gln Gly His Cys Val Ala Ala Ile
130                 135                 140

Asp Ala Leu Asn Val Leu Thr Gly Asn Leu His Pro Glu Gln Glu Arg
145                 150                 155                 160

Ala Tyr Ala Asp Gly Glu Glu Gly Leu Asn Arg Leu Leu Gln Asp Phe
                165                 170                 175

Tyr Gly Tyr Ala Gln Ala Pro Asn Gly Ala Pro Ala Ala Pro Leu Gly
            180                 185                 190

Ser His Val Asn Pro His Thr Ala Gly Gly Ile Ala Glu Gly Gly Tyr
        195                 200                 205

Leu Gly Phe Ala Glu Leu Gln Tyr Ala His Met Pro Leu Pro Gly Glu
210                 215                 220

Thr Leu Val Ala Phe Leu Ser Asp Gly Ala Ala Glu Glu Gln Arg Gly
225                 230                 235                 240

Ser Asp Trp Ile Pro Arg Trp Arg Ala Glu Asp Cys Gly Ala Ala
                245                 250                 255

Leu Pro Val Met Ile Ala Asn Gly Arg Arg Ile Glu Gln Arg Thr Glu
            260                 265                 270

Leu Gly Thr His Glu Gly Leu Glu Gly Phe Lys Leu His Leu Arg Arg
        275                 280                 285

Cys Gly Phe Asp Pro Ile Ser Phe Asp Gly Arg Asp Pro Ala Ala Phe
    290                 295                 300

Val Cys Thr Leu Trp Glu Met Glu Gln Arg Leu Glu Arg Val Gln
305                 310                 315                 320

Glu Lys Asn Ser Gly Ile Leu Arg Tyr Pro Leu Pro Ile Pro Tyr Gly
                325                 330                 335

Ile Ala Glu Thr Val Lys Gly Phe Gly Phe Tyr Gly Ala Gly Ser Asn

-continued

```
                340                 345                 350
Ala Ala His Asn Leu Pro Leu Pro Gly Asn Pro His Asn Asp Glu Gln
            355                 360                 365

Ala Arg Gln Leu Phe Asn Gln His Ala Asn Glu Leu Trp Val Glu Pro
    370                 375                 380

Glu Ala Leu Glu Leu Ala Arg Arg Leu Phe Ala Glu Gln Arg Gly Glu
385                 390                 395                 400

Arg Pro Leu Glu Arg Asp Asn Pro Leu Ala Leu Arg His Pro Ile Glu
                405                 410                 415

Pro Ile Ile Pro Pro Leu Arg Tyr Arg Asp Asp Ala Cys Ser Pro Met
            420                 425                 430

Ala Ala Leu Asp Arg Phe Tyr Thr Glu Leu Val Glu Ala Asn Pro Asp
        435                 440                 445

Leu Arg Ala Arg Val Gly Asn Pro Asp Glu Leu Ala Ser Asn Arg Leu
        450                 455                 460

Gly Gly Val Leu Lys Ala Leu Lys His Arg Val Ser Glu Pro Glu Ser
465                 470                 475                 480

Glu Leu Glu Ser Val Ser Gly Arg Val Ile Thr Ala Leu Asn Glu Glu
                485                 490                 495

Ala Val Val Ser Ala Cys Leu Ala Asn Gln Gly Gly Leu Asn Leu Val
            500                 505                 510

Ala Ser Tyr Glu Ala Phe Cys Val Lys Met Leu Gly Ala Val Arg Gln
        515                 520                 525

Thr Leu Ile Phe Ala Arg Gln Gln Lys Glu Val Gly Arg Pro Ala Gly
        530                 535                 540

Trp Leu Gly Trp Pro Leu Val Ala Thr Ser His Thr Trp Glu Asn Gly
545                 550                 555                 560

Lys Asn Gln Gln Ser His Gln Asp Thr Thr Phe Cys Glu Ala Leu Leu
                565                 570                 575

Gly Glu Met Ser Asp Met Val Arg Val Leu Phe Pro Ala Asp His Asn
            580                 585                 590

Ser Ala Leu Ala Leu Leu Pro Thr Ile Tyr Arg Ser Arg Gly Gln Leu
        595                 600                 605

Ala Cys Leu Val Ile Pro Lys Arg Asp Arg Pro Met Val Phe Asp Ala
        610                 615                 620

Val Gln Ala Glu Arg Leu Ala Arg Asp Gly Ala Ile Leu Val Glu Glu
625                 630                 635                 640

Arg Cys Gly Ser Asp Pro Leu Leu Ile Ala Asn Gly Ser Tyr Gln
                645                 650                 655

Leu Glu Gln Met Arg Arg Ala Ala Gln Arg Leu Ala Glu Ala Gly Gln
            660                 665                 670

Ala Tyr Arg Leu Val Tyr Leu Gln Glu Pro Gly Arg Phe Arg Ala Pro
        675                 680                 685

Arg Asp Arg Trp Glu Val Glu Ala Val Ala Asp Glu Ala Leu Val Glu
        690                 695                 700

Arg Leu Phe Pro Asp Ser His Glu Arg Arg Val Leu Leu Thr His Met
705                 710                 715                 720

Arg Ala Glu Val Ala Arg Gly His Leu Trp Pro Ile Leu Pro Asp Ala
                725                 730                 735

Arg Arg Thr Ser Val Leu Gly Tyr Arg Asn Arg Gly Gly Thr Leu Asp
            740                 745                 750

Glu Ala Gly Met Gln Phe Ala Asn Arg Ala Cys Trp Gly Asn Val Leu
        755                 760                 765
```

```
Ala Ala Cys Ala Arg Leu Met Glu Val Pro Arg Thr Ala Leu Leu Thr
            770                 775                 780

Pro Glu Glu Ala Ala Val Ala Gly Lys Gly Asp Pro Ala Leu Leu
785                 790                 795                 800

Arg

<210> SEQ ID NO 56
<211> LENGTH: 326
<212> TYPE: PRT
<213> ORGANISM: Geobacillus stearothermophilus

<400> SEQUENCE: 56

Met Thr Thr Asp Leu Phe Thr Ala Leu Lys Ala Lys Val Thr Asp Thr
1               5                   10                  15

Gly Arg Lys Ile Val Phe Pro Glu Gly Thr Asp Arg Ile Leu Thr
            20                  25                  30

Ala Ala Ser Arg Leu Ala Thr Glu Gln Val Leu Gln Pro Ile Val Leu
            35                  40                  45

Gly Asp Glu Gln Ala Val Arg Val Lys Ala Ala Leu Gly Leu Pro
        50                  55                  60

Leu Glu Gly Val Glu Ile Val Asn Pro Arg Arg Tyr Gly Gly Phe Asp
65                  70                  75                  80

Glu Leu Val Ser Ala Phe Val Glu Arg Arg Lys Gly Lys Val Thr Glu
                85                  90                  95

Glu Thr Ala Arg Glu Leu Leu Phe Asp Glu Asn Tyr Phe Gly Thr Met
            100                 105                 110

Leu Val Tyr Thr Gly Ala Ala Asp Gly Leu Val Ser Gly Ala Ala His
            115                 120                 125

Ser Thr Ala Asp Thr Val Arg Pro Ala Leu Gln Ile Ile Lys Thr Lys
130                 135                 140

Pro Gly Val Gly Lys Thr Ser Gly Val Phe Ile Met Val Arg Gly Asp
145                 150                 155                 160

Glu Lys Tyr Val Phe Ala Asp Cys Ala Ile Asn Ile Ala Pro Asn Ser
                165                 170                 175

His Asp Leu Ala Glu Ile Ala Val Glu Ser Ala Arg Thr Ala Lys Met
            180                 185                 190

Phe Gly Leu Thr Pro Arg Val Ala Leu Leu Ser Phe Ser Thr Lys Gly
        195                 200                 205

Ser Ala Ser Ser Pro Glu Thr Glu Lys Val Val Glu Ala Val Arg Leu
210                 215                 220

Ala Lys Glu Met Ala Pro Asp Leu Ile Leu Asp Gly Glu Phe Gln Phe
225                 230                 235                 240

Asp Ala Ala Phe Val Pro Glu Val Ala Lys Lys Lys Ala Pro Asp Ser
                245                 250                 255

Val Ile Gln Gly Asp Ala Asn Val Phe Ile Phe Pro Ser Leu Glu Ala
            260                 265                 270

Gly Asn Ile Gly Tyr Lys Ile Ala Gln Arg Leu Gly Gly Phe Glu Ala
        275                 280                 285

Val Gly Pro Ile Leu Gln Gly Leu Asn Lys Pro Val Asn Asp Leu Ser
290                 295                 300

Arg Gly Cys Ser Ala Glu Asp Ala Tyr Lys Leu Ala Leu Ile Thr Ala
305                 310                 315                 320

Ala Gln Ser Leu Gly Glu
                325
```

<210> SEQ ID NO 57
<211> LENGTH: 449
<212> TYPE: PRT
<213> ORGANISM: Geobacillus thermodenitrificans

<400> SEQUENCE: 57

```
Met Thr His Ile Arg Phe Asp Tyr Ser Lys Ala Leu Ala Phe Phe Gly
1               5                   10                  15

Glu His Glu Leu Thr Tyr Leu Arg Asp Ala Val Lys Val Ala His His
            20                  25                  30

Ser Leu His Glu Lys Thr Gly Val Gly Asn Asp Phe Leu Gly Trp Leu
        35                  40                  45

Asp Trp Pro Val Asn Tyr Asp Lys Glu Glu Phe Ala Arg Ile Lys Gln
    50                  55                  60

Ala Ala Lys Lys Ile Gln Ser Asp Ser Asp Val Leu Leu Val Ile Gly
65                  70                  75                  80

Ile Gly Gly Ser Tyr Leu Gly Ala Arg Ala Ala Ile Glu Met Leu His
                85                  90                  95

His Ser Phe Tyr Asn Ala Leu Pro Lys Glu Lys Arg Ser Thr Pro Gln
            100                 105                 110

Ile Ile Phe Val Gly Asn Asn Ile Ser Ser Thr Tyr Met Lys Asp Val
        115                 120                 125

Ile Asp Phe Leu Glu Gly Lys Asp Phe Ser Ile Asn Val Ile Ser Lys
    130                 135                 140

Ser Gly Thr Thr Thr Glu Pro Ala Ile Ala Phe Arg Ile Phe Arg Lys
145                 150                 155                 160

Leu Leu Glu Asp Lys Tyr Gly Lys Glu Ala Arg Arg Ile Tyr
                165                 170                 175

Ala Thr Thr Asp Arg Ala Arg Gly Ala Leu Arg Thr Leu Ala Asp Glu
            180                 185                 190

Glu Gly Tyr Glu Thr Phe Val Ile Pro Asp Asp Ile Gly Gly Arg Tyr
        195                 200                 205

Ser Val Leu Thr Ala Val Gly Leu Leu Pro Ile Ala Ala Ser Gly Ala
    210                 215                 220

Asp Ile Asp Ala Met Met Glu Gly Ala Ala Lys Ala Arg Glu Asp Phe
225                 230                 235                 240

Ser Arg Ser Glu Leu Glu Glu Asn Ala Ala Tyr Gln Tyr Ala Ala Ile
                245                 250                 255

Arg Asn Ile Leu Tyr Asn Lys Gly Lys Thr Ile Glu Leu Leu Val Asn
            260                 265                 270

Tyr Glu Pro Ala Leu His Tyr Phe Ala Glu Trp Trp Lys Gln Leu Phe
        275                 280                 285

Gly Glu Ser Glu Gly Lys Asp Gln Lys Gly Ile Tyr Pro Ala Ser Ala
    290                 295                 300

Asp Phe Ser Thr Asp Leu His Ser Leu Gly Gln Tyr Ile Gln Glu Gly
305                 310                 315                 320

Arg Arg Asp Leu Phe Glu Thr Val Leu Lys Leu Glu Glu Pro Arg His
                325                 330                 335

Glu Leu Val Ile Glu Ala Glu Ser Asp Leu Asp Gly Leu Asn Tyr
            340                 345                 350

Leu Ala Gly Gln Thr Val Asp Phe Val Asn Thr Lys Ala Phe Glu Gly
        355                 360                 365

Thr Leu Leu Ala His Thr Asp Gly Gly Val Pro Asn Leu Val Val Thr
```

-continued

```
              370                 375                 380
Leu Pro Lys Leu Asp Glu Tyr Thr Phe Gly Tyr Leu Val Tyr Phe Phe
385                 390                 395                 400

Glu Lys Ala Cys Ala Met Ser Gly Tyr Leu Leu Gly Val Asn Pro Phe
                405                 410                 415

Asp Gln Pro Gly Val Glu Ala Tyr Lys Lys Asn Met Phe Ala Leu Leu
                420                 425                 430

Gly Lys Pro Gly Tyr Glu Glu Leu Lys Asp Glu Leu Glu Lys Arg Leu
                435                 440                 445

Lys

<210> SEQ ID NO 58
<211> LENGTH: 592
<212> TYPE: PRT
<213> ORGANISM: Aerococcus viridans

<400> SEQUENCE: 58

Met Ser Asp Asn Lys Ile Asn Ile Gly Leu Ala Val Met Lys Ile Leu
1               5                   10                  15

Glu Ser Trp Gly Ala Asp Thr Ile Tyr Gly Ile Pro Ser Gly Thr Leu
                20                  25                  30

Ser Ser Leu Met Asp Ala Met Gly Glu Glu Asn Asn Val Lys Phe
            35                  40                  45

Leu Gln Val Lys His Glu Glu Val Gly Ala Met Ala Ala Val Met Gln
        50                  55                  60

Ser Lys Phe Gly Gly Asn Leu Gly Val Thr Val Gly Ser Gly Gly Pro
65                  70                  75                  80

Gly Ala Ser His Leu Ile Asn Gly Leu Tyr Asp Ala Ala Met Asp Asn
                85                  90                  95

Ile Pro Val Val Ala Ile Leu Gly Ser Arg Pro Gln Arg Glu Leu Asn
                100                 105                 110

Met Asp Ala Phe Gln Glu Leu Asn Gln Asn Pro Met Tyr Asp His Ile
                115                 120                 125

Ala Val Tyr Asn Arg Arg Val Ala Tyr Ala Glu Gln Leu Pro Lys Leu
            130                 135                 140

Val Asp Glu Ala Ala Arg Met Ala Ile Ala Lys Arg Gly Val Ala Val
145                 150                 155                 160

Leu Glu Val Pro Gly Asp Phe Ala Lys Val Glu Ile Asp Asn Asp Gln
                165                 170                 175

Trp Tyr Ser Ser Ala Asn Ser Leu Arg Lys Tyr Glu Pro Ile Ala Pro
            180                 185                 190

Ala Ala Gln Asp Ile Asp Ala Ala Val Glu Leu Leu Asn Asn Ser Lys
                195                 200                 205

Arg Pro Val Ile Tyr Ala Gly Ile Gly Thr Met Gly His Gly Pro Ala
        210                 215                 220

Val Gln Glu Leu Ala Arg Lys Ile Lys Ala Pro Val Ile Thr Thr Gly
225                 230                 235                 240

Lys Asn Phe Glu Thr Phe Glu Trp Asp Phe Glu Ala Leu Thr Gly Ser
                245                 250                 255

Thr Tyr Arg Val Gly Trp Lys Pro Ala Asn Glu Thr Ile Leu Glu Ala
                260                 265                 270

Asp Thr Val Leu Phe Ala Gly Ser Asn Phe Pro Phe Ser Glu Val Glu
                275                 280                 285

Gly Thr Phe Arg Asn Val Asp Asn Phe Ile Gln Ile Asp Ile Asp Pro
```

290                 295                 300

Ala Met Leu Gly Lys Arg His His Ala Asp Val Ala Ile Leu Gly Asp
305                 310                 315                 320

Ala Gly Leu Ala Ile Asp Glu Ile Leu Asn Lys Val Asp Ala Val Glu
                325                 330                 335

Glu Ser Ala Trp Trp Thr Ala Asn Leu Lys Asn Ile Ala Asn Trp Arg
            340                 345                 350

Glu Tyr Ile Asn Met Leu Glu Thr Lys Glu Gly Asp Leu Gln Phe
        355                 360                 365

Tyr Gln Val Tyr Asn Ala Ile Asn Asn His Ala Asp Glu Asp Ala Ile
    370                 375                 380

Tyr Ser Ile Asp Val Gly Asn Ser Thr Gln Thr Ser Ile Arg His Leu
385                 390                 395                 400

His Met Thr Pro Lys Asn Met Trp Arg Thr Ser Pro Leu Phe Ala Thr
                405                 410                 415

Met Gly Ile Ala Ile Pro Gly Gly Leu Gly Ala Lys Asn Thr Tyr Pro
            420                 425                 430

Asp Arg Gln Val Trp Asn Ile Ile Gly Asp Gly Ala Phe Ser Met Thr
        435                 440                 445

Tyr Pro Asp Val Val Thr Asn Val Arg Tyr Asn Met Pro Val Ile Asn
    450                 455                 460

Val Val Phe Ser Asn Thr Glu Tyr Ala Phe Ile Lys Asn Lys Tyr Glu
465                 470                 475                 480

Asp Thr Asn Lys Asn Leu Phe Gly Val Asp Phe Thr Asp Val Asp Tyr
                485                 490                 495

Ala Lys Ile Ala Glu Ala Gln Gly Ala Lys Gly Phe Thr Val Ser Arg
            500                 505                 510

Ile Glu Asp Met Asp Arg Val Met Ala Glu Ala Val Ala Ala Asn Lys
        515                 520                 525

Ala Gly His Thr Val Val Ile Asp Cys Lys Ile Thr Gln Asp Arg Pro
    530                 535                 540

Ile Pro Val Glu Thr Leu Lys Leu Asp Ser Lys Leu Tyr Ser Glu Asp
545                 550                 555                 560

Glu Ile Lys Ala Tyr Lys Glu Arg Tyr Glu Ala Ala Asn Leu Val Pro
                565                 570                 575

Phe Arg Glu Tyr Leu Glu Ala Glu Gly Leu Glu Ser Lys Tyr Ile Lys
            580                 585                 590

<210> SEQ ID NO 59
<211> LENGTH: 369
<212> TYPE: PRT
<213> ORGANISM: Geobacillus stearothermophilus
<220> FEATURE:
<221> NAME/KEY: misc_feature
<222> LOCATION: (298)..(298)
<223> OTHER INFORMATION: Xaa can be any naturally occurring amino acid

<400> SEQUENCE: 59

Met Gly Val Lys Thr Phe Gln Phe Pro Phe Ala Glu Gln Leu Glu Lys
1               5                   10                  15

Val Ala Glu Gln Phe Pro Thr Phe Gln Ile Leu Asn Glu Glu Gly Glu
            20                  25                  30

Val Val Asn Glu Glu Ala Met Pro Glu Leu Ser Asp Glu Gln Leu Lys
        35                  40                  45

Glu Leu Met Arg Arg Met Val Tyr Thr Arg Ile Leu Asp Gln Arg Ser
    50                  55                  60

```
Ile Ser Leu Asn Arg Gln Gly Arg Leu Gly Phe Tyr Ala Pro Thr Ala
 65                  70                  75                  80

Gly Gln Glu Ala Ser Gln Ile Ala Ser His Phe Ala Leu Glu Lys Glu
                 85                  90                  95

Asp Phe Ile Leu Pro Gly Tyr Arg Asp Val Pro Gln Ile Ile Trp His
            100                 105                 110

Gly Leu Pro Leu Tyr Gln Ala Phe Leu Phe Ser Arg Gly His Phe His
            115                 120                 125

Gly Asn Gln Ile Pro Glu Gly Val Asn Val Leu Pro Pro Gln Ile Ile
130                 135                 140

Ile Gly Ala Gln Tyr Ile Gln Ala Ala Gly Val Ala Leu Gly Leu Lys
145                 150                 155                 160

Met Arg Gly Lys Lys Ala Val Ala Ile Thr Tyr Thr Gly Asp Gly Gly
                165                 170                 175

Thr Ser Gln Gly Asp Phe Tyr Glu Gly Ile Asn Phe Ala Gly Ala Phe
            180                 185                 190

Lys Ala Pro Ala Ile Phe Val Val Gln Asn Asn Arg Phe Ala Ile Ser
            195                 200                 205

Thr Pro Val Glu Lys Gln Thr Val Ala Lys Thr Leu Ala Gln Lys Ala
210                 215                 220

Val Ala Ala Gly Ile Pro Gly Ile Gln Val Asp Gly Met Asp Pro Leu
225                 230                 235                 240

Ala Val Tyr Ala Ala Val Lys Ala Ala Arg Glu Arg Ala Ile Asn Gly
                245                 250                 255

Glu Gly Pro Thr Leu Ile Glu Thr Leu Cys Phe Arg Tyr Gly Pro His
            260                 265                 270

Thr Met Ser Gly Asp Asp Pro Thr Arg Tyr Arg Ser Lys Glu Leu Glu
            275                 280                 285

Asn Glu Trp Ala Lys Lys Asp Pro Leu Xaa Arg Phe Arg Lys Phe Leu
290                 295                 300

Glu Ala Lys Gly Leu Trp Ser Glu Glu Glu Asn Asn Val Ile Glu
305                 310                 315                 320

Gln Ala Lys Glu Glu Ile Lys Glu Ala Ile Lys Lys Ala Asp Glu Thr
                325                 330                 335

Pro Lys Gln Lys Val Thr Asp Leu Ile Ser Ile Met Phe Glu Glu Leu
            340                 345                 350

Pro Phe Asn Leu Lys Glu Gln Tyr Glu Ile Tyr Lys Glu Lys Glu Ser
            355                 360                 365

Lys

<210> SEQ ID NO 60
<211> LENGTH: 325
<212> TYPE: PRT
<213> ORGANISM: Geobacillus stearothermophilus

<400> SEQUENCE: 60

Met Ala Gln Met Thr Met Val Gln Ala Ile Thr Asp Ala Leu Arg Ile
  1               5                  10                  15

Glu Leu Lys Asn Asp Pro Asn Val Leu Ile Phe Gly Glu Asp Val Gly
                 20                  25                  30

Val Asn Gly Gly Val Phe Arg Ala Thr Glu Gly Leu Gln Ala Glu Phe
             35                  40                  45

Gly Glu Asp Arg Val Phe Asp Thr Pro Leu Ala Glu Ser Gly Ile Gly
         50                  55                  60
```

Gly Leu Ala Ile Gly Leu Ala Leu Gln Gly Phe Arg Pro Val Pro Glu
65                  70                  75                  80

Ile Gln Phe Phe Gly Phe Val Tyr Glu Val Met Asp Ser Ile Cys Gly
                85                  90                  95

Gln Met Ala Arg Ile Arg Tyr Arg Thr Gly Arg Tyr His Met Pro
            100                 105                 110

Ile Thr Ile Arg Ser Pro Phe Gly Gly Val His Thr Pro Glu Leu
            115                 120                 125

His Ser Asp Ser Leu Glu Gly Leu Val Ala Gln Gln Pro Gly Leu Lys
    130                 135                 140

Val Val Ile Pro Ser Thr Pro Tyr Asp Ala Lys Gly Leu Leu Ile Ser
145                 150                 155                 160

Ala Ile Arg Asp Asn Asp Pro Val Ile Phe Leu Glu His Leu Lys Leu
                165                 170                 175

Tyr Arg Ser Phe Arg Gln Glu Val Pro Glu Gly Glu Tyr Thr Ile Pro
            180                 185                 190

Ile Gly Lys Ala Asp Ile Lys Arg Glu Gly Lys Asp Ile Thr Ile Ile
            195                 200                 205

Ala Tyr Gly Ala Met Val His Glu Ser Leu Lys Ala Ala Ala Glu Leu
    210                 215                 220

Glu Lys Glu Gly Ile Ser Ala Glu Val Val Asp Leu Arg Thr Val Gln
225                 230                 235                 240

Pro Leu Asp Ile Glu Thr Ile Ile Gly Ser Val Glu Lys Thr Gly Arg
                245                 250                 255

Ala Ile Val Val Gln Glu Ala Gln Arg Gln Ala Gly Ile Ala Ala Asn
            260                 265                 270

Val Val Ala Glu Ile Asn Glu Arg Ala Ile Leu Ser Leu Glu Ala Pro
    275                 280                 285

Val Leu Arg Val Ala Ala Pro Asp Thr Val Tyr Pro Phe Ala Gln Ala
    290                 295                 300

Glu Ser Val Trp Leu Pro Asn Phe Lys Asp Val Ile Glu Thr Ala Lys
305                 310                 315                 320

Lys Val Met Asn Phe
            325

<210> SEQ ID NO 61
<211> LENGTH: 428
<212> TYPE: PRT
<213> ORGANISM: Geobacillus stearothermophilus

<400> SEQUENCE: 61

Met Ala Phe Glu Phe Lys Leu Pro Asp Ile Gly Glu Gly Ile His Glu
1               5                   10                  15

Gly Glu Ile Val Lys Trp Phe Val Lys Pro Gly Asp Glu Val Asn Glu
            20                  25                  30

Asp Asp Val Leu Cys Glu Val Gln Asn Asp Lys Ala Val Val Glu Ile
        35                  40                  45

Pro Ser Pro Val Lys Gly Lys Val Leu Glu Ile Leu Val Pro Glu Gly
    50                  55                  60

Thr Val Ala Thr Val Gly Gln Thr Leu Ile Thr Leu Asp Ala Pro Gly
65                  70                  75                  80

Tyr Glu Asn Met Thr Phe Lys Gly Gln Glu Gln Glu Ala Lys Lys
                85                  90                  95

Glu Glu Lys Thr Glu Thr Val Ser Lys Glu Glu Lys Val Asp Ala Val

```
                100             105             110
Ala Pro Asn Ala Pro Ala Ala Glu Ala Glu Ala Gly Pro Asn Arg Arg
            115                 120                 125
Val Ile Ala Met Pro Ser Val Arg Lys Tyr Ala Arg Glu Lys Gly Val
        130                 135                 140
Asp Ile Arg Leu Val Gln Gly Thr Gly Lys Asn Gly Arg Val Leu Lys
145                 150                 155                 160
Glu Asp Ile Asp Ala Phe Leu Ala Gly Ala Lys Pro Ala Pro Ala
                165                 170                 175
Ala Ala Glu Glu Lys Ala Ala Pro Ala Ala Lys Pro Ala Thr Thr
            180                 185                 190
Glu Gly Glu Phe Pro Glu Thr Arg Glu Lys Met Ser Gly Ile Arg Arg
            195                 200                 205
Ala Ile Ala Lys Ala Met Val His Ser Lys His Thr Ala Pro His Val
        210                 215                 220
Thr Leu Met Asp Glu Ala Asp Val Thr Lys Leu Val Ala His Arg Lys
225                 230                 235                 240
Lys Phe Lys Ala Ile Ala Ala Glu Lys Gly Ile Lys Leu Thr Phe Leu
                245                 250                 255
Pro Tyr Val Val Lys Ala Leu Val Ser Ala Leu Arg Glu Tyr Pro Val
            260                 265                 270
Leu Asn Thr Ser Ile Asp Asp Glu Thr Glu Glu Ile Ile Gln Lys His
            275                 280                 285
Tyr Tyr Asn Ile Gly Ile Ala Ala Asp Thr Asp Arg Gly Leu Leu Val
        290                 295                 300
Pro Val Ile Lys His Ala Asp Arg Lys Pro Ile Phe Ala Leu Ala Gln
305                 310                 315                 320
Glu Ile Asn Glu Leu Ala Glu Lys Ala Arg Asp Gly Lys Leu Thr Pro
                325                 330                 335
Gly Glu Met Lys Gly Ala Ser Cys Thr Ile Thr Asn Ile Gly Ser Ala
            340                 345                 350
Gly Gly Gln Trp Phe Thr Pro Val Ile Asn His Pro Glu Val Ala Ile
            355                 360                 365
Leu Gly Ile Gly Arg Ile Ala Glu Lys Pro Ile Val Arg Asp Gly Glu
        370                 375                 380
Ile Val Ala Ala Pro Met Leu Ala Leu Ser Leu Ser Phe Asp His Arg
385                 390                 395                 400
Met Ile Asp Gly Ala Thr Ala Gln Lys Ala Leu Asn His Ile Lys Arg
                405                 410                 415
Leu Leu Ser Asp Pro Glu Leu Leu Leu Met Glu Ala
            420                 425

<210> SEQ ID NO 62
<211> LENGTH: 470
<212> TYPE: PRT
<213> ORGANISM: Geobacillus stearothermophilus
<220> FEATURE:
<221> NAME/KEY: misc_feature
<222> LOCATION: (255)..(255)
<223> OTHER INFORMATION: Xaa can be any naturally occurring amino acid

<400> SEQUENCE: 62

Met Val Val Gly Asp Phe Ala Ile Glu Thr Glu Thr Leu Val Val Gly
1               5                   10                  15

Ala Gly Pro Gly Gly Tyr Val Ala Ala Ile Arg Ala Ala Gln Leu Gly
            20                  25                  30
```

```
Gln Lys Val Thr Ile Val Glu Lys Gly Asn Leu Gly Gly Val Cys Leu
        35                  40                  45

Asn Val Gly Cys Ile Pro Ser Lys Ala Leu Ile Ser Ala Ser His Arg
 50                  55                  60

Tyr Glu Gln Ala Lys His Ser Glu Glu Met Gly Ile Lys Ala Glu Asn
 65                  70                  75                  80

Val Thr Ile Asp Phe Ala Lys Val Gln Glu Trp Lys Ala Ser Val Val
                     85                  90                  95

Lys Lys Leu Thr Gly Gly Val Glu Gly Leu Leu Lys Gly Asn Lys Val
                100                 105                 110

Glu Ile Val Lys Gly Glu Ala Tyr Phe Val Asp Ala Asn Thr Val Arg
                115                 120                 125

Val Val Asn Gly Asp Ser Ala Gln Thr Tyr Thr Phe Lys Asn Ala Ile
        130                 135                 140

Ile Ala Thr Gly Ser Arg Pro Ile Glu Leu Pro Asn Phe Lys Phe Ser
145                 150                 155                 160

Asn Arg Ile Leu Asp Ser Thr Gly Ala Leu Asn Leu Gly Glu Val Pro
                    165                 170                 175

Lys Ser Leu Val Val Ile Gly Gly Tyr Ile Gly Ile Glu Leu Gly
                180                 185                 190

Thr Ala Tyr Ala Asn Phe Gly Thr Lys Val Thr Ile Leu Glu Gly Ala
                195                 200                 205

Gly Glu Ile Leu Ser Gly Phe Glu Lys Gln Met Ala Ala Ile Ile Lys
        210                 215                 220

Lys Arg Leu Lys Lys Gly Val Glu Val Val Thr Asn Ala Leu Ala
225                 230                 235                 240

Lys Gly Ala Glu Glu Arg Glu Asp Gly Val Thr Val Thr Tyr Xaa Ala
                    245                 250                 255

Asn Gly Glu Thr Lys Thr Ile Asp Ala Asp Tyr Val Leu Val Thr Val
                260                 265                 270

Gly Arg Arg Pro Asn Thr Asp Glu Leu Gly Leu Glu Gln Ile Gly Ile
        275                 280                 285

Lys Met Thr Asn Arg Gly Leu Ile Glu Val Asp Gln Gln Cys Arg Thr
290                 295                 300

Ser Val Pro Asn Ile Phe Ala Ile Gly Asp Ile Val Pro Gly Pro Ala
305                 310                 315                 320

Leu Ala His Lys Ala Ser Tyr Glu Gly Lys Val Ala Ala Glu Ala Ile
                325                 330                 335

Ala Gly His Pro Ser Val Val Asp Tyr Ile Ala Ile Pro Ala Val Val
                340                 345                 350

Phe Ser Asp Pro Glu Cys Ala Ser Val Gly Tyr Phe Glu Gln Gln Ala
                355                 360                 365

Lys Asp Glu Gly Ile Asp Val Ile Ala Ala Lys Phe Pro Phe Ala Ala
        370                 375                 380

Asn Gly Arg Ala Leu Ala Leu Asn Asp Thr Asp Gly Phe Leu Lys Leu
385                 390                 395                 400

Val Val Arg Lys Glu Asp Gly Val Val Ile Gly Ala Gln Ile Ile Gly
                405                 410                 415

Pro Asn Ala Ser Asp Met Ile Ala Glu Leu Gly Leu Ala Ile Glu Ala
                420                 425                 430

Gly Met Thr Ala Glu Asp Ile Ala Leu Thr Ile His Ala His Pro Thr
        435                 440                 445
```

Leu Gly Glu Ile Ala Met Glu Ala Ala Glu Val Ala Leu Gly Thr Pro
            450                 455                 460

Ile His Ile Ile Thr Lys
465                 470

<210> SEQ ID NO 63
<211> LENGTH: 470
<212> TYPE: PRT
<213> ORGANISM: Artificial Sequence
<220> FEATURE:
<223> OTHER INFORMATION: Mutant G.stearothermophilus dihydrolipoamide
      dehydrogenase
<220> FEATURE:
<221> NAME/KEY: misc_feature
<222> LOCATION: (255)..(255)
<223> OTHER INFORMATION: Xaa can be any naturally occurring amino acid

<400> SEQUENCE: 63

Met Val Val Gly Asp Phe Ala Ile Glu Thr Glu Thr Leu Val Val Gly
1               5                   10                  15

Ala Gly Pro Gly Gly Tyr Val Ala Ala Ile Arg Ala Ala Gln Leu Gly
            20                  25                  30

Gln Lys Val Thr Ile Val Glu Lys Gly Asn Leu Gly Gly Val Cys Leu
        35                  40                  45

Asn Val Gly Cys Ile Pro Ser Lys Ala Leu Ile Ser Ala Ser His Arg
50                  55                  60

Tyr Glu Gln Ala Lys His Ser Glu Met Gly Ile Lys Ala Glu Asn
65                  70                  75                  80

Val Thr Ile Asp Phe Ala Lys Val Gln Glu Trp Lys Ala Ser Val Val
                85                  90                  95

Lys Lys Leu Thr Gly Gly Val Glu Gly Leu Leu Lys Gly Asn Lys Val
            100                 105                 110

Glu Ile Val Lys Gly Glu Ala Tyr Phe Val Asp Ala Asn Thr Val Arg
        115                 120                 125

Val Val Asn Gly Asp Ser Ala Gln Thr Tyr Thr Phe Lys Asn Ala Ile
    130                 135                 140

Ile Ala Thr Gly Ser Arg Pro Ile Glu Leu Pro Asn Phe Lys Phe Ser
145                 150                 155                 160

Asn Arg Ile Leu Asp Ser Thr Gly Ala Leu Asn Leu Gly Glu Val Pro
                165                 170                 175

Lys Ser Leu Val Val Ile Gly Gly Gly Tyr Ile Ala Ile Glu Leu Ala
            180                 185                 190

Thr Ala Tyr Ala Asn Phe Gly Thr Lys Val Thr Ile Leu Val Arg Lys
        195                 200                 205

Gly Glu Ile Leu Arg Gly Phe Glu Lys Gln Met Ala Ala Ile Ile Lys
    210                 215                 220

Lys Arg Leu Lys Lys Lys Gly Val Glu Val Val Thr Asn Ala Leu Ala
225                 230                 235                 240

Lys Gly Ala Glu Glu Arg Glu Asp Gly Val Thr Val Thr Tyr Xaa Ala
                245                 250                 255

Asn Gly Glu Thr Lys Thr Ile Asp Ala Asp Tyr Val Leu Val Thr Val
            260                 265                 270

Gly Arg Arg Pro Asn Thr Asp Glu Leu Gly Leu Glu Gln Ile Gly Ile
        275                 280                 285

Lys Met Thr Asn Arg Gly Leu Ile Glu Val Asp Gln Gln Cys Arg Thr
    290                 295                 300

Ser Val Pro Asn Ile Phe Ala Ile Gly Asp Ile Val Pro Gly Pro Ala

```
                    305                 310                 315                 320
Leu Ala His Lys Ala Ser Tyr Glu Gly Lys Val Ala Glu Ala Ile
                325                 330                 335
Ala Gly His Pro Ser Val Val Asp Tyr Ile Ala Ile Pro Ala Val Val
                340                 345                 350
Phe Ser Asp Pro Glu Cys Ala Ser Val Gly Tyr Phe Glu Gln Gln Ala
                355                 360                 365
Lys Asp Glu Gly Ile Asp Val Ile Ala Ala Lys Phe Pro Phe Ala Ala
    370                 375                 380
Asn Gly Arg Ala Leu Ala Leu Asn Asp Thr Asp Gly Phe Leu Lys Leu
385                 390                 395                 400
Val Val Arg Lys Glu Asp Gly Val Val Ile Gly Ala Gln Ile Ile Gly
                405                 410                 415
Pro Asn Ala Ser Asp Met Ile Ala Glu Leu Gly Leu Ala Ile Glu Ala
                420                 425                 430
Gly Met Thr Ala Glu Asp Ile Ala Leu Thr Ile His Ala His Pro Thr
                435                 440                 445
Leu Gly Glu Ile Ala Met Glu Ala Ala Glu Val Ala Leu Gly Thr Pro
    450                 455                 460
Ile His Ile Ile Thr Lys
465                 470

<210> SEQ ID NO 64
<211> LENGTH: 470
<212> TYPE: PRT
<213> ORGANISM: Artificial Sequence
<220> FEATURE:
<223> OTHER INFORMATION: Mutant E.coli dihydrolipoyl dehydrogenase

<400> SEQUENCE: 64

Thr Glu Ile Lys Thr Gln Val Val Val Leu Gly Ala Gly Pro Ala Gly
1               5                   10                  15
Tyr Ser Ala Ala Phe Arg Cys Ala Asp Leu Gly Leu Glu Thr Val Ile
                20                  25                  30
Val Glu Arg Tyr Asn Thr Leu Gly Gly Val Cys Leu Asn Val Gly Cys
            35                  40                  45
Ile Pro Ser Lys Ala Leu Leu His Val Ala Lys Val Ile Glu Glu Ala
    50                  55                  60
Lys Ala Leu Ala Glu His Gly Ile Val Phe Gly Glu Pro Lys Thr Asp
65                  70                  75                  80
Ile Asp Lys Ile Arg Thr Trp Lys Glu Lys Val Ile Asn Gln Leu Thr
                85                  90                  95
Gly Gly Leu Ala Gly Met Ala Lys Gly Arg Lys Val Lys Val Val Asn
                100                 105                 110
Gly Leu Gly Lys Phe Thr Gly Ala Asn Thr Leu Glu Val Glu Gly Glu
            115                 120                 125
Asn Gly Lys Thr Val Ile Asn Phe Asp Asn Ala Ile Ile Ala Ala Gly
    130                 135                 140
Ser Arg Pro Ile Gln Leu Pro Phe Ile Pro His Glu Asp Pro Arg Ile
145                 150                 155                 160
Trp Asp Ser Thr Asp Ala Leu Glu Leu Lys Glu Val Pro Glu Arg Leu
                165                 170                 175
Leu Val Met Gly Gly Gly Ile Ile Ala Leu Glu Met Ala Thr Val Tyr
            180                 185                 190
His Ala Leu Gly Ser Gln Ile Asp Val Val Val Arg Lys His Gln Val
```

```
                195                 200                 205
Ile Arg Ala Ala Asp Lys Asp Ile Val Lys Val Phe Thr Lys Arg Ile
    210                 215                 220

Ser Lys Lys Phe Asn Leu Met Leu Glu Thr Lys Val Thr Ala Val Glu
225                 230                 235                 240

Ala Lys Glu Asp Gly Ile Tyr Val Thr Met Glu Gly Lys Lys Ala Pro
                245                 250                 255

Ala Glu Pro Gln Arg Tyr Asp Ala Val Leu Val Ala Ile Gly Arg Val
            260                 265                 270

Pro Asn Gly Lys Asn Leu Asp Ala Gly Lys Ala Gly Val Glu Val Asp
        275                 280                 285

Asp Arg Gly Phe Ile Arg Val Asp Lys Gln Leu Arg Thr Asn Val Pro
    290                 295                 300

His Ile Phe Ala Ile Gly Asp Ile Val Gly Gln Pro Met Leu Ala His
305                 310                 315                 320

Lys Gly Val His Glu Gly His Val Ala Ala Glu Val Ile Ala Gly Lys
                325                 330                 335

Lys His Tyr Phe Asp Pro Lys Val Ile Pro Ser Ile Ala Tyr Thr Glu
            340                 345                 350

Pro Glu Val Ala Trp Val Gly Leu Thr Glu Lys Glu Ala Lys Glu Lys
        355                 360                 365

Gly Ile Ser Tyr Glu Thr Ala Thr Phe Pro Trp Ala Ala Ser Gly Arg
    370                 375                 380

Ala Ile Ala Ser Asp Cys Ala Asp Gly Met Thr Lys Leu Ile Phe Asp
385                 390                 395                 400

Lys Glu Ser His Arg Val Ile Gly Gly Ala Ile Val Gly Thr Asn Gly
                405                 410                 415

Gly Glu Leu Leu Gly Glu Ile Gly Leu Ala Ile Glu Met Gly Cys Asp
            420                 425                 430

Ala Glu Asp Ile Ala Leu Thr Ile His Ala His Pro Thr Leu His Glu
        435                 440                 445

Ser Val Gly Leu Ala Ala Glu Val Phe Glu Gly Ser Ile Thr Asp Leu
    450                 455                 460

Pro Asn Pro Lys Ala Lys
465                 470
```

CELL-FREE METABOLIC PATHWAY FOR GLUCOSE METABOLISM WITH A MOLECULAR PURGE VALVE

CROSS REFERENCE TO RELATED APPLICATIONS

This application is a U.S. National Stage Application filed under 35 U.S.C. § 371 and claims priority to International Application No. PCT/US2016/043,260, filed Jul. 21, 2016, which application claims priority to U.S. Provisional Application Ser. No. 62/195,142, filed Jul. 21, 2015, the disclosures of which are incorporated herein by reference in their entirety.

STATEMENT REGARDING FEDERALLY SPONSORED RESEARCH

This invention was made with government support under Grant No. DE-AR0000556 awarded by the U.S. Department of Energy. The government has certain rights in the invention.

REFERENCE TO SEQUENCE LISTING

The present application is being filed along with a Sequence Listing in electronic format. The Sequence Listing is provided as a file entitled Sequencelisting_ST25.txt, created Jul. 21, 2016, which is 273 Kb in size. The information in the electronic format of the Sequence Listing is incorporated herein by reference in its entirety.

TECHNICAL FIELD

The disclosure provides compositions, pathways and methods for producing chemicals by contacting a suitable substrate with an enzymatic preparations of the disclosure.

BACKGROUND

Pyruvate is a key central metabolite to both cell growth as well as biosynthesis of multiple cell constituents and products, including fatty acids, polyketides, amino acids, isoprenoids, and alcohols. Typically, the Embden-Meyerhof-Parnas (EMP) pathway, the Entner-Doudoroff (ED) pathway, and their variations are used to produce acetyl-CoA from sugars through oxidative decarboxylation of pyruvate. Similarly, the CBB, RuMP, and DHA pathways incorporate Ci compounds, such as $CO_2$ and methanol, to synthesize sugar-phosphates and pyruvate, which then produce acetyl-CoA through decarboxylation of pyruvate. Thus, in all heterotrophic organisms and those autotrophic organisms that use the sugar-phosphate-dependent pathways for Ci incorporation, acetyl-coA is derived from oxidative decarboxylation of pyruvate.

SUMMARY

The disclosure provides a recombinant, artificial or engineered metabolic pathway comprising a plurality of enzymatic steps that converts a substrate to acetyl-phosphate, pyruvate, or acetyl-CoA, wherein the pathway includes an unbalanced production and utilization of a co-factor, the pathway comprising a non-naturally occurring purge valve pathway that recycles the co-factor, wherein the purge valve pathway comprises an enzyme that uses the co-factor to convert a metabolite to an intermediate or product in one or more of the plurality of enzymatic steps. In one embodiment, the co-factors are oxidizing/reducing co-factors. In a further embodiment, the oxidizing/reducing co-factors are $NAD^+/NADH$, $NADP^+/NADPH$ or $FAD^+/FADH$. In yet a further embodiment of any of the foregoing, a first cofactor comprises $NAD^+/NADH$ and a second cofactor comprises $NADP^+/NADPH$. In another embodiment the first cofactor comprises ADP/ATP and a second comprises a different nucleotide triphosphate (ex. GDP/GTP, CDP/CTP, or TDP/TTP). In still a further embodiment of any of the foregoing, the purge valve pathway comprises a NADH oxidase. In yet a further embodiment, the NADH oxidase is a NoxE or homolog thereof. In still a further embodiment, the NADH oxidase comprises a sequence that is at least 50% identical to SEQ ID NO:18. In another embodiment, the pathway carries out the following reactions: (i) converts glucose to glucose-6-phosphate; (ii) converts glucose-6-phosphate to 6-phospho-D-glucono-1,5-lactone; (iii) converts 6-phospho-D-glucono-1,5-lactone to 6-phospho-D-gluconate; (iv) converts 6-phospho-D-gluconate to ribulose-5-phosphate; (v) converts ribulose-5-phosphate to xylulose-5-phosphate; (vi) converts xylulose-5-phosphate to glyceraldehyde-3-phosphate and acetyl-phosphate; (vii) produces acetyl-phosphate and erythrose-4-phosphate (E4P) from fructose-6-phosphate; (viii) converts glyceraldehyde-3-phosphate to dihydroxyacetone phosphate or the reverse thereof; (ix) convert glyceraldehyde-3-phosphate and dihydroxyacetone phosphate to fructose-1,6-bisphosphate; and (x) converts fructose 1,6-biphosphate to fructose-6-phosphate and a polyphosphate. In a further embodiment, the pathway comprises the following enzymes: (a) a phosphoketolase (F/Xpk or Xfp); (b) a transaldolase (Tal); (c) a transketolase (Tkt); (d) a ribose-5-phosphate isomerase (Rpi); (e) a ribulose-5-phosphate epimerase (Rpe); (f) a triose phosphate isomerase (Tpi); (g) a fructose 1,6 bisphosphate aldolase (Fba); (h) a glucokinase (Glk); (i) a glucose-6-phosphate dehydrogenase (Zwf); (j) a 6-phospho-gluconolactonase (pgl); (k) 6-phosphogluconate dehydrogenase (Gnd) (1) a phosphoglucoisomerase (Pgi); and (m) a phosphofructokinase (pfk). In another embodiment of any of the foregoing embodiments, the pathway is in a cell-free system. In still another embodiment, the pathway is engineered and expressed in a microorganism. In a further embodiment, the microorganism is a prokaryote or eukaryote. In a further embodiment, the microorganism is yeast. In yet further embodiment, the microorganism is a prokaryote. In yet a further embodiment, the microorganism is derived from an *E. coli* microorganism. In another embodiment, the purge valve pathway comprises an enzyme that converts a nucleoside tri-phosphate or di-phosphate to a di- or -monophosphate, respectively. In a further embodiment, the purge valve pathway recycles ATP. In another embodiment, the pathway produces acetyl-coA from glucose. In a further embodiment, the pathway is a cell free system and comprises: (a) a glucokinase having a sequence that is at least 85% identical to SEQ ID NO:19 and which converts glucose to glucose-6-phosphate; (b) a glucose-6-phosphate dehydrogenase that is at least 85% identical to SEQ ID NO:22 or 24 and which converts glucose-6-phosphate to 6-phospho-D-glucono 1,5-lactone; (c) an NAD(P)H oxidase having a sequence that is at least 85% identical to SEQ ID NO:18 and which converts NAD(P)H to $NAD(P)^+$; (d) a 6-phosphgluconolactonase having a sequence that is at least 85% identical to SEQ ID NO:26 and which converts 6-phospho-D-glucono 1,5-lactone to 6-phospho-D-gluconate; (e) a 6-phosphogluconate dehydrogenase having a sequence that is at least 85% identical to SEQ ID NO:27 and which converts 6-phospho-D-gluconate to ribulose-5-phosphate; (f) a ribulose-5-phosphate epimerase having a sequence that is at least 85% identical to SEQ ID NO:6 and which converts ribulose-5-phosphate to xylulose-5-phosphate; (g) a ribose-5-phosphate isomerase having a sequence that is at least 85% identical to SEQ ID NO:8 and which converts ribulose-5-phosphate to ribose-5-phosphate; (h) a xylulose-5-phosphate/fructose-6-phosphate phosphoketolase having a sequence that is at least 85% identical to SEQ ID NO:2 or 55 and which converts (1) xylulose-5-phosphate to glyceraldehyde-3-phosphate and/or (2) fructose-6-phosphate to erythrose-4-phosphate; (i) a glucose-6-phosphate isomerase that is at least 85% identical to SEQ ID NO:57 and which converts fructose-6-phosphate to glucose-6-phosphate; (j) a phosphofructokinase that is at least 85% identical to SEQ ID NO:20, 52 or 53 and which converts fructose 1,6-bisphosphate to fructose-6-phosphate; (k) a fructose-1,6-bisphosphate aldolase that is at least 85% identical to SEQ ID NO: 16 or 51 and which converts glyceraldehyde-3-phosphate to fructose-1,6-bis-phosphate and/or fructose-1,6-bis-phosphate to dihydroxyacetone phosphate; (l) a triose phosphate isomerase that is at least 85% identical to SEQ ID NO:14 and which converts dihydroxyacetone phosphate to glyceraldehyde-3-phosphate; (m) a transaldolase that is at least 85% identical to SEQ ID NO:10 and produces sedoheptulose-7-phosphate from a substrate that includes erythrose-4-phosphate and fructose-6-phosphate; (n) a transketolase that is at least 85% identical to SEQ ID NO:12 and produces a metabolite that includes (1) ribose-5-phosphate and xylulose-5-phosphate from sedoheptulose-7-phosphate and glyceraldehyde-3-phosphate; and/or (2) glyceraldehyde-3-phosphate and fructose-6-phosphate from xylulose-5-phosphate and erythrose-4-phosphate; and (o) a phosphotransacetylase that is at least 85% identical to SEQ ID NO:56 and acetyl-phosphate to acetyl-CoA. In still a further embodiment, the cell-free system can further comprise enzymes for the production of n-butanol, n-hexanol, hexanoic acid, acetoacetyl-CoA, 3-hydroxybutyryl-CoA, and/or PhB. In a further embodiment, that pathway further comprising one or more enzymes selected from the group consisting of AtoB, Hbd, Crt, Ter, BktB, and AdhE. In one embodiment, during operation 2 glucose molecules enter the cycle and are converted to glucose-6-phosphate (G6P) through the action of glucokinase, consuming 2 ATP. The first phase of the cycle then passes through the oxidative branch, which breaks down 2 G6P to 2 xylulose-5-phosphate (X5P), producing 4 NAD(P)H in the process. In the second phase of the cycle, X5P phosphoketolase (Xfp) from the *bifidobacterium* shunt splits the 2 X5P molecules into 2 acetylphosphate and 2 glyceraldehyde-3-phosphate (G3P) molecules. Acetylphosphate is subsequently converted into acetyl-CoA by phosphotransacetylase (Pta) and then used as a carbon building block for additional chemical production (e.g., PHB, n-butanol, n-hexanol etc.), while G3P is recycled in the third phase. In the third phase, using glycolysis enzymes, 2 G3P molecules (from 2 input G6P) are condensed into fructose-1,6-bisphosphate (FBP) by fructose bisphosphate aldolase (Fba) and then recycled back to G6P, making 1 ATP in the process via the reverse reaction of phosphofructokinase B (PfkB). The identification of an efficient ATP-recycling PfkB is described herein. The ATP produced is then consumed by glucokinase, which allows another molecule of glucose to enter the cycle as G6P, thus completing the cycle. Overall, the PBG cycle produces a net of 2 acetyl-CoA, 4 NAD(P)H, and 0 ATP for each glucose molecule and 66.6% theoretical molar yield of carbon due to the release of $CO_2$. Two purge valves for regulating NAD(P)H levels and (ii) a metabolite salvage pathway to account for the promiscuity of the Xfp enzyme are included.

The disclosure provides an invention as substantially described herein with reference to the Figures, sequences and description. In one embodiment, the disclosure provides an in vitro or recombinant in vivo pathway as set out FIG. 1A-B.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the polypeptide" includes reference to one or more polypeptides, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising"

"include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Figure 1A:
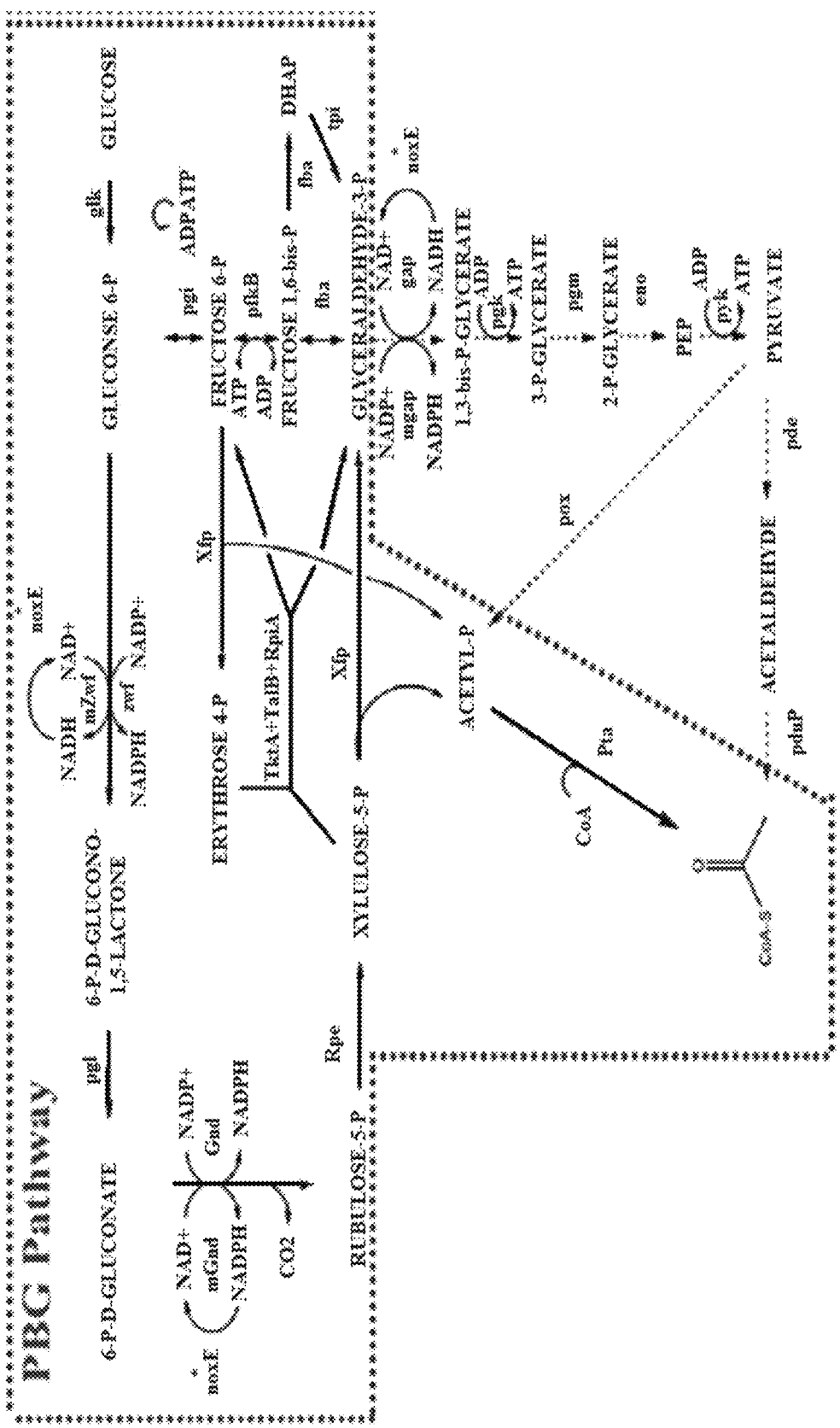
FIG. 1A-D show metabolic pathways of the disclosure. (A) shows an outline of the pentose-bifido-glycolysis (PGB) pathway of the disclosure. (B) shows an outline of a glucose breakdown pathway of the disclosure. (C) shows an outline of a glucose breakdown pathway of the disclosure comprising an NAD(P)H and ATP purge valve system. (D) shows an outline of the PBG pathway (phosphate is denoted by "P" for brevity). The PBG cycle consists of components from the pentose phosphate pathway, the *bifidobacterium* shunt, and the first half of the glycolytic pathway. The PBG cycle yields acetyl-CoA, which enters the PHB pathway for conversion into PHB bioplastic. Because the Xfp enzyme has dual specificity, acting on fructose-6-phosphate to produce the unwanted side product erythrose-4-phosphate, a salvage pathway was added to allow re-entry of erythrose-4-phosphate into the cycle. The PBG cycle employs two purge valves, used to maintain NAD(P)H levels, that are highlighted with stars.
Figure 1B:
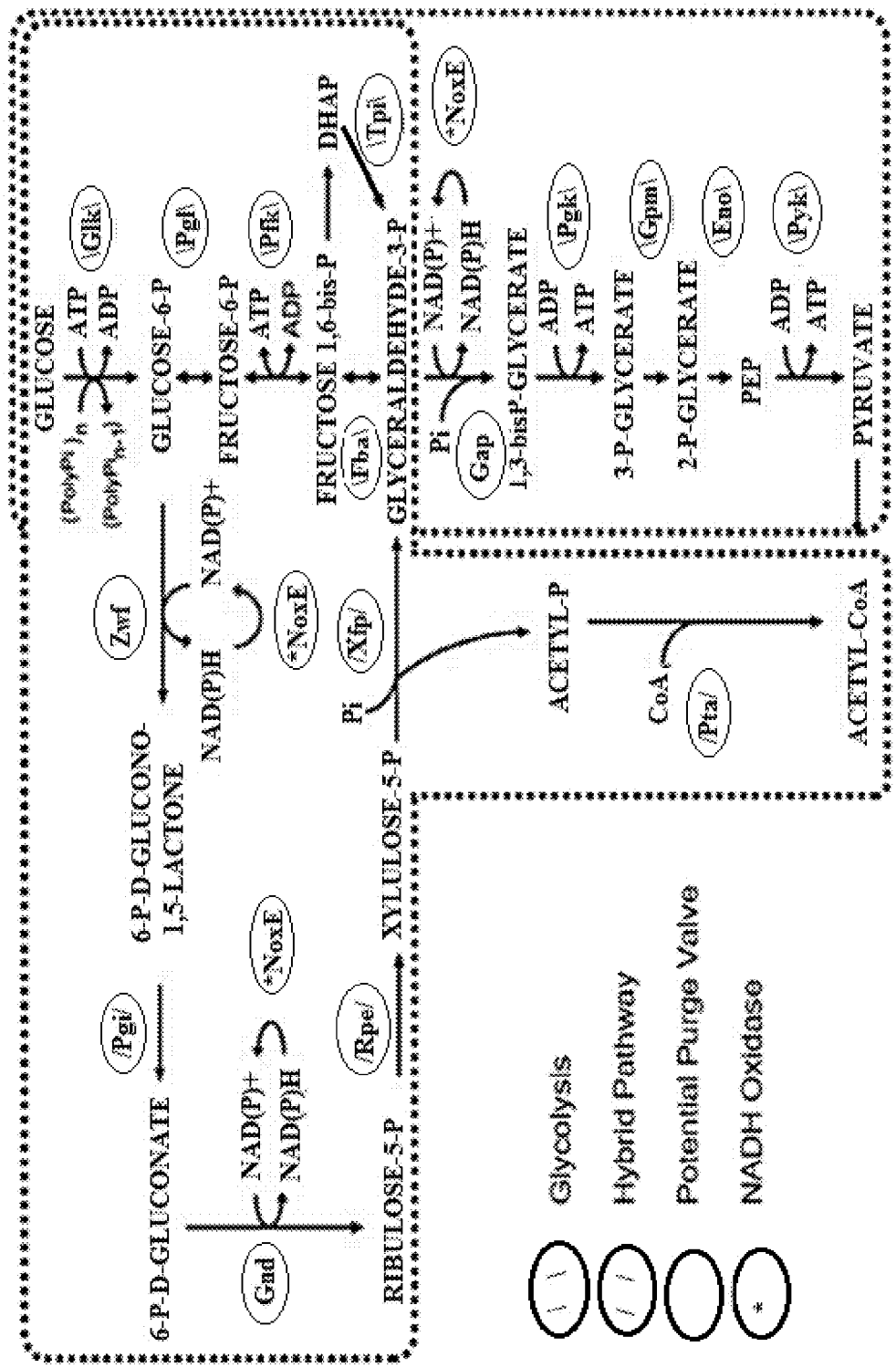
Figure 1C:
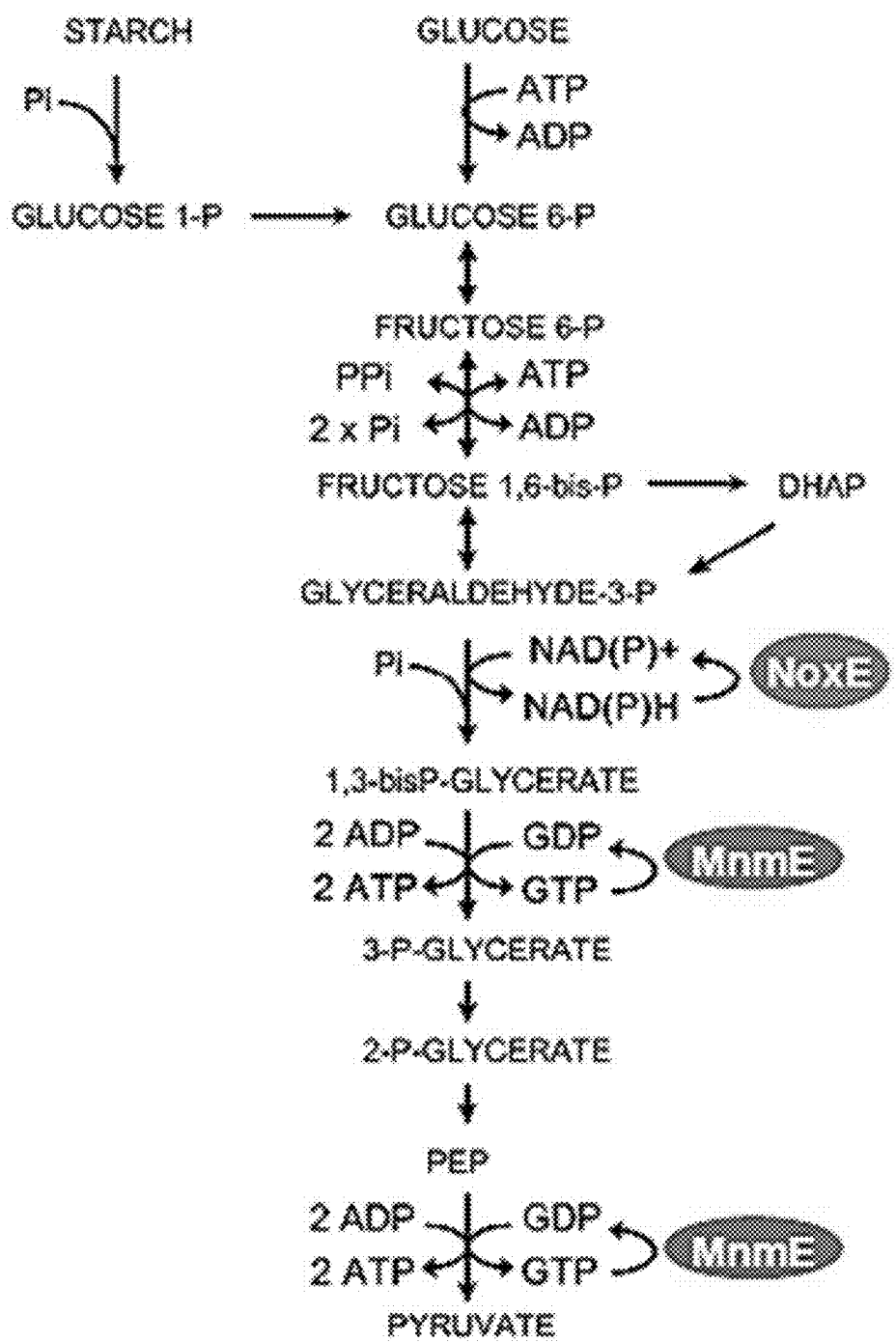
Figure 1D:
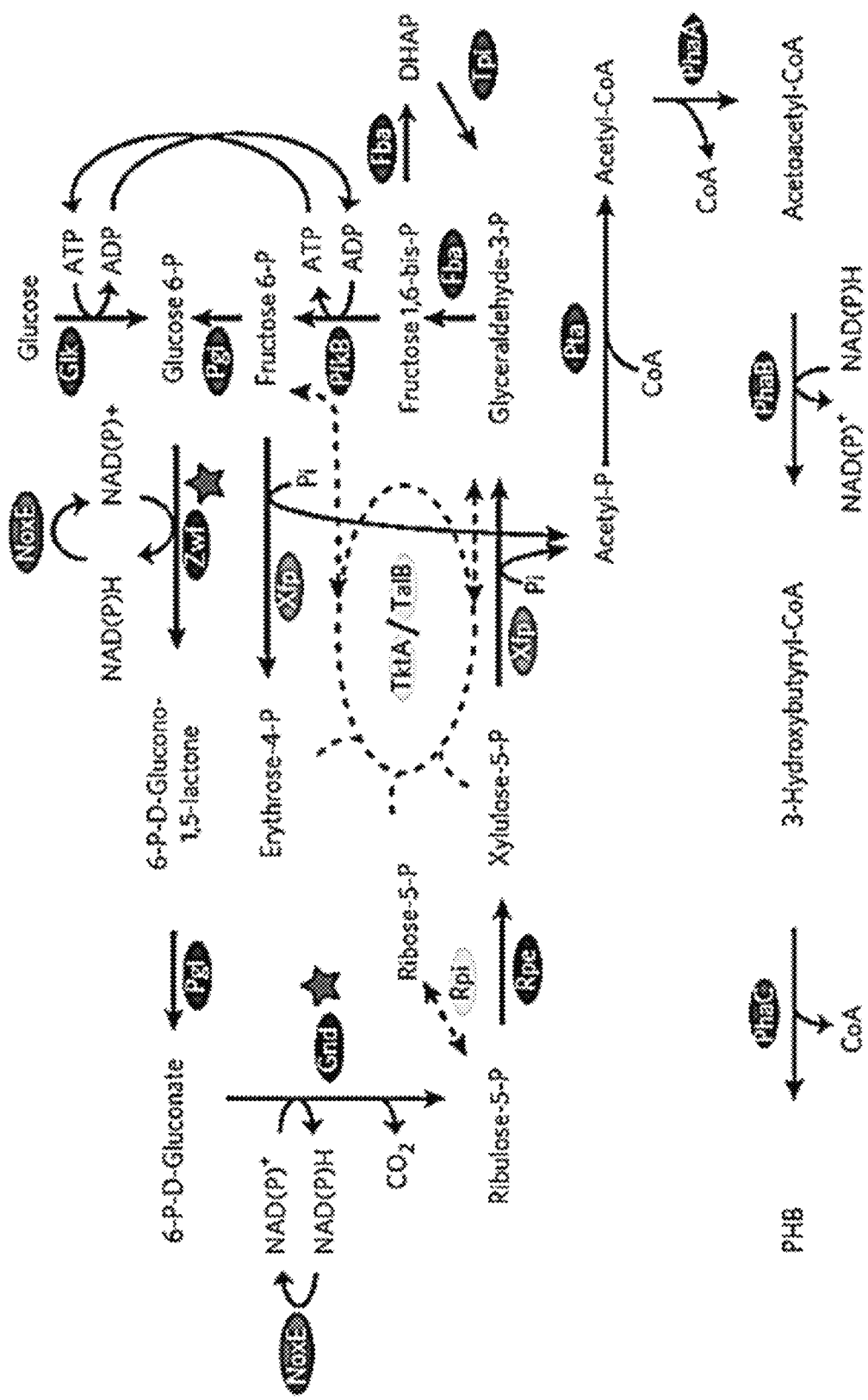
Figure 2A:
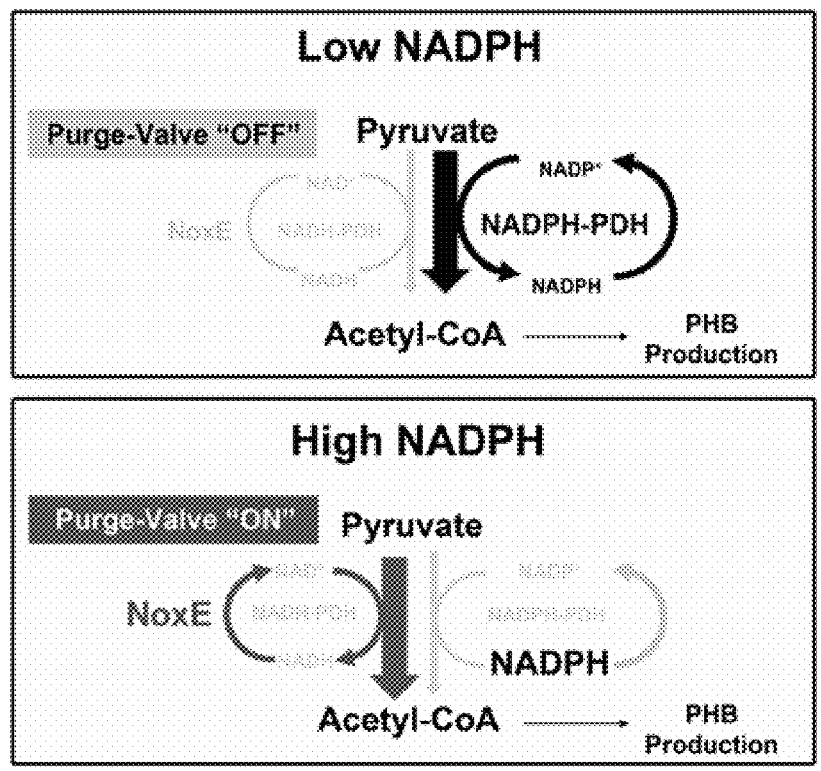
FIG. 2A-B shows an exemplary purge valve designs and system of the disclosure.
Figure 2A:
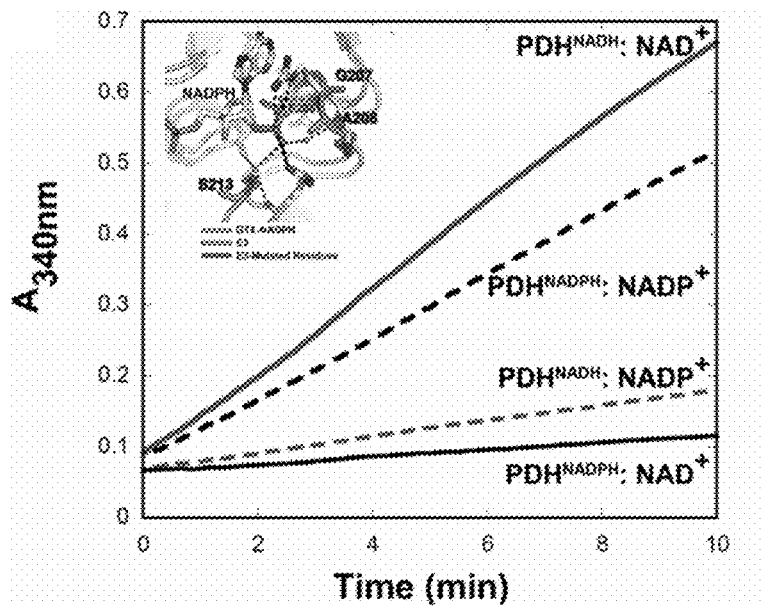
Figure 2A:
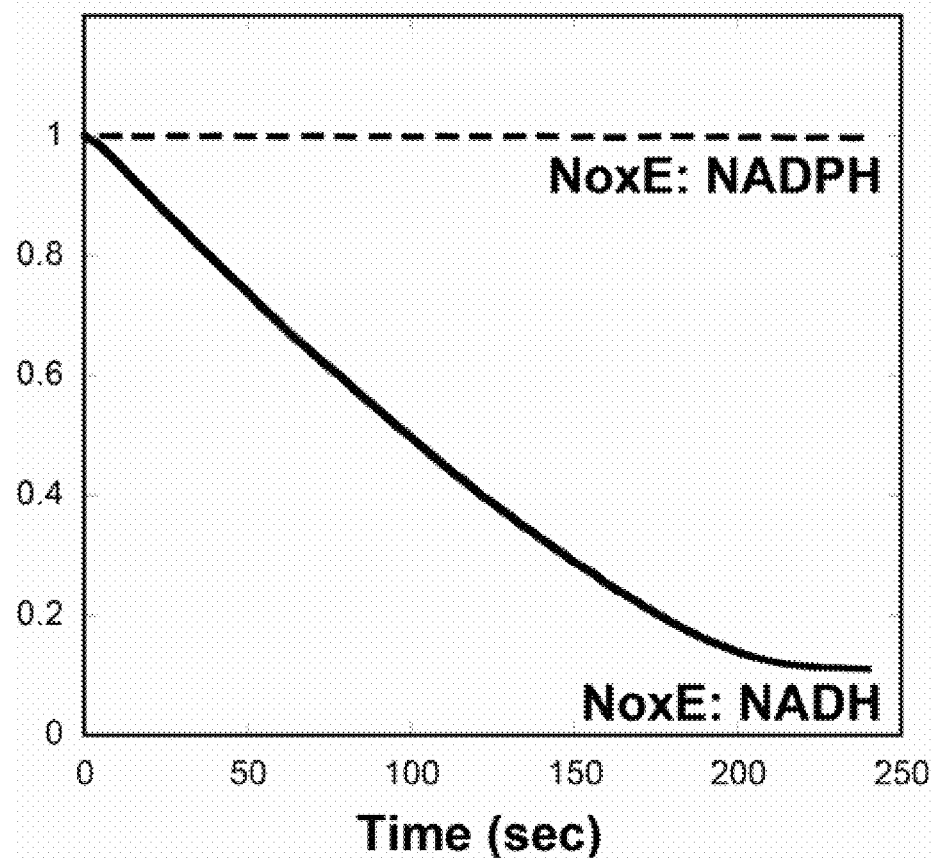
Figure 2A:
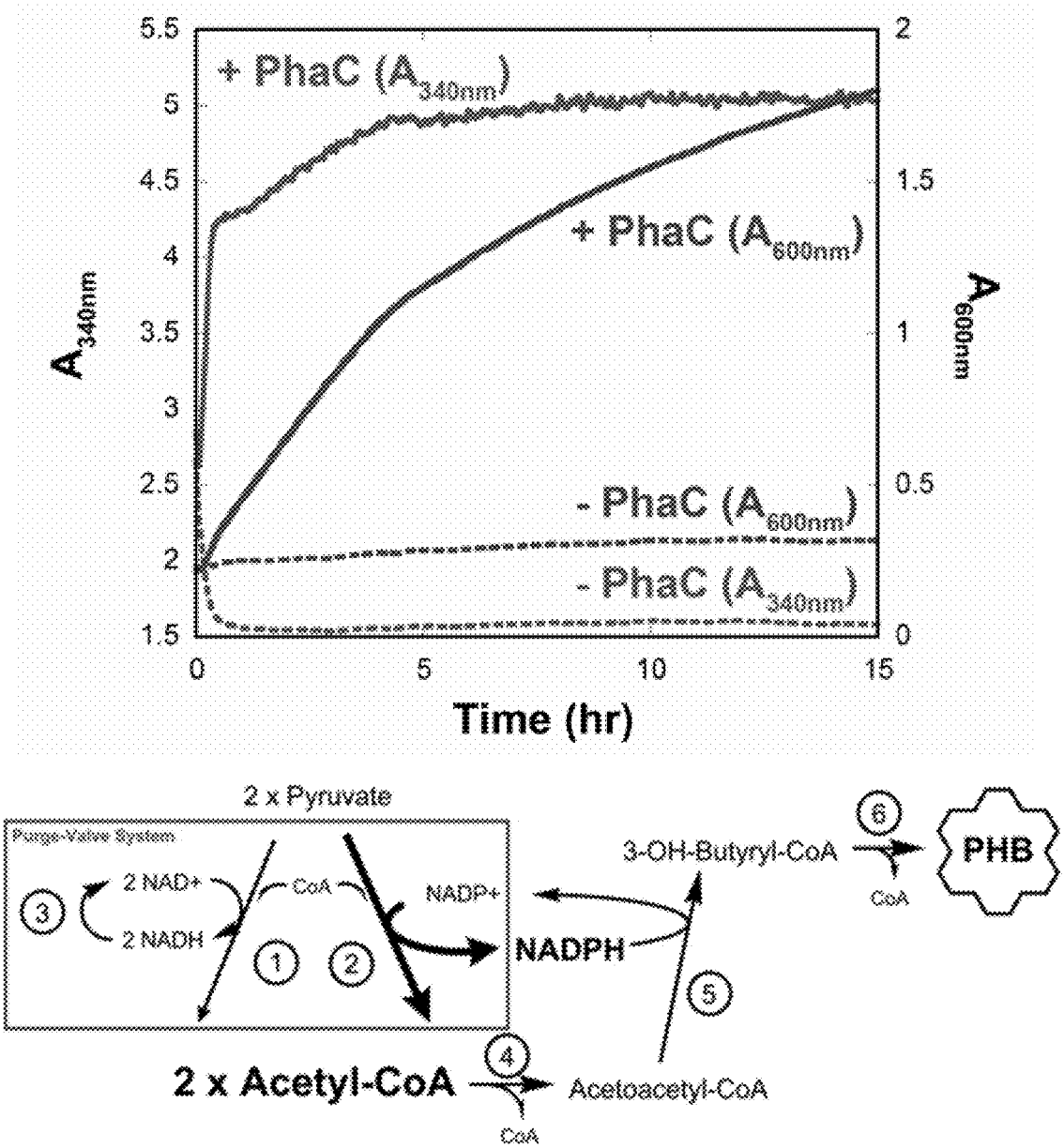
Figure 2A:
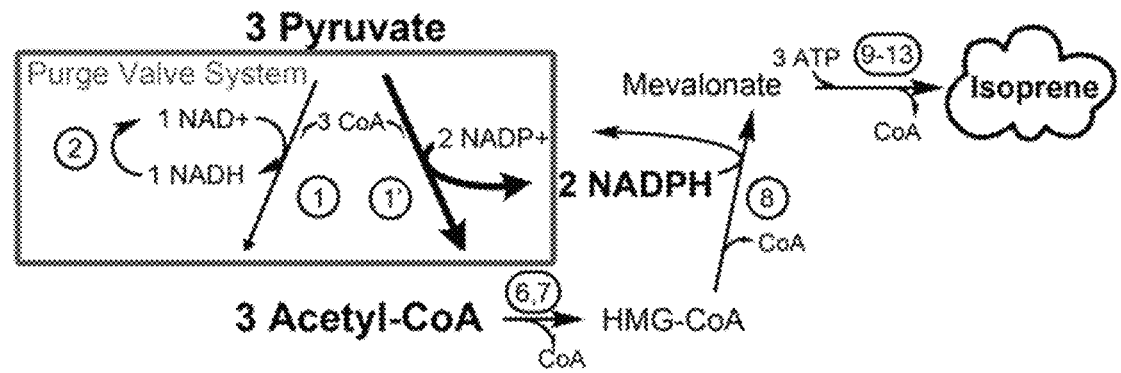
Figure 2A:
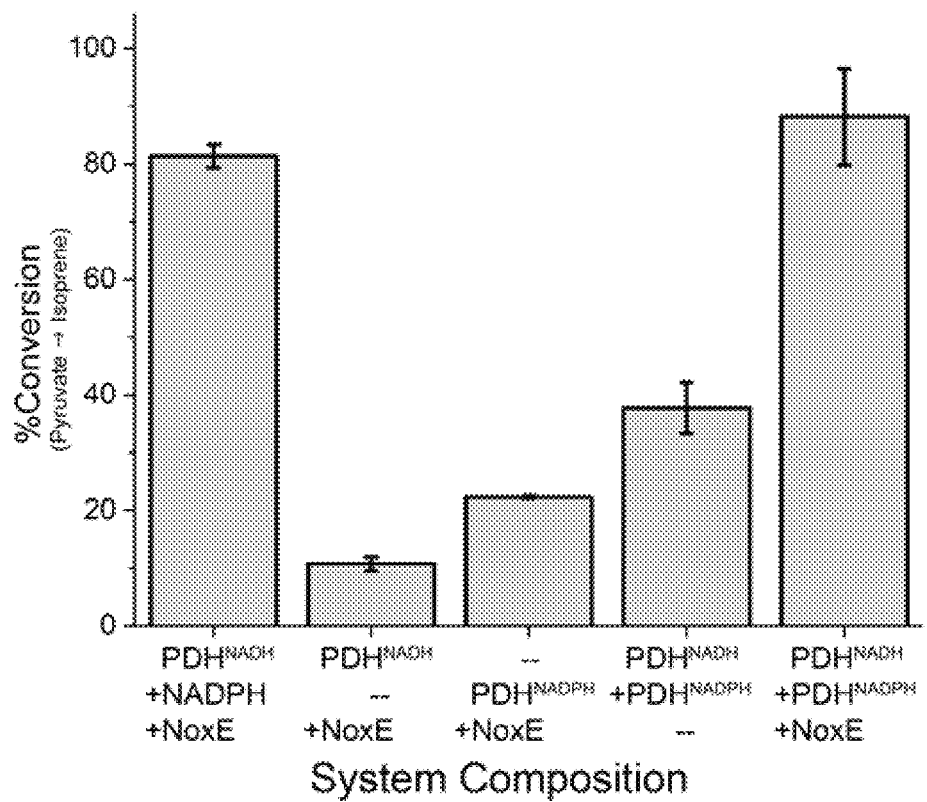
Figure 2B:
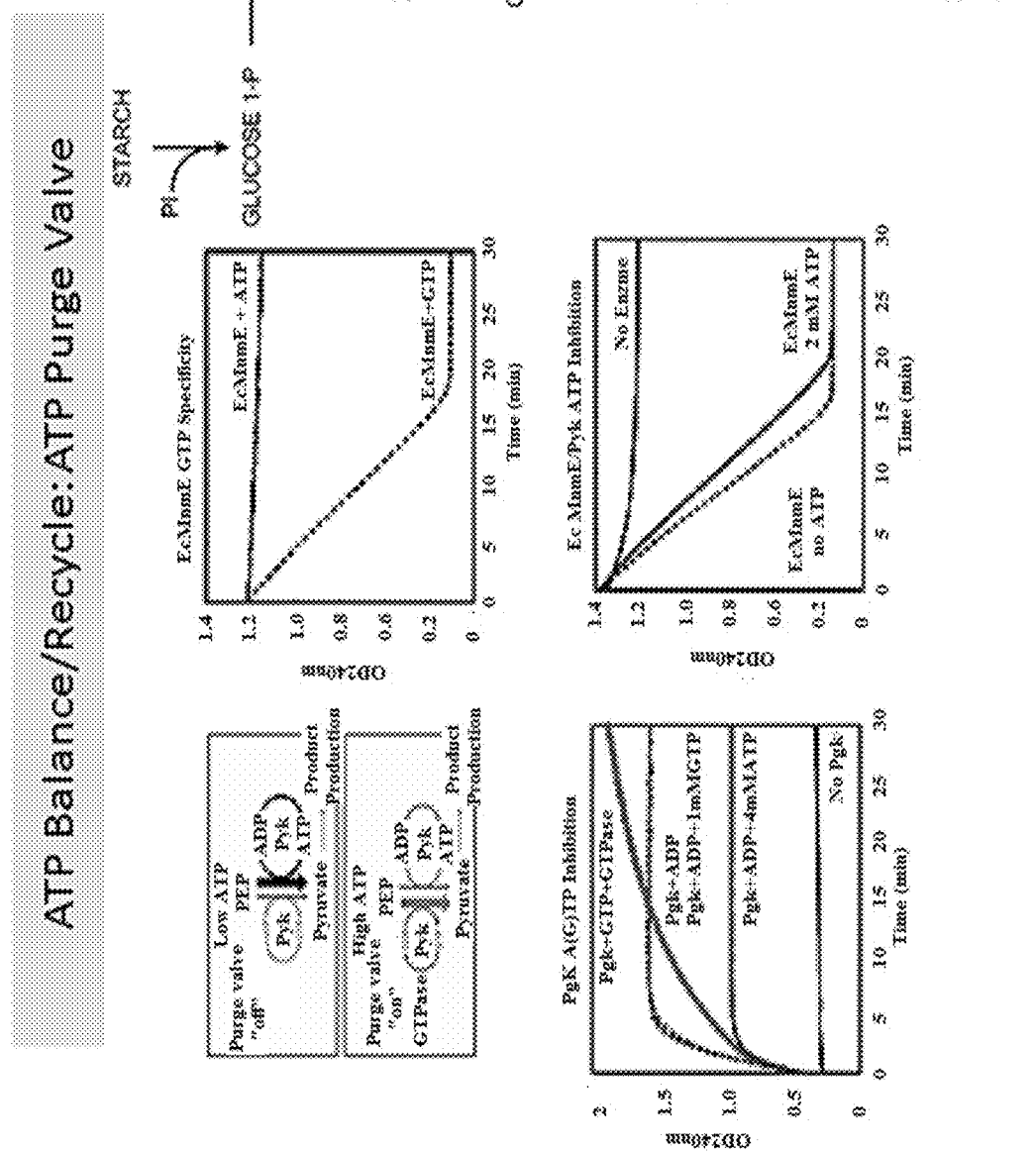

The assembly of self-regulating synthetic biochemical pathways in vitro has great potential as alternative catalysts for the high-yield production of low value/high volume commodity chemicals from biomass. The disclosure provides in vitro and in vivo metabolic engineering, called synthetic biochemistry, where the glycolysis pathway of central metabolism was deconstructed and then reconstituted in vitro with an anabolic pathway that can produce useful compounds at high yield. In the synthetic biochemistry system described, reducing equivalents, ATP, and carbon from glycolysis are funneled through the anabolic pathways to produce acetyl-phosphate, pyruvate, and acetyl-CoA from glucose. The implementation of the in vitro pathway use a molecular purge-valve consisting of an $NAD^+$ and $NADP^+$ specific enzymes (i.e., wild-type and/or mutant), and NADH oxidase, NoxE, to maintain proper $NADP^+$/NADPH cofactor balance while allowing continuous carbon flux. This purge-valve concept is readily transportable to other NAD(P)H generating steps in central metabolism (see, e.g., FIG. 2). Similarly, an ATP purge valve system can be utilized to regenerate ADP. FIG. 1C shows one such pathway utilizing a GTPase enzyme.

Figure 3:
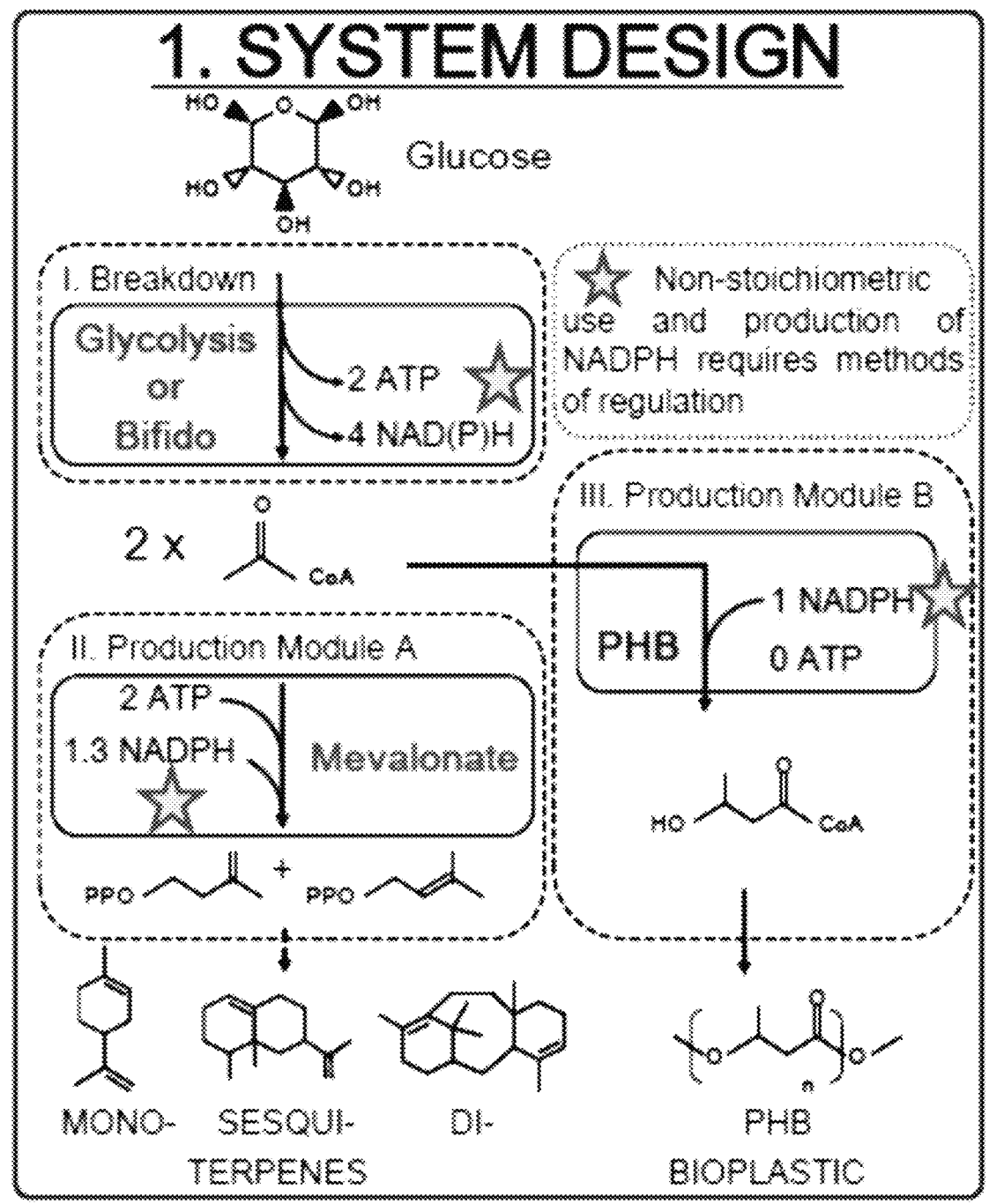
FIGS. 3 and 4 show a schematic design and development of a pathway of the disclosure.
Figure 4:
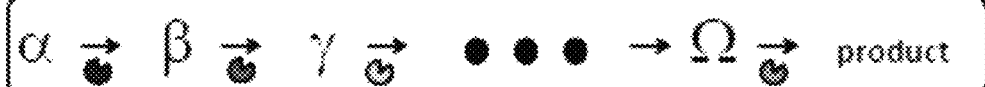
Figure 5:
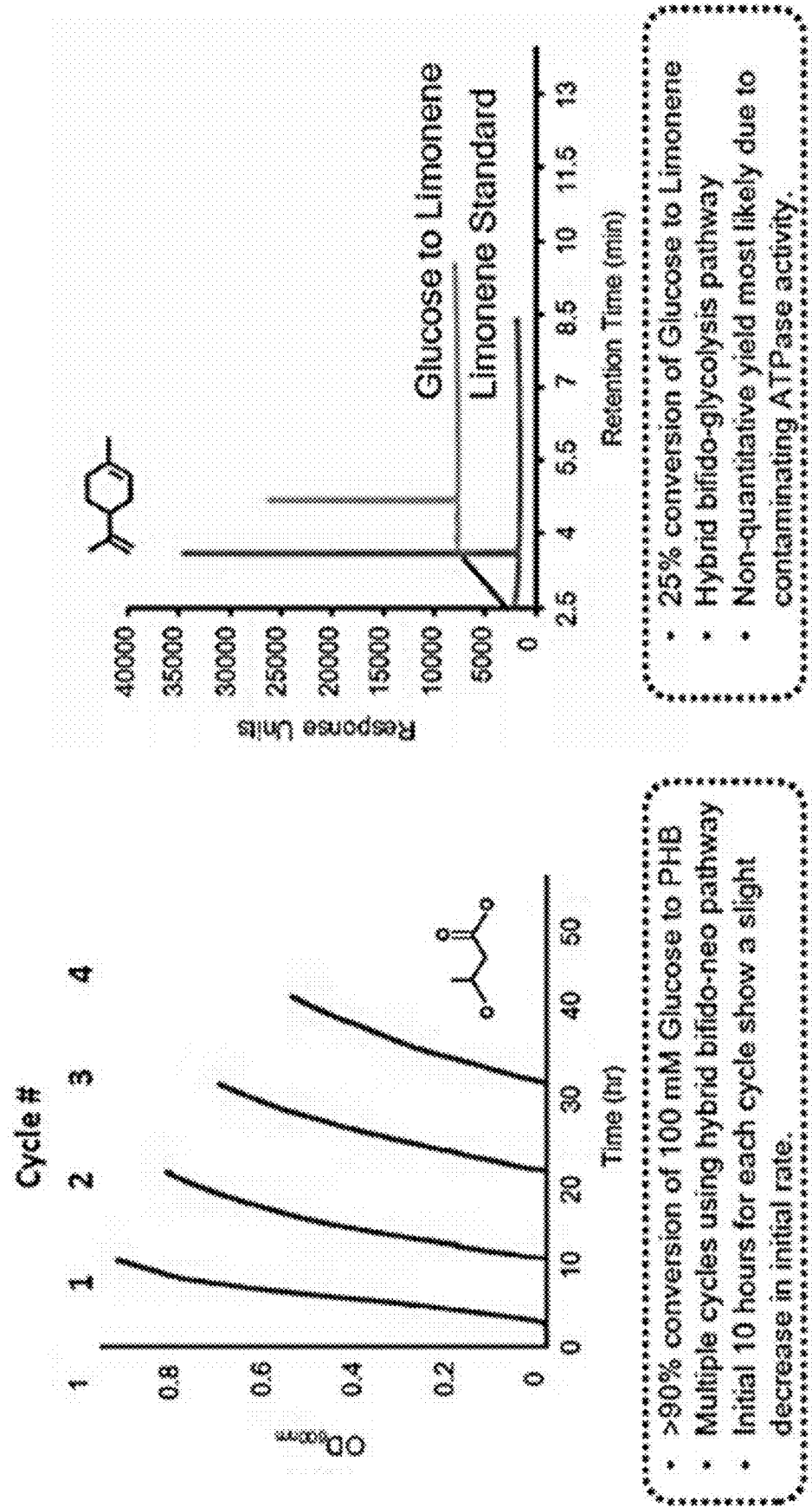
FIG. 5 shows data obtained for the conversion of glucose to product using a purge valve system.
Figure 6:
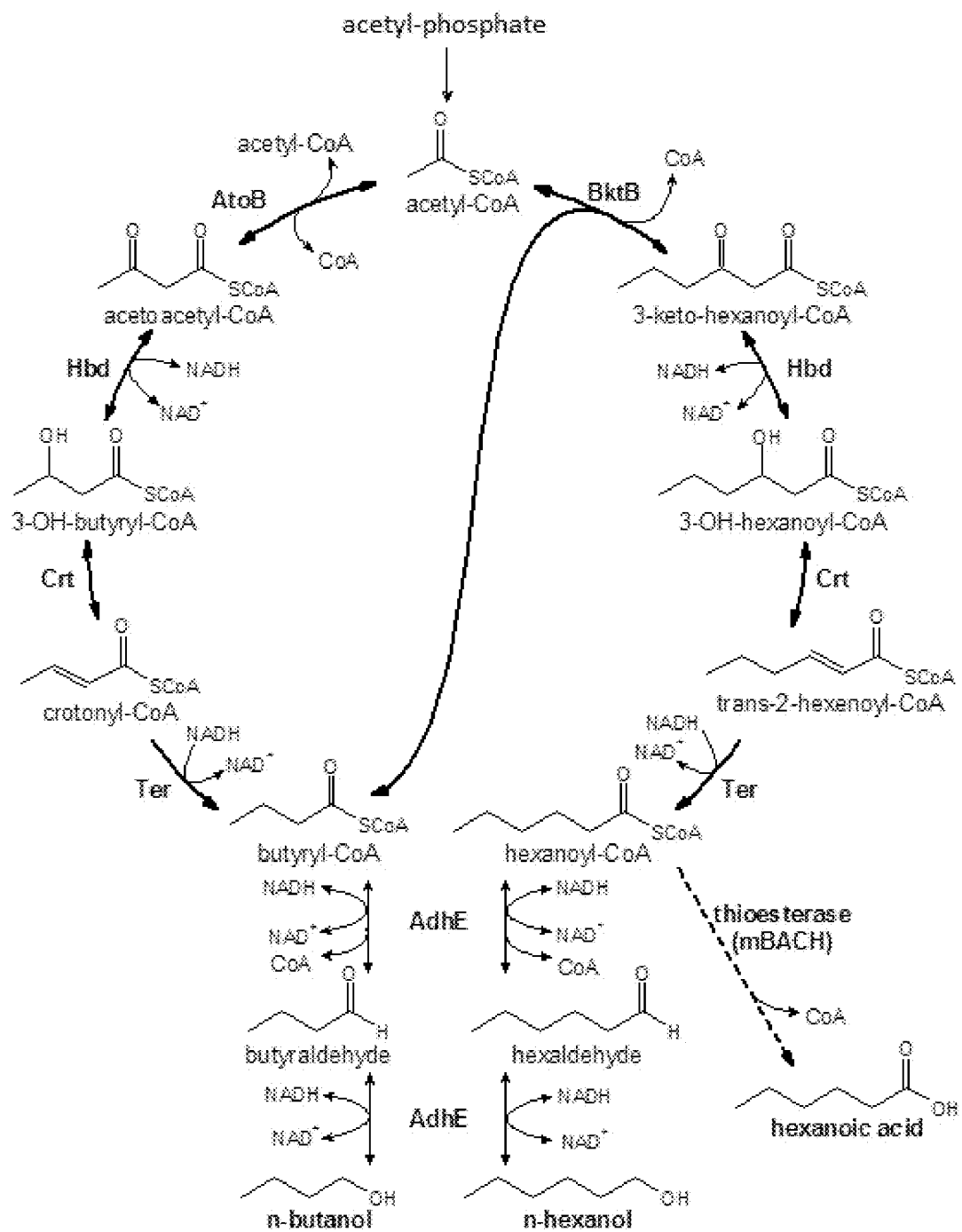
FIG. 6 shows additional enzymes and pathway for converting acetyl-phosphate and acetyl-CoA to various chemicals and biofuels.

A general concept is schematically depicted in FIGS. 3 and 4. This general concept is characterized in FIG. 4 as (i) designing catabolic and anabolic pathways, including cofactor balancing; (ii) choosing appropriate enzymes (e.g., clone, express and isolate); and (iii) mixing the enzymes with cofactors and substrate and running the reaction.

The disclosure provides methods and compositions (including cell free systems) for the production of pyruvate or acetyl-CoA from glucose or other suitable carbon source.

In the pathways shown in FIG. 1A-D, for example, glucose (Glu) is the input molecule, which is converted to glucose-6-phosphate (G6P) using a glucokinase (Glk) (e.g., as provided in SEQ ID NO:19, or a homolog or variant thereof that is at least 80% identical thereto). The G6P is converted to 6 phospho-D-glucono-1,5-lactone by glucose-6 phosphate dehydrogenase (Zwf or mutant thereof; see, e.g., SEQ ID NOs: 22, 23 and 24). One or a combination of Zwf enzymes can be used. In one embodiment, a wild-type Zwf is used that uses $NADP^+$ as a cofactor. In another embodiment, a mutant Zwf (mZwf; e.g., having an A47D mutation; see SEQ ID NO:24) is used that uses $NAD^+$ as a cofactor. In yet another embodiment, a combination of Zwf and mZwf are used. A molecular purge valve comprising a water generating NADH oxidase (NoxE; e.g., as provided in SEQ ID NO:18, or a homolog or variant thereof that is at least 80% identical thereto) that specifically oxidizes NADH, but not NADPH can be used to recycle ("purge") NADH when a mutant Zwf is used that preferentially uses $NAD^+$. A 6-phosphogluconolactonase (pgl; e.g., as provided in SEQ ID NO:26, or a homolog or variant thereof that is at least 80% identical thereto) converts 6 phospho-D-glucono-1,5-lactone to 6-phospho-D-gluconate. The 6-phospho-D-gluconate is then converted to ribulose-5-phosphate with a release of $CO_2$ by 6-phosphogluconate dehydrogenase (gnd; e.g., as provided in SEQ ID NO:27, or a homolog or variant thereof that is at least 80% identical thereto) or a mutant thereof. One or a combination of Gnd enzymes can be used. In one embodiment, a wild-type Gnd is used that uses $NADP^+$ as a cofactor. In another embodiment, a mutant Gnd (mGnd; e.g., having an N33D/R34Y/K38L mutation relative to the sequence of SEQ ID NO:27 and as provided in SEQ ID NO:28) is used that uses $NAD^+$ as a cofactor. In yet another embodiment, a combination of Gnd and mGnd are used. A molecular purge valve comprising a water generating NADH oxidase (NoxE) that specifically oxidizes NADH, but not NADPH can be used to recycle ("purge") NADH when a mutant Gnd is used that preferentially uses $NAD^+$. A ribulose 5-phosphate epimerase (Rpe; e.g., as provided in SEQ ID NO:6, or a homolog or variant thereof that is at least 80% identical thereto) then catalyzes the formation of xylulose 5-phosphate from ribulose 5-phosphate. Phosphoketolases (either fructose 6-phosphate phosphoketolase, Fpk, or xylulose 5-phosphate phosphoketolase, Xpk (aka Xfp); or a bifunctional F/Xpk) are used to convert xylulose-5-phosphate to glyceride-3-phosphate or fructose-6-phosphate to erythrose-4-phosphate while generating acetyl-phosphate (AcP) as an output. Xylulose-5-phosphate and erythrose-4-phosphate can also be metabolized by a transketolase (tkt; e.g., as provided in SEQ ID NO:12, or a homolog or variant thereof that is at least 80% identical thereto). The pathway can comprise a transaldolase (talB; e.g., as provided in SEQ ID NO:10, or a homolog or variant thereof that is at least 80% identical thereto) and a ribulose-5 phosphate isomerase (RpiA; e.g., as provided in SEQ ID NO:8, or a homolog or variant thereof that is at least 80% identical thereto). This primary pathway produces acetyl-CoA from glucose.

In a secondary or further pathway, glyceraldehyde-3-phosphate can be further converted to acetyl-coA. For example, glyceraldehyde-3-phosphate dehydrogenase (Gap, Tdh) converts glyceraldehyde-3-phosphate to 1,3-bisphospho-glycerate. In one embodiment, the Gap or Tdh enzyme may be knocked-out to promote flux of metabolites and co-factors in a desired direction. Alternatively, one or a combination of Gap enzymes can be used. In one embodiment, a wild-type Gap is used that uses $NAD^+$ as a cofactor (see, e.g., SEQ ID NO:29) or a mutant gap comprising a P188D mutation (relative to the sequence of SEQ ID NO:29 and as shown in SEQ ID NO:31). In another embodiment, a mutant gap (mGap; e.g., having a D34A/L35R/T35K mutation; relative to the sequence of SEQ ID NO:29 and as shows in SEQ ID NO:30) is used that uses $NADP^+$ as a cofactor. In yet another embodiment, a combination of gap and mGap are used. A molecular purge valve comprising a water generating NADH oxidase (NoxE) that specifically oxidizes NADH, but not NADPH can be used to recycle ("purge") NADH when a wild-type gap or P118D mutant gap is used that preferentially uses $NAD^+$. 1,3-bis-glycerate can be converted by phosphoglycerate kinase (EC 2.7.2.3) (PGK; e.g., as provided in SEQ ID NO:32, or a homolog or variant thereof that is at least 80% identical thereto) which catalyzes the reversible transfer of a phosphate group from 1,3-bisphosphoglycerate (1,3-BPG) to ADP producing 3-phosphoglycerate (3-PG) and ATP. A molecular purge valve for ATP can be present to recycle ADP using, for example, a GTPase or other enzyme as provided in SEQ ID NOs: 34, 36, 38, 40, or 42 or a homolog or variant thereof that is at least 80% identical thereto) The 3-phospho-glycerate can then be converted by a phosphoglycerate mutase (pgm; e.g., as provided in SEQ ID NO:27, or a homolog or variant thereof that is at least 80% identical thereto) to 2-phosphoglycerate. An enolase (eno; e.g., as provided in SEQ ID NO:44, or a homolog or variant thereof that is at least 80% identical thereto) can then convert the 2-phosphoglycerate to phosphenolpyruvate (PEP). A pyruvate kinase (pyk; e.g., as provided in SEQ ID NOs:45, 46, and 47, or a homolog or variant thereof that is at least 80% identical thereto) converts PEP to pyruvate. A pyruvate decarboxylase (PDC; e.g., as provided in SEQ ID NO:48, or a homolog or variant thereof that is at least 80% identical thereto) converts pyruvate to acetaldehyde which can then be converted to acetyl-CoA by the actions of propionaldehyde dehydrogenase (PduP; e.g., as provided in SEQ ID NO:49, or a homolog or variant thereof that is at least 80% identical thereto). Alternatively, a pyruvate oxidase (Pox, e.g., SEQ ID NO:58, or homolog or variant thereof that is at least 80% identical thereto) can be used to convert pyruvate to acetyl-phosphate. Alternatively, a pyruvate dehydrogenase (PDH; e.g., as provided in SEQ ID NO:59-63, i.e., the PDH complex, or a homolog or variant thereof that is at least 80% identical thereto) can be used to convert pyruvate directly to acetyl-CoA and NADH. One or a combination of PDH enzymes can be used. In one embodiment, a wild-type PDH is used that uses $NAD^+$ as a cofactor. In another embodiment, a mutant PDH (mPDH; e.g., having a G185A/G189A/E203V/M204R/F205K/D206H/P210R mutation; see, e.g., Bocanegra et al., Biochemistry, 32(11):2737-2740, 1993, incorporated herein by reference; SEQ ID NO:64) is used that uses $NADP^+$ as a cofactor. In yet another embodiment, a combination of PDH and mPDH are used. A molecular purge valve comprising a water generating NADH oxidase (NoxE) that specifically oxidizes NADH, but not NADPH can be used to recycle ("purge") NADH when a wild-type gap or P118D mutant gap is used that preferentially uses $NAD^+$.

In some embodiments, where ADP is a limiting co-factor an ATP purge valve can be employed to regenerate ADP. In this embodiment, a GTPase can be used to recycle ADP. An example of this is depicted in FIG. 1C. In this embodiment, an enzyme encoded by MnmE from E. coli (or a homolog or variant thereof) can be used. For example, SEQ ID NOs: 34, 36, 38, 40, and 42, provide various enzymes that can serve as purge valves for ATP accumulation.

AcP can be converted to acetyl-CoA by acetyltransferase (Pta, Pta variant or homolog thereof), or to acetate by acetate kinase (Ack, Ack variant or homolog thereof). Pyruvate or Acetyl-CoA can be converted to alcohols. Acetyl-CoA can be converted to fatty acids, or other products if additional ATP or reducing power is provided.

Both in vitro and in vivo systems are contemplated herein and provide a robust and effective metabolic pathway for the production of acetyl-phosphate, pyruvate, glyceraldehyde-3-phosphate, and acetyl-CoA. Thus, the disclosure provides both a cell-free (in vitro) pathway and a recombinant microorganism pathway for the production of acetyl-phosphate and acetyl-CoA.

The disclosure provides an in vitro method of producing acetyl-phosphate, pyruvate, glyceraldehyde-3-phosphate, acetyl-CoA and chemicals and biofuels that use pyruvate or acetyl-CoA as a substrate. In this embodiment, of the disclosure cell-free preparations can be made through, for example, three methods. In one embodiment, the enzymes of the pathway, as described more fully elsewhere herein, are purchased and mixed in a suitable buffer and a suitable substrate is added and incubated under conditions suitable for acetyl-phosphate and/or pyruvate or glyceraldehyde-3-phosphate and/or acetyl-CoA production. In another embodiment, one or more polynucleotides encoding one or more enzymes of the pathway are cloned into one or more microorganisms under conditions whereby the enzymes are expressed. Subsequently the cells are lysed and the lysed preparation comprising the one or enzymes derived from the cell are combined with a suitable buffer and substrate (and one or more additional enzymes of the pathway) to produce acetyl-phosphate and/or pyruvate or glyceraldehyde-3-phosphate or acetyl-CoA from the substrate. Alternatively, the enzymes can be isolated from the lysed preparations and then recombined in an appropriate buffer. In yet another embodiment, a combination of purchased enzymes and expressed enzymes are used to provide a pathway in an appropriate buffer.

For example, to construct an in vitro system, all the enzymes are acquired commercially or purified by affinity chromatography, tested for activity, and mixed together in a properly selected reaction buffer. The system can comprise at least 13 enzymes: Fpk/Xpk (aka Xfp), fructose bisphosphate aldolase (Fba), triose phosphate isomerase (Tpi), ribulose-5-phosphate 3-epimerase (Rpe), ribose-5-phosphate isomerase (Rpi), transketolase (Tkt), phosphoglucoisomerase (Pgi), transaldolase (Tal), phosphofructokinase (pfk), glucokinase (glk), phosphogluconolactonase (pgl), phosphogluconate dehydrogenase (gnd), glucose-6-phosphate dehydrogenase (zwf), and an NADH oxidase (noxE). Acetyl-phosphate concentration is measured using an end-point colorimetric hydroxamate method. Using this in vitro system a 10 mM amount of glucose (Glu) is completely converted to stoichiometric amounts of AcP (within error) at room temperature after 1.5 hours.

To extend the production further to acetate, Ack is added to the in vitro system. When Ack is added, it is useful to include a phosphofructokinase to maintain ATP-balance. Since the ADP (the substrate for acetate kinase) is regenerated, only a catalytic amount is necessary.

The disclosure also provides recombinant organisms comprising metabolically engineered biosynthetic pathways that comprise the enzymatic pathway above (e.g., the pathway depicted in FIG. 1) for the production of acetyl-phosphate, pyruvate, glyceraldehyde-3-phosphate, acetyl-CoA and/or products derived therefrom.

In one embodiment, the disclosure provides a recombinant microorganism comprising elevated expression of at least one target enzyme as compared to a parental microorganism or encodes an enzyme not found in the parental organism. In another or further embodiment, the microorganism comprises a reduction, disruption or knockout of at least one gene encoding an enzyme that competes with a metabolite necessary for the production of a desired metabolite or which produces an unwanted product. The recombinant microorganism produces at least one metabolite involved in a biosynthetic pathway for the production of, for example, acetyl-phosphate, pyruvate, glyceraldehyde-3-phosphate and/or acetyl-CoA. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of, for example, acetyl-phosphate, pyruvate, glyceraldehyde-3-phosphate and/or acetyl-CoA. The target enzyme is encoded by, and expressed from, a polynucleotide derived from a suitable biological source. In some embodiments, the polynucleotide comprises a gene derived from a bacterial or yeast source and recombinantly engineered into the "recombinant" microorganism of the disclosure.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. The disclosure provides in vitro systems and recombinant microorganism having a biosynthetic pathway or metabolically engineered pathway for the production of a desired product or intermediate.

As used herein, the term "metabolically engineered" or "metabolic engineering" involves rational pathway design and assembly of biosynthetic genes, genes associated with operons, and control elements of such polynucleotides, for the production of a desired metabolite, such as an acetyl-phosphate, pyruvate, glyceraldehyde-3-phosphate and/or acetyl-CoA, higher alcohols or other chemical, in a microorganism. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogeneic to the host organism, the polynucleotide can be codon optimized.

Accordingly, an in vitro biosynthetic pathway is produced via the introduction of enzymes into a buffer system that leads to the production of desired intermediate(s). A buffer system can be a single fluid buffer that includes all the desired enzymes or may include a plurality of fluid buffers each comprising a set or subset of enzymes. For example, a microfluidic device can comprise a plurality of reaction wells that each contain a set of enzymes in the biosynthetic pathway for the production of acetyl-phosphate and/or pyruvate and or glyceraldehyde-3-phosphate and/or acetyl-CoA. A substrate (which can include intermediates) is flowed through the various channels and wells to produce a product or additional intermediates. As described herein, the enzymes can be purchased from vendors, expressed from microorganisms and purified or expressed from microorganisms and unpurified. In addition, it is contemplated that the biosynthetic pathway can comprise a combination of in vitro enzyme reactions and whole cells (e.g., prokaryotic and/or eukaryotic) that express a subset of the enzymes in the pathway, wherein the microorganism can utilize or provide metabolites from or to the in vitro system, respectively.

An "enzyme" means any substance, typically composed wholly or largely of amino acids making up a protein or polypeptide that catalyzes or promotes, more or less specifically, one or more chemical or biochemical reactions.

A "protein" or "polypeptide", which terms are used interchangeably herein, comprises one or more chains of chemical building blocks called amino acids that are linked together by chemical bonds called peptide bonds. A protein or polypeptide can function as an enzyme.

A "native" or "wild-type" protein, enzyme, polynucleotide, gene, or cell, means a protein, enzyme, polynucleotide, gene, or cell whose primary sequence occurs in nature. A "native" or "wild-type" protein may be "recombinantly expressed".

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., a carbohydrate, a sugar phosphate, pyruvate etc.), an intermediate in (e.g., acetyl-coA), or an end product (e.g., 1-butanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. In an illustrative embodiment, the introduction of genetic material into a parental microorganism results in a new or modified ability to produce acetyl-phosphate, pyruvate and/or acetyl-CoA or to produce such metabolites at different levels compared to a non-engineered microorganism. The genetic material introduced into the parental microorganism contains gene(s), or parts of gene(s), coding for one or more of the enzymes involved in a biosynthetic pathway for the production of acetyl-phosphate and/or acetyl-CoA, and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produced a new or greater quantities of an intercellular metabolite, improve the flux of a metabolite down a desired pathway, and/or reduce the production of undesirable by-products). This can be particularly relevant in the preparation of in vitro systems where a disrupted cell preparation is used. In such preparations, the knocking out or disruption of a competing pathway comprising enzymes can be useful.

A "parental microorganism" refers to a cell used to generate a recombinant microorganism. The term "parental microorganism" describes a cell that occurs in nature, i.e. a "wild-type" cell that has not been genetically modified. The term "parental microorganism" also describes a cell that serves as the "parent" for further engineering.

For example, a wild-type microorganism can be genetically modified to express or over express a first target enzyme such as a phosphoketolase. This microorganism, in turn, can act as a parental microorganism in the generation of a microorganism modified to express or over-express a third target enzyme e.g., a transaldolase. In turn, the microorganism can be modified to express or over express e.g., a transketolase and a ribose-5 phosphate isomerase, which can be further modified to express or over express a third target enzyme, e.g., a ribulose-5-phosphate epimerase.

Accordingly, a parental microorganism functions as a reference cell for successive genetic modification events. Each modification event can be accomplished by introducing one or more nucleic acid molecules in to the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

Polynucleotides that encode enzymes useful for generating metabolites (e.g., enzymes such as phosphoketolase, transaldolase, transketolase, ribose-5-phosphate isomerase, ribulose-5-phosphate epimerase, fructose 1,6-bisphosphate aldolase, fructose 1,6 bisphosphates etc.) including homologs, variants, fragments, related fusion proteins, or functional equivalents thereof, are used in recombinant nucleic acid molecules that direct the expression of such polypeptides in appropriate host cells, such as bacterial or yeast cells. Exemplary polynucleotide sequences encoding polypeptides useful in the methods are described herein. It is understood that the addition of sequences which do not alter the encoded activity of a nucleic acid molecule, such as the addition of a non-functional or non-coding sequence, is a conservative variation of the basic nucleic acid.

It is understood that a polynucleotide described above include "genes" and that the nucleic acid molecules described above include "vectors" or "plasmids." For example, a polynucleotide encoding a phosphoketolase can comprise an Fpk gene or homolog thereof, or an Xpk gene or homolog thereof, or a bifunctional F/Xpk gene or homolog thereof. Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

The term "polynucleotide," "nucleic acid" or "recombinant nucleic acid" refers to polynucleotides such as deoxyribonucleic acid (DNA), and, where appropriate, ribonucleic acid (RNA).

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate preferred embodiments of the disclosure. The methods of the disclosure describe ways to measure whether a modified polypeptide has a required or desired activity.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (e.g., not pure, but existing in a preparation in an abundance and/or concentration not found in nature) and purified (e.g., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

The term "recombinant microorganism" and "recombinant host cell" are used interchangeably herein and refer to microorganisms that have been genetically modified to express or over-express endogenous polynucleotides, or to express non-endogenous sequences, such as those included in a vector. The polynucleotide generally encodes a target enzyme involved in a metabolic pathway for producing a desired metabolite as described above, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway associated with a metabolically engineered microorganism as described herein. With respect to the pathway described herein, a starting material can be any suitable carbon source including, but not limited to, glucose, fructose or other biomass sugars etc. These starting materials may be metabolized to a suitable sugar or sugar phosphate that enters the pathway as set forth in FIG. 1.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

The disclosure provides methods for the heterologous expression of one or more of the biosynthetic genes or polynucleotides involved in acetyl-phosphate synthesis, acetyl-CoA biosynthesis or other metabolites derived therefrom and recombinant DNA expression vectors useful in the method. Thus, included within the scope of the disclosure are recombinant expression vectors that include such nucleic acids.

Recombinant microorganisms provided herein can express a plurality of target enzymes involved in pathways for the production of, or enzymatic preparations for the production of, acetyl-phosphate, pyruvate, glyceraldehyde-3-phosphate, and/or acetyl-CoA or other metabolites derived therefrom from a suitable carbon substrate such as, for example, glucose, fructose or other biomass sugars and the like.

A "biomass derived sugar" includes, but is not limited to, molecules such as glucose, sucrose, cellobiose, mannose, xylose, and arabinose. The term biomass derived sugar encompasses suitable carbon substrates of 1 to 7 carbons ordinarily used by microorganisms, such as 3-7 carbon sugars, including but not limited to glucose, lactose, sorbose, fructose, idose, galactose and mannose all in either D or L form, or a combination of 3-7 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2

KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, and lignin can be generally treated by a variety of chemical, mechanical and enzymatic means to release primarily hexose and pentose sugars. These sugars can then be "fed" into the pathway described herein.

The disclosure demonstrates that the expression or over expression of one or more heterologous polynucleotide or over-expression of one or more native polynucleotides, or an enzymatic in vitro system comprising (i) a polypeptide that catalyzes the production of glucose-6-phosphate from glucose (in one embodiment, using a polyphosphate); (ii) a polypeptide that catalyzes the production of acetyl-phosphate and erythrose-4-phosphate (E4P) from Fructose-6-phosphate; (iii) a polypeptide the catalyzes the conversion of ribulose-5-phosphate to xylulose-5-phosphate; (iv) a polypeptide that converts xylulose-5-phosphate to G3P and acetyl-phosphate; (v) a polypeptide that converts glyceraldehyde-3-phosphate to dihydroxyacetone phosphate (DHAP); (vi) a polypeptide that converts dihydroxyacetone phosphate and glyceraldehyde-3-phosphate to fructose 1,6 biphosphate; (vii) a polypeptide that converts glucose-6-phosphate to 6-phospho-D-glucono-1,5-lactone; (viii) a polypeptide that oxidizes NADH to $NAD^+$; (ix) a polypeptide that converts 6-phospho-D-glucono-1,5-lactone to 6-phospho-D-gluconate; and (x) a polypeptide that converts 6-phospho-D-gluconate to ribulose-5-phosphate.

Accordingly, the disclosure provides systems and recombinant microorganisms that produce acetyl-phosphate, pyruvate, glyceraldehyde-3-phosphate, acetyl-CoA and/or other metabolites derived therefrom wherein the system or microorganism comprises an enzyme that oxidizes NADH to $NAD^+$ and further comprises target enzymes such as one or more of a glucokinase (Glk or variant of homolog thereof, including a polyphosphate-dependent glucokinase), a phosphoketolase (e.g., Fpk, Xpk, or Fpk/Xpk or variant of homolog thereof), a transaldolase (e.g., Tal or variant thereof), a transketolase (e.g., Tkt or variant of homolog thereof), ribose-5-phosphate isomerase (e.g., Rpi or variant of homolog thereof), a ribulose-5-phosphate epimerase (e.g., Rpe or variant of homolog thereof), a triose phosphate isomerase (e.g., Tpi or variant of homolog thereof), a fructose 1,6 bisphosphate aldolase (e.g., Fba or variant of homolog thereof), a phosphoglucoisomerase (e.g., Pgi or variant of homolog thereof), and any combination thereof. In addition, the microorganism may include a disruption, deletion or knockout of expression of an alcohol/acetaldehyde dehydrogenase that preferentially uses acetyl-coA as a substrate (e.g. adhE gene), as compared to a parental microorganism. In some embodiments, further knockouts may include knockouts in a lactate dehydrogenase (e.g., ldh) and frdBC. In other embodiments, knockouts or reductions in expression or activity of one or more of gapA, eda, edd and mgsA may be performed to remove other glycolysis pathways in the microorganism. Other enzymes that can be knocked out or expression reduced include Fbp, glpX, pfkAB and homologs and variants thereof.

It will be recognized that subsystems or organism that have one or more (but not all) of the foregoing enzymes can be utilized and then combined with an organism or other subsystems comprising remaining enzymatic members of the pathway. As described more fully below, a system or microorganism of the disclosure may further include additional enzymes that extend the acetyl-phosphate product to acetyl-CoA, which can then be extended to produce, for example, butanol, isobutanol, 2-pentanone and the like.

A s previously noted, the target enzymes described throughout this disclosure generally produce metabolites. In addition, the target enzymes described throughout this disclosure are encoded by polynucleotides. For example, a fructose-6-phosphoketolase can be encoded by an Fpk gene, polynucleotide or homolog thereof. The Fpk gene can be derived from any biologic source that provides a suitable nucleic acid sequence encoding a suitable enzyme having fructose-6-phosphoketolase activity.

Accordingly, in one embodiment, a system or recombinant microorganism provided herein comprises a glucokinase (Glk, polyphosphate-dependent glucokinase or homolog or variant thereof). This expression may be combined with other enzymes in the metabolic pathway for the production of acetyl-phosphate, acetyl-coA or other metabolites derived therefrom. The Glk can be derived from *G. stearothermophilus* (SEQ ID NO:19). In another embodiment, an engineered variant of Glk can be used so long as it has glucokinase activity and can convert glucose to glucose-6-phosphate. Such engineered variants can be obtained by site-directed mutagenesis, directed evolutions and the like. Thus included within the disclosure are polypeptides that are at least 85-99% identical to the sequence of SEQ ID NO:19 and having glucokinase activity.

In another or further embodiment, a system or recombinant microorganism provided herein includes expression of a phosphofructokinase (Pfk, polyphosphate-dependent Pfk or homolog or variants thereof). This expression may be combined with other enzymes in the metabolic pathway for the production of acetyl-phosphate, acetyl-coA or other metabolites derived therefrom. The Pfk can be derived from *G. stearothermophilus* (SEQ ID NO:20). In another embodiment, an engineered variant of Pfk can be used so long as it has phosphofructokinase activity and can convert fructose 1,6 bisphosphate to fructose-6-phosphate. Such engineered variants can be obtained by site-directed mutagenesis, directed evolutions and the like. Thus included within the disclosure are polypeptides that are at least 85-99% identical to a sequence as set forth in SEQ ID NO:20 and having phosphofructokinase activity (see, e.g., SEQ ID NOs:52-53).

In another or further embodiment, a system or recombinant microorganism provided herein includes a phosphoketolase (e.g., Xpk, Fpk or Xfp). This expression may be combined with the expression or over-expression with other enzymes for the production of acetyl-phosphate, acetyl-CoA or other metabolites derived therefrom as described herein above and below. The phosphoketolase can be derived from various organisms including *Pseudomonas aeruginosa*.

Phosphoketolase enzymes (F/Xpk or Xfp) catalyze the formation of acetyl-phosphate and glyceraldehyde 3-phosphate or erythrose-4-phosphate from xylulose 5-phosphate or fructose 6-phosphate.

In addition to the foregoing, the terms "phosphoketolase" or "F/Xpk" or "Xfp" refer to proteins that are capable of catalyzing the formation of acetyl-phosphate and glyceraldehyde 3-phosphate or erythrose-4-phosphate from xylulose 5-phosphate or fructose 6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:2. Additional homologs include: *Gardnerella vaginalis* 409-05 ref|YP_003373859.1| having 91% identity to SEQ ID NO:2; *Bifidobacterium breve* ref|ZP_06595931.1| having 89% to SEQ ID NO:2; *Cellulomonas fimi* ATCC 484 YP_004452609.1 having 55% to SEQ ID NO:2; *Methylomonas methanica* YP_004515101.1 having 50% identity to SEQ ID NO:2; and *Thermosynechococcus elongatus* BP-1] NP_681976.1 having 49% identity to SEQ ID NO:2. The sequences associated with the foregoing accession numbers are incorporated herein by reference.

In another or further embodiment, a system or recombinant microorganism provided herein includes a ribulose-5-phosphate epimerase. This enzyme may be combined with other enzymes in the metabolic pathway for the production of acetyl-phosphate, acetyl-CoA or other metabolites derived therefrom as described herein above and below. The enzyme produces a metabolite that includes xylulose 5-phosphate from a substrate that includes ribulose 5-phosphate. The ribulose-5-phosphate epimerase can be encoded by a Rpe gene, polynucleotide or homolog thereof. The Rpe gene or polynucleotide can be derived from various microorganisms including *E. coli*.

In addition to the foregoing, the terms "ribulose 5-phosphate epimerase" or "Rpe" refer to proteins that are capable of catalyzing the formation of xylulose 5-phosphate from ribulose 5-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:6. Additional homologs include: *Shigella boydii* ATCC 9905 ZP_11645297.1 having 99% identity to SEQ ID NO:6; *Shewanella loihica* PV-4 YP_001092350.1 having 87% identity to SEQ ID NO:6; *Nitrosococcus halophilus* Nc4 YP_003526253.1 having 75% identity to SEQ ID NO:6; *Ralstonia eutropha* JMP134 having 72% identity to SEQ ID NO:6; and *Synechococcus* sp. CC9605 YP_381562.1 having 51% identity to SEQ ID NO:6. The sequences associated with the foregoing accession numbers are incorporated herein by reference.

In another embodiment, a system or recombinant microorganism provided herein includes a ribose-5-phosphate isomerase. This enzyme may be combined with other enzymes in the metabolic pathway for the production of acetyl-phosphate, acetyl-CoA or other metabolites derived therefrom as described herein above and below. The enzyme produces a metabolite that includes ribulose-5-phosphate from a substrate that includes ribose-5-phosphate. The ribose-5-phosphate isomerase can be encoded by an Rpi gene, polynucleotide or homolog thereof. The Rpi gene or polynucleotide can be derived from various microorganisms including *E. coli*.

In addition to the foregoing, the terms "ribose-5-phosphate isomerase" or "Rpi" refer to proteins that are capable of catalyzing the formation of ribulose-5-phosphate from ribose 5-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:8. Additional homologs include: *Vibrio sinaloensis* DSM 21326 ZP_08101051.1 having 74% identity to SEQ ID NO:8; *Aeromonas media* WS ZP_15944363.1 having 72% identity to SEQ ID NO:8; *Thermosynechococcus elongatus* BP-1 having 48% identity to SEQ ID NO:8; *Lactobacillus suebicus* KCTC 3549 ZP_09450605.1 having 42% identity to SEQ ID NO:8; and *Homo sapiens* AAK95569.1 having 37% identity to SEQ ID NO:8. The sequences associated with the foregoing accession numbers are incorporated herein by reference.

In another embodiment, a system or recombinant microorganism provided herein a transaldolase. This enzyme may be combined with other enzymes in the metabolic pathway for the production of acetyl-phosphate, acetyl-CoA or other metabolites derived therefrom as described herein above and below. The enzyme produces a metabolite that includes sedoheptulose-7-phosphate from a substrate that includes erythrose-4-phosphate and fructose-6-phosphate. The transaldolase can be encoded by a Tal gene, polynucleotide or homolog thereof. The Tal gene or polynucleotide can be derived from various microorganisms including *E. coli*.

In addition to the foregoing, the terms "transaldolase" or "Tal" refer to proteins that are capable of catalyzing the formation of sedoheptulose-7-phosphate from erythrose-4-phosphate and fructose-6-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:10. Additional homologs include: *Bifidobacterium breve* DSM 20213 ZP_06596167.1 having 30% identity to SEQ ID NO:10; *Homo sapiens* AAC51151.1 having 67% identity to SEQ ID NO:10; Cyanothece sp. CCY0110 ZP_01731137.1 having 57% identity to SEQ ID NO:10; *Ralstonia eutropha* JMP134 YP_296277.2 having 57% identity to SEQ ID NO:10; and *Bacillus subtilis* BEST7613 NP_440132.1 having 59% identity to SEQ ID NO:10. The sequences associated with the foregoing accession numbers are incorporated herein by reference.

In another embodiment, a system or recombinant microorganism provided herein includes a transketolase. This enzyme may be combined with the expression or overexpression with other enzymes in the metabolic pathway for the production of acetyl-phosphate, acetyl-CoA or other metabolites derived therefrom as described herein above and below. The enzyme produces a metabolite that includes (i) ribose-5-phosphate and xylulose-5-phosphate from sedoheptulose-7-phosphate and glyceraldehyde-3-phosphate; and/or (ii) glyceraldehyde-3-phosphate and fructose-6-phosphate from xylulose-5-phosphate and erythrose-4-phosphate. The transketolase can be encoded by a Tkt gene, polynucleotide or homolog thereof. The Tkt gene or polynucleotide can be derived from various microorganisms including *E. coli*.

In addition to the foregoing, the terms "transketolase" or "Tkt" refer to proteins that are capable of catalyzing the formation of (i) ribose-5-phosphate and xylulose-5-phosphate from sedoheptulose-7-phosphate and glyceraldehyde-3-phosphate; and/or (ii) glyceraldehyde-3-phosphate and fructose-6-phosphate from xylulose-5-phosphate and erythrose-4-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:12. Additional homologs include: *Neisseria meningitidis* M13399 ZP_11612112.1 having 65% identity to SEQ ID NO:12; *Bifidobacterium breve* DSM 20213 ZP_06596168.1 having 41% identity to SEQ ID NO:12; *Ralstonia eutropha* JMP134 YP_297046.1 having 66% identity to SEQ ID NO:12; *Synechococcus elongatus* PCC 6301 YP_171693.1 having 56% identity to SEQ ID NO:12; and *Bacillus subtilis* BEST7613 NP_440630.1 having 54% identity to SEQ ID NO:12. The sequences associated with the foregoing accession numbers are incorporated herein by reference.

In another embodiment, a system or recombinant microorganism provided herein includes a triose phosphate isomerase. This enzyme may be combined with other enzymes in the metabolic pathway for the production of acetyl-phosphate, pyruvate, acetyl-CoA or other metabolites derived therefrom as described herein above and below. The enzyme produces a metabolite that includes dihydroxyacetone phosphate from glyceraldehyde-3-phosphate. The triose phosphate isomerase can be encoded by a Tpi gene, polynucleotide or homolog thereof. The Tpi gene or polynucleotide can be derived from various microorganisms including *G. stearothermophilus* and *E. coli*.

In addition to the foregoing, the terms "triose phosphate isomerase" or "Tpi" refer to proteins that are capable of catalyzing the formation of dihydroxyacetone phosphate from glyceraldehyde-3-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:14. Additional homologs include: *Rattus norvegicus* AAA42278.1 having 45% identity to SEQ ID NO:14; *Homo sapiens* AAH17917.1 having 45% identity to SEQ ID NO:14; *Bacillus subtilis* BEST7613 NP_391272.1 having 40% identity to SEQ ID NO:14; *Synechococcus elongatus* PCC 6301 YP_171000.1 having 40% identity to SEQ ID NO:14; and *Salmonella enterica* subsp. *enterica* serovar *Typhi* str. AG3 ZP_06540375.1 having 98% identity to SEQ ID NO:14. The sequences associated with the foregoing accession numbers are incorporated herein by reference.

In another embodiment, a system or recombinant microorganism provided herein includes a fructose 1,6 bisphosphate aldolase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes fructose 1,6-bisphosphate from a substrate that includes dihydroxyacetone phosphate and glyceraldehyde-3-phosphate. The fructose 1,6 bisphosphate aldolase can be encoded by a Fba gene, polynucleotide or homolog thereof. The Fba gene or polynucleotide can be derived from various microorganisms including *G. stearothermophilus* and *E. coli*.

In addition to the foregoing, the terms "fructose 1,6 bisphosphate aldolase" or "Fba" refer to proteins that are capable of catalyzing the formation of fructose 1,6-bisphosphate from a substrate that includes dihydroxyacetone phosphate and glyceraldehyde-3-phosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:16. Additional homologs include: *Synechococcus elongatus* PCC 6301 YP_170823.1 having 26% identity to SEQ ID NO:16; *Vibrio nigripulchritudo* ATCC 27043 ZP_08732298.1 having 80% identity to SEQ ID NO:16; *Methylomicrobium album* BG8 ZP_09865128.1 having 76% identity to SEQ ID NO:16; *Pseudomonas fluorescens* Pf0-1 YP_350990.1 having 25% identity to SEQ ID NO:16; and *Methylobacterium nodulans* ORS 2060 YP_002502325.1 having 24% identity to SEQ ID NO:16. The sequences associated with the foregoing accession numbers are incorporated herein by reference.

In the design, a synthetic biochemistry "purge valve" was developed that effectively decouples the stoichiometric production of NAD(P)H from Acetyl-CoA (see, e.g., FIG. 1). To this end a mixture of both an NADP$^+$-utilizing wild-type enzymes, a mutant that utilizes NAD$^+$ and a water generating NADH oxidase (NoxE) that specifically oxidizes NADH, but not NADPH was utilized. By employing this metabolic node, excess reducing equivalents were dissipated in an auto-regulatory manner.

For example, the system comprises a core set of enzymes and comprises a "purge valve" for the synthesis of a desired chemical or biofuel. The purge valve system can be utilized in combination with any in vitro system that converts one set of metabolites (e.g., a first carbon source) to a second metabolite (e.g., a desired chemical product). In such instances a purge valve system can be utilized to balance the cofactors. Upon utilization of the available NADP$^+$ at, for example, the conversion of Glucose-6-phosphate to 6-phospho-D-glucono-1,5-lactone, the system would stop and no further metabolites would be made. However, in the purge valve system of the disclosure, the purge valve can oxidize the reducing equivalents thereby maintaining the production.

In one embodiment, the purge valve for use in an in vitro system comprises: a combination of both an NADH-dehydrogenase enzyme and an NADPH-dehydrogenase and a NADH or NADPH-oxidase. It should be noted that other dehydrogenase pairs can be used.

In all of the foregoing embodiments, a system or recombinant microorganism provided herein includes an NADH-oxidase (NoxE). The NADH oxidase can be encoded by a NoxE gene, polynucleotide or homolog thereof. The NoxE gene or polynucleotide can be derived from various microorganisms including *L. Lactis* (see, e.g., Accession number YP_007507681).

In addition to the foregoing, the terms "NADH oxidase" or "NoxE" refer to proteins that are capable of oxidizing NADH to NAD$^+$, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:18.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

In some instances "isozymes" can be used that carry out the same functional conversion/reaction, but which are so dissimilar in structure that they are typically determined to not be "homologous". For example, glpX is an isozyme of fbp, tktB is an isozyme of tktA, talA is an isozyme of talB and rpiB is an isozyme of rpiA.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

The disclosure provides accession numbers for various genes, homologs and variants useful in the generation of recombinant microorganism or in the enzymes systems described herein. In addition, sequences of various enzymes useful in the practice of the disclosure as set forth in FIG. 1A-B are also provided. One of skill in the art will recognize that any and all sequences provided herein can be varied by 1 to 10 conservative amino acid substitutions (e.g., 1, 2, 3, 4, 5, 6, 7, 8, 9 or 10, and in some cases more). It will be further understood that performing BLAST searches using the sequences provided herein will identify sequences that are 80-99% identical (e.g., 81, 82, 83, 84, 85, 86, 87, 88, 89, 90, 91, 92, 93, 94, 95, 96, 97, 98, or 99% identical) to the sequences herein and having the desired activity. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Culture conditions suitable for the growth and maintenance of a recombinant microorganism provided herein are known. The skilled artisan will recognize that such conditions can be modified to accommodate the requirements of each microorganism. Appropriate culture conditions useful in producing a acetyl-phosphate, pyruvate, glyceraldehyde-3-phosphate, acetyl-CoA or other metabolites derived therefrom including, but not limited to 1-butanol, n-hexanol, 2-pentanone and/or octanol products comprise conditions of culture medium pH, ionic strength, nutritive content, etc.; temperature; oxygen/$CO_2$/nitrogen content; humidity; light and other culture conditions that permit production of the compound by the host microorganism or enzyme system, e.g., by the metabolic action of the microorganism or enzymes. Appropriate culture conditions are well known for microorganisms that can serve as host cells.

It is understood that a range of microorganisms can be modified to include a recombinant metabolic pathway, or portions thereof, suitable for the production of chemical entities (e.g., acetl-CoA, pyruvate, G3P, n-butanol, n-hexanol, octanol and others. It is also understood that various microorganisms can act as "sources" for genetic material encoding target enzymes suitable for use in a recombinant microorganism provided herein.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; and (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

In another embodiment, as mentioned previously, a recombinant organism as set forth in any of the embodiments above, is cultured under conditions to express any or all of the enzymatic polypeptide and the culture is then lysed or a cell free preparation is prepared having the necessary enzymatic activity to carry out the pathway set forth in FIG. 1.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C & EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

It should be noted and apparent to one of skill in the art, that where a cell-free system is used, expression and metabolic flux for cell viability are not factors that need be considered. Rather, the enzymes can be any enzymes that have the desired activity. Such enzymes are easily identified in the art, readily available by expression/cloning and can be purchased from various manufacturers.

The invention is illustrated in the following examples, which are provided by way of illustration and are not intended to be limiting.

EXAMPLES

To construct an in vitro system, all the enzymes are acquired commercially or purified by affinity chromatography, tested for activity, and mixed together in a properly selected reaction buffer.

Materials.

Miller LB media or Miller LB agar (BD Difco) was used for growth of bacterial strains in liquid or solid media cultures. *E. coli* BL21Gold(DE3) [B, F—, ompT, hsdSB, (rB—, mB—), dcm+, Tetr, galλ, (DE3) endA, Hte] (Agilent) was used as host for both cloning and expression of recombinant proteins using pET vectors. Plasmid pET28a(+) was purchased from Novagen. HotStart Taq Mastermix (Denville) was used for gene amplification from genomic or plasmid DNA. KOD Xtreme DNA polymerase (Toyobo), Taq DNA ligase (MCLab), and T5 Exonuclease (Epicenter) were purchased separately and used to make the assembly master mix (AMM) used for cloning 21. ATP, glucose, coenzyme A, NADP+, glutathione, and NAD+ were from Sigma.

Enzyme abbreviations and EC numbers are listed in Table A.

TABLE A

Enzyme abbreviations and EC numbers:

| Name | Abbrev. | EC# |
|---|---|---|
| F6P-Phosphoketolase | Fpk | 4.1.2.22 |
| X5P-Phosphoketolase | Xpk | 4.1.2.9 |
| Transaldolase | Tal | 2.2.1.2 |
| Transketolase | Tkt | 2.2.1.1 |
| Triose Phosphate Isomerase | Tpi | 5.3.1.1 |
| Fructose 1,6 Bisphosphatase | Fbp | 3.1.3.11 |
| Fructose 1,6 bisphosphate Aldolase | Fba | 4.1.2.13 |
| Ribose-5-phosphate isomerase | Rpi | 5.3.1.6 |
| Ribulose-3-phosphate epimerase | Rpe | 5.1.3.1 |
| Glucokinase | Glk | 2.7.1.2 |
| Glucose-6-phosphate Dehydrogenase | Zwf | 1.1.1.49 |
| Phopshoglucose isomerase | Pgi | 5.3.1.9 |
| Phosphotransacetylase | Pta | 2.3.18 |

Plasmid Construction.

The expression plasmids for the PHB enzymes were constructed from the pET28a plasmid backbone using the Nde1 and Sac1 cut sites to produce constructs with an N-terminal 6×His tag for purification. Expression constructs for TktA, TalB, and RpiA were from the ASKA collection (RIKEN) cloned into vector pCAN24 (Kitagawa et al., DNA Res. Int. J. Rapid Publ. Rep Genes Genomes, 12:291-299, 2005). The genes used in this study are listed in Table B. The gene encoding polyhydroxybutyrate synthase (phaC; HE_610111) was synthesized and codon optimized for expression in an *E. coli* host before being subcloned into the pET28a expression vector.

TABLE B

Enzyme activity and units added for the final reaction

| Enzyme | Name | activity (u/mg) | stock conc (mg/mL) | activity/rxn |
|---|---|---|---|---|
| Glk | Glucose kinase | 0.56 | 2 | 5.6 |
| Zwf | Glucose-6-phosphate dehydrogenase | 3.7 | 1.5 | 5.6 |
| Zwf mutant | Glucose-6-phosphate dehydrogenase | 1.1 | 2.7 | 14.9 |
| Pgi | 6-phosphoglucolactonase | not measured | 7.7 | — |
| Gnd | 6-phosphogluconate dehydrogenase | 12.6 | 5.2 | 65.5 |
| Gnd mutant | 6-phosphogluconate dehydrogenase | 5.6 | 4.8 | 134.4 |
| Rpe | ribulose-5-phosphate epimerase | not measured | 2.4 | — |
| Xfp | xyululose-5-phosphate phosphoketolase | 0.14 | 11.5 | 32.2 |
| Pta | phosphotrans acetylase | 2.3 | 3.6 | 16.6 |
| TktA | Transketolase A | 50.4 | 20.1 | 2026.1 |
| TalB | Transaldolase B | 60 | 14.3 | 1716.0 |
| RpiA | Ribose-5-phosphate isomerase A | 77.4 | 18.2 | 2817.4 |
| Tpi | Triosephosphate isomerase | 331.7 | 8 | 5307.2 |
| Fba | Fructosebisphosphate aldolase | 0.87 | 4.8 | 20.9 |
| PfkB | Phosphofructokinase B | 0.29 | 2.3 | 6.7 |
| phaA | Acetly-CoA acetyltransferase | 76.2 | 12.9 | 1965.9 |
| phaB | 3-hydroxybutyl-CoA reductase | 6.1 | 13.9 | 169.8 |
| phaC | Polyhydroxybutyrate synthase | 142.7 | 1.8 | 1284.3 |
| noxE | NADH oxidase (H2) forming) | 0.35 | 7.5 | 5.3 |

Enzyme Purification.

Cells from 1 L of culture were harvested by centrifugation and resuspended in 150 mM Tris pH 7.5, 100 mM NaCl. The cells were lysed on ice with sonication and the cell debris was removed by 12,000 g centrifugation at 4° C. The supernatant was then mixed with 5 mL nickel-nitrilotriacetic acid (NTA) agarose and after 30 min, the slurry was loaded onto a column and washed with five column volumes of 100 mM Tris pH 7.5, 100 mM NaCl, 15 mM imidazole. The enzymes were then eluted with 250 mM imidazole, 100 mM Tris pH 7.5. The resulting enzyme was dialyzed into 50 mM Tris pH 7.5, 50 mM NaCl and stored at 4° C.

Enzyme Activity Assays.

All of the enzymes used in this work were assayed as outlined in Table B. The enzymes were assayed in 50 mM Tris buffer, pH 7.5, 5 mM MgCl, and 5 mM KCl which mirrors the final glucose to PHB reaction conditions. The activity of NAD(P)H producing or consuming reactions were monitored at 340 nm. The activity of ATP consuming enzymes were monitored using a coupled assay with Zwf and $NADP^+$ at 340 nm.

Initial Glucose to PHB Reactions and Optimization.

Initial reactions for the self-sustaining biotransformation of glucose into PHB were composed of 50 mM Tris pH 7.5, 5 mM MgCl, 5 mM KCl, 1 mM CoA, 0.5 mM $NAD^+$, 0.5 mM $NADP^+$, 50 mM glucose, 0.1 mM thiamine pyrophosphate, 2 mM glutathione, and 10 mM inorganic phosphate in a final volume of 200 μL. The enzyme concentrations are given in the Table B. The reactions were initiated with the addition of glucose and PHB production monitored by absorbance at 600 nm or using a GC assay.

To find the bottleneck enzyme(s) and optimize the enzymatic levels in the reaction, we decreased single enzyme concentrations systematically and monitored the reaction for a similar decrease in PHB. The reaction was reconstituted with the same buffers and cofactors as the initial biotransformation of glucose to PHB, and 19 out of the 20 PBG pathway enzymes were held constant while a single enzyme was decreased 5-fold and 25-fold. This was systematically carried out for each of the 20 enzymes and the PHB accumulation after 10 h was monitored by $A_{600}$.

Final Semicontinuous Glucose-to-PHB Reactions and Analysis.

Initial reactions for the self-sustaining semicontinuous biotransformation of glucose into PHB were composed of 50 mM Tris, pH 7.5, 5 mM MgCl, 5 mM KCl, 1 mM CoA, 0.5 mM $NAD^+$, 0.5 mM $NADP^+$, 50 mM glucose, 0.1 mM thiamine pyrophosphate, 2 mM glutathione, and 10 mM inorganic phosphate in a final volume of 200 μL. The enzyme concentrations are given in the Table B. The reaction was initiated with the addition of glucose and incubated at room temperature for 10 h. The PHB was harvested by centrifugation, the supernatant pipetted off, and additional PhaC was added to replace the PhaC that precipitated with the bioplastic. Each addition was identical to the starting amount of PhaC. Residual glucose was measured at the start of each reaction at when and after each 10 h run through an enzyme linked assay from Megazyme (K-GLOX 04/14). The reaction was monitored at 600 nm and PHB was quantified after each 10 h cycle. Each reaction was set up in triplicate, and the data represent the mean and standard deviation of both residual glucose and PHB produced.

To assay for PHB, the granules were harvested from the reaction mix and dried at 60° C. for 4 h. The dry PHB was dissolved in 0.5 mL chloroform and 0.25 mL PHA solution (85 mL methanol, 15 mL $H_2SO_4$, and 0.7 g benzoic acid) and incubated at 95° C. for 4 h.

The reactions were extracted with 0.5 mL water and 1 μL of the organic layer was injected on a 0.25 micron HP-Innowax column in an HP5890 Series II gas chromatogram. The gas chromatography method used an injection temperature that was held at 45° C. for 5 min and then increased to 275° C. over 40 min. The peak area was compared with an authentic standard to quantify concentrations.

Enzyme Engineering for Purge Valves.

Both Zwf and Gnd wild-type enzymes have a strong preference for $NADP^+$ over $NAD^+$. Accordingly, the enzymes need to be "re-engineered" to favor $NAD^+$ rather than $NADP^+$. To flip the cofactor specificity of Zwf and Gnd, mutations in the $NADP^+$ binding pocket were designed based on structural models. First, a homology model of the Zwf enzyme from *Geobacillus stearothermophilus* was generated based on the crystal structure of Glucose-6-phosphate dehydrogenase from *Leuconostoc mesenteroides* with NADPH bound (see, PDBID 1E7Y, incorporated herein by reference). A comparison of the model with the NADPH bound structure shows that A47 in GsZwf would come within 4.0 Å of the phosphate at the 2' position of the ribose. As a result, the A47D mutant of GsZwf was generated and assayed for cofactor specificity. Kinetic parameters shown in Table B indicate that the A47D mutation reverses the specificity of the enzyme. In particular, for the wild-type GsZwf, kcat/Km is 14-fold higher for $NADP^+$ than $NAD^+$, while for the re-engineered mutant kcat/Km is nearly 5-fold higher for $NAD^+$.

For Gnd, there is a crystal structure of the enzyme from *G. stearothermophilus* (GsGnd) albeit without $NADP^+$ bound. To model the $NADP^+$ binding site and identify residues that may be important for binding in GsGnd, the GsGnd structure was aligned with the $NADP^+$ bound structure 1PGN from *Ovis aries*. Based on sequence comparison with $NAD^+$ dependent reductases as well as proximity to the 2' phosphate, a series of mutations were introduced (R34Y, N33D and K38L) in an effort to exclude $NADP^+$. The R34Y mutation was chosen because R34 is changed to Y in the bispecific enzyme gntZ from *B. subtilis* while the N33D mutation was chosen because the conserved N33 is Asp in $NAD^+$ dependent dehydrogenases. The K38L mutation was designed to sterically interfere with the phosphate $NADP^+$. The kinetics and specificity for the GsGnd triple mutant N33D/R34Y/K38L are shown in Table B. The wild type Gnd enzyme has a slight preference for $NADP^+$ but the triple mutant sufficiently excludes $NADP^+$ (kcat/Km=0.5) and retains activity with $NAD^+$ (Kcat/Km=1.2) to serve in the purge valve node.

Identification of an ATP Generating Phosphofructokinase.

A aspect of the PBG pathway is quantitative regeneration of ATP during the conversion of fructose 1,6 bisphosphate into fructose-6-phosphate. Although a similar reaction is performed in natural gluconeogenesis by fructose-1,6-bisphosphatase, it generates inorganic phosphate rather than ATP. Normally, Pfk catalyzes the ATP dependent phosphorylation of F6P to FBP and is a key regulatory step in the EMP pathway. While two different isoforms of Pfk, PfkA and PfkB, have been identified and characterized from various organisms, it is generally thought that the reverse reaction (FBP and ADP to F6P and ATP) does not occur in vivo, hence the use of a non-phosphorylating Fbpase in gluconeogenesis. Prior to implementing the PBG pathway, effort was made to find a Pfkenzyme that would efficiently generate ATP in a reverse reaction. It has been reported that PfkA and PfkB can catalyze the reverse reaction in vitro so multiple enzymes were screened including the *E. coli* PfkA, *E. coli* PfkB, *G. sterothermophilus* Pfk, and a regulatory mutant of *G. sterothermophilus* Pfk (R211A) that abolishes the allosteric inhibition by PEP and GDP. From this screen the *E. coli* PfkB was found to efficiently generated ATP at high enough flux to be used in the PBG cycle.

Obtaining and Purifying Enzymes.

In an alternative process six proteins (Fba, Glk, Zwf, Tpi, Pgi, and Pfk) are purchased from Sigma-Aldrich while others (e.g., Tkt, Tal, Rpe, Rpi) are purified in-house. All commercial enzymes are purchased from Sigma Chemical Co. (St. Louis, Mo.). Rabbit muscle is the source for Tpi and Fba, Baker's yeast for Glk, Zwf, and Pgi, and *Bacillus stearothermophilus* for Pfk.

All non-commercial proteins are put on the high expression plasmid pQE9 (Qiagen, Chatsworth, Calif.) with an N-terminal 6× histidine tag and cloned into XL1-Blue (Stratagene). Expression in the same cloning strain yield high yields when cells are induced at an OD of 0.4-0.6 and induced at 0.1 mM IPTG for four hours. The purification is done according to the protocol listed in His-Spin Protein Miniprep kit (Zymo Research, Orange, Calif.). All of the genetic sequences except F/Xpk can be obtained from *E. coli*'s JCL16 gDNA. Specifically, rpe, rpiA, tktA, talB, and ackA are cloned from *E. coli*. F/Xpk is cloned from *Bifidobacterium adolenscentis* (ATCC 15703 gDNA). Between 0.5-3 milligrams of protein can be obtained from each elution and the purity analyzed by SDS-PAGE by loading 10 uL of diluted protein sample using the MINI PROTEAN II (Bio-Rad Laboratories, Hercules, Calif.). To verify the activity of each purified enzyme, a system of several NADPH-linked coupled assays are used. Using the "Enzyme Buffer" consisting of 50 mM 3-(N-morpholino)propanesulfonic acid (MOPS) pH 7.5, 5 mM $MgCl_2$, and 1 mM TPP, using the commercial enzymes described above (Glk, Zwf, and Pgi) high activity is established. The Zwf linked assay is used because the production of NADPH produces less noise then the degradation of NADH by glycerol-3-phosphate dehydrogenase. All the coupled assays end with the formation of G6P, which becomes oxidized by glucose-6 phosphate dehydrogenase (Zwf) to 6-phospho D-glucono-1,5-lactone (PGL).

Enzyme Activity and Optimization.

NoxE was assayed by monitoring the oxidation of NAD(P)H at 340 nm. The assay was carried out in 100 mM tris-HCl pH 7.5, 5 mM $MgCl_2$, 5 mM KCl, and 0.2 mM NAD(P)H.

As an initial test of the synthetic biochemistry system, all the PBG enzymes (See, FIG. 1) (except the salvage pathway described below) and the PHB biosynthetic pathway were mixed with cofactors, after which 50 mM glucose was added to initiate the reaction.

A clear increase in turbidity was observed at 600 nm compared to that of a control lacking PhaC (the PHB synthase), indicating that PHB was produced. Nevertheless, the rates and yields in the initial test were poor.

The PBG cycle is complicated by the fact that Xfp has phosphoketolase activity with both X5P and fructose-6-phosphate (F6P). The secondary reaction with F6P would create a potentially wasteful trap by producing erythrose-4-phosphate (E4P) as a dead-end product. To solve this problem, three additional enzymes were added from the non-oxidative pentose phosphate pathway, transketolase A (TktA), transaldolase B (TalB), and ribose-5-phosphate isomerase (RpiA), so that E4P could be fed back into the PBG cycle (see FIG. 1). When the E4P salvage pathway enzymes were added (TktA, TalB, and RpiA), a dramatic enhancement in the flux through the pathway was observed.

The efficiency of each purge valve node was analyzed to determine whether both purge valves were required to maintain NADPH levels and carbon flux to drive this system. The full in vitro system, including the salvage pathway, was reconstituted with the either the Zwf purge valve only (i.e., eliminating the $NADP^+$-specific Gnd enzyme), the Gnd purge valve only, or both, and the rate of PHB accumulation assessed. Omitting the Gnd purge valve produced only about half of the flux obtained when using the Gnd purge valve only or both purge valves simultaneously. The dependence of PHB production on the Gnd node is likely due to the fact that Gnd is the committed step of the oxidative pentose phosphate pathway driven by the release of $CO_2$.

To determine whether enzymatic bottlenecks were present in the system, the pathway was systematically reconstituted with ⅕th or 1/25th the starting amount of each enzyme while the other enzymes were kept constant. For most of the enzymes, lowering the concentration 25-fold had little to no effect; the exceptions were Glk and Xfp, indicating that these represent potential bottlenecks. Glk and Xfp concentrations were thus increased two-fold in the final system.

To evaluate the efficiency and longevity of the PBG pathway, the ability of the system to process a single large initial input of glucose was examined. A practical constraint, however, is the fact that the type 1 PHB synthase (PhaC) that was used remains covalently bound to the end of the growing PHB chain, so when PHB was removed to quantitatively assay the amount produced, PhaC was also removed. Thus, the system was run in a semicontinuous fashion: at regular time points the bioplastic were removed by centrifugation for quantitative assays, and then added new PhaC to allow the reactions to proceed. In these experiments, there were no additions with the exception of PhaC.

To monitor the function and stability of the optimized system, the PBG pathway was used to convert either 60.7 or 109.2 mM glucose into PHB from a single addition of glucose. The reaction started with the addition of glucose and was allowed to proceed for up to 55 h (2.3 d) without any addition of cofactors or metabolites to maintain flux in the system. The reaction could be roughly monitored continuously by absorbance at 600 nm, but for a more rigorous quantitative assessment, a GC assay was used. After each 10 h cycle, precipitated PHB was pelleted and removed by centrifugation and assayed.

When the reaction was started with 60.7 mM glucose, a rapid production of PHB in the initial 10 h cycles was observed, but then reaction rates diminished as the glucose was consumed. By the end of the third cycle, the reaction stopped because there was simply no more glucose to consume. The reaction produced 57±6 mM PHB (monomer equivalents), corresponding to a 94% yield.

To see whether the system could process glucose for longer periods of time, the initial concentration of glucose was increased to 109.2 mM. The results showed robust activity for five cycles with the higher glucose starting concentrations, ultimately providing 93.8±6.1 mM PHB (monomer equivalents), corresponding to an 86% yield. The maximum productivity of the PBG cycle was 0.7 g/L/h of PHB, and the system maintained >50% of the maximum activity over the entire 55-h run at room temperature, with titers of 9.8 g/L of PHB from 19.7 g/L of glucose.

The high yield and high titers achieved are particularly notable considering that glucose was used and all cofactors were fully recycled, whereas other attempts to produce PHB in vitro have relied on sacrificial substrates and expensive building blocks. Based on experience from the ethanol industry, the production values are already close to generally accepted thresholds needed for industrial production 20 (90% yields with a productivity of 1 g/L/h and titers of 40 g/L), even though little effort was made to maximize production.

The accompany sequence listing submitted herewith includes the sequence for the protein and enzymes described in Table C. One of skill in the art will be readily apprised of homologs and variants using the accompany Table and sequence listing. For example, the use of BLAST using any of the sequences identified herein will identify additional sequences that can readily be substituted for the sequences provided in the sequence listing. Moreover, one of skill in the art can readily identify the biological steps and reactions in FIGS. 1A-D and the enzymes in Table C to define and understand the reactions and methods of the disclosure.

TABLE C

| Sequences | | | |
|---|---|---|---|
| Enzyme | Acronym | Organism | Sequence |
| Xylulose-5-phosphate/fructose-6-phosphate phospohoketolase | Xfp | *Bifidobacterium adolescentis* | SEQ ID NO: 1 (Nucleic Acid) |
| Xylulose-5-phosphate/fructose-6-phosphate phospohoketolase | Xfp | *Bifidobacterium adolescentis* | SEQ ID NO: 2 (Polypeptide) |
| Fructose 1,6-bisphosphatase | FBP1 | *E. coli* | SEQ ID NO: 3 (Nucleic Acid) |
| Fructose 1,6-bisphosphatase | FBP1 | *E. coli* | SEQ ID NO: 4 (Polypeptide) |
| ribulose-5-phosphate epimerase | Rpe | *E. coli* | SEQ ID NO: 5 (Nucleic acid) |
| ribulose-5-phosphate epimerase | Rpe | *E. coli* | SEQ ID NO: 6 (Polypeptide) |
| Ribose-5-phosphate isomerase | Rpi | *E. coli* | SEQ ID NO: 7 (Nucleic acid) |
| Ribose-5-phsophate isomerase | Rpi | *E. coli* | SEQ ID NO: 8 (Polypeptide) |
| Transaldolase | Tal | *E. coli* | SEQ ID NO: 9 (Nucleic acid) |
| Transaldolase | Tal | *E. coli* | SEQ ID NO: 10 (Polypeptide) |
| Transketolase | Tkt | *E. coli* | SEQ ID NO: 11 (Nucleic acid) |
| Transketolase | Tkt | *E. coli* | SEQ ID NO: 12 (Polypeptide) |
| Triose phosphate isomerase | Tpi | *E. coli* | SEQ ID NO: 13 (Nucleic acid) |
| Triose phosphate isomerase | Tpi | *E. coli* | SEQ ID NO: 14 (Polypeptide |
| Fructose 1,6 bisphosphate aldolase | Fba | *E. coli* | SEQ ID NO: 15 (Nucleic acid) |
| Fructose 1,6 bisphosphate aldolase | Fba | *E. coli* | SEQ ID NO: 16 (Polypeptide) |
| NADH oxidase | NoxE | *Lactococcus lactis* | SEQ ID NO: 17 (Nucleic acid) |
| NADH oxidase | NoxE | *Lactococcus lactis* | SEQ ID NO: 18 (Polypeptide) |
| Glucokinase | Glk | *Geobacillus stearothermophilus* | SEQ ID NO: 19 (Polypeptide) |
| Phosphofructokinase | Pfk | *Geobacillus stearothermophilus* | SEQ ID NO: 20 (Polypeptide) |
| Glucose-6-phosphate dehydrogenase | Zwf | *E. coli* | SEQ ID NO: 21 (Nucleic acid) |
| Glucose-6-phosphate dehydrogenase | Zwf | *E. coli* | SEQ ID NO: 22 (Polypeptide) |
| Glucose-6-phosphate dehydrogenase | Zwf | *Geobacillus stearothermophilus* | SEQ ID NO: 23 (Polypeptide) |
| Glucose-6-phosphate dehydrogenase | Zwf | *Geobacillus stearothermophilus* | SEQ ID NO: 24 (Polypeptide) |
| 6-phosphoglucono-lactonase | Pgl | *E. coli* | SEQ ID NO: 25 (Nucleic acid) |
| 6-phosphoglucono-lactonase | Pgl | *E. coli* | SEQ ID NO: 26 (Polypeptide) |
| 6-phosphogluconate dehydrogenase | Gnd | *Geobacillus thermodenitrificans* | SEQ ID NO: 27 (Polypeptide) |
| 6-phosphogluconate dehydrogenase | mGnd | Mutant sequence | SEQ ID NO: 28 (Polypeptide) |
| Glyceraldehyde-3-phosphate dehydrogenase | Gap | *Geobacillus stearothermophilus* | SEQ ID NO: 29 (Polypeptide) |
| Glyceraldehyde-3-phosphate dehydrogenase | mGap | Mutant sequence (D34A/L35R/T35K) | SEQ ID NO: 30 (Polypeptide) |
| Glyceraldehyde-3-phosphate dehydrogenase | mGap | Mutant sequence (P188D | SEQ ID NO: 31 (Polypeptide) |

TABLE C-continued

Sequences

| Enzyme | Acronym | Organism | Sequence |
| --- | --- | --- | --- |
| Phosphoglycerate Kinase | Pgk | *Geobacillus stearothermophilus* | SEQ ID NO: 32 (Polypeptide) |
| tRNA 5-methylamino methyl-2-thiouridine modification GTPase | MnmE, also called TrmE and previously designated ThdF (thiophene and furan oxidation protein) | *E. coli* | SEQ ID NO: 33 (Nucleic acid) |
| tRNA 5-methylamino methyl-2-thiouridine modification GTPase | MnmE, also called TrmE and previously designated ThdF (thiophene and furan oxidation protein) | *E. coli* | SEQ ID NO: 34 (Polypeptide) |
| tRNA 5-methylamino methyl-2-thiouridine modification GTPase | MnmE, also called TrmE and previously designated ThdF (thiophene and furan oxidation protein) | *Geobacillus thermodenitrificans* | SEQ ID NO: 35 (Nucleic acid) |
| tRNA 5-methylamino methyl-2-thiouridine modification GTPase | MnmE, also called TrmE and previously designated ThdF (thiophene and furan oxidation protein) | *Geobacillus thermodenitrificans* | SEQ ID NO: 36 (Polypeptide) |
| GTP-binding tubulin-like cell division protein | FtsZ | *E. coli* | SEQ ID NO: 37 (Nucleic acid) |
| GTP-binding tubulin-like cell division protein | FtsZ | *E. coli* | SEQ ID NO: 38 (Polypeptide) |
| 5-methylcytosine-specific restriction enzyme McrBC, subunit McrB | McrB | *E. coli* | SEQ ID NO: 39 (Nucleic acid) |
| 5-methylcytosine-specific restriction enzyme McrBC, subunit McrB | McrB | *E. coli* | SEQ ID NO: 40 (Polypeptide) |
| 5-methylcytosine-specific restriction enzyme McrBC, subunit McrC | McrC | *E. coli* | SEQ ID NO: 41 (Nucleic acid) |
| 5-methylcytosine-specific restriction enzyme McrBC, subunit McrC | McrC | *E. coli* | SEQ ID NO: 42 (Polypeptide) |
| 2,3-bisphosphoglycerate-independent phosphoglycerate mutase | Pgm | *Geobacillus stearothermophilus* | SEQ ID NO: 43 (Polypeptide) |
| Enolase | Eno | *E. coli* | SEQ ID NO: 44 (Polypeptide) |
| Pyruvate kinase | Pyk | *Geobacillus stearothermophilus* | SEQ ID NO: 45 (Polypeptide) |
| Pyruvate kinase | Pyk | *Zymomonas mobilis* | SEQ ID NO: 46 (Polypeptide) |
| Pyruvate kinase | Pyk | *Oryctolagus cuniculus* | SEQ ID NO: 47 (Polypeptide) |
| Pyruvate decarboxylase | Pdc | *Zymomonas mobilis* | SEQ ID NO: 48 (Polypeptide) |
| Aldehyde dehydrogenase | pduP | *Salmonella enterica* | SEQ ID NO: 49 (Polypeptide) |
| Triosephosphate isomerase | Tpi | *Geobacillus stearothermophilus* | SEQ ID NO: 50 (Polypeptide) |
| Fructose-bisphosphate aldolase | FBA | *Geobacillus stearothermophilus* | SEQ ID NO: 51 (Polypeptide) |
| 6-phosphofructokinase II | pfkB | *E. coli* | SEQ ID NO: 52 (Polypeptide) |
| ATP-dependent 6-phosphofructokinase | mpfkB | *Geobacillus stearothermophilus* | SEQ ID NO: 53 (Polypeptide) |
| polyphosphate kinase | Ppk | *Mycobacterium tuberculosis* | SEQ ID NO: 54 (Polypeptide) |
| phosphoketolase D-xylulose 5-phosphate/D-fructose 6-phosphate phosphoketolase | Xfp | *Pseudomonas aeruginosa* | SEQ ID NO: 55 (Polypeptide) |
| phosphotransacetylase | Pta | *Geobacillus stearothermophilus* | SEQ ID NO: 56 (Polypeptide) |
| glucose-6-phosphate isomerase | Pgi | *Geobacillus thermodenitrificans* | SEQ ID NO: 57 (Polypeptide) |
| Pyruvate oxidase | Pox | *Aerococcus viridans* | SEQ ID NO: 58 (Polypeptide) |
| Pyruvate dehydrogenase | PdhE1a | *Geobacillus stearothermophilus* | SEQ ID NO: 59 (Polypeptide) |
| Pyruvate dehydrogenase | PdhE1b | *Geobacillus stearothermophilus* | SEQ ID NO: 60 (Polypeptide) |
| Pyruvate dehydrogenase (dihydrolipamide acetyltransferase subunit) | PdhE2 | *Geobacillus stearothermophilus* | SEQ ID NO: 61 (Polypeptide) |

TABLE C-continued

Sequences

| Enzyme | Acronym | Organism | Sequence |
| --- | --- | --- | --- |
| Pyruvate dehydrogenase (dihydrolipamide dehydrogenase subunit) | PdhE3 | *Geobacillus stearothermophilus* | SEQ ID NO: 62 (Polypeptide) |
| Pyruvate dehydrogenase (dihydrolipamide dehydrogenase subunit) | mPdhE3 | Mutant sequence (G188A/G192A/E206V/ G207R/A208K/S213R) | SEQ ID NO: 63 (Polypeptide) |
| Pyruvate dehydrogenase (dihydrolipamide dehydrogenase subunit) | mPdhE3 | Mutant sequence (G185A/G189A/E203V/ M204R/F205K/D206H/ P210R) | SEQ ID NO: 64 (Polypeptide) |

A number of embodiments of the invention have been described. Nevertheless, it will be understood that various modifications may be made without departing from the spirit and scope of the invention. Accordingly, other embodiments are within the scope of the following claims.

---

What is claimed is:

1. A cell-free in vitro metabolic pathway comprising a plurality of enzymatic steps that converts a substrate to acetyl-phosphate, pyruvate, glyceraldehyde-3-phosphate, or acetyl-CoA, wherein the pathway includes an unbalanced production and utilization of a co-factor, the pathway comprising a non-naturally occurring purge valve pathway that recycles the co-factor, wherein the non-naturally occurring purge valve pathway comprises (i) a wild-type enzyme that utilizes NADP+, (ii) a mutant of the wild-type enzyme that utilizes NAD+ and (iii) an NADH oxidase, wherein the wild-type enzyme of (i) is a glucose-6-phosphate dehydrogenase and/or a 6-phosphogluconate dehydrogenase and wherein the pathway comprises pentose phosphate pathway enzymes including glucose-6-phosphate dehydrogenase and 6-phosphogluconate dehydrogenase, wherein (1) the wild-type enzyme of (i) has a sequence that is 95% identical to SEQ ID NO:23 and has glucose-6-phosphate dehydrogenase activity and uses NADP+ as a cofactor and the mutant enzyme of (ii) has a sequence that is 95% identical to SEQ ID NO:24 and has glucose-6-phosphate dehydrogenase activity and uses NAD+ as a cofactor; and/or (2) wherein the wild-type enzyme of (i) has a sequence that is 95% identical to SEQ ID N0:27 and has 6-phosphogluconate dehydrogenase activity and uses NADP+ as a cofactor and the mutant enzyme of (ii) has a sequence that is 95% identical to SEQ ID NO:28 and has 6-phosphogluconate dehydrogenase activity and uses NAD+ as a cofactor; and wherein the NADH oxidase of (iii) has a sequence that is at least 80% identical to SEQ ID NO:18 and has NADH oxidase activity.

2. The cell-free in vitro pathway of claim 1, further comprising the following enzymes:
(a) a phosphoketolase (F/Xpk or Xfp);
(b) a transaldolase (Tal);
(c) a transketolase (Tkt);
(d) a ribose-5-phosphate isomerase (Rpi);
(e) a ribulose-5-phosphate epimerase (Rpe);
(f) a triose phosphate isomerase (Tpi);
(g) a fructose 1,6 bisphosphate aldolase (Fba);

(h) a glucokinase (Glk);
(i) a 6-phospho-gluconolactonase (pgl);
(j) a phosphoglucoisomerase (Pgi);
(k) a phosphofructokinase (pfk).

3. The cell-free in vitro pathway of claim 1, wherein the pathway is a cell-free system.

4. The cell-free in vitro pathway of claim 1, wherein the pathway is engineered and expressed in a microorganism.

5. The cell-free in vitro pathway of claim 4, wherein the microorganism is a prokaryote or eukaryote.

6. A cell-free in vitro pathway for producing acetyl-phosphate from glucose comprising:
   (a) a phosphoketolase (F/Xpk or Xfp);
   (b) a transaldolase (tal);
   (c) a transketolase (tkt);
   (d) a ribose-5phosphate isomerase (Rpi);
   (e) a ribulose-5phospate epimerase (Rpe);
   (f) a triose phosphate isomerase (Tpi);
   (g) a fructose 1,6 bisphosphate aldolase (Fba);
   (h) a glucokinase (Glk);
   (i) a glucose-6-phosphate dehydrogenase (Zwf) having the sequence of SEQ ID NO:23;
   (j) a 6-phosphogluconolactonase (pgl);
   (k) a 6-phosphogluconate dehydrogenase (Gnd) having the sequence of SEQ ID NO:27;
   (l) a phosphoglucoisomerase (pgi);
   (m) a phosphofructokinase (pfk);
   (n) a mutant 6-phosphogluconate (mGnd) having the sequence of SEQ ID NO:28;
   (o) a mutant glucose-tphosphate dehydrogenase (mZwf) having the sequence of SEQ ID NO:24; and
   (p) an NADH oxidase.

* * * * *